(12) United States Patent
Kimple et al.

(10) Patent No.: US 7,309,575 B2
(45) Date of Patent: Dec. 18, 2007

(54) PROTEIN PURIFICATION AND DETECTION METHODS

(75) Inventors: Michelle E. Kimple, Chapel Hill, NC (US); John Sondek, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 543 days.

(21) Appl. No.: 10/345,574

(22) Filed: Jan. 16, 2003

(65) Prior Publication Data

US 2003/0215897 A1    Nov. 20, 2003

Related U.S. Application Data

(60) Provisional application No. 60/353,225, filed on Feb. 1, 2002, provisional application No. 60/349,818, filed on Jan. 16, 2002.

(51) Int. Cl.
*G01N 33/53* (2006.01)
*C07K 14/00* (2006.01)
(52) U.S. Cl. .................. 435/7.1; 530/350; 435/183
(58) Field of Classification Search .......... 435/7.1, 435/21, 28, 29, 71.1, 69.1, 968, 975, 183; 530/350
See application file for complete search history.

(56) References Cited

U.S. PATENT DOCUMENTS 7,087,388 B1 * 8/2006 Zuker et al. ................. 435/7.1

FOREIGN PATENT DOCUMENTS

WO    WO 91/17239    * 11/1991

OTHER PUBLICATIONS van Huizen et al, The EMBO J., vol. 17, pp. 2285-2297, (1998).*
Kimple, M. et al, The EMBO J., vol. 20(16), pp. 4414-4422, (2001).*
Reina et al., Computer-aided design of a PDZ domain to recognize new target sequences, *Nature Structural Biology—advance online publication* pp. 1-7 (Jun. 24, 2002).

* cited by examiner

*Primary Examiner*—Karen Cochrane Carlson
(74) *Attorney, Agent, or Firm*—Jenkins, Wilson, Taylor & Hunt, P.A.

(57) ABSTRACT

The present invention relates to methods for purifying and for detecting the presence of a protein. The invention employs a NorpA sequence and a PDZ1 domain. A protein tagged with a NorpA sequence can associate with PDZ1 domain. Similarly, a protein tagged with a PDZ1 domain can associate with a NorpA sequence. This interaction forms an aspect of the protein purification methods and protein detection methods of the present invention. Recombinant expression vectors and a protein purification solid phase are also disclosed, as well as protein detection and purification kits.

18 Claims, 10 Drawing Sheets

NorpA  AP-PDZ1

Figure 3A

PROTEIN PURIFICATION AND DETECTION METHODS

CROSS REFERENCE TO RELATED APPLICATIONS

This application is based on and claims priority to U.S. Provisional Application Ser. Nos. 60/349,818, filed Jan. 16, 2002, and 60/353,225, filed Feb. 1, 2002, each of which is herein incorporated by reference in its entirety.

GRANT STATEMENT

This work was supported by NIH grant R01-GM57391. Thus, the U.S. Government has rights in the invention.

TECHNICAL FIELD

The present invention relates to purification of proteins in general and purification of proteins by affinity tags in particular. The present invention also relates to detection of proteins in a background of proteins.

| Abbreviations | |
|---|---|
| ABP | albumin binding protein |
| ADP | adenosine diphosphate |
| AMP | adenosine monophosphate |
| AP | alkaline phosphatase |
| BCCP | biotin carboxyl carrier protein |
| BCIP | 5-bromo-4-chloro-3-indolyl phosphate |
| BME | β-mercaptoethanol |
| BSA | bovine serum albumin |
| CaMV | cauliflower mosaic virus, CaMV |
| CBP | calmodulin binding protein |
| CNBr | cyanogen bromide |
| $CT_{Dm}$ | C-terminal domain of NorpA |
| $ddH_2O$ | double distilled water |
| DNA | deoxyribonucleic acid |
| DTE | dithioerythritol |
| DTT | dithiothreitol |
| EGTA | ethylene glycol-bis(2-aminoethyl)-N,N,N',N'-tetraacetic acid |
| ELISA | enzyme-linked immunosorbent assay |
| FRET | fluorescence resonance energy transfer |
| GFP | green fluorescent protein |
| GSH | reduced glutathione |
| GST | glutathione S transferase |
| HA | hemaglutinin |
| hIgG | human immunoglobulin gamma |
| $His_6$ | hexahistidine |
| HRP | horseradish peroxidase |
| HSPs | high scoring sequence pairs |
| InaD | inactivation no after-potential |
| IPTG | isopropyl-thio-β-D-galactopyranoside |
| LB | Luria broth |
| Mab | monoclonal antibody |
| MBP | maltose binding protein |
| NAD | nicotine adenine dinucleotide |
| NBT | nitro blue tetrazolium |
| NCBI | National Center for Biotechnology Information |
| NHS | N-hydroxysuccinimide |
| NorpA | no receptor potential A |
| nt | nucleotide(s) |
| $OD_{600}$ | optical density at 600 nm |
| PBS | phosphate buffered saline |
| PCR | polymerase chain reaction |
| PDZ | post-synaptic density 95, discs-large and zonular occludens |
| RNA | ribonucleic acid |
| RU | response unit |
| SBP | streptavidin binding peptide |
| SDS | sodium dodecyl sulfate |

-continued

| Abbreviations | |
|---|---|
| SDS/PAGE | sodium dodecyl sulfate polyacrylamide gene electrophoresis |
| SPA | staphylococcal protein A |
| SPG | staphylococcal protein G |
| SPR | surface plasmon resonance |
| SSC | standard saline citrate |
| TBS | tris-buffered saline |
| TBS-T | tris-buffered saline plus Tween-20 |
| TCEP | tris(2-carboxyethyl)phosphine |
| TMV | tobacco mosaic virus |
| TSB | tryptic soy broth |

Amino Acid Abbreviation and Corresponding mRNA Codons

| Amino Acid | 3-Letter | 1-Letter | mRNA Codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic Acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Proline | Pro | P | CCA CCC CCG CCU |
| Phenylalanine | Phe | F | UUC UUU |
| Serine | Ser | S | ACG AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

BACKGROUND ART

Proteins and polypeptides play an important role in a variety of applications. For example, proteins and polypeptides can be employed as research compounds, drug candidates, and in other therapeutic applications. One of the more significant challenges in the development of these and other applications is the development of cost effective and efficient processes for purification of proteins and polypeptides, particularly on a commercial scale. It is also challenging to develop feasible methods of producing proteins of suitable purity and amounts for research purposes as well. While many methods are now available for large-scale production of proteins, crude preparations contain not only the desired product but also closely related impurities that are difficult to separate from the desired product. Moreover, biological sources of proteins usually produce complex mixtures of materials.

Procedures for purification of proteins from cell debris can initially depend on the site of expression of the protein. Some proteins can be engineered so that they are secreted directly from the cell into the surrounding growth media; others are retained within the cell. For the latter proteins, the first step of a purification process involves lysis of the cell, which can be done by a variety of methods, including mechanical shear, osmotic shock, or enzymatic treatments. Such disruption releases the entire contents of the cell into the homogenate and, in addition, produces subcellular fragments that can be difficult to remove due to their small size. These are generally removed by differential centrifugation or by filtration, leading to a clarified solution. The same problem arises, although on a smaller scale, with directly secreted proteins due to the natural death of cells and release of intracellular host cell proteins in the course of the protein production run.

Once a clarified solution containing a protein of interest has been obtained, its separation from the other proteins produced by the cell is usually attempted using a combination of various chromatography techniques. These techniques separate mixtures of proteins on the basis of their charge, degree of hydrophobicity, size, or affinity, to name but a few separation criteria. Several different chromatography resins are available for each of these techniques, allowing accurate tailoring of the purification scheme to the particular protein involved.

The essence of each of these separation methods is that proteins can be caused either to move at different rates down a long column, achieving a physical separation that increases as they pass further down the column, or to adhere selectively to the separation medium, being then differentially eluted by different solvents. Alternatively, the separation can be based on the association of a protein with a column matrix material and thus depends on the sample not moving down the column until it is eluted therefrom. In some cases, the desired protein is separated from impurities when the impurities specifically adhere to the column and the protein of interest does not; that is, the protein of interest is present in the "flow-through".

Affinity chromatography and hydrophobic interaction chromatography techniques have been developed to supplement the more traditional size exclusion and ion exchange chromatographic protocols. Affinity chromatography relies on the interaction of a target protein with an immobilized ligand. The ligand can be specific for the particular protein of interest in which case the ligand can be, for example, a substrate, substrate analog, inhibitor, or antibody. Alternatively, the ligand can be adapted to react with another protein. General ligands, such as adenosine monophosphate (AMP), adenosine diphosphate (ADP), nicotine adenine dinucleotide (NAD), or certain dyes can be employed to recover one or more classes of proteins.

In a common affinity chromatography isolation scheme, a specific interaction between an insoluble immobilized ligand and a soluble target protein can be advantageously employed (see generally, Janson & Rydén (eds), (1998) *Protein Purification: Principles, High Resolution Methods, and Applications* ($2^{nd}$ ed.), Wiley-Liss, New York; Johnstone & Thorpe, (1987) *Immunochemistry in Practice*, ($2^{nd}$ ed.), Blackwell Scientific Publications, pp. 207-240). By interacting with the ligand, the target protein is temporarily rendered insoluble and is retained on the solid support on which the ligand is immobilized while the soluble contaminants are eluted. The binding of the target protein to the ligand conventionally takes place in an aqueous buffer at a neutral pH. The target protein is subsequently released from the immobilized ligand by a change in the elution conditions, such as a change in the pH; an increase in temperature; elution with a denaturing agent, an organic solvent, or an unphysiologically high concentration of a salt; or elution with a compound that competes for a binding site on the target protein. As a result of these procedures, the target protein is often recovered in a denatured form and must be subjected to further manipulations in order to become refolded into its native conformation.

Examples of commonly employed ligands are antibodies, in particular monoclonal antibodies (Mabs), which can be made to be more selective and to bind more firmly than most other known ligands. As a result, monoclonal antibodies can result in a higher purity of the eluted protein product. In order to obtain an antibody in sufficient quantities, however, the protein to be purified usually must be available in substantially pure form for the immunization procedure. Often, this is an insurmountable limitation.

Colorimetric methods are often based on a primary and secondary antibody-conjugate system. Antibodies have the advantage of being very specific and sensitive. However, antibody-based methods also have the potential for non-specific interactions due to antibody and antibody-conjugate adsorption to the peptide library itself. These two-step methods also consist of more variables than simple one-step methods, thus requiring additional optimization. With direct fluorescent detection methods, autofluorescence of the resin beads can be a major drawback, depending on the type of resin used. Thus, antibody-based approaches to protein purification and detection can be cumbersome and nonspecific.

Radiological techniques have also been employed in protein purification schemes. In these approaches, a protein is labeled with a detectable radioactive moiety. Disadvantages of these radiological techniques include the need to handle hazardous radioactive material, radiolysis of the labeled protein, and the potential structural modification of target protein due to radiolabeling. Exposure times can also be a limiting factor.

Additionally, most of these methods are not appropriate for the large-scale production of a target protein, since they are inefficient in target protein recovery or are only partially effective in removing impurities. Large scale purification methods which employ immunoaffinity chromatography (see e.g., Wallen et al. (1983) *Eur. J. Biochem.* 133: 681-686) are limited by the cost of antibody resins, the difficulty associated with sterilizing these resins, and by the potential for the antibodies, or fragments thereof, to contaminate the recovered target protein. Radiological methods require the use of radioactivity, which, as disclosed hereinabove, can be undesirable. All of the methods discussed suffer from a lack of specificity. Furthermore, fusion proteins can require the fusion of a target protein with a sequence that can be longer than that of the target protein, or alternatively, can interfere with the activity of the target protein. In cases where the retention of the biological activity of the protein is essential, the removal of the fused moiety would be necessary, as well as the purification of the target protein from the fused moiety, which can result in drastically reduced yields.

Therefore, the need for a cost-effective affinity ligand to purify target proteins remains. In order to obtain a high degree of purity, a ligand with a high avidity towards a target protein is needed. Additionally, there is a concurrent need for a short tag that can associate with the ligand. Such a tag can be associated with a target protein sequence to aid in purification and/or detection of the target protein. Preferably, the tag is short enough that it does not interfere with the structure or function of the target protein. The problem then, is to identify a ligand with a high avidity for a short tag, yet without such high avidity that the target protein cannot be disassociated from the ligand without denaturation. The present invention solves this and other problems associated with protein purification and detection.

SUMMARY OF THE INVENTION

A method of purifying a target protein comprising a tag sequence from a mixture of components is disclosed. In one embodiment, the tag sequence is one of a "post-synaptic density 95, discs-large and zonular occludens" (PDZ1) domain and a "no receptor potential A" (NorpA) sequence. In another embodiment, the method comprises: (a) contacting the mixture with one of a PDZ1 domain and a NorpA sequence to form a complex comprising the target protein and the PDZ1 domain or the NorpA sequence; (b) removing uncomplexed components; and (c) recovering the target protein, whereby a target protein comprising a tag sequence is purified from a mixture of components. In one embodiment, the tag sequence provides for selective binding to the PDZ1 domain.

Further, a method of detecting the presence of a target protein comprising a tag sequence in a mixture of components is disclosed. In one embodiment, the tag sequence is one of a PDZ1 domain and a NorpA sequence. In another embodiment, the method comprises: (a) contacting the mixture with one of a PDZ1 domain or a NorpA sequence to form a complex comprising the target protein and the PDZ1 domain or the NorpA sequence; and (b) detecting the complex. In one embodiment, the tag sequence provides for selective binding to the PDZ1 domain.

A protein purification solid phase is also disclosed. In one embodiment, the solid phase comprises: (a) a non-soluble matrix; and (b) one of a PDZ1 domain polypeptide and a NorpA polypeptide sequence.

Additionally, a recombinant expression vector is disclosed. In one embodiment, the vector comprises: (a) a nucleic acid sequence encoding one of a PDZ1 domain and a NorpA tag; and (b) a cloning site flanking of one of one side and both sides of the PDZ1 domain or the NorpA tag.

A kit is disclosed. In one embodiment, the kit comprises: (a) a first container containing a vector comprising a nucleic acid sequence encoding a tag sequence, wherein the tag sequence is one of a PDZ1 domain and a NorpA sequence; and (b) a second container containing one of a PDZ1 domain polypeptide and a polypeptide comprising a NorpA sequence. In one embodiment, the tag sequence provides for selective binding to the PDZ1 domain.

In another aspect of the present invention a protein purification kit is disclosed. In one embodiment, the protein purification kit comprises: (a) a first container containing a vector comprising a nucleic acid sequence encoding a tag sequence, wherein the tag sequence is one of a PDZ1 domain and a NorpA sequence; (b) a second container containing one of a PDZ1 domain polypeptide and a polypeptide comprising a NorpA sequence; and (c) a third container containing an elution component. In one embodiment, the tag sequence provides for selective binding to the PDZ1 domain.

Additionally, a protein detection kit is disclosed. In one embodiment of this aspect of the present invention, the kit comprises: (a) a first container containing a vector comprising a nucleic acid sequence encoding a tag sequence, wherein the tag sequence is one of a PDZ1 domain and a NorpA sequence; (b) a second container containing one of a PDZ1 domain polypeptide and a polypeptide comprising a NorpA sequence; (c) an elution component; and (d) a detection component. In one embodiment, the tag sequence provides for selective binding to the PDZ1 domain.

It is thus an object of the present invention to provide a vector and a method of purifying proteins. It is another object of the present invention to provide a vector and a method of detecting the presence of a protein. These and other objects are achieved in whole or in part by the present invention.

Some of the objects of the invention having been stated hereinabove, other objects will become evident as the description proceeds, when taken in connection with the accompanying Drawings and Examples as best described hereinbelow.

BRIEF DESCRIPTION OF THE DRAWINGS

Figure 3A:
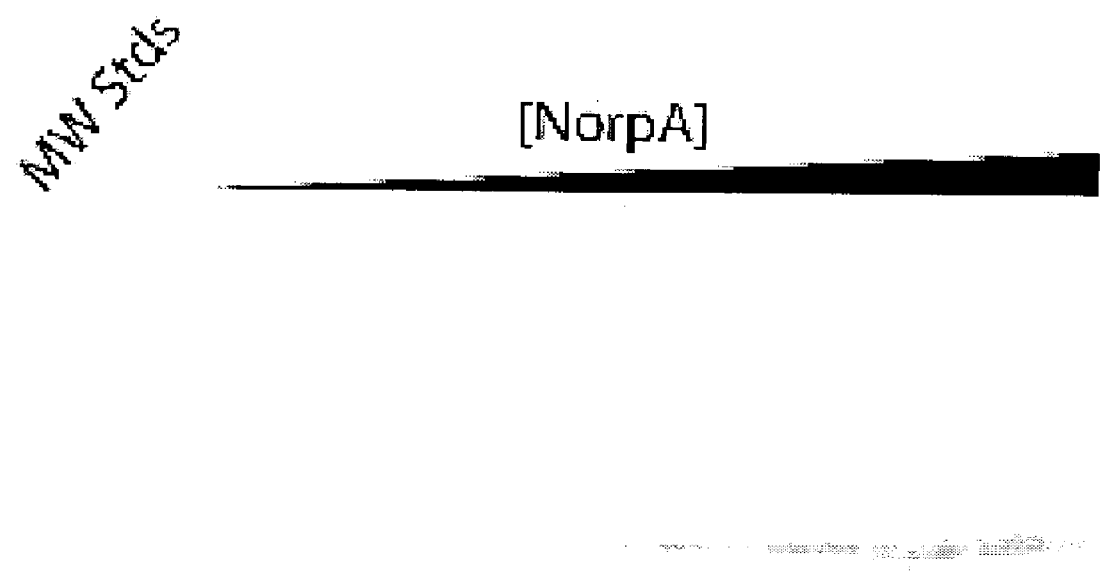

FIG. 3A is blot depicting the observation that AP-PDZ1 interacts specifically with $CT_{Dm}$ in a background of bacterial proteins. Varying amounts of purified $CT_{Dm}$ were added to BL21(DE3) whole-cell lysate and separated by sodium dodecyl sulfate polyacrylamide gene electrophoresis (SDS/PAGE), followed by transfer to nitrocellulose. The membrane was blocked and incubated with AP-PDZ1 for 4 hours, followed by extensive washing.

BRIEF DESCRIPTION OF THE SEQUENCES IN THE SEQUENCE LISTING

Figure 1A:
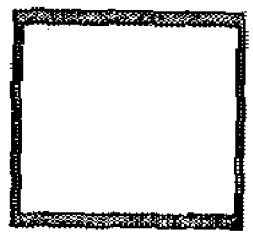
FIG. 1A is a blot depicting the observation that AP-PDZ1 has an active alkaline phosphatase (AP) activity, while the C-terminal domain of NorpA ($CT_{Dm}$) alone does not. $CT_{Dm}$ (left) and AP-PDZ1 (right) were dotted onto a nitrocellulose membrane, dried, blocked, and washed.
Figure 1A:

SEQ ID NO: 1 is an amino acid sequence of an exemplary 5-residue tag sequence.

SEQ ID NO: 2 is an amino acid sequence of a variable tag sequence.

SEQ ID NO: 3 is a DNA sequence encoding an InaD polypeptide.

SEQ ID NO: 4 is an amino acid sequence of an InaD AA polypeptide.

SEQ ID NO: 5 is a DNA sequence encoding a NorpA polypeptide.

SEQ ID NO: 6 is an amino acid sequence of a NorpA AA polypeptide.

SEQ ID NO: 7 is a DNA sequence encoding PDZ1 polypeptide.

SEQ ID NO: 8 is an amino acid sequence of a PDZ1 polypeptide.

SEQ ID NO: 9 is an amino acid sequence of a NorpA peptide co-crystallized with a PDZ1 domain.

SEQ ID NO: 10 is a nucleic acid sequence encoding a primer.

SEQ ID NO: 11 is a nucleic acid sequence encoding a primer.

SEQ ID NO: 12 is a nucleic acid sequence encoding a primer.

SEQ ID NO: 13 is a nucleic acid sequence encoding a primer.

DETAILED DESCRIPTION OF THE INVENTION

In one embodiment, the present invention provides a system in which a protein tagged with a NorpA tag of the present invention (e.g. Thr-Glu-Phe-Cys-Ala (SEQ ID NO: 1) or $X_1$-$X_2$-$X_3$-C-$X_4$ (SEQ ID NO: 2)) can be purified and/or detected by a PDZ1 fusion protein (such as an alkaline phosphatase (AP)-PDZ1 fusion protein), based on a covalent and specific interaction between the tag and a PDZ1 domain. In one aspect of the present invention, an AP-PDZ1 fusion protein can be employed to specifically detect a target protein tagged with a tag of the present invention against a background of bacterial proteins.

In another aspect of the present invention, the tag can be spliced onto a target protein that does not normally interact with a PDZ1 domain. In this aspect of the present invention, the addition of the tag confers PDZ1 domain binding ability on the target protein and the interaction between the target protein and a labeled PDZ1 domain can be specifically detected against a background of proteins.

In yet another aspect of the present invention, this system can be employed in a protein purification method. In this embodiment, a PDZ1 domain polypeptide can be associated with an insoluble support. A mixture of proteins, including a target protein comprising the NorpA tag, is then contacted with the support. The tag on the tagged target protein will associate with the PDZ1 domain polypeptide on the support, while those proteins not labeled with the tag will not associate with the support. The target protein can then be eluted from the support and recovered. Due to its short length, its role in protein detection and purification, and its covalent and specific interaction with a PDZ1 domain polypeptide, the methods and apparatus of the present invention is an improvement over presently available affinity tags and methods.

Until disclosure of the present invention, the ability to purify proteins by employing a short, highly specific tag has not been fully realized. And until disclosure of the present invention, the ability to detect the presence of a target protein tagged with a short highly specific tag has not been realized. The present invention solves these and other problems.

I. Definitions

Following long-standing patent law convention, the terms "a" and "an" refer to "one or more" when used in this application, including the claims.

As used herein, the term "mutation" carries its traditional connotation and refers to a change, inherited, naturally occurring, or introduced, in a nucleic acid or polypeptide sequence, and is used in its sense as generally known to those of skill in the art.

As used herein, the term "labeled" refers to the attachment of a moiety, capable of detection by spectroscopic, radiologic, or other methods, to a probe molecule. A label can be a small molecule or it can be a functional domain derived from an enzyme.

As used herein, the term "transcription" refers to a cellular process involving the interaction of an RNA polymerase with a gene that directs the expression as RNA of the structural information present in the coding sequences of the gene. The process includes, but is not limited to the following steps: (a) transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

As used herein, the term "expression" generally refers to the cellular processes by which a polypeptide is produced from RNA.

As used herein, the term "detecting" refers to confirming the presence of a target entity by observing the occurrence of a detectable signal, such as a radiologic, calorimetric, or spectroscopic signal that will appear exclusively in the presence of the target entity.

As used herein, the term "sequencing" refers to determining the ordered linear sequence of nucleic acids or amino acids of a DNA or protein target sample, using conventional manual or automated laboratory techniques.

As used herein, the terms "isolated" and "purified" are used interchangeably and refer to oligonucleotides substantially free of other nucleic acids, proteins, lipids, carbohydrates, or other materials with which they can be associated, such association being either in cellular material or in a synthesis medium. The term can also be applied to polypeptides, in which case the polypeptide will be substantially free of nucleic acids, carbohydrates, lipids, and other undesired polypeptides.

When "isolating" or "purifying" a sample, the degree of purity of an oligonucleotide or polypeptide of interest is increase by removing (completely or partially) at least one contaminant from the composition. A "purification step" can comprise a part of an overall purification process resulting in a "substantially pure" composition.

As used herein, the term "substantially pure" refers to a sample in which a polynucleotide or polypeptide is substantially free of the sequences and molecules with which it is associated in its natural state, and those molecules used in the isolation procedure. The term "substantially free" refers to that the sample is in one embodiment at least 50%, in another embodiment at least 70%, in another embodiment 80% and in still another embodiment 90% free of the materials and compounds with which is it associated in nature.

As used herein, the term "primer" refers to a sequence comprising in one embodiment two or more deoxyribonucleotides or ribonucleotides, in another embodiment more than three, in another embodiment more than eight, and in still another embodiment at least about 20 nucleotides (nt) of an exonic or intronic region. In one embodiment, such oligonucleotides are between ten and thirty bases in length.

As used herein, the term "DNA segment" refers to a DNA molecule that has been isolated free of total genomic DNA of a particular species. For example, in one embodiment, a DNA segment encoding a NorpA polypeptide refers to a DNA segment that comprises SEQ ID NO: 5, a DNA segment encoding a PDZ1 domain refers to a DNA segment that comprises SEQ ID NO: 7, and a DNA segment encoding an InaD polypeptide refers to a DNA segment that comprises SEQ ID NO: 3. A DNA segment of the present invention can optionally comprise fewer or additional nucleic acids, yet is isolated away from, or purified free from, total genomic DNA of a source species, such as *Homo sapiens* or *Escherichia coli*. Included within the term "DNA segment" are DNA segments and smaller fragments of such segments, and also recombinant vectors, including, for example, plasmids, cosmids, phages, viruses, and the like.

As used herein, the term "biological activity" refers to any observable effect flowing from interaction between a tag of the present invention, a PDZ domain polypeptide, or target protein, and a ligand. A representative, but non-limiting, biological activity is the association of a protein tagged with a tag of the present invention with a PDZ1 domain.

As used herein, the term "modified" refers to an alteration from an entity's normally occurring state. An entity can be modified by removing discrete chemical units or by adding discrete chemical units. The term "modified" encompasses detectable labels as well as those entities added as aids in purification.

As used herein, the term "NorpA" refers to nucleic acids (e.g. SEQ ID NO: 5) encoding a "no receptor potential A" polypeptide (e.g. SEQ ID NO: 6). The term also refers to the protein encoded by such a nucleic acid sequence. The term "NorpA" includes vertebrate homologs; however, NorpA nucleic acids and polypeptides can also be isolated from invertebrate sources. In one embodiment, a NorpA nucleic acid or polypeptide is isolated from *Drosophila melanogaster*. "NorpA" further includes vertebrate homologs of NorpA family members, including, but not limited to mammalian and avian homologs. Representative mammalian homologs of NorpA family members include, but are not limited to murine and human homologs.

As used herein, the terms "NorpA gene product", "NorpA protein", "NorpA polypeptide", and "NorpA peptide" are used interchangeably and refer to peptides having amino acid sequences which are substantially identical to native amino acid sequences from an organism of interest (for example, *Drosophila*) and which are biologically active in that they comprise all or a part of the amino acid sequence of a NorpA polypeptide, cross-react with antibodies raised against a NorpA polypeptide, or retain all or some of the biological activity (in one embodiment, the ability to associate with a PDZ1 domain) of the native amino acid sequence or protein. Such biological activity can include the ability to associate with a PDZ1 domain polypeptide.

As used herein, the terms "NorpA gene product", "NorpA protein", "NorpA polypeptide", and "NorpA peptide" also include derivatives of a NorpA polypeptide. By "derivative" it is intended that a DNA or peptide sequence can comprise alterations relative to the sequences disclosed herein, yet retain all or some of the biological activity of those sequences. Derivatives can be derived from genomic nucleotide sequences as are disclosed herein or from other organisms, or can be created synthetically. Those skilled in the art will appreciate that other derivatives, as yet undisclosed or undiscovered, can be used to design and/or construct NorpA derivatives.

There is no need for a "NorpA gene product", "NorpA protein", "NorpA polypeptide", or "NorpA peptide" to comprise all or substantially all of the amino acid sequence of a NorpA polypeptide. Shorter or longer sequences are antici-pated to be of use in the invention; shorter sequences are herein referred to as "segments". Thus, the terms "NorpA gene product", "NorpA protein", "NorpA polypeptide", and "NorpA peptide" also include fusion, chimeric, or recombinant NorpA polypeptides and proteins comprising sequences of the present invention. Methods of preparing such polypeptides are disclosed herein and are known in the art.

As used herein, the terms "NorpA gene" and "recombinant NorpA gene" refer to a nucleic acid molecule comprising an open reading frame encoding a NorpA polypeptide of the present invention, including both exon and (optionally) intron sequences.

As used herein, the term "DNA sequence encoding a NorpA polypeptide" can refer to one or more coding sequences within a particular individual. Moreover, certain differences in nucleotide sequences can exist between individual organisms, which are called alleles. It is possible that such allelic differences might or might not result in differences in amino acid sequence of the encoded polypeptide yet still encode a protein with the same biological activity. As is well known, genes for a particular polypeptide can exist in single or multiple copies within the genome of an individual. Such duplicate genes can be identical or can have certain modifications, including nucleotide substitutions, additions, or deletions, all of which still code for polypeptides having substantially the same activity.

As used herein, the term "PDZ1" refers to nucleic acids (e.g. SEQ ID NO: 7) encoding domain 1 of a "post synaptic density 95, discs-large and zonular occludens" (PDZ1) polypeptide (e.g. SEQ ID NO: 8) that can associate with a tag of the present invention. The term "PDZ1 domain" includes vertebrate homologs; however, in alternative embodiments, PDZ1 nucleic acids and polypeptides are isolated from invertebrate sources, such as *Drosophila melanogaster*. "PDZ1" further includes vertebrate homologs of PDZ1 family members, including, but not limited to mammalian and avian homologs. Representative mammalian homologs of PDZ1 domain family members include, but are not limited to murine and human homologs.

As used herein, the terms "PDZ1 domain gene product", "PDZ1 domain protein", "PDZ1 domain polypeptide", and "PDZ1 domain peptide" are used interchangeably and refer to peptides having amino acid sequences which are substantially identical to native amino acid sequences from an organism of interest (in one embodiment, *Drosophila*) and which are biologically active in that they comprise all or a part of the amino acid sequence of a PDZ1 domain polypeptide, cross-react with antibodies raised against a PDZ1 domain polypeptide, or retain all or some of the biological activity (in one embodiment, the ability to associate with the C-terminal five amino acids of a NorpA polypeptide) of the native amino acid sequence or protein. Such biological activity can include the ability to associate with a tag of the present invention.

As used herein, the terms "PDZ1 domain gene product", "PDZ1 domain protein", "PDZ1 domain polypeptide", and "PDZ1 domain peptide" also include derivatives of a PDZ1 domain polypeptide. By "derivative" it is intended that a DNA or peptide sequence can contain alterations relative to the sequences disclosed herein, yet retain all or some of the biological activity of those sequences. Derivatives can be derived from genomic nucleotide sequences as are disclosed herein or from other organisms, or can be created synthetically. Those skilled in the art will appreciate that other derivatives, as yet undisclosed or undiscovered, can be used to design and/or construct PDZ1 domain derivatives.

There is no need for a "PDZ1 domain gene product", "PDZ1 protein", "PDZ1 domain polypeptide", or "PDZ1 domain peptide" to comprise all or substantially all of the amino acid sequence of a PDZ1 domain polypeptide gene product. Shorter or longer sequences are anticipated to be of use in the invention; shorter sequences are herein referred to as "segments". Thus, the terms "PDZ1 domain gene product", "PDZ1 domain protein", "PDZ1 domain polypeptide", and "PDZ1 domain peptide" also include fusion, chimeric, or recombinant PDZ1 domain polypeptides and proteins comprising sequences of the present invention. Methods of preparing such proteins are disclosed herein and are known in the art.

As used herein, the terms "PDZ1 domain gene" and "recombinant PDZ1 domain gene" refer to a nucleic acid molecule comprising an open reading frame encoding a PDZ1 domain polypeptide of the present invention, including both exon and (optionally) intron sequences.

As used herein, the term "DNA sequence encoding a PDZ1 domain polypeptide" can refer to one or more coding sequences within a particular individual. Moreover, certain differences in nucleotide sequences can exist between individual organisms, which are called alleles. It is possible that such allelic differences might or might not result in differences in amino acid sequence of the encoded polypeptide yet still encode a protein with the same biological activity. As is well known, genes for a particular polypeptide can exist in single or multiple copies within the genome of an individual. Such duplicate genes can be identical or can have certain modifications, including nucleotide substitutions, additions, or deletions, all of which still code for polypeptides having substantially the same activity.

As used herein, the term "gene" is used for simplicity to refer to a functional protein, polypeptide, or peptide encoding unit. As will be understood by those in the art, this functional term includes both genomic sequences and cDNA sequences. Representative embodiments of genomic and cDNA sequences are disclosed herein.

As used herein, the term "polypeptide" refers to any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. As used herein, the terms "protein", "polypeptide", and "peptide" are used interchangeably herein when referring to a gene product.

As used herein, the term "intron" refers to a DNA sequence present in a given gene that is not translated into protein and/or is removed by splicing from a RNA molecule prior to that RNA being translated.

As used herein, the term "interact" refers to undetectable interactions between molecules as well as detectable interactions between molecules, such as can be detected using, for example, a yeast two-hybrid assay. The term "interact" is also meant to include "binding" interactions between molecules. Interactions can, for example, be protein-protein or protein-nucleic acid in nature.

As used herein, the terms "cells", "host cells", or "recombinant host cells" are used interchangeably and refer to not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

A "contaminant" is a material that is different from the desired polypeptide product. The contaminant can be a variant of the desired polypeptide or another polypeptide, nucleic acid, endotoxin, etc.

A "variant" or "amino acid sequence variant" of a starting polypeptide is a polypeptide that comprises an amino acid sequence different from that of the starting polypeptide. Generally, a variant will possess in one embodiment at least 80% sequence identity, in another embodiment at least 90% sequence identity, in another embodiment at least 95% sequence identity, and in yet another embodiment at least 98% sequence identity with the native polypeptide. Percentage sequence identity can be determined, for example, by the Fitch et al. version of the algorithm (Fitch et al., *Proc. Natl. Acad. Sci. U.S.A.* 80: 1382-1386 (1983)) described by Needleman et al., (Needleman et al., *J. Mol. Biol.* 48: 443-453 (1970)), after aligning the sequences to provide for maximum homology. Other alignment techniques are disclosed herein below. Amino acid sequence variants of a polypeptide can be prepared by introducing appropriate nucleotide changes into DNA encoding the polypeptide, or by peptide synthesis. Such variants include, for example, deletions from, and/or insertions into, and/or substitutions of, residues within the amino acid sequence of the polypeptide of interest. Any combination of deletion, insertion, and substitution is made to arrive at the final construct, provided that the final construct possesses the desired characteristics. The amino acid changes also can alter post-translational processes of the polypeptide, such as changing the number or position of glycosylation sites. Methods for generating amino acid sequence variants of polypeptides are described, for example, in U.S. Pat. No. 5,534,615, incorporated herein by reference.

As used herein, the term "recombinant polypeptide" refers to a polypeptide that has been produced in a host cell which has been transformed or transfected with a nucleic acid encoding the polypeptide, or produces the polypeptide as a result of homologous recombination.

As used herein the terms "transformation" and "transfection" are used interchangeably and refer to the process of introducing a nucleic acid into a cell. Following transformation or transfection, the nucleic acid can integrate into the host cell genome or can exist as an extrachromosomal element. The "host cell" includes a cell in in vitro cell culture as well as a cell within a host animal.

As used herein, the term "buffer" refers to a solution that resists changes in pH by the action of its acid-base conjugate components. Various buffers that can be employed depending, for example, on the desired pH of the buffer are described in *Buffers. A Guide for the Preparation and Use of Buffers in Biological Systems*, (Gueffroy, ed.) Calbiochem Corporation, San Diego, Calif., United States of America (1975). In one embodiment, a buffer has a pH in the range from about 6 to about 8. Examples of buffers that will control the pH in this range include MES, MOPS, MOPSO, TRIS, TBS, TSE, TBS-T, phosphate, acetate, citrate, succinate, and ammonium buffers, as well as combinations of these.

As used herein, the terms "binding activity" and "binding affinity" are used interchangeably and refer to the tendency of one protein or polypeptide to bind or not to bind to another protein or polypeptide. The energetics of protein-protein interactions are significant in "binding activity" and "binding affinity" because they define the necessary concentrations of interacting partners, the rates at which these partners are capable of associating, and the relative concentrations of bound and free proteins in a solution.

As used herein, the term "solid phase" refers to a non-aqueous matrix to which a target protein can adhere. Representative solid phases comprise a glass, silica, polymeric, nitrocellulose, or carbohydrate surface. The solid phase can comprise a purification column or a discontinuous phase of discrete particles. In one embodiment, a solid phase comprises a polysaccharide-based gel. Representative polysaccharide-based gels include, but are not limited to SEPHAROSE® (available from Amersham Biosciences, Piscataway, N.J., United States of America) and AFFI-GEL® (available from Bio-Rad Laboratories, Hercules, Calif., United States of America).

As used herein, the terms "tag", "tag of the present invention", and "NorpA tag" are used interchangeably and refer to a short amino acid sequence that can associate with a PDZ1 domain polypeptide. In one embodiment, a tag encompasses the C-terminal 5 amino acids of a NorpA protein derived from *Drosophila* and recited in SEQ ID NOs: 1 and 2, but can also comprise any sequence of contiguous amino acids derived from SEQ ID NO: 6 or modified versions thereof.

As used herein, the term "host cell" refers to a cell into which a heterologous nucleic acid molecule has been introduced. Transformed cells, tissues, or organisms are understood to encompass not only the end product of a transformation process, but also transgenic progeny thereof. Exemplary host cells of the present invention include *E. coli* cells. In one embodiment, a host cell is *E. coli* strain BL21 (DE3).

A host cell strain can be chosen which modulates the expression of the inserted sequences, or modifies and processes the gene product in the specific fashion desired. For example, different host cells have characteristic and specific mechanisms for the translational and post-transactional processing and modification (for example, glycosylation and/or phosphorylation of proteins). Appropriate cell lines or host systems can be chosen to ensure the desired modification and processing of the foreign protein expressed. Expression in a bacterial system can be used to produce a non-glycosylated core protein product. Expression in yeast will produce a glycosylated product. Expression in animal cells can be used to ensure "native" glycosylation of a heterologous protein.

II. General Considerations

The purification of proteins is an increasingly important problem for commercial and academic biotechnology efforts. Thus, a need exists for methods and apparatuses that can be employed to generate highly pure protein samples. Typically, proteins are produced by cell culture, using either mammalian or bacterial cell lines engineered to produce the protein of interest by insertion of a recombinant plasmid containing the gene for that protein. Since the cell lines employed are living organisms, they must be fed with a complex growth medium containing sugars, amino acids, and growth factors, usually supplied from preparations of animal serum.

Separation of a desired protein from such a mixture of compounds fed to the cells, and from the by-products of the cells themselves, to a purity level sufficient for use as a research tool or even as a human therapeutic poses a formidable challenge. Often, the separation procedure is a complex multi-step process requiring expensive apparatus and chromatography media. See, e.g., Oqez et al., (1989) *Biotech. Adv.* 7: 467-488 and Sofer, (1986) *Bio/Technology* 4: 712-715.

Procedures for purifying proteins from cell debris initially depend on the site of expression of the protein. Some proteins can be engineered to be secreted from the cell into the surrounding growth media, while other proteins remain within the cell. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved.

Affinity chromatography, which exploits a specific interaction between the protein to be purified and a second protein (such as a specific antibody), can also be employed for the purification of some proteins. Various chromatography techniques are known in the art for purifying proteins. Procedures such as molecular sieve chromatography, ion exchange chromatography, and electrophoresis are commonly utilized to purify proteins. Separation of proteins that have very similar molecular weights and similar net charges, however, requires the use of alternative purification methods due to the absence of any significant differential in the features (for example, molecular weight and net charge) which known separation processes exploit. Complete and efficient separation of proteins is critical for research and is also important when a protein is intended for therapeutic use, particularly if the purified protein is to be employed in the treatment of hypersensitive individuals such as immunodeficient or immunocompromised patients.

III. Tag of the Present Invention

The NorpA protein is found in *Drosophila* and is involved in at least visual signal transduction. See the *Drosophila* database "Flybase", available online at flybase.bio.indiana.edu/. NorpA is a cytoplasmic protein that functions in vivo as a 1-phosphatidylinositol-4,5-bisphosphate phosphodiesterase (similar to phospholipase C). In the cell, NorpA catalyzes the degradation of phospholipids, forming inositol trisphosphate and diacylglycerol.

The NorpA protein can exist in one of two subtypes. Subtype I comprises 1305 amino acid residues in its primary sequence. Subtype II comprises 1312 amino acid residues in its primary sequence. In the present disclosure, both subtypes are encompassed by the term "NorpA". Thus, the term "NorpA tag" encompasses a sequence derived from either subtype I and subtype II.

A tag of the present invention can be of any length or sequence. In one embodiment, however, a tag of the present invention is derived from the NorpA protein (i.e., a NorpA tag) and in another embodiment from the C-terminus of a NorpA protein (SEQ ID NO: 1). In still another embodiment, the tag comprises the amino acid sequence $X_1$-$X_2$-$X_3$-C-$X_4$, (SEQ ID NO: 2) where C is an invariant cysteine and $X_1$, $X_2$, $X_3$, and $X_4$ can be any residue. In alternative embodiments, these variable amino acids are as follows: $X_1$ is threonine, serine, or tyrosine; $X_2$ is glutamic acid or aspartic acid; $X_3$ is phenylalanine or tyrosine, and $X_4$ is alanine, glycine, leucine, isoleucine, or valine. Indeed, a tag of the present invention can comprise any segment or fragment of a NorpA polypeptide (representative NorpA polypeptide set forth in SEQ ID NO: 6), or functional equivalent thereof as defined herein, so long as the segment, fragment, or functional equivalent thereof exhibits the functional characteristic of binding a PDZ1 domain polypeptide as defined herein.

III.A. Designing a Tag of the Present Invention

A general formula for one embodiment of a tag of the present invention is $X_1$-$X_2$-$X_3$-C-$X_4$, (SEQ ID NO: 2) where C is an invariant cysteine and $X_1$, $X_2$, $X_3$, and $X_4$ can be any residue. In alternative embodiments, these variable amino acids are as follows: $X_1$ is threonine, serine, or tyrosine; $X_2$ is glutamic acid or aspartic acid; $X_3$ is phenylalanine or tyrosine and $X_4$ is alanine, glycine, leucine, isoleucine, or valine. Additionally, another sequence known to associate with a PDZ1 domain polypeptide can also be employed as a tag of the present invention and comprises the sequence T-E-F-C-A (SEQ ID NO: 1). But the present disclosure transcends these specific examples and discloses processes for designing a tag that can associate with a PDZ1 domain polypeptide, as well as tags designed by this process. Indeed, a tag of the present invention can comprise any segment or fragment of a NorpA polypeptide (representative NorpA polypeptide set forth in SEQ ID NO: 6), or functional equivalent thereof as defined herein, so long as the segment, fragment, or functional equivalent thereof exhibits the functional characteristic of binding a PDZ1 domain polypeptide as defined herein.

When designing a tag of the present invention, various properties can be considered. For example, it might be desirable to design a tag that has a hydrophobicity or hydrophilicity value that is higher or lower than that of a sequence corresponding to SEQ ID NOs: 1 and 2. Additionally, it might be desirable to design a tag that is longer in length than the five-residue sequence of SEQ ID NOs: 1 and 2. Further, it might be desirable to design a tag that has an overall charge (or imparts an overall charge to a target protein with which the tag will be associated). These and other properties can be varied when designing a tag based on an amino sequence of the present invention (for example, SEQ ID NO: 6).

More often, though, it will be desirable for a tag to interact with the tagged protein to a minimal extent. Indeed, this is an advantage of the present invention: a tag of the present invention is relatively small (on the order of about five amino acids) compared to the protein that is tagged. The small size of the tag can be advantageous since it will minimally interact with the tagged protein while still maintaining a high specificity for a PDZ1 domain of the present invention. These factors can also be considerations when designing a tag of the present invention.

III.B. The PDZ1-NorpA Crystal Structure

The crystal structure of PDZ1 in complex with a peptide corresponding to the C-terminus of NorpA (G-L-T-E-F-C-A) (SEQ ID NO: 9) has been solved (Kimple et al., (2001) *EMBO J.* 20: 4414-4422). This crystal structure indicates that PDZ1 interacts with the C-terminus of NorpA via a disulfide bond. This disulfide bond forms a basis for the high-affinity interaction between the InaD and NorpA proteins in vivo (Kimple et al., (2001) *EMBO J.* 20: 4414-4422). Those of ordinary skill in the art can advantageously employ this crystal structure in the design of a tag of the present invention, as described hereinbelow.

The three-dimensional structure of NorpA in complex with a PDZ1 domain can be used in the development of tag sequences that can interact with a PDZ1 domain. Computer programs that use crystallography data can be used in the rational design of tags that can be employed in protein purification and/or detection protocols. Programs such as RASMOL (Biomolecular Structures Group, GlaxoWellcome Research & Development Stevenage, Hertfordshire, UK, Version 2.6, August 1995, Version 2.6.4, December 1998, Copyright © Roger Sayle 1992-1999) can be employed to display the atomic structural coordinates from the NorpA-PDZ1 crystal structure, and/or can be used to generate three-dimensional models and/or to determine the structures of candidate tag sequences. Computer programs and software suites, such as those sold under the registered trademark INSIGHT II® and such as GRASP (Nicholls et al., (1991) *Proteins* 11: 282), allow for further manipulations and the ability to introduce new structures. In addition, high throughput binding and biological activity assays can be devised employing one or more purified recombinant proteins and modern reporter gene transcription assays known to those of ordinary skill in the art in order to refine the length and/or specificity of a tag of the present invention.

A method of designing a tag based on the NorpA-PDZ1 crystal structure is thus provided in accordance with the present invention. The method comprises designing a potential tag that will make interactions with amino acids of PDZ1, based upon the NorpA-PDZ1 crystal structure; synthesizing the tag; and determining whether, to what degree, and in what fashion the potential tag associates with a PDZ1 domain polypeptide. A tag designed by this method is also provided.

In an alternative embodiment, another method of designing a tag in accordance with the present invention is disclosed. The method comprises selecting a candidate tag; determining which amino acid or amino acids of a PDZ1 domain polypeptide interact with the tag based on an analysis of a three-dimensional model of the crystallized NorpA-PDZ1 complex; identifying in a binding assay a degree to which the tag binds to a PDZ1 domain polypeptide; selecting a chemical modification of the tag wherein the interaction between the amino acids of the PDZ1 domain polypeptide and the tag is predicted to be modulated by the chemical modification; synthesizing a tag having the chemical modification to form a modified tag; contacting the modified tag with the PDZ1 domain polypeptide; identifying in a binding assay a degree to which the modified tag modulates the binding of the tag to the PDZ1 domain polypeptide; and comparing the binding of the tag to the PDZ1 domain polypeptide to the modified tag with the binding of the PDZ1 domain polypeptide in the presence of the unmodified tag. A tag designed by this method is also provided.

An additional method of designing tags of the present invention can comprise: (a) determining which amino acid or amino acids of a PDZ1 domain polypeptide interacts with a first chemical moiety (at least one) of the tag using the three dimensional model of the crystallized NorpA-PDZ1 complex; and (b) selecting one or more chemical modifications of the first chemical moiety to produce a second chemical moiety with a structure that either decreases or increases an interaction between the interacting amino acid and the second chemical moiety compared to the interaction between the interacting amino acid and the first chemical moiety. This is a general strategy only, however, and variations on this disclosed protocol would be apparent to those of ordinary skill in the art upon consideration of the present disclosure. A tag designed by this method is also provided.

In each of foregoing embodiments, the PDZ1 domain polypeptide can comprise the amino acid sequence of SEQ ID NO: 8 and/or can be encoded by the nucleic acid sequence of SEQ ID NO: 7. In alternative embodiments, a tag of the present invention comprises the amino acid sequence of SEQ ID NOs: 1, 2, or 9.

Once a candidate tag is synthesized as described herein and as will be apparent to those of ordinary skill in the art upon contemplation of the disclosure of the present invention set forth herein, it can be tested using assays to establish its binding affinity. After such testing, a candidate tag can be further refined by generating crystals comprising the candidate tag bound to the PDZ1 domain polypeptide. The structure of the candidate tag can then be further refined using the chemical modification methods described herein for three dimensional models to improve the activity or affinity of the candidate tag and make second generation tags with improved properties.

A further aspect of the present invention is that sterically similar compounds can be formulated to mimic the key portions of a PDZ1 domain polypeptide. Such compounds are functional equivalents, as discussed further hereinbelow. The generation of a structural functional equivalent can be achieved by the techniques of modeling and chemical design known to those of skill in the art and described herein. Modeling and chemical design of PDZ1 domain structural equivalents can be based on the structure coordinates of a crystalline tag-PDZ1 domain polypeptide complex. It will be understood that all such sterically similar constructs fall within the scope of the present invention.

IV. A PDZ1 Domain Sequence of the Present Invention

Inactivation no after-potential D (InaD) is a critical protein in the *Drosophila* phototransduction pathway, a well-characterized G protein-coupled, phospholipase C-mediated signaling cascade (Scott & Zuker, (1998) *Nature* 395: 805-808; Xu et al., (1998) *J. Cell Biol.* 142: 545-555; Scott et al., (1995) *Neuron* 15: 919-927). InaD is composed nearly completely of five PDZ domains (van Huizen et al., (1998) *EMBO J.* 17: 2285-2297; Tsunoda et al., (1997) *Nature* 388: 243-249; Shieh et al., (1997) *Proc. Natl. Acad. Sci. U.S.A.* 94: 12682-12687), so named for the first three proteins in which this domain was characterized: Post-synaptic density 95, Discs-large, and Zonular occludens (Kennedy, (1995) *Trends Biochem Sci* 20: 350; Morais Cabral et al., (1996) *Nature* 382: 649-652; Doyle et al., (1996) *Cell* 85: 1067-1076). PDZ domains generally interact with the C-terminal 3-4 amino acids of their protein targets, including the free carboxylate group (Hillier et al., (1999) *Science* 284: 812-815). Type I PDZ domains bind to the consensus sequence S/T-X-V/L, where X is any residue (Doyle et al., (1996) *Cell* 85: 1067-1076; Songyang et al., (1997) *Science* 275: 73-77), while type II PDZ domains bind to the more general sequence φ-X-φ, where φ is usually a large, hydrophobic residue (Daniels et al., (1998) *Nat. Struct. Biol.* 5: 317-325). Each of the PDZ domains of InaD has been implicated in binding one or more of the proteins involved in phototransduction, bringing the complex together in the proper cellular location for efficient signaling (Tsunoda et al., (1997) *Nature* 388: 243-249; Wes et al., (1999) *Nat Neurosci* 2: 447-453; Montell, (1999) *Annu Rev Cell Dev Biol* 15: 231-268; Fanning & Anderson, (1999) *Curr. Opin. Cell Biol.* 11: 432-439).

Two further properties of PDZ domains, or proteins that contain them, can expand their potential activities. First, some PDZ domains can bind internal peptide sequences and, indeed, have a propensity to undergo homotypic or heterotypic interactions with other PDZ domains (Brenman et al., 1996). Second, proteins with PDZ domains frequently contain other interaction modules, including SH3 and LIM domains, and catalytic elements such a tyrosine phosphatase or nitric oxide synthase domains. PDZ domains can therefore both coordinate the localization and clustering of receptors and channels, and provide a bridge to the cytoskeleton or intracellular signaling pathways.

The InaD protein of *Drosophila* comprises 674 amino acids (SEQ ID NO: 3), has a molecular weight of 74332 daltons and comprises five PDZ domains. These five PDZ domains form the majority of the protein's structure. The domains are numbered PDZ1 through PDZ5. PDZ1, the N-terminal domain of InaD, which forms an embodiment of the present invention, comprises residues 17-106 of the InaD protein. In the disclosure presented herein PDZ1 is referred to specifically in some embodiments; however, the disclosure and discussion of embodiments, methods, and techniques can also be applied to another PDZ domain, such as PDZ2, PDZ3, PDZ4, and PDZ5.

Thus, in one embodiment a PDZ domain (e.g. a PDZ1 domain) of the present invention is derived from the InaD protein found in *Drosophila*. However, a PDZ domain (e.g. a PDZ1 domain) of the present invention need not be derived from *Drosophila* and can be derived from any species (for example, *Caenorhabditis elegans*, *Calliphora vicina*, *Homo sapiens*, *Mus musculus*, etc.).

The N-terminal PDZ domain of InaD (PDZ1) is known to bind the C-terminus of NorpA. Until the present disclosure, however, the precise nature of this interaction was not known. As disclosed herein, this interaction is mediated by a disulfide bond formed between these two proteins and constitutes an aspect of the present invention. As disclosed herein, this disulfide bond plays a role in the observed reversible high-affinity interaction between a tag of the present invention (i.e., a NorpA tag) and a PDZ1 domain of the present invention.

IV.A. Preparing a PDZ1 Domain Polypeptide of the Present Invention

A PDZ1 domain polypeptide of the present invention can be prepared by at least three different methods. First, a PDZ1 domain polypeptide can be isolated from an InaD polypeptide. Second, a PDZ1 domain can be expressed and isolated from a host cell. Third, a PDZ1 domain can be synthesized using standard peptide synthesis techniques. Each of these methods is discussed further hereinbelow. This list of preparation methods is not a complete list and is presented not to limit but to illustrate this aspect of the present invention.

IV.A.1. Preparing a PDZ1 Domain from an InaD Polypeptide

In one method of preparing a PDZ1 domain polypeptide of the present invention, the InaD polypeptide can be expressed and isolated from *Drosophila*. Alternatively, a host cell can be transfected or transformed with a vector comprising a nucleic acid sequence encoding the InaD polypeptide. Transfection and transformation techniques are known in the art (see e.g., Sambrook et al., (1989) *Molecular Cloning: A Laboratory Manual*, Cold Spring Harbor Press, New York, United States of America) and can be employed in preparing a PDZ1 domain from an InaD polypeptide. The InaD polypeptide can be expressed and isolated. Subsequently, the PDZ1 domain can be chemically or proteolytically cleaved from the remainder of the InaD polypeptide and isolated.

IV.A.2. Preparing a PDZ1 Domain in a Host Cell

In another method of preparing a PDZ1 domain polypeptide of the present invention, a nucleic acid sequence encoding a PDZ1 domain can be cleaved from the InaD sequence. The PDZ1 sequence can be ligated into a vector. A host cell can then be transfected or transformed with the vector comprising a nucleic acid sequence encoding the PDZ1 domain of InaD, as disclosed herein and as well known in the art. The PDZ1 domain can then be expressed and isolated, again, by employing standard recombinant DNA methods known in the art. See, e.g., Sambrook et al., (1989) *Molecular Cloning: A Laboratory Manual*, Cold Spring Harbor Press, New York, United States of America.

IV.A.3. Preparing a PDZ1 Domain Polypeptide of the Present Invention by Synthesis In yet another embodiment of the present invention, a PDZ1 domain can be prepared by peptide synthesis techniques. Such techniques are contemplated for preparing a PDZ1 domain polypeptide of the present invention, which in one embodiment comprises about 100 amino acid residues or less.

A PDZ1 domain polypeptide of the present invention can be synthesized by any of the techniques that are known to those skilled in the polypeptide art, including recombinant DNA techniques, as disclosed herein above. Synthetic chemistry techniques, such as a solid-phase Merrifield-type synthesis, can be employed and, for syntheses, are preferred for reasons of purity, antigenic specificity, freedom from undesired side products, ease of production, and the like. A summary of the many techniques available can be found in Steward et al. (1969) *Solid Phase Peptide Synthesis*, W. H. Freeman Co., San Francisco, Calif., United States of America; Bodanszky et al. (1976) *Peptide Synthesis*, Second Edition, John Wiley & Sons, New York, N.Y., United States of America; Meienhofer, J. (1983) *Hormonal Proteins and Peptides*, Vol. 2, p. 46, Academic Press, New York, N.Y., United States of America; Merrifield (1969) *Adv. Enzymol.* 32:221-96; Fields et al. (1990) *Int. J. Peptide Protein Res.*, 35:161-214; U.S. Pat. No. 4,244,946 for solid phase peptide synthesis; and Schroder et al. (1965) *The Peptides*, Vol. 1, Academic Press, New York, N.Y., United States of America for classical solution synthesis, each of which is incorporated herein by reference. Appropriate protective groups useful in such syntheses are described in the above texts and in McOmie, J. F. W. (1973) *Protective Groups in Organic Chemistry*, Plenum Press, New York, N.Y., United States of America, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a selectively removable protecting group. A different, selectively removable protecting group is typically utilized for amino acids containing a reactive side group such as lysine.

Employing a solid phase synthesis as an example, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming an amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently to afford the final linear polypeptide.

The above-presented synthesis techniques can also be employed, for example, in the chemical modification of a tag of the present invention. As disclosed herein above, chemical modification can be employed in the design of a tag of the present invention.

IV.B. Modifying a PDZ1 Domain Polypeptide of the Present Invention

A PDZ1 domain polypeptide of the present invention can be modified from the native sequence of the PDZ1 domain of the InaD complex found in *Drosophila* (SEQ ID NO: 3) and can still associate with a tag of the present invention. Biological and functional equivalents of the wild type PDZ1 domain polypeptide (SEQ ID NO: 3) therefore form an aspect of the present invention. Modifications and/or substitutions in SEQ ID NO: 3 can be achieved via the one or more of the following techniques.

Modifications to a PDZ1 domain polypeptide of the present invention as described herein can be carried out by employing techniques such as site-specific mutagenesis. Site-specific mutagenesis is a technique that is useful in the preparation of individual peptides, or biologically functional equivalent proteins or peptides, through specific mutagenesis of the underlying DNA. The technique further provides a ready ability to prepare and test sequence variants by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is employed, with about 5 to 10 residues on both sides of the junction of the sequence being altered.

In general, the technique of site-specific mutagenesis is well known in the art as exemplified by publications (see, e.g., Adelman et al. (1983) *DNA* 2:183). As will be appreciated, the technique typically employs a phage vector, which exists in both a single stranded and double stranded form.

Typical vectors useful in site-directed mutagenesis include vectors such as the M13 phage (Messing et al., (1981) *Third Cleveland Symposium on Macromolecules and Recombinant DNA*, (Walton, ed.). Elsevier, Amsterdam, The Netherlands). These phages are readily commercially available and their use is generally well known to those or ordinary skill in the art. Double stranded plasmids are also routinely employed in site directed mutagenesis and eliminate the step of transferring the gene of interest from a plasmid to a phage. A polymerase chain reaction (PCR) based site-directed mutagenesis technique can also be employed to introduce modifications to a sequence.

In general, site-directed mutagenesis is performed by obtaining a single-stranded vector or by melting apart the two strands of a double stranded vector. The vector includes within its sequence a DNA sequence that encodes, for example, the PDZ1 domain of *Drosophila* InaD. An oligonucleotide primer bearing the desired mutated sequence is prepared, generally synthetically, for example by the method of Crea et al. (Crea et al., (1978) *Proc. Nat. Acad. Sci. U.S.A.* 75: 5765). This primer is then annealed to the single-stranded vector and subjected to DNA polymerizing enzymes such as the Klenow fragment of *E. coli* DNA polymerase I in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells (in one embodiment, BL21 (DE3) cells), and clones are selected which include recombinant vectors bearing the mutated sequence arrangement.

A PCR technique can also be used in modifying a polypeptide of interest such that it contains a different amino acid composition than when initially selected. In a specific non-limiting example of PCR mutagenesis, template plasmid DNA encoding the polypeptide of interest (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and 25 picomoles of each oligonucleotide primer, to a final volume of 50 μl. The reaction mixture is overlaid with 35 μl mineral oil. The reaction is denatured for 5 minutes at 100° C., placed briefly on ice, and then 1 μl *Thermus aguaticus* (Taq) DNA polymerase (5 units/μl) is added below the mineral oil layer. The reaction mixture is then inserted into a thermocycler.

At the end of the program, the reaction vial is removed from the thermocycler and the aqueous phase transferred to a new vial, extracted with phenol/chloroform (50:50 by volume), and the amplified DNA is recovered by standard procedures (e.g., ethanol precipitation). This material is subsequently subjected to appropriate treatments for insertion into a vector and expression of the encoded modified polypeptide.

Other methods for modifying a polypeptide of interest so that it contains a different composition of amino acids than when originally selected include cassette mutagenesis which is based on the technique described by Wells et al. (Wells et al., (1985) *Gene* 34: 315) and phagemid display.

V. Engineering a Tagged Target Protein

A tagged target protein can be engineered by inserting a nucleic acid sequence encoding a target protein into a vector such that it is flanked either on one side or on both sides by a nucleic acid sequence encoding a tag of the present invention (e.g. SEQ ID NOs: 1, 2 or 9). In one embodiment, the vector comprises the tag sequence and is flanked on one or both sides by a multiple cloning region comprising one or more restriction sites. Such vectors are disclosed herein.

Factors to be considered when engineering a tagged target protein include, but are not limited to assuring that the nucleic acid sequence encoding a target protein is inserted so that it is contiguous with the nucleic acid sequence encoding a tag of the present invention. Additionally, it is important to ensure that the sequences encoding the tag and the protein are inserted in frame, thereby assuring translation of the desired tagged protein. In one embodiment, the nucleic acid sequence encoding the tag further comprises a stop codon.

VI. Expressing of a Tagged Target Protein

A tagged target protein of the present invention, and fragments thereof, can be chemically synthesized in whole or in part using techniques disclosed herein above. See also, Creighton, (1983) *Proteins: Structures and Molecular Principles*, W. H. Freeman & Co., New York, N.Y., United States of America, incorporated herein in its entirety. Alternatively, in accordance with methods disclosed herein and known in the art, expression vectors containing a partial or the entire tag/target protein coding sequence and appropriate transcriptional/translational control signals are prepared. These methods include in vitro recombinant DNA techniques, synthetic techniques, and in vivo recombination/genetic recombination. See e.g., the techniques described throughout Sambrook et al., (1989) *Molecular Cloning: A Laboratory Manual*, Cold Spring Harbor Laboratory, New York, N.Y., United States of America, and Ausubel et al., (1989) *Current Protocols in Molecular Biology*, Greene Publishing Associates and Wiley Interscience, New York, N.Y., United States of America, both incorporated herein in their entirety.

A variety of host-expression vector systems can be employed to express a tagged target protein coding sequence. These include, but are not limited to microorganisms such as bacteria transformed with recombinant bacteriophage DNA, plasmid DNA, or cosmid DNA expression vectors containing a PDZ1 domain polypeptide coding sequence or a tagged target protein coding sequence; yeast transformed with recombinant yeast expression vectors containing a tagged target protein coding sequence; insect cell systems infected with recombinant virus expression vectors (e.g., baculovirus) containing a PDZ1 domain polypeptide or a tagged target protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a tagged target protein coding sequence; or animal cell systems. The expression elements of these systems vary in their strength and specificities.

Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter), and the like can be used. When cloning in insect cell systems, promoters such as the baculovirus polyhedrin promoter can be used. When cloning in plant cell systems, promoters derived from the genome of plant cells, such as heat shock promoters, the promoter for the small subunit of RUBISCO, the promoter for the chlorophyll a/b binding protein, or from plant viruses (e.g., the 35S RNA promoter of CaMV; the coat protein promoter of TMV) can be used. When cloning in mammalian cell systems, promoters derived from the genome of mammalian cells (e.g., metallothionein promoter) or from mammalian viruses (e.g., the adenovirus late promoter; the vaccinia virus 7.5 K promoter) can be used. When generating cell lines that contain multiple copies of the tyrosine kinase domain DNA, SV40-, BPV- and EBV-based vectors can be used with an appropriate selectable marker.

VII. Design and Preparation of Tags and PDZ1 Domain Polypeptides and Structural Equivalents thereof The present invention provides for the generation of tags and PDZ1 domain polypeptides and tags and PDZ1 domain mutants. It is noted that Table 2 discloses a crystal structure comprising a NorpA polypeptide associated with a PDZ1 domain polypeptide through a disulfide bond. In accordance with method disclosed herein above, by employing the three-dimensional structure of a NorpA-PDZ1 domain structure, sites on either the PDZ1 domain or a tag that are candidates for mutation can be identified.

VII.A. Sterically Similar Compounds

A further aspect of the present invention is that sterically similar compounds can be formulated to mimic the key portions of a NorpA sequence or a PDZ1 domain polypeptide, such as regions comprising disulfide-forming residues. Such compounds are functional equivalents. The generation of a structural functional equivalent can be achieved by the techniques of modeling and chemical design known to those of skill in the art and described herein. Modeling and chemical design of tags of the present invention and PDZ1 domain structural equivalents can be based on the structure coordinates of Table 2. It will be understood that all such sterically similar constructs fall within the scope of the present invention.

VII.B. Sequence Similarity and Identity

As used herein, the term "substantially similar" as applied to a tag or a PDZ1 domain polypeptide as disclosed herein refers to that a particular sequence varies from nucleic acid sequence of SEQ ID NO: 7, or the amino acid sequence of SEQ ID NO: 8 by one or more deletions, substitutions, or additions, the net effect of which is to retain at least some of biological activity of the natural gene, gene product, or sequence. Such sequences include "mutant" or "polymorphic" sequences, and sequences in which the biological activity and/or the physical properties are altered to some degree but retains at least some or an enhanced degree of the original biological activity and/or physical properties. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

VII.B.1. Sequences That Are Substantially Identical to Disclosed Tags and PDZ1 Domain Polypeptides or a PDZ1 Domain Mutant Sequence of the Present Invention Nucleic acids that are substantially identical to a nucleic acid sequence of a tag disclosed in the present invention or a PDZ1 domain or a PDZ1 domain mutant of the present invention (e.g, allelic variants, genetically altered versions of the gene, etc.) bind to tags and PDZ1 domain polypeptide sequences disclosed herein, or to a PDZ1 domain mutant sequence under stringent hybridization conditions. By using probes, particularly labeled probes of DNA sequences, one can isolate homologous or related genes. The source of homologous genes can be any species including, but not limited to primate species; rodents, such as rats and mice, canines, felines, bovines, equines, yeast, and nematodes.

Between species, homologs have substantial sequence similarity: i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nt long, more usually at least about 30 nt long, and can extend to the complete sequence that is being compared. Algorithms for sequence analysis are known in the art, such as BLAST, described in Altschul et al., (1990) *J. Mol. Biol.* 215: 403-10.

Software for performing BLAST analyses is publicly available through the, National Center for Biotechnology Information (NCBI; www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=-4, and a comparison of both strands. For amino acid sequences, the BLASTP program uses as defaults a wordlength W=3, an expectation E=10, and the BLOSUM62 scoring matrix. See Henikoff & Henikoff, (1989) *Proc Natl Acad Sci U.S.A.* 89: 10915.

In addition to calculating percent sequence identity, the BLAST algorithm also performs a statistical analysis of the similarity between two sequences. See e.g., Karlin and Altschul, (1993) *Proc Natl Acad Sci U.S.A.* 90: 5873-5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in yet another embodiment less than about 0.001.

Percent identity or percent similarity of a DNA or peptide sequence can be determined, for example, by comparing sequence information using the GAP computer program (available from Accelrys Inc., San Diego, Calif., United States of America). The GAP program utilizes the alignment method of Needleman et al., (1970) *J. Mol. Biol.* 48: 443, as revised by Smith et al., (1981) *Adv. Appl. Math.* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See e.g., Schwartz et al., eds., (1979), *Atlas of Protein Sequence and Structure*, National Biomedical Research Foundation, Silver Spring, Md., United States of America, pp. 357-358, and Gribskov et al., (1986) *Nucl. Acids. Res.* 14: 6745.

The term "similarity" is contrasted with the term "identity". Similarity is defined as above; "identity", however, refers to a nucleic acid or amino acid sequence having the same amino acid at the same relative position in a given family member of a gene family. Homology and similarity are generally viewed as broader terms than the term identity. Biochemically similar amino acids, for example leucine/ isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

As used herein, DNA analog sequences are "substantially identical" to specific DNA sequences disclosed herein if: (a) the DNA analog sequence is derived from coding regions of the nucleic acid sequence shown in SEQ ID NOs: 3, 5 and 7; or (b) the DNA analog sequence is capable of hybridization with DNA sequences of (a) under stringent conditions and which encode a tag disclosed herein or a biologically active PDZ1 domain gene product; or (c) the DNA sequences are degenerate as a result of alternative genetic code to the DNA analog sequences defined in (a) and/or (b). Substantially identical analog proteins and nucleic acids will have in one embodiment between about 70% and 80%, in another embodiment between about 81% to about 90%, and in still another embodiment between about 91% and 99% sequence identity with the corresponding sequence of the native protein or nucleic acid. Sequences having lesser degrees of identity but comparable biological activity are considered to be equivalents.

As used herein, "stringent conditions" refers to conditions of high stringency, for example 6× standard saline citrate (SSC; 1×SSC is 150 mM NaCl/15 mM sodium citrate), 0.2% polyvinylpyrrolidone, 0.2% Ficoll, 0.2% bovine serum albumin (BSA), 0.1% sodium dodecyl sulfate (SDS), 100 µg/ml salmon sperm DNA, and 15% formamide at 68° C. For the purposes of specifying additional conditions of high stringency, representative conditions are salt concentration of about 200 mM and temperature of about 45° C. One example of such stringent conditions is hybridization at 4×SSC at 65° C., followed by a washing in 0.1×SSC at 65° C. for one hour. Another exemplary stringent hybridization scheme uses 50% formamide and 4×SSC at 42° C.

In contrast, nucleic acids having sequence similarity are detected by hybridization under lower stringency conditions. Thus, sequence identity can be determined by hybridization under lower stringency conditions, for example, at 50° C. or higher and 0.1×SSC and the sequences will remain bound when subjected to washing at 55° C. in 1×SSC.

VII.B.2. Complementarity and Hybridization to Disclosed Tags, a PDZ1 Domain or a PDZ1 Domain Mutant Sequence of the Present Invention As used herein, the term "complementary sequences" refers to nucleic acid sequences that are base-paired according to the standard Watson-Crick complementarity rules. The present invention also encompasses the use of nucleotide segments that are complementary to the sequences of the present invention.

Hybridization can also be used for assessing complementary sequences and/or isolating complementary nucleotide sequences. As discussed above, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., in one embodiment in excess of about 37° C., and in another embodiment in excess of about 45° C. Stringent salt conditions will be in one embodiment less than about 1,000 mM, in another embodiment less than about 500 mM, and in still another embodiment less than about 200 mM. However, the combination of parameters is much more important than the measure of any single parameter. See e.g., Wetmur & Davidson, (1968) *J. Mol. Biol.* 31: 349-70. Determining appropriate hybridization conditions to identify and/or isolate sequences containing high levels of homology is well known in the art. See e.g., Sambrook et al., (1989) *Molecular Cloning: A Laboratory Manual*, Cold Spring Harbor, New York, N.Y., United States of America.

VII.B.3. Functional Equivalents of Disclosed Tags, a PDZ1 Domain or a PDZ1 Domain Mutant Sequence of the Present Invention As used herein, the term "functionally equivalent codon" is used to refer to codons that encode the same amino acid, such as the ACG and AGU codons for serine. For example, tag-encoding nucleic acid sequences comprising SEQ ID NO: 5 and those encoding SEQ ID NOs: 1, 2 and 9 and a PDZ1 domain-encoding nucleic acid sequence comprising SEQ ID NO: 7 that have functionally equivalent codons are covered by the present invention. Thus, when referring to the sequence example presented in SEQ ID NOs: 3, 5 and 7, and those encoding the amino acid sequences of SEQ ID NOs: 1, 2 and 9, applicants contemplate substitution of functionally equivalent codons into these sequences. Thus, applicants are in possession of amino acid and nucleic acids sequences which include such substitutions but which for convenience are not set forth herein in their entirety.

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where polypeptide expression is concerned. The addition of terminal sequences particularly applies to nucleic acid sequences which can, for example, include various non-coding sequences flanking either of the 5' or 3' portions of the coding region or can include various internal sequences, such as introns, which are known to occur within genes.

VII.B.4. Biological Equivalents

The present invention envisions and includes biological equivalents of tags and PDZ1 domain polypeptides and mutant PDZ1 domain polypeptides disclosed herein. The term "biological equivalent" refers to proteins having amino acid sequences which are substantially identical to the amino acid sequence of a tag or a PDZ1 domain polypeptide and mutants thereof of the present invention and which are capable of exerting a biological effect in that they are capable of forming a disulfide bond or cross-reacting with anti-tag, anti-PDZ1 domain polypeptide antibodies, or antibodies raised against a tag or a PDZ1 domain polypeptide of the present invention.

For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the protein, but this need not be the case, and the biological activity of the invention is not limited to a particular mechanism of action. It is thus in accordance with the present invention that various changes can be made in the amino acid sequence of tags disclosed herein, PDZ1 domain polypeptides, and PDZ1 domain mutant polypeptides disclosed herein, or their underlying nucleic acid sequences without appreciable loss of biological utility or activity. In one embodiment, a biological equivalent of a tag of the present invention is a polypeptide that interacts with a PDZ1 domain.

Biologically equivalent polypeptides, as used herein, are polypeptides in which certain, but not most or all, of the amino acids can be substituted. Thus, when referring to the sequence examples presented in SEQ ID NOs: 3, 5, and 7, and those encoding the amino acid sequences of SEQ ID NOs: 1, 2, and 9, applicants envision substitution of codons that encode biologically equivalent amino acids, as described herein, into these sequences. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology in which changes in the protein structure can be engineered based on considerations of the properties of the amino acids being exchanged, for example substitution of Ile for Leu. Changes designed by man can be introduced through the application of site-directed mutagenesis techniques, for example, to introduce improvements to the antigenicity of the protein or to test an engineered mutant polypeptide of the present invention in order to modulate lipid-binding or other activity, at the molecular level.

Amino acid substitutions, such as those which might be employed in modifying an engineered mutant polypeptide of the present invention are generally, but not necessarily, based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all of similar size; and that phenylalanine, tryptophan, and tyrosine all have a generally similar shape. Therefore, based upon these considerations, arginine, lysine, and histidine; alanine, glycine, and serine; and phenylalanine, tryptophan, and tyrosine; are defined herein as biologically functional equivalents. Those of skill in the art will appreciate other biologically functionally equivalent changes. It is implicit in the above discussion, however, that one of skill in the art can appreciate that a radical, rather than a conservative, substitution is warranted in a given situation. Non-conservative substitutions in tags and PDZ1 domain polypeptides disclosed herein are also an aspect of the present invention.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, (1982), $J.$ $Mol.$ $Biol.$ 157: 105-132, incorporated herein by reference). It is known that certain amino acids can be substituted for other amino acids having a similar hydropathic index or score and still retain a similar biological activity. The substitution of amino acids whose hydropathic indices are in one embodiment within ±2 of the original value, in another embodiment within ±1 of the original value, and in yet another embodiment within ±0.5 of the original value are chosen in making changes based upon the hydropathic index.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

The substitution of amino acids whose hydrophilicity values are in one embodiment within ±2 of the original value, in another embodiment within ±1 of the original value, and in still another embodiment within ±0.5 of the original value are chosen in making changes based upon similar hydrophilicity values.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid. Thus, it will also be understood that this invention is not limited to the particular amino acid and nucleic acid sequences of SEQ ID NOs: 3, 5, and 7, and those encoding the amino acid sequences of SEQ ID NOs: 1, 2, and 9.

Recombinant vectors and isolated DNA segments can variously include a tag, a PDZ1 domain polypeptide, or a PDZ1 domain mutant polypeptide-encoding region, and can also include coding regions bearing selected alterations or modifications in the basic coding region. Such vectors can also include larger polypeptides that nevertheless comprise a tag, a PDZ1 domain polypeptide or a PDZ1 domain mutant polypeptide-encoding region, or can encode biologically functional equivalent proteins or polypeptides that have variant amino acid sequences. Biological activity of a tag, a PDZ1 domain polypeptide, or a PDZ1 domain mutant polypeptide can be determined, for example, by transcription assays known to those of skill in the art.

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. Therefore, a nucleic acid fragment of almost any length can be employed, with the total length being influenced by the ease of preparation and use in the intended recombinant DNA protocol. For example, nucleic acid fragments can be prepared which include a short stretch complementary to a nucleic acid sequence set forth in SEQ ID NOs: 3, 5, and 7, and those encoding the amino acid sequences of SEQ ID NOs: 1, 2, and 9, such as about 10 nucleotides, and which are up to 10,000 or 5,000 base pairs in length. DNA segments with total lengths of about 4,000, 3,000, 2,000, 1,000, 500, 200, 100, and about 50 base pairs in length are also useful.

The DNA segments of the present invention encompass biologically functional equivalents of disclosed tags, PDZ1 domain polypeptides, and PDZ1 domain mutant polypeptides. Such sequences can arise as a consequence of codon redundancy and functional equivalency that are known to occur naturally within nucleic acid sequences and the proteins thus encoded. Alternatively, functionally equivalent proteins or polypeptides can be created via the application of recombinant DNA technology, in which changes in the protein structure can be engineered based on considerations of the properties of the amino acids being exchanged. Changes can be introduced through the application of site-directed mutagenesis techniques, for example to introduce improvements to the antigenicity of the protein or to test variants of an engineered mutant of the present invention in order to examine the degree of lipid-binding activity, or other activity at the molecular level. Various site-directed mutagenesis techniques are known to those of skill in the art and can be employed in the present invention.

The invention further encompasses fusion proteins and peptides wherein an engineered mutant coding region of the present invention is aligned within the same expression unit with other proteins or peptides having desired functions, such as for purification or immunodetection purposes.

VII.B.5. Recombinant Vectors

Recombinant vectors form important further aspects of the present invention. Particularly useful vectors are those in which the coding portion of the DNA segment is positioned under the control of a promoter. The promoter can be that naturally associated with a NorpA polypeptide or a PDZ1 domain gene, as can be obtained by isolating the 5' non-coding sequences located upstream of the coding segment or exon, for example, using recombinant cloning and/or PCR technology and/or other methods known in the art, in conjunction with the compositions disclosed herein.

In other embodiments, certain advantages will be gained by positioning the coding DNA segment under the control of a recombinant, or heterologous, promoter. As used herein, a recombinant or heterologous promoter is a promoter that is not normally associated with a NorpA polypeptide or a PDZ1 domain gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See e.g., Sambrook et al., (1989) *Molecular Cloning: A Laboratory Manual*, Cold Spring Harbor Laboratory, New York, United States of America, specifically incorporated herein by reference). The promoters employed can be constitutive or inducible and can be used under the appropriate conditions to direct high level expression of the introduced DNA segment, such as is advantageous in the large-scale production of recombinant proteins or peptides.

VIII. Matrix Preparation

A PDZ1 domain can be associated with a matrix material. Suitable matrix materials can comprise polysaccharide-based gels including, but not limited to SEPHAROSE® (available from Amersham Biosciences, Piscataway, N.J., United States of America) and AFFI-GEL®, (available from Bio-Rad Laboratories, Hercules, Calif., United States of America), to name just two matrix materials. Additionally, a PDZ1 domain can be labeled before or after the PDZ1 domain has been associated with a matrix material. After a PDZ1 domain has been associated with a matrix material, the matrix material can be associated with a support, such as a chromatography column, membrane or plastic plate. These processes are described herein below.

VIII.A. Association of a PDZ1 Domain with a Matrix

A PDZ1 domain can be associated with a matrix by employing standard chemical techniques. Additionally, many matrix materials are commercially available and are adapted for easy protein-matrix association. For example, a protein can be associated with the matrix AFFI-GEL® (available from Bio-Rad Laboratories, Hercules, Calif., United States of America) by incubating the protein with the matrix in the presence of a coupling buffer, as described in the product literature. In another example, N-hydroxysuccinimide (NHS)-activated SEPHAROSE®, a highly cross-linked agarose (available from Amersham Biosciences, Piscataway, N.J., United States of America) can be employed in the present invention.

Easy coupling of antibodies, small proteins, peptides, or other ligands containing —NH2 groups can also be achieved by employing a spacer moiety, such as a 15-atom spacer arm. In this example, a ligand can be immobilized by covalent attachment of the ligand's primary amino groups to the NHS linkage to form a very stable amide bond, especially at high pH. Coupling can be performed at 4° C. or 25° C. between pH 6 to 9, and is typically complete in 2-4 hours.

Cyanogen bromide (CNBr) activated SEPHAROSE® (Amersham Biosciences, Piscataway, N.J., United States of America) can also couple ligands via their primary amino groups to a matrix material. This method is commonly used, but because it does not include a spacer arm it is typically employed for attaching large proteins or antibodies to a matrix material. The coupling conditions for this approach are typically pH 8-10, 4-25° C., for 2-16 hours. There are many more chemistries available for coupling proteins to gel matrices, but they are less commonly used. Those of skill in the art will recognize the steps and applicability of these additional chemistries upon consideration of the pertinent literature in view of the present disclosure.

VIII.B. PDZ1 Labeling

A PDZ1 domain of the present invention can be labeled with a detectable label. Suitable labels include, but are not limited to fluorescent moieties, radioactive moieties, absorptive moieties, and even functional enzymes. By labeling a PDZ1 domain of the present invention, the presence of a PDZ1 domain-tagged protein complex can be directly detected.

Labeling can be achieved by employing standard protein labeling methods. Such methods are well recognized in the art. For example, fluorescent moieties can be covalently attached to proteins through cysteine residues or N-terminal groups.

In another approach, proteins can be phosphorylated with $^{32}$P as the only phosphorous source if a protein kinase site is already present in the protein or is engineered into it. This approach can be employed to incorporate a radioactive label. In vitro translation in the presence of $^{35}$S-methionine can also be employed to incorporate the radioactive label. Additionally, protein labeling kits are commercially available that can be employed in the present invention.

When it is desired to fuse a functional enzyme with a PDZ1 domain, such a fusion can be achieved by employing standard recombinant DNA methods. In one embodiment, a nucleotide sequence coding for the desired enzyme is isolated and linked to a nucleotide sequence coding for the PDZ1 domain polypeptide. The hybrid gene can then be incorporated into a desired expression vector, such as those disclosed herein or other commercial or generally accessible plasmids, using standard methods. Such methodology can be found, for example in Sambrook et al., (1989) *Molecular Cloning: A Laboratory Manual*, Cold Spring Harbor Laboratory Press, New York, United States of America.

Methods for the expression of the fusion proteins of this invention are also described by Sambrook et al. Generally, expression methods include the following procedures: (a) transformation of a suitable host organism, in one embodiment *E. coli*, with an expression vector in which the hybrid gene is operatively linked to an expression control sequence; (b) cultivation of the transformed host organism under suitable growth conditions; and (c) extraction and isolation of the desired fusion protein from the host organism. All of these procedures are apparent to those of skill in the ordinary art upon contemplation of the present disclosure.

Suitable host cells that can be used to express a fusion protein comprising a PDZ1 domain include, but are not limited to gram-negative and gram-positive bacteria such as *E. coli* and *B. subtilis*.

IX. Applications

The methods and reagents of the present invention can be employed in a variety of applications. Several representative applications of the present invention are disclosed herein below. For example, the present invention encompasses a protein purification method and a protein detection method. Other applications include a solid support for use in chromatography and in other processes. A recombinant vector adapted to express a tagged protein forms another application of the present invention. In another application, the present invention is collected as kits that are adapted for protein purification, protein detection, and the like. While this list of applications is not meant to be complete or exhaustive, the applications named above are discussed is further detail herein below.

IX.A. Protein Purification

The methods and reagents of the present invention can be employed in a protein purification method. In one embodiment, the present invention comprises a method of purifying a target protein comprising a tag sequence from a mixture of components. The method can be advantageously employed to isolate a target protein from a mixture of proteins, carbohydrates, lipids, and other compounds. Such a mixture is typically present in crude cell lysates that are formed when cells expressing the target protein are lysed.

In one embodiment, the method comprises contacting the mixture with a PDZ1 domain polypeptide to form a complex comprising the target protein and a PDZ1 domain polypeptide. In one embodiment, a PDZ1 domain polypeptide comprises SEQ ID NO: 8 and a tag comprises SEQ ID NO: 1, 2, or 9. However, functional and biological equivalents of PDZ1 sequence SEQ ID NO: 8 and tag sequences SEQ ID NO: 1, 2, and 9 are also within the scope of the present invention.

A PDZ1 domain polypeptide can also be labeled with another moiety. For example, a PDZ1 domain polypeptide can be labeled with a detectable moiety including, but not limited to a chemiluminescent moiety, a radioactive moiety, and a fluorescent moiety. In another example, a PDZ1 domain polypeptide can comprise an enzyme, such as alkaline phosphatase or horseradish peroxidase. Representative enzymes include those that generate a detectable product, for example a product that is detectable by absorbance spectroscopy.

The contacting can be conveniently achieved by passing the mixture over a chromatography column in which a PDZ1 domain polypeptide is disposed. The PDZ1 domain polypeptide can be associated with a column matrix material. For example, as discussed further hereinbelow, the PDZ1 polypeptide domain can be associated with a column matrix material such as SEPHAROSE®, AFFI-GEL®, glass beads or other column matrix material. Association of a protein with a column matrix material is known in the art and can be performed using any of the commonly known chemical processes to achieve the association.

As disclosed hereinabove, N-hydroxysuccinimide (NHS)-activated SEPHAROSE®, a highly cross-linked agarose available from Amersham Biosciences of Piscataway, N.J., United States of America, can be employed in the present invention.

Easy coupling of antibodies, and small proteins and peptides, or other ligands containing —NH2 groups can also be achieved by employing a spacer moiety, such as a 15-atom spacer arm. In this example, a ligand can be immobilized by covalent attachment of the ligand's primary amino groups to the NHS linkage to form a very stable amide bond, especially at high pH. In one embodiment, coupling is performed at 4° C. or 25° C. between pH 6 to 9, and is typically complete in 2-4 hours.

CNBr-activated SEPHAROSE® (Amersham Biosciences, Piscataway, N.J., United States of America) can also couple ligands via their primary amino groups to a matrix material. This method is commonly used, but because it does not include a spacer arm it is typically employed for attaching large proteins or antibodies to a matrix material. In one embodiment, the coupling conditions for this approach are pH 8-10, 4-25° C., and incubation for 2-16 hours. There are many more chemistries available for coupling proteins to gel matrices, but they are less-commonly used. Those of ordinary skill in the art will recognize the steps and applicability of these additional chemistries upon consideration of the pertinent literature in view of the present disclosure. In another embodiment, a protein comprising a tag of the present invention is associated with a matrix material.

Following association of a PDZ1 domain polypeptide (or a protein comprising a tag of the present invention) with the matrix material, the derivatized matrix material can be disposed on a support. In one embodiment, a support is a glass chromatography column; however plastic columns, membranes, polymer discs, and other structures can also function as a support. In one embodiment, the column is vertically oriented and adapted for gravity-controlled flow of liquids placed on the top of the column. The column can be stored at 4° C.

A mixture can then be contacted with the PDZ1 domain polypeptide (or a protein comprising a tag of the present invention). When the PDZ1 domain polypeptide (or a protein comprising a tag of the present invention) is associated with a matrix material and disposed in a column, the mixture can be placed on the top of the matrix material disposed in the column. The mixture can be placed on the exposed top face of the matrix material by pipeting or by a vacuum created by a peristaltic or other pump communicatively attached to the bottom end of the column.

The mixture can then be moved through the column either by gravity or can be assisted by a peristaltic or other pump communicatively attached to the bottom end of the column. This process enables the mixture to contact a greater number of PDZ1 domain polypeptides (or proteins comprising a tag of the present invention). Target proteins in the mixture that comprise a tag of the present invention will associate with the PDZ1 domain polypeptide to form a complex, and not flow through the column. Alternatively, target proteins in the mixture that comprise a PDZ1 domain polypeptide will associate with a protein comprising a tag of the present invention to form a complex and not flow through the column. Uncomplexed components of the mixture (e.g. proteins, carbohydrates, nucleic acids, and other compounds) can be removed by virtue of the fact that they do not comprise a tag of the present invention and thus do not associate with the PDZ1 domain polypeptides.

When a column is employed as a support, it can be desirable to employ a buffer to aid in washing the mixture through the column. Suitable buffers include, but are not limited to TSE, TRIS, and MOPS. The selection of a buffer will depend, in part, on the nature of the tagged protein. Methods of preparing and selecting a suitable buffer are known in the art. In one embodiment, the pH of the buffer is between about 6.0 and 9.0. In another embodiment, the pH of the buffer is 8.0.

As disclosed hereinabove, a disulfide bond formed between a PDZ1 domain polypeptide and a tag of the present invention forms a basis for the association of these two structures. In one embodiment, the structures are disposed in a non-reducing environment in order for this interaction to occur. Thus, in one embodiment the pH of any buffer that is selected takes this fact into account. In another embodiment, such a buffer does not comprise a reducing compound, such as dithiothreitol (DTT), β-mercaptoethanol (BME), dithioerythritol (DTE), reduced glutathione (GSH), or the like.

After the mixture is contacted with a PDZ1 domain polypeptide (or a protein comprising a tag of the present invention) and the uncomplexed material is removed, the tagged target protein can be recovered. The recovery of the protein can be achieved by reducing the disulfide bond that forms between a tag of the present invention and a PDZ1 domain polypeptide, which associates these two structures. Washing the complex with a buffer comprising a reducing agent can reduce the disulfide bond. Suitable reducing agents include DTT and BME. The reducing agent will reduce the disulfide bond and enable the tagged target protein to elute from the PDZ1 domain polypeptide.

The above procedure for purifying a protein tagged represents a single embodiment. Additional steps and variations on the above steps will be apparent to those of ordinary skill in the art upon consideration of the present disclosure. For example, depending on the subcellular localization of a tagged target protein, one or more centrifugation steps can be employed prior to the contacting. Steps and conditions designed to modulate the solubility of the target protein or any of the components of a mixture can also be performed.

IX.B. Protein Detection

The methods and reagents of the present invention can be employed in a protein detection method. In one embodiment, the present invention comprises a method to detect the presence of a target protein comprising a tag sequence in a mixture of components against a background of other proteins, carbohydrates, lipids and other structures. The method can be advantageously employed to detect the presence of a target protein in a mixture of proteins, carbohydrates, lipids, and other compounds. Such a mixture is typically present in crude cell lysates that are formed when cells expressing the target protein are lysed.

In one embodiment, a method of detecting the presence of a target protein comprising a tag sequence in a mixture of components, wherein the tag sequence is one of a PDZ1 domain and a NorpA sequence, comprises: (a) contacting the mixture with one of a PDZ1 domain and a NorpA sequence to form a complex comprising the target protein and the PDZ1 domain or the NorpA sequence; and (b) detecting the complex. In one embodiment, a PDZ1 domain polypeptide comprises SEQ ID NO: 8 and a tag comprises SEQ ID NO: 1, 2, or 9. However, functional and biological equivalents of PDZ1 sequence SEQ ID NO: 8 and tag sequences SEQ ID NO: 1, 2, and 9 are also within the scope of the present invention.

In another embodiment of the method, a target protein is contacted with a detectable PDZ1 domain polypeptide to form a complex. By detectable PDZ1 domain polypeptide it is meant that the PDZ1 domain polypeptide is adapted to be qualitatively (or quantitatively) identified using standard methods. For example, a detectable PDZ1 domain polypeptide can comprise a label that can be detected spectrophotometrically (e.g., a fluorescent label, a radioactive label, a label detectable via absorbance spectroscopy, a chemiluminescent label, etc.).

The discussion of contacting disclosed hereinabove is equally applicable in the present method. However, in the present method of detecting the presence of a target protein tagged with a tag of the present invention, there is no need to remove components from the mixture. Indeed, an advantage of this application of the present invention is that it can detect the presence of a protein comprising a tag of the present invention against a background of other proteins, carbohydrates, other molecules, and cellular material.

The method includes the step of detecting the complex. The complex comprises a labeled PDZ1 domain polypeptide and a protein comprising a tag of the present invention. The complex can be detected by employing any of a variety of techniques known to those of skill in the art. Primarily, the selection of a detection technique is dictated, in part, by the nature of the label associated with a PDZ1 domain polypeptide. For example, if a PDZ1 domain polypeptide is labeled with a fluorescent tag, the complex can be detected by fluorescence spectroscopy. Alternatively, if the PDZ1 domain polypeptide is labeled with a radioactive moiety, the complex can be detected by employing a technique that is sensitive to emitted radiation.

A complex can also be detected by, for example, a labeled antibody. In this example, an antibody specific for PDZ1 polypeptide can be employed. The antibody can comprise any label that makes the presence of the antibody detectable. Representative labels include radioactive labels, chemiluminescent labels, and absorptive labels.

Further, a complex can be detected by surface plasmon resonance, which is made possible in part by the high affinity of a tag of the present invention for a PDZ1 domain polypeptide. Surface plasmon resonance strategies are discussed further hereinbelow.

The detecting can be a qualitative detection or a quantitative detection. Most commonly, however, the detection will be qualitative. When the detecting is qualitative, the detecting can indicate the presence of the complex, and thus, the presence of a protein comprising a tag of the present invention. When the detecting is quantitative, however, the detecting can indicate the amount of protein comprising a tag of the present invention present in a sample. Detecting can also comprise performing a dot blot experiment or a western blot, as disclosed in the Laboratory Examples presented hereinbelow.

The disclosed method can comprise additional steps. For example, after the presence of a complex has been identified, the complex and/or its components can be isolated. In this example, a complex can be separated from other cellular materials by filtration, centrifugation, or another method. At a desired time and under desired conditions (which can be after a separation step), the complex can be dissociated by reducing the disulfide bond joining a tag of the present invention and a PDZ1 domain polypeptide. Suitable reducing agents include, but are not limited to DTT and BME. This process will generate free protein comprising a tag of the present invention, which can then be isolated from the mixture of other components by employing the method disclosed above.

It is noted that a target protein can also comprise a PDZ1 domain polypeptide. In this embodiment, a protein comprising a tag of the present invention can be associated with a matrix material. Thus, a mixture can comprise a target protein comprising a PDZ1 domain polypeptide. The methodology disclosed above can be employed as written.

Thus, the methods of the present invention can be employed to identify the presence of a protein comprising a tag of the present invention. The binding specificity of a tag of the present invention for a PDZ1 domain polypeptide ensures that only proteins comprising a tag of the present invention are identified.

IX.C. A Protein Purification and/or Detection Solid Phase

In another aspect of the present invention, a protein purification and/or detection solid phase is disclosed. Such a solid phase can be employed in the purification or detection of a protein comprising a tag of the present invention.

A protein purification and/or detection solid phase of the present invention comprises a non-soluble matrix. A representative but non-limiting list of non-soluble matrices includes polysaccharide-based gels (for example, SEPHAROSE® and AFFI-GEL®) glass beads, nitrocellulose or nylon membranes, polymeric structures such as beads, and carboxymethylated dextran.

A protein purification and/or detection solid phase of the present invention also comprises a PDZ1 domain polypeptide or a protein comprising a tag of the present invention associated with the matrix. Various methods exist for associating a PDZ1 domain polypeptide or a protein comprising a tag of the present invention with a matrix, several of which are disclosed herein above. (See e.g., the protocol for associating NHS-activated SEPHAROSE® with a matrix, disclosed hereinabove.)

In one embodiment, a PDZ1 domain polypeptide comprises SEQ ID NO: 8. However, functional and biological equivalents of PDZ1 sequence SEQ ID NO: 8 are also within the scope of the present invention. In one embodiment, a tag of the present invention comprises a sequence selected from the group consisting of SEQ ID NOs: 1, 2, and 9. Functional and biological equivalents of sequences SEQ ID NOs: 1, 2, and 9 are also within the scope of the present invention.

A protein purification and/or detection solid phase of the present invention can be prepared as described and stored in a container. In one embodiment, the protein purification and/or detection solid phase of the present invention is stored at about 4° C. in order to preserve the integrity of the PDZ1 protein or the protein comprising a tag. A protein purification and/or detection solid phase of the present invention can be stored as a slurry in the presence of a suitable buffer, such as TRIS, MOPS, TBS-T, or TSE, at a pH of about 6-8. The composition of these buffers as well as protocols for making them is known in the art (see, e.g., Buffers. *A Guide for the Preparation and Use of Buffers in Biological Systems*, (Gueffroy, ed.) Calbiochem Corporation (1975)). Alternatively, when the matrix is a membrane or a similar structure, the membranes can also be stored under a buffer at about 4° C. A solid phase can form a component of a kit, including kits for protein purification and protein detection.

IX.D. A Recombinant Expression Vector

A recombinant expression vector forms an aspect of the present invention. Such a vector can be employed to express a protein comprising a NorpA tag of the present invention. A recombinant expression vector of the present invention can form a component of a kit, including kits for protein purification and protein detection.

A recombinant expression vector of the present invention can comprise a nucleic acid sequence encoding a tag of the present invention (e.g. a NorpA tag) or a PDZ1 domain polypeptide. A NorpA tag employed in a recombinant expression vector, or any application of the present invention, can comprise the complete sequence of SEQ ID NO: 6 or any contiguous sequence of nucleic acids derived therefrom. Representative NorpA tag sequences include SEQ ID NOs: 1, 2, and 9. NorpA tag sequences can be designed based on the coordinates disclosed in Table 2, as discussed herein.

A recombinant expression vector of the present invention also comprises a cloning site flanking one of one side and both sides of the NorpA tag or the PDZ1 domain. The term "cloning site" is employed in its usual sense and refers to a sequence of nucleic acids that form one or more sites recognized by one or more restriction enzymes. One or more cloning sites can be situated on either side or both sides of the nucleic acid sequence encoding the NorpA tag or the PDZ1 domain. The cloning region(s) can be advantageously employed to insert a nucleic acid sequence encoding a protein of interest adjacent to and in frame with the NorpA tag or the PDZ1 domain, thereby forming a nucleic acid sequence encoding a fusion protein comprising the protein of interest and either the PDZ1 domain or the NorpA tag.

Cloning methods and methods of forming fusion proteins are well known in the art (see e.g., Sambrook et al., (1989) *Molecular Cloning: A Laboratory Manual*, Cold Spring Harbor Laboratory, New York, United States of America; and Ausubel et al., (1989) *Current Protocols in Molecular Biology*, Greene Publishing Associates and Wiley Interscience, New York, N.Y., United States of America, both incorporated herein in their entirety).

A recombinant expression vector of the present invention can comprise additional features, such as one or more nucleic acid sequences selected from the group consisting of a selectable marker, a restriction site, a promoter, an operon, and an origin of replication. These terms take their ordinary meanings and are well known to those of skill in the art. When a recombinant expression vector comprises a selectable marker, a suitable selectable marker includes, but is not limited to an antibiotic resistance gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complimentary to a PCR primer sequence.

A host cell comprising a recombinant expression vector of the present invention also forms an aspect of the present invention. A host cell can be selected based on the nature of a recombinant vector. Alternatively, a recombinant vector can be designed and/or selected based on the nature of a host cell.

Cells derived from any species can be employed as host cells in the present invention. Representative host cells include single celled organisms such as yeast and bacteria. In one embodiment, a host cell is an *E. coli* cell. A recombinant expression vector of the present invention can be introduced into a host cell in a variety of ways, including transfection and transformation. For example, expression constructs can be transfected into a host cell by any standard method including, but not limited to electroporation, calcium phosphate precipitation, DEAE-Dextran transfection, liposome-mediated transfection, and infection using a retrovirus.

Protocols for transfection and/or transformation of a host cell are well known to those of skill in the art. Guidance in transfection and transformation can be found in the relevant literature. See, e.g., Maniatis et al., (1982) *Molecular Cloning: A Laboratory Manual*, Cold Spring Harbor Press, Cold Spring Harbor, N.Y., United States of America; *DNA Cloning: A Practical Approach*, Volumes I and II (1985) (Glover, ed.), IRL Press, Oxford, England; *Oligonucleotide Synthesis* (1984) (Gait, ed.), IRL Press, Oxford, England; *Nucleic Acid Hybridization* (1985) (Hames & Higgins, eds.), IRL Press, Oxford, England; *Transcription and Translation* (1984) (Hames & Higgins, eds), IRL Press, Oxford, England; *Animal Cell Culture* (1986) (Freshney, ed.), IRL Press, Oxford, England; *Immobilized Cells and Enzymes* (1986), IRL Press, Oxford, England; Perbal, (1984) *A Practical Guide to Molecular Cloning*, John Wiley & Sons, New York, N.Y., United States of America; and Sambrook et al., (1989) *Molecular Cloning: a Laboratory Manual*, Cold Spring Harbor Press, Cold Spring Harbor, United States of America, all of which are incorporated herein in their entirety.

IX.E. A Kit Comprising a Tag of the Present Invention and a PDZ1 Domain Polypeptide In a further aspect of the present invention a kit is disclosed. In one embodiment, the kit comprises: (a) a first container containing a vector comprising a nucleic acid sequence encoding a tag sequence, wherein the tag sequence is one of a PDZ1 domain and a NorpA sequence; and (b) a second container containing one of a PDZ1 domain polypeptide and a polypeptide comprising a NorpA sequence.

In one embodiment, the vector contained in the first container comprises a vector. In another embodiment, the vector comprises a nucleic acid sequence encoding a tag of the present invention. In one embodiment, the nucleic acid sequence encoding a tag is selected from hose encoding the peptides of SEQ ID NOs: 1, 2, and 9. The vector can also comprise one or more additional nucleic acid sequences, such as a sequence selected from the group consisting of a selectable marker, a restriction site, a promoter, an operon, an origin of replication, and a cloning site flanking one of one side and both sides of the tag. A suitable selectable marker includes, but is not limited to an antibiotic resistance gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complimentary to a PCR primer sequence, although others are possible.

In another embodiment, the kit also comprises a second container containing a PDZ1 domain polypeptide. In one embodiment, the PDZ1 domain polypeptide comprises the amino acid sequence SEQ ID NO: 8, although shorter fragments of SEQ ID NO: 8 can also be employed in the kit. Additionally, the PDZ1 domain polypeptide can be detectably labeled. This can be advantageous when the kit is employed in a protein detection application. A representative but non-limiting list of suitable labels includes a fluorescent moiety, a chemiluminescent moiety, an absorptive moiety, an emissive moiety, and a radioactive moiety. The PDZ1 domain polypeptide can also comprises an enzyme fused to the PDZ1 domain polypeptide. Enzymes that can be fused to a PDZ1 domain polypeptide include, but are not limited to alkaline phosphatase and horseradish peroxidase.

The PDZ1 domain polypeptide can optionally be associated with a non-soluble matrix, as disclosed above. In this embodiment, it can be desirable to maintain the PDZ1 domain polypeptide under a suitable buffer. A representative but non-limiting list of suitable non-soluble matrix material includes polysaccharide-based gels (for example, SEPHAROSE®0 or AFFI-GEL®) glass, nitrocellulose, nylon, a polymer, and a membrane. Association of a PDZ1 domain polypeptide with a matrix is disclosed hereinabove. Additionally, a PDZ1 domain polypeptide associated with a matrix can be further associated with a support. Suitable supports include, but are not limited to a glass column, a plastic column, a membrane, and a plastic plate.

The kit can further comprise a set of instructions. The instruction set can describe representative step-by-step methods for using the kit in various applications. Although cloning methods are well known in the art, the set of instructions can include a map of the vector, including any restriction sites that can be employed in an insertion of a nucleic acid encoding a protein of interest. It can also describe exemplary protocols for preparing the kit, as well as conditions for storing the kit. Additionally, a set of instructions can also describe how to interpret the results of an experiment performed using the kit.

IX.F. A Protein Purification Kit

A protein purification kit is another aspect of the present invention. The protein purification kit can comprise three containers. In one embodiment, the kit comprises: (a) a first container containing a vector comprising a nucleic acid sequence encoding a tag sequence, wherein the tag sequence is one of a PDZ1 domain and a NorpA sequence; (b) a second container containing one of a PDZ1 domain polypeptide and a polypeptide comprising a NorpA sequence; and (c) an elution component.

The first container contains an expression vector comprising a nucleic acid sequence encoding a tag or a PDZ1 domain. In one embodiment, the nucleic acid sequence encoding a NorpA tag is selected from those encoding the peptides of SEQ ID NOs: 1, 2, and 9. The vector can also comprise one or more additional nucleic acid sequences, such as a sequence selected from the group consisting of a selectable marker, a restriction site, a promoter, an operon, an origin of replication, and a cloning site flanking one of one side and both sides of the tag. A suitable selectable marker includes, but is not limited to an antibiotic resistance gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complimentary to a PCR primer sequence, although others are possible.

The second container of the protein purification contains one of a PDZ1 domain polypeptide and a polypeptide comprising a NorpA sequence. As noted throughout the present disclosure, in one embodiment the PDZ1 domain polypeptide comprises the amino acid sequence SEQ ID NO: 8, although shorter fragments of SEQ ID NO: 8 can also be employed in the kit. Additionally, the PDZ1 domain polypeptide can be detectably labeled. This can be advantageous when the kit is employed in a protein detection application. A representative but non-limiting list of suitable labels includes a fluorescent moiety, a chemiluminescent moiety, an absorptive moiety, an emissive moiety, and a radioactive moiety. The PDZ1 domain polypeptide can also comprises an enzyme fused to the PDZ1 domain polypeptide. Enzymes that can be fused to a PDZ1 domain polypeptide include, but are not limited to alkaline phosphatase and horseradish peroxidase.

The third container of the protein purification kit contains an elution component. The elution component is employed to reduce the disulfide bond between the tag and the PDZ1 domain polypeptide. Various reducing agents can be employed as elution components. Suitable elution components include, but are not limited to DTT, BME, and Tris(2-carboxyethyl)phosphine (TCEP), to name just a few.

The kit can further comprise a set of instructions. The instruction set can describe step-by-step representative methods for using the kit in a protein purification operation. Additionally, although cloning methods are well known in the art, the set of instructions can include a map of the vector, including any restriction sites that can be employed in an insertion of a nucleic acid encoding a protein of interest. It can also describe exemplary protocols for preparing the kit, as well as conditions for storing the kit. Additionally, a set of instructions can also describe how to interpret the results of an experiment performed using the kit.

IX.G. A Protein Detection Kit

Another kit that forms an aspect of the present invention is a protein detection kit. The contents of this kit can be employed to detect the presence of a protein in a background of other proteins, carbohydrates, lipids, small molecules, and other cellular material. This kit can be employed as a step in a screening process, for example. Thus, in one embodiment the protein detection kit comprises: (a) a first container containing a vector comprising a nucleic acid sequence encoding a tag sequence, wherein the tag sequence is one of a PDZ1 domain and a NorpA sequence; (b) a second container containing one of a PDZ1 domain polypeptide and a polypeptide comprising a NorpA sequence; (c) a third container containing an elution component; and (d) a fourth container containing a detection component.

In one embodiment, the kit comprises a first container containing an expression vector comprising a nucleic acid sequence encoding a tag. In one embodiment, the nucleic acid sequence encoding a tag is selected from those encoding the peptides of SEQ ID NOs: 1, 2, and 9. The vector can also comprise one or more additional nucleic acid sequences, such as a sequence selected from the group consisting of a selectable marker, a restriction site, a promoter, an operon, an origin of replication, and a cloning site flanking one of one side and both sides of the tag. A suitable selectable marker includes, but is not limited to an antibiotic resistance gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complimentary to a PCR primer sequence, although others are possible.

Continuing with the present embodiment, the second container of a protein detection kit contains a PDZ1 domain polypeptide. As noted throughout the present disclosure, in one embodiment the PDZ1 domain polypeptide comprises the amino acid sequence SEQ ID NO: 8, although shorter fragments of SEQ ID NO: 8 can also be employed in the kit. Additionally, the PDZ1 domain polypeptide can be detectably labeled. This can be advantageous when the kit is employed in a protein detection application. Suitable labels include, but are not limited to a fluorescent moiety, a chemiluminescent moiety, an absorptive moiety, an emissive moiety, and a radioactive moiety. The PDZ1 domain polypeptide can also comprises an enzyme fused to the PDZ1 domain polypeptide. Enzymes that can be fused to a PDZ1 domain polypeptide include, but are not limited to alkaline phosphatase and horseradish peroxidase.

The third container of a protein detection kit contains an elution component. The elution component is employed to reduce the disulfide bond between the tag and the PDZ1 domain polypeptide. Various reducing agents can be employed as elution components. Suitable elution components include, but are not limited to DTT, BME, and TCEP, to name just a few.

The fourth container of a protein detection kit contains a detection component. The identity of a detection component can be dependent on the properties of the PDZ1 domain. For example, when a PDZ1 domain polypeptide is fused to an enzyme such as alkaline phosphatase, a detection component can comprise a substrate for that enzyme. A detection component can also be an antibody that is specific for a PDZ1 domain polypeptide or a tag. Other detection components can also be employed, and in one embodiment exhibit the property of association with a PDZ1 domain polypeptide or a tag.

The kit can further comprise a set of instructions. The instruction set can describe step-by-step representative methods of using the kit in a protein purification operation. Additionally, although cloning methods are well known in the art, the set of instructions can include a map of the vector, including any restriction sites that can be employed in an insertion of a nucleic acid encoding a protein of interest. It can also describe exemplary protocols for preparing the kit, as well as conditions for storing the kit. Additionally, a set of instructions can also describe how to interpret the results of an experiment performed using the kit.

IX.H. Detection of Protein-protein Interactions by Surface Plasmon Resonance

Surface plasmon resonance (SPR) can be employed in the nondestructive study of surfaces, interfaces, and very thin layers, and has recently been found to be particularly adapted for the study of biological phenomenon such as protein-protein interactions (e.g. antigen-antibody reactions and antigen stimulation of tissue). A surface plasmon is an oscillation of free electrons propagated along the surface of a conductor that is typically in the form of a thin metal film of gold, silver, or copper. Transverse-magnetic polarized energy in an evanescent field excites surface plasmons on the thin metal film. The characteristics of the resonance are directly related to the refractive indices of materials on both sides of the metal film. By including the sample to be measured as a layer on one side of the metal film, changes in the refractive index of the sample can be monitored by measuring changes in the evanescent field to surface plasmon coupling efficiency. Surface plasmons represent the quanta of oscillations of surface charges produced by application of an external electric field to a conducting medium.

The surface selectivity of SPR arises from the enhancement of the optical electric fields at metal surfaces when surface plasmon polaritons (SPPs) are created at the metal/dielectric surface. SPPs are coupled photon-plasmon surface electromagnetic waves that propagate parallel to the metal/dielectric interface. The intensity of the optical electric fields associated with an SPP decays exponentially in distance away from the metal surface, with a typical decay length for an SPP into the dielectric being on the order or 200 nm. SPPs cannot be created on an isolated planar metal surface, but rather require a prism or grating coupling geometry for exciting SPPS. Thus, surface plasmon resonance is achieved by employing the evanescent wave, which is generated when a p-polarized light beam is totally internally reflected at the boundary of a medium having a high dielectric constant, such as glass. The free electron oscillation is affected by the refractive index of the material adjacent the metal surface which forms the basis of SPR measurements.

Protein-protein interactions can be detected by SPR. In one SPR detection scheme, PDZ1 is not the detection agent, but the matrix. A PDZ1 domain polypeptide can be covalently-coupled to the carboxymethylated dextran of an SPR chip. Methods of achieving this association are well known in the literature and will be known to those of skill in the art upon consideration of the present disclosure.

Next, a tagged protein of interest (e.g. a NorpA-protein fusion protein comprising a sequence of SEQ ID NOs: 1, 2, and 9) can be prepared as disclosed herein. The tagged protein can then be contacted with the PDZ1 domain polypeptide. The two proteins can covalently couple to PDZ1, due to the inherent affinity of a tagged protein for a PDZ1 domain polypeptide. This entire complex can comprise the "surface" of the SPR chip.

Subsequently, a test protein can then be contacted the surface. The contacting can be achieved by contacting a solution comprising a test protein with the surface. If the test protein associates with the surface (i.e. the tagged protein of interest), an increase in response units (RU) will be observed. A series of test proteins can be contacted with the surface in order to identify (e.g. screen) those proteins that associate with the tagged protein of interest. The covalent interaction between a tagged protein of interest and a PDZ1 domain polypeptide is advantageous because it maintains a consistent surface throughout an SPR experiment.

IX.I. "Proteins on a Chip" Applications

The present invention can also be employed in applications in which a "protein on a chip" approach is desired. Such applications include the identification of test proteins that associate with a protein of interest. In these applications, a substrate can be a chip and a tagged protein of interest can comprise a tag derived from a NorpA polypeptide, such as those of SEQ ID NOs: 1, 2, and 9. These applications can form the basis of a high-throughout detection protocol.

In one application, a protein of interest can be generated or provided that comprises a tag of the present invention. Such proteins can be prepared by employing the techniques disclosed herein. Similarly, a PDZ1 domain polypeptide can be prepared by employing the techniques disclosed herein.

A PDZ1 domain polypeptide can then be associated with a chip. When it is desired to employ SPR to detect an interaction between a protein of interest (which is a preferred method of detecting protein-protein interactions), a chip can comprise an SPR chip. When a microfluidics-based application is contemplated, a chip can comprise a chip designed for that application. Generally, a chip can comprise any material or dimension, each of which can be selected based on the context in which the chip will be applied (e.g., SPR, microfluidics, etc). In one embodiment, a chip is adapted to facilitate association of a protein (e.g. a PDZ1 domain polypeptide) with the chip.

Continuing with this example, a tagged protein of interest can then be provided. Fusion proteins comprising a protein of interest and a tag of the present invention can be prepared by employing the methods disclosed hereinabove and recombinant methods that will be known to those of skill in the art upon contemplation of the present invention.

The tagged protein can then be contacted with the PDZ1 domain polypeptide. The contacting can take the form of passing a solution comprising the tagged protein over the PDZ1 domain polypeptide. An interaction can then be detected. The detecting can be via any of a range of methods; in one embodiment, a method comprising SPR.

X. Conclusions

The methods and reagents of the present invention can be employed in a variety of applications, such as protein purification and detection applications. Additionally, the present invention discloses recombinant expression vectors and non-soluble solid phase materials that can be employed in protein purification and detection operations.

The methods and reagents of the present invention are based, in part, on the interaction between the NorpA protein and a PDZ1 domain of the InaD protein, both of which are found in *Drosophila*. The observation that a five residue peptide is sufficient to form the association between these two proteins forms an aspect of the present invention. Specifically, SEQ ID NOs: 1, 2, and 9 are sufficient to facilitate this association. The present invention further discloses the observation that these two proteins interact via a disulfide bond that is formed between the proteins.

The present invention offers many advantages over known protein purification and detection systems. First, the methods and apparatuses of the present invention can be employed to detect and purify a protein of interest. Very few systems can be employed for both of these applications.

Next, the interaction between a PDZ1 domain polypeptide and a tag of the present invention is highly specific. This offers an advantage over antibodies and other proteins and small molecules that can be promiscuous and can bind to proteins other than a protein of interest. This can lead to false positives in protein detection applications and can impart additional impurities to a protein purification protocol.

Further, a tag of the present invention is shorter than almost any other known tag. Hexahistidine ($His_6$) tags are available, which are a single residue longer than a NorpA tag of the present invention. However, hexahistidine tags have the disadvantage that they are not consistently recognized by anti-hexahistidine antibodies, which are typically employed in protein purification and detection protocols. Additionally, since a tag of the present invention can be functional and comprise only about 5 residues in length, this fact minimizes adverse interactions of the tag with the protein of interest.

Moreover, the PDZ1 domain polypeptide can be easily labeled, eliminating any need for a secondary detection component, such as an antibody. Thus, for protein detection applications, the presence of a complex, and therefore a tagged target protein, can be ascertained by detecting the presence of the labeled PDZ1 domain polypeptide. This eliminates the need to for a secondary component.

Additionally, the kits of the present invention comprise all reagents and materials needed to perform any of a range of applications. Therefore, a researcher desiring to purify a protein can employ a protein purification kit of the present invention and does not need to supply additional materials beyond standard laboratory solvents and the like.

It will be understood that various details of the invention may be changed without departing from the scope of the invention. Furthermore, the foregoing description is for the purpose of illustration only, and not for the purpose of limitation—the invention being defined by the claims.

LABORATORY EXAMPLES

The following Laboratory Examples have been included to illustrate exemplary modes of the invention. Certain aspects of the following Laboratory Examples are described in terms of techniques and procedures found or contemplated by the present co-inventors to work well in the practice of the invention. These Laboratory Examples are exemplified through the use of standard laboratory practices of the co-inventors. In light of the present disclosure and the general level of skill in the art, those of skill will appreciate that the following Laboratory Examples are intended to be exemplary only and that numerous changes, modifications, and alterations can be employed without departing from the spirit and scope of the invention.

Materials and Methods for Laboratory Examples
1-2 Plasmid Construction cDNA encoding the C-terminal domain of NorpA ($CT_{Dm}$) was cloned into pPROEX™ HTa (Invitrogen Life Technologies, Carlsbad, Calif., United States of America), which codes for a cleavable N-terminal $His_6$ tag.

Gαi1 was cloned into pPROEX™ HTb (Invitrogen Life Technologies, Carlsbad, Calif., United States of America). In order to express Gαi1 with the NorpA tail, the stop codon of pPRO/Gαi1 was removed using the QUIKCHANGE™ site-directed mutagenesis kit (Stratagene, La Jolla, Calif., United States of America). Oligonucleotides that encoded for the C-terminal five amino acids of NorpA (Thr-Glu-Phe-Cys-Ala) (SEQ ID NO: 1) flanked by NotI and XbaI half-sites (5'-GGCCGCACGGAATTTT GTGCCTAAT-3' (sense) (SEQ ID NO: 10) and 5'-CTAGATTAGG CACAAAATTCCGTGC-3' (antisense) (SEQ ID NO: 11) were annealed by denaturation at 94° C. for 5 minutes followed by cooling to room temperature for 15 minutes, and ligated into the pPRO/Gαi1 vector cut with Not I and Xba I.

cDNA corresponding to residues 13-107 of InaD was amplified from a plasmid template by employing PDZ1-specific primers. A KpnI restriction site was engineered into the sense primer, and a BglII restriction site into the antisense primer. The sequences of the PDZ1 primers used were 5'-TGGTACCGAGCTCATTCACATGGTGACCCT-3' (sense) (SEQ ID NO: 12) and 5'-C AGATCTTCTTGTCGAAGGTCTGAATCTC-3' (antisense) (SEQ ID NO: 13). The PDZ1 cDNA was ligated into the pCR®2.1-TOPO® vector and transformed into TOP10 chemically competent cells using the TOPO TA® cloning system (Invitrogen Life Technologies, Carlsbad, Calif., United States of America). pCR2.1/PDZ1 was purified from an overnight culture of a positive transformant and digested with Kpn I and Bgl II. The Kpn I/Bgl II-cut PDZ1 was separated from the vector by agarose gel electrophoresis followed by gel purification (QIAQUICK® Gel Extraction Kit, Qiagen Inc., Valencia, Calif., United States of America). Purified insert was ligated into Kpn I/Bgl II-cut pQUANTagen(kx) (PHOA* COLOR™ System, Qbiogene, Montreal, Quebec, Canada), which encodes for a C-terminal alkaline phosphatase (AP) fusion protein.

Recombinant Protein Expression and Purification $CT_{Dm}$ was expressed and purified. Gαi1 and Gαi1-NorpA were expressed and purified. Briefly, pPRO/Gαi1 or pPRO/Gαi1-NorpA was transformed into BL21(DE3) *E. Coli*, and 50 μL of the transformation reactions were used to inoculate overnight starter cultures. 1 mL of the pPRO/Gαi1 or pPRO/Gαi1-NorpA starter culture was used to inoculate 100 mL of Luria broth (LB: 10 g tryptone, 5 g yeast extract, 10 g NaCl per liter, pH 7.5) containing 100 μg/mL ampicillin, which was grown at 37° C. with shaking to an optical density at 600 nm ($OD_{600}$) of about 1.0. An uninduced sample of each culture was saved, and 1 mM isopropyl-thio-β-D-galactopyranoside (IPTG) was added to the remainder to induce Gαi1 or Gαi1-NorpA protein expression. Growth was continued for about 4 hours at 37° C. A post-induction sample of each culture was taken.

pQUANT/PDZ1 was transformed into *E. coli* strain XL1-Blue (Stratagene, La Jolla, Calif., United States of America), and the cells plated on LB agar containing 200 μg/mL ampicillin and 0.004% 5-bromo-4-chloro-3-indolyl phosphate (BCIP) (Qbiogene, Montreal, Quebec, Canada). Colonies containing the PDZ1 insert in the correct reading frame appeared blue after incubation for about 16 hours at 37° C. An overnight culture of one positive colony was used to inoculate 100 mL of tryptic soy broth (TSB: 17 g tryptone, 3 g soytone, 5 g yeast extract, 5 g sodium chloride, 2.5 g dipotassium phosphate per liter, pH 7.5) containing 200 μg/mL ampicillin, which was grown at 37° C. with shaking to an $OD_{600}$ of about 0.7. AP-PDZ1 expression was induced by adding IPTG to 0.5 mM and growing for an additional 3.5 hours at 37° C.

The periplasmic AP-PDZ1 protein was extracted by lysozymic shock according to standard protocol. Briefly, the culture was pelleted by centrifugation and resuspended in 10 mL TSB (20 mM Tris-HCl pH 8.0, 20% sucrose, 0.5 mM EDTA) containing one COMPLETE® EDTA-free protease cocktail tablet (available from Roche Molecular Biochemicals, Indianapolis, Ind., United States of America) per 50 mL. Lysozyme (Sigma, St. Louis, Mo., United States of America) was added to a final concentration of 0.1 mg/mL, and the cell suspension agitated for 20 min at 4° C. followed by centrifugation for 30 minutes at 20,000 g. The supernatant, containing the periplasmic AP-PDZ1, was either used immediately or flash-frozen on dry ice and stored at −80° C. for use within 24 hours.

Dot Blots

5 μL of purified AP-PDZ1 or $CT_{Dm}$ was pipetted onto a nitrocellulose membrane and dried at room temperature. The membranes were blocked with 10% nonfat dry milk in Tris-buffered saline (TBS: 20 mM Tris-HCl, 50 mM NaCl, pH 7.5) containing 0.01% Tween 20 (TBS-T). Control blots were washed 3× with TBS for 15 minutes each, followed by addition of 5-bromo-4-chloro-3-indolyl phosphate/nitro blue tetrazolium (BCIP/NBT) (Sigma Chemical Co., St. Louis, Mo., United States of America), an alkaline phosphatase substrate solution. Color development proceeded for about 10 minutes, followed by extensive washing in double distilled water ($ddH_2O$) to stop the reaction. Test blots were incubated with 1 mL of purified AP-PDZ1 in 10 mL 10% milk/TBS-T for 4 hours at room temperature. Blots were washed and developed as described above.

Western Blots

Uninduced and induced $CT_{Dm}$, Gαi1, and Gαi1-NorpA bacterial samples were loaded onto 15% SDS/PAGE gels to separate the species by molecular weight. Duplicate gels were stained for total protein with Coomassie blue. Separated proteins were transferred to nitrocellulose membranes using a tank transfer system according to standard protocol. Membranes were dried, blocked, incubated with AP-PDZ1, washed, and developed as above for dot blots.

Laboratory Example 1

AP-PDZ1 Binds to NorpA Specifically

Figure 1B:
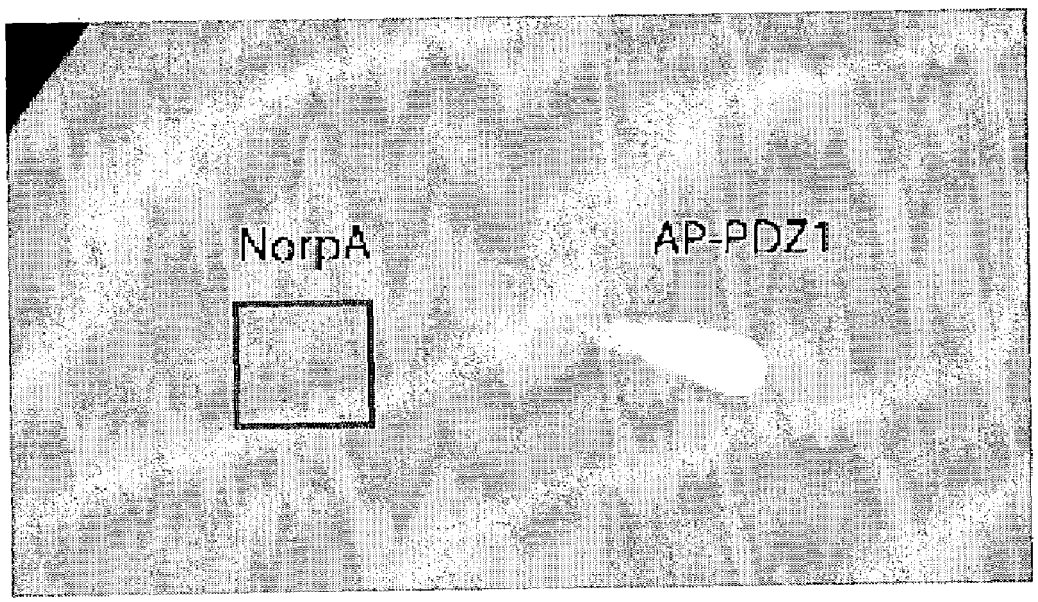
FIG. 1B is a blot depicting the observation that AP remains active. The membrane was incubated with 5-bromo-4-chloro-3-indolyl phosphate and nitro blue tetrazolium (BCIP/NBT) for 10 minutes, and the color change of the AP-PDZ1 dot indicates AP activity. $CT_{Dm}$ is shown on the left and AP-PDZ1 is shown on the right.

PDZ1 was expressed and purified as an alkaline phosphatase (AP) fusion protein. To test for phosphatase activity, AP-PDZ1 was dotted onto a nitrocellulose membrane, along with purified $CT_{Dm}$ as a negative control. The color change of the PDZ1 dot but not the $CT_{Dm}$ dot after the addition of the AP substrate BCIP/NBT (FIGS. 1A and 1B) indicated that AP-PDZ1 contains an active phosphatase, while $CT_{Dm}$ alone does not.

Figure 2A:
FIG. 2A is a blot depicting the observation that AP-PDZ1 binds to and confers AP activity onto $CT_{Dm}$. $CT_{Dm}$ was dotted onto a nitrocellulose membrane, which was dried, blocked, and incubated with AP-PDZ1 for 4 hours.
Figure 2B:
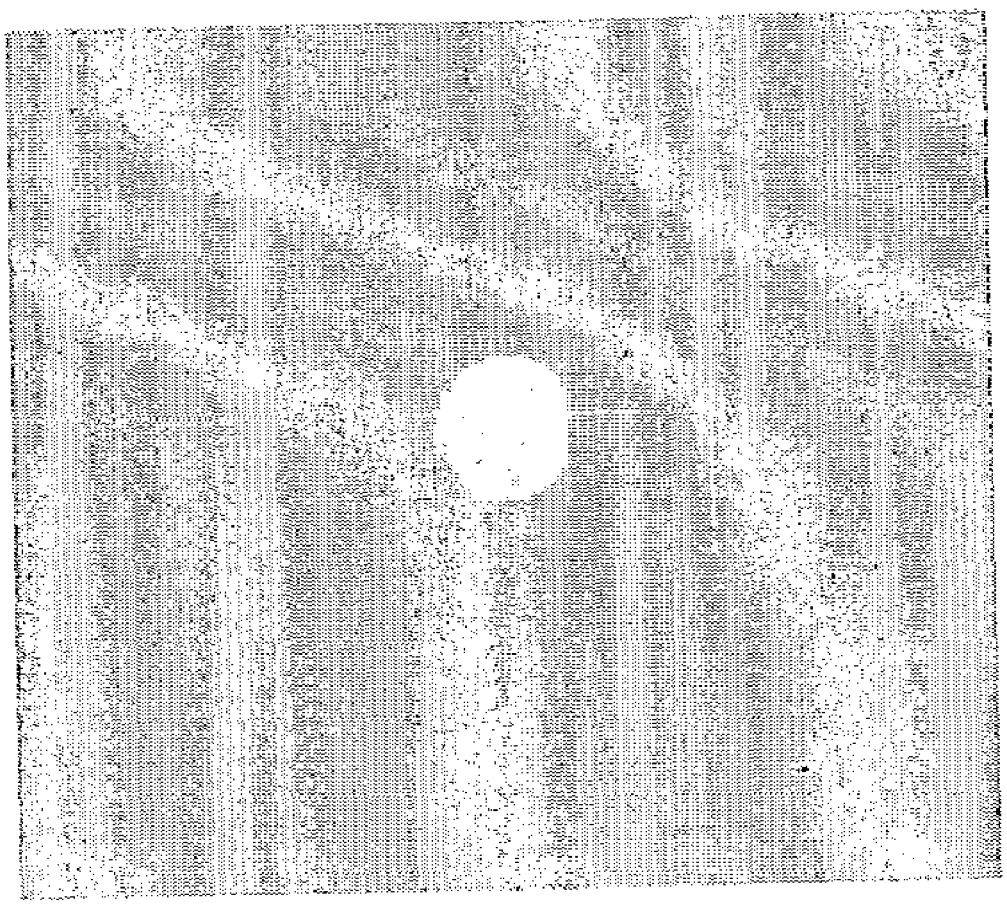
FIG. 2B is a blot depicting the observation that AP-PDZ1 remained bound to $CT_{Dm}$. The membrane was extensively washed, and the color change of the $CT_{Dm}$ dot after incubation with BCIP/NBT indicates that AP-PDZ1 remained bound to $CT_{Dm}$.
Figure 3B:
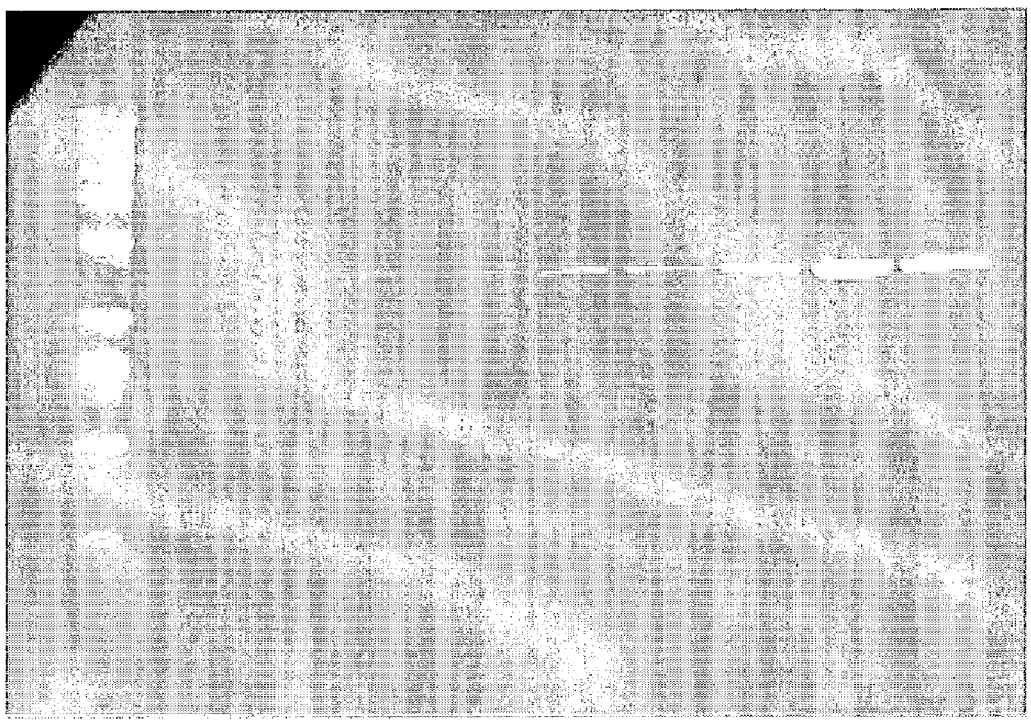
FIG. 3B is a blot depicting the observation that after the addition of BCIP/NBT, AP-PDZ1 interacts specifically with $CT_{Dm}$ in a background of bacterial proteins.
Figure 3C:
FIG. 3C is a Coomassie-stained gel of the bacterial lysate that was loaded in each lane, except the purified $CT_{Dm}$ lane.
Figure 4A:
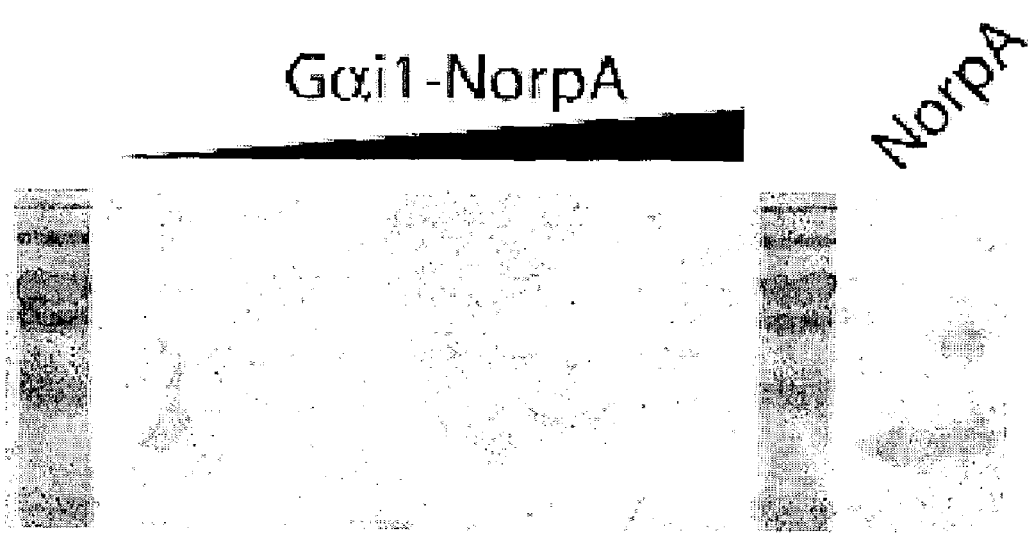
FIG. 4A is a polyacrylamide gel depicting the specificity of AP-PDZ1 for Gαi1-NorpA. Varying ratios of uninduced:induced Gαi1-NorpA cell lysate samples were separated by SDS/PAGE and transferred to nitrocellulose. The membrane was incubated with AP-PDZ1 for 4 hours, followed by extensive washing.
Figure 4B:
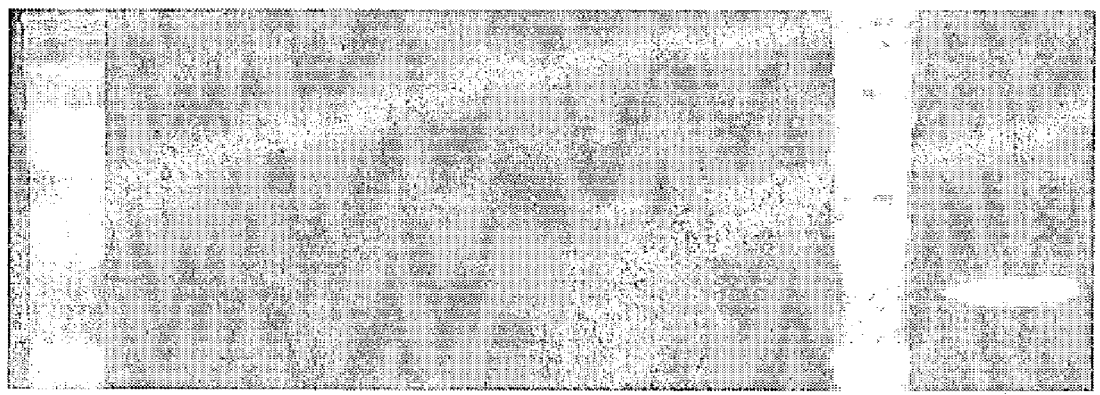
FIG. 4B is a blot depicting the observation that after addition of BCIP/NBT, AP-PDZ1 specifically interacts with Gαi1-NorpA in a background of bacterial proteins.
Figure 4C:
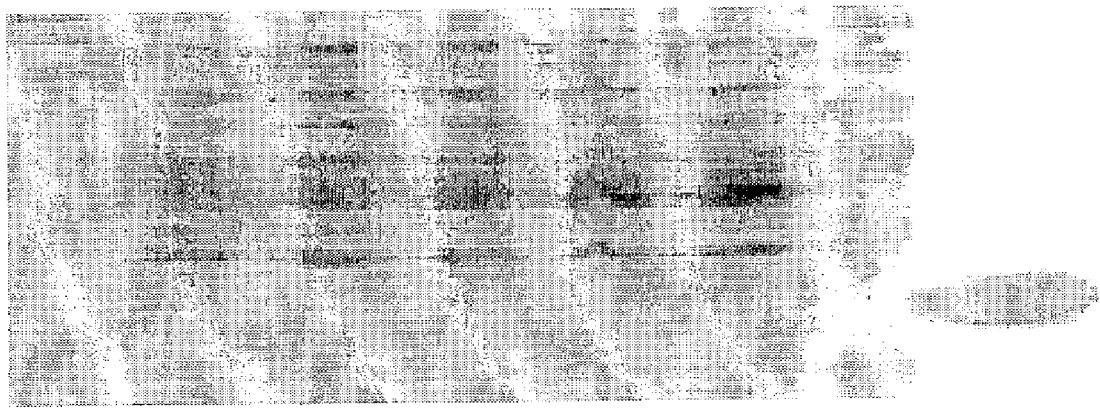
FIG. 4C is a duplicate Coomassie-stained gel of the protein that was transferred to nitrocellulose in FIG. 4A. Purified $CT_{Dm}$ was added to the last lane as a positive control.

To show that AP-PDZ1 can bind to and confer its phosphatase activity onto its physiological ligand, $CT_{Dm}$ was dotted onto a nitrocellulose membrane and incubated with a solution of AP-PDZ1 for 4 hours. The membrane was extensively washed, and since $CT_{Dm}$ alone does not have AP activity (FIGS. 1A and 1B), the color change after addition of BCIP/NBT (FIGS. 2A and 2B) indicated that AP-PDZ1 remained bound to $CT_{Dm}$.

In order to demonstrate that AP-PDZ1 can be used to detect $CT_{Dm}$ specifically out of a pool of other proteins, varying amounts of purified $CT_{Dm}$ were added to BL21 (DE3) whole-cell lysate and separated by gel electrophoresis, along with a control lane of purified $CT_{Dm}$ alone. Proteins were transferred to a nitrocellulose membrane, blocked, and incubated with AP-PDZ1 for 4 hours. After extensive washing, the membrane was developed with BCIP/NBT. The color change of the $CT_{Dm}$ bands indicated that AP-PDZ1 interacts specifically with $CT_{Dm}$ even in a background of cellular lysate (FIGS. 3A-3C), and that this interaction can be exploited to detect $CT_{Dm}$ colorimetrically.

Laboratory Example 2

Addition of the NorpA Tail Confers PDZ1 Binding to Heterologous Proteins

As a final test, the NorpA tail was spliced onto Gαi1, a signaling protein that does not interact with PDZ1. Varying ratios of uninduced and induced Gαi1-NorpA bacterial samples were separated by gel electrophoresis and transferred to a nitrocellulose membrane, along purified $CT_{Dm}$ alone as a positive control. As above for $CT_{Dm}$, the membrane was blocked, incubated with AP-PDZ1, washed, and developed with BCIP/NBT. Although the Gαi1-NorpA/PDZ1 interaction did not seem to be as strong as that of the $CT_{Dm}$ /PDZ1 complex, Gαi1 was still detected using colorimetric methods in a background of bacterial cell proteins (FIGS. 4A-4C).

Discussion of Laboratory Examples 1-2

The NorpA tagging system is a powerful affinity tag and detection system improves upon currently available methods. Table 1 shows a summary of several characteristics of commonly-employed epitope tags (above dotted line) and less commonly-used epitope tags (below dotted line), including their molecular weights, uses, advantages, and disadvantages (summarized from Jones et al., (1995) *J Chromatogr A* 707: 3-22; Bornhorst & Falke, (2000) *Method. Enzymol*. 326: 245-254; Skerra & Schmidt, (2000) *Method. Enzymol*. 326: 271-304; 22. Smith, (2000) *Method. Enzymol* 326: 254-270; Nilsson et al., (1997) *Protein Expr. Purif* 11: 1-16; Sheibani, (1999) *Prep. Biochem. Biotechnol*. 29: 77-90; and Fritze & Anderson, (2000) *Method. Enzymol*. 327: 3-16). The most desirable affinity tag would comprise a short, linear recognition motif (i.e. one that is less likely to affect the structure or function of the protein of interest) useful for both protein detection and protein purification on a regenerable, reusable affinity matrix.

The first four tags (c-Myc, Hemaglutinin (HA), FLAG®, and Green fluorescent protein (GFP)) are limiting in that they are normally used for protein detection only. FLAG®-tagged proteins can be purified using calcium-dependent affinity chromatography to the M1 antibody (Nilsson et al., (1997) *Protein Expr. Purif* 11: 1-16), but this method is difficult to scale-up due to the prohibitive cost of creating a large quantity of affinity resin and the fact that the resin is only reusable until the antibody begins to degrade. Anti-FLAG® M1 affinity gel is available from Sigma Aldrich, St. Louis, Mo., United States of America. Cost and reuse are also problems that are present in purification of c-Myc-tagged proteins by antibody affinity chromatography (Hillman et al., (2001) *Protein Expr. Purif.* 23: 359-368), along with the low pH elution conditions that can cause protein aggregation. In addition, c-Myc antibodies are somewhat promiscuous (Fritze & Anderson, (2000) *Method. Enzymol*. 327: 3-16), leading to a higher background binding during both protein purification and protein detection than is optimal.

In contrast, HA- and FLAG®-tag antibodies are quite specific (Fritze & Anderson, (2000) *Method. Enzymol*. 327: 3-16), but the tags themselves are longer, and the anti-FLAG® antibody M1 requires the tag be placed at the N-terminus of the protein of interest (Nilsson et al., (1997) *Protein Expr. Purif* 11: 1-16). GFP is the largest of the commonly-used affinity tags, but because of its fluorescent properties it is quite versatile. GFP-tagged proteins have been used to study processes such as intracellular transport, cell secretion, membrane dynamics, and nuclear membrane translocation (Gerdes & Kaether, (1996) *FEBS Lett* 389: 44-47), as well as in vitro protein-protein interactions (Day et al., (2001) *Methods* 25: 4-18; Kiessig et al., (2001) *Electrophoresis* 22: 428-1435). Care must be taken in analyzing experiments involving sub-cellular localization of GFP-tagged proteins, however, because some GFP fusions are non-specifically targeted to the nucleus (Olson et al., (1995) *J. Cell Biol*. 130: 639-650; Pines, (1995) *Trends Genet*. 11: 326-327; Ogawa et al., (1995) *Proc. Natl. Acad. Sci. U.S.A*. 92: 11899-11903).

Only two commonly-employed affinity tags are employed regularly for both protein detection and purification: glutathione S transferase (GST) and $His_6$ (Bornhorst & Falke, (2000) *Methods Enzymol*. 326: 245-254; Smith, (2000) *Methods Enzymol*. 326: 254-270; Sheibani, (1999) *Prep. Biochem. Biotechnol*. 29: 77-90). GST is a large tag, sometimes larger than the protein or peptide of interest, and it readily homodimerizes (Tudyka & Skerra, (1997) *Protein Sci*. 6: 2180-2187), which can lead to experimental artifacts. $His_6$ tags can be as short as 6 residues, depending on the expression vector, are quite useful for protein purification, but $His_6$ antibodies are notoriously promiscuous and can require additional residues for specificity (Fritze & Anderson, (2000) *Method. Enzymol*. 327: 3-16).

The affinity tags listed below the line on Table 1 are not commonly-employed, but each has one or more characteristics that warrant their inclusion in the molecular biologist's repertoire. These advantages include increased solubility (maltose binding protein (MBP) Staphylococcal proteins A and G (SPA and SPG), and albumin binding protein (ABP)), $^{32}P$ labeling ability (calmodulin binding protein (CBP)), heat-stability (thioredoxin), or extracellular secretion (biotin carboxyl carrier protein (BCCP)). Proteins with any of these fusion tags can be purified on antibody or protein affinity resins, however these resins are not easily reusable or commercially available (except for immobilized streptavidin). In addition, because these tags are not used very often, there have not been AP- or horseradish peroxidase (HRP)-conjugated primary antibodies developed to detect them without using a secondary antibody.

The five-residue NorpA tag of the present invention is the shortest of any of the tags listed in Table 1, and is useful for protein detection. PDZ1 binds specifically and covalently to the NorpA epitope, and the development of an AP-PDZ1 fusion that can detect NorpA-tagged proteins negates primary antibody generation. HRP-PDZ1 is useful for chemiluminescent detection, a more sensitive method than the colorimetric assay described here. The NorpA tag system is also advantageous for protein purification.

This makes the NorpA tail one of the more advantageous affinity tagging systems, comparable with the $His_6$ tag in length, but more useful for protein-protein interaction techniques, such as SPR, where a strong attachment of the protein of interest to the substrate is necessary for valid data recovery.

TABLE 1

| Affinity Tag | MW (kD) | Use Detection | Use Purification | Ligand | Elution | Other Advantages | Other Disadvantages | Other Uses |
|---|---|---|---|---|---|---|---|---|
| c-Myc | 1.2 | yes | yes% | immobilized hIgG | Low pH | Tag at N-or C-term; linear recognition | α-cMyc ABs promiscuous; Low pH elution may cause aggregation | Protein-protein interactions& |
| Hemaglutinin (HA) | 3.5 | yes | no | N/A | N/A | Tag at N-or C-term; α-HA ABs specific | | Protein-protein interactions |
| FLAG | 4.0 | yes | yes% | Immobilized M1 mAB | EGTA or free FLAG peptide | α-Flag ABs specific; linear recognition | M1 mAB can only bind FLAG at N-terminus of fusion | Protein-protein interactions |
| Green fluorescent protein (GFP) | 31.0 | yes | no | N/A | N/A | Tag at N-or C-term; α-GFP ABs specific; GFP is fluorescent | Very large tag; Some GFP fusions non-specifically targeted to nucleus | Real-time cell biology studies; protein-protein interactions |
| Glutathione S transferase (GST) | 28.0 | yes | yes | Immobilized glutathione | Reduced glutathione | Tag at N- or C-term; α-GST ABs specific | Very large tag; GST dimerizes and is highly antigenic; glutathione may affect disulfide-containing proteins | Protein-protein interactions |
| $His_6$ | 0.8-3.0 | yes | yes | Immobilized $Ni^{2+}$ | Low pH, imidazole, or EDTA | Tag at N- or C-terminus; linear recognition; native or denatured protein purification | Non-specific binding to Ni2+; α-$His_6$ ABs promiscuous; pH or imidazole may cause aggregation | Protein-protein interactions |
| Maltose binding protein (MBP) | 40.0 | yes# | yes% | immobilized amylose | maltose | Tag at N- or C-terminus; May improve solubility | Very large tag; Polylinker contains 10 Asn residues | |
| Calmodulin binding peptide (CBP) | 4.0 | yes# | yes% | calmodulin affinity resin with $Ca^{2+}$ | EGTA | PKA target sequence allows $^{32}P$ labeling | | |
| Thioredoxin | 11.8 | yes# | yes% | Immobilized phenylarsine oxide | β-ME | Heat-stable; May be targeted to periplasm for purification | Elution with reducing agent may disrupt disulfide-containing proteins | |
| Streptavidin binding peptide (SBP) | 1.0 | yes# | yes | Immobilized streptavidin | biotin | Linear recognition | Tag at C-terminus only | Protein-protein interactions |
| Staphylococcal protein A and G (SPA and SPG) | 31.0 | yes# | yes% | immobilized hIgG | Low pH | Proteolytically stable; May improve solubility | Very large tag; Low pH elution may cause protein aggregation | |
| Albumin binding protein (ABP) | 15.0 | yes# | yes% | immobilized albumin | Low pH | Proteolytically stable; May improve solubility | Low pH elution may cause protein aggregation | |
| Biotin carboxyl carrier protein (BCCP) | 11.1$ | yes# | yes% | Immobilized avidin | biotin | Biotinylation of tag In vivo; Fusion protein secreted | High background binding to avidin | |
| NorpA | 0.6 | yes | yes** | Immobilized PDZ1 | β-ME or DTT | Very short tag; linear recognition; PDZ1 binds specifically and covalently; no need for AB. | Tag at C-terminus only; elution with reductant may disrupt disulfide-containing proteins | Protein-protein interactions |

TABLE 2

| ATOM | ATOM TYPE | RESIDUE | PROTEIN # | # | X | Y | Z | OCC | B |
|---|---|---|---|---|---|---|---|---|---|
| 1 | N | GLY | A | 12 | 2.867 | 0.935 | −21.408 | 1.00 | 38.47 |
| 2 | CA | GLY | A | 12 | 4.215 | 0.909 | −20.769 | 1.00 | 37.68 |
| 3 | C | GLY | A | 12 | 4.116 | 0.957 | −19.259 | 1.00 | 35.86 |
| 4 | O | GLY | A | 12 | 3.438 | 1.817 | −18.703 | 1.00 | 39.12 |
| 5 | N | GLU | A | 13 | 4.802 | 0.039 | −18.590 | 1.00 | 33.00 |
| 6 | CA | GLU | A | 13 | 4.763 | −0.014 | −17.138 | 1.00 | 29.65 |
| 7 | C | GLU | A | 13 | 6.004 | 0.617 | −16.523 | 1.00 | 26.81 |
| 8 | O | GLU | A | 13 | 6.999 | 0.864 | −17.208 | 1.00 | 22.44 |
| 9 | CB | GLU | A | 13 | 4.630 | −1.468 | −16.688 | 1.00 | 33.26 |
| 10 | CG | GLU | A | 13 | 3.604 | −2.234 | −17.508 | 1.00 | 40.78 |
| 11 | CD | GLU | A | 13 | 3.341 | −3.625 | −16.979 | 1.00 | 44.76 |
| 12 | OE1 | GLU | A | 13 | 4.306 | −4.406 | −16.842 | 1.00 | 47.95 |
| 13 | OE2 | GLU | A | 13 | 2.161 | −3.936 | −16.705 | 1.00 | 48.03 |
| 14 | N | LEU | A | 14 | 5.945 | 0.879 | −15.225 | 1.00 | 22.97 |
| 15 | CA | LEU | A | 14 | 7.080 | 1.483 | −14.552 | 1.00 | 20.14 |
| 16 | C | LEU | A | 14 | 7.057 | 1.194 | −13.062 | 1.00 | 20.58 |
| 17 | O | LEU | A | 14 | 5.993 | 1.164 | −12.442 | 1.00 | 20.33 |
| 18 | CB | LEU | A | 14 | 7.063 | 2.994 | −14.764 | 1.00 | 20.96 |
| 19 | CG | LEU | A | 14 | 8.285 | 3.740 | −14.234 | 1.00 | 24.69 |
| 20 | CD1 | LEU | A | 14 | 9.469 | 3.476 | −15.157 | 1.00 | 24.07 |
| 21 | CD2 | LEU | A | 14 | 7.985 | 5.222 | −14.150 | 1.00 | 27.83 |
| 22 | N | ILE | A | 15 | 8.236 | 0.976 | −12.494 | 1.00 | 19.83 |
| 23 | CA | ILE | A | 15 | 8.349 | 0.738 | −11.060 | 1.00 | 19.22 |
| 24 | C | ILE | A | 15 | 8.862 | 2.043 | −10.475 | 1.00 | 18.99 |
| 25 | O | ILE | A | 15 | 9.871 | 2.574 | −10.934 | 1.00 | 18.46 |
| 26 | CB | ILE | A | 15 | 9.363 | −0.373 | −10.736 | 1.00 | 20.50 |
| 27 | CG1 | ILE | A | 15 | 8.870 | −1.707 | −11.298 | 1.00 | 20.02 |
| 28 | CG2 | ILE | A | 15 | 9.565 | −0.467 | −9.224 | 1.00 | 20.78 |
| 29 | CD1 | ILE | A | 15 | 9.881 | −2.825 | −11.196 | 1.00 | 24.78 |
| 30 | N | HIS | A | 16 | 8.156 | 2.579 | −9.487 | 1.00 | 17.55 |
| 31 | CA | HIS | A | 16 | 8.590 | 3.818 | −8.862 | 1.00 | 17.30 |
| 32 | C | HIS | A | 16 | 8.323 | 3.767 | −7.365 | 1.00 | 18.86 |
| 33 | O | HIS | A | 16 | 7.703 | 2.826 | −6.873 | 1.00 | 17.50 |
| 34 | CB | HIS | A | 16 | 7.904 | 5.029 | −9.504 | 1.00 | 17.51 |
| 35 | CG | HIS | A | 16 | 6.422 | 5.084 | −9.295 | 1.00 | 20.72 |
| 36 | ND1 | HIS | A | 16 | 5.554 | 4.168 | −9.849 | 1.00 | 23.90 |
| 37 | CD2 | HIS | A | 16 | 5.653 | 5.967 | −8.615 | 1.00 | 22.27 |
| 38 | CE1 | HIS | A | 16 | 4.314 | 4.487 | −9.522 | 1.00 | 19.05 |
| 39 | NE2 | HIS | A | 16 | 4.346 | 5.574 | −8.774 | 1.00 | 26.27 |
| 40 | N | MET | A | 17 | 8.810 | 4.768 | −6.640 | 1.00 | 17.15 |
| 41 | CA | MET | A | 17 | 8.651 | 4.795 | −5.192 | 1.00 | 16.16 |
| 42 | C | MET | A | 17 | 7.677 | 5.865 | −4.748 | 1.00 | 18.93 |
| 43 | O | MET | A | 17 | 7.691 | 6.980 | −5.263 | 1.00 | 17.47 |
| 44 | CB | MET | A | 17 | 10.001 | 5.054 | −4.510 | 1.00 | 19.32 |
| 45 | CG | MET | A | 17 | 11.053 | 3.991 | −4.745 | 1.00 | 25.14 |
| 46 | SD | MET | A | 17 | 10.517 | 2.370 | −4.196 | 1.00 | 27.79 |
| 47 | CE | MET | A | 17 | 10.587 | 2.546 | −2.443 | 1.00 | 28.81 |
| 48 | N | VAL | A | 18 | 6.836 | 5.521 | −3.780 | 1.00 | 17.29 |
| 49 | CA | VAL | A | 18 | 5.869 | 6.470 | −3.251 | 1.00 | 18.77 |
| 50 | C | VAL | A | 18 | 5.873 | 6.395 | −1.733 | 1.00 | 19.33 |
| 51 | O | VAL | A | 18 | 5.719 | 5.324 | −1.158 | 1.00 | 18.68 |
| 52 | CB | VAL | A | 18 | 4.442 | 6.170 | −3.763 | 1.00 | 20.80 |
| 53 | CG1 | VAL | A | 18 | 3.426 | 7.062 | −3.045 | 1.00 | 21.60 |
| 54 | CG2 | VAL | A | 18 | 4.370 | 6.410 | −5.270 | 1.00 | 22.60 |
| 55 | N | THR | A | 19 | 6.064 | 7.538 | −1.086 | 1.00 | 20.69 |
| 56 | CA | THR | A | 19 | 6.051 | 7.580 | 0.366 | 1.00 | 21.51 |
| 57 | C | THR | A | 19 | 4.762 | 8.259 | 0.810 | 1.00 | 20.83 |
| 58 | O | THR | A | 19 | 4.419 | 9.335 | 0.324 | 1.00 | 22.34 |
| 59 | CB | THR | A | 19 | 7.254 | 8.369 | 0.927 | 1.00 | 25.34 |
| 60 | OG1 | THR | A | 19 | 8.455 | 7.613 | 0.727 | 1.00 | 25.97 |
| 61 | CG2 | THR | A | 19 | 7.071 | 8.641 | 2.421 | 1.00 | 27.50 |
| 62 | N | LEU | A | 20 | 4.038 | 7.607 | 1.709 | 1.00 | 22.18 |
| 63 | CA | LEU | A | 20 | 2.801 | 8.157 | 2.238 | 1.00 | 22.51 |
| 64 | C | LEU | A | 20 | 3.008 | 8.449 | 3.721 | 1.00 | 24.08 |
| 65 | O | LEU | A | 20 | 3.640 | 7.672 | 4.441 | 1.00 | 24.09 |
| 66 | CB | LEU | A | 20 | 1.643 | 7.168 | 2.073 | 1.00 | 20.32 |
| 67 | CG | LEU | A | 20 | 1.196 | 6.814 | 0.650 | 1.00 | 23.26 |
| 68 | CD1 | LEU | A | 20 | 0.049 | 5.814 | 0.714 | 1.00 | 22.02 |
| 69 | CD2 | LEU | A | 20 | 0.769 | 8.080 | −0.094 | 1.00 | 21.56 |
| 70 | N | ASP | A | 21 | 2.476 | 9.579 | 4.160 | 1.00 | 23.33 |
| 71 | CA | ASP | A | 21 | 2.571 | 10.003 | 5.549 | 1.00 | 21.50 |
| 72 | C | ASP | A | 21 | 1.128 | 10.232 | 5.982 | 1.00 | 19.85 |
| 73 | O | ASP | A | 21 | 0.448 | 11.095 | 5.428 | 1.00 | 20.07 |
| 74 | CB | ASP | A | 21 | 3.357 | 11.310 | 5.632 | 1.00 | 25.93 |
| 75 | CG | ASP | A | 21 | 3.633 | 11.731 | 7.058 | 1.00 | 31.04 |
| 76 | OD1 | ASP | A | 21 | 2.750 | 11.526 | 7.910 | 1.00 | 28.00 |

TABLE 2-continued

| ATOM | ATOM TYPE | RESIDUE | PROTEIN # | # | X | Y | Z | OCC | B |
|---|---|---|---|---|---|---|---|---|---|
| 77 | OD2 | ASP | A | 21 | 4.728 | 12.275 | 7.321 | 1.00 | 33.70 |
| 78 | N | LYS | A | 22 | 0.648 | 9.458 | 6.951 | 1.00 | 18.08 |
| 79 | CA | LYS | A | 22 | −0.732 | 9.622 | 7.389 | 1.00 | 19.71 |
| 80 | C | LYS | A | 22 | −0.893 | 10.580 | 8.557 | 1.00 | 20.37 |
| 81 | O | LYS | A | 22 | −1.927 | 10.583 | 9.220 | 1.00 | 20.90 |
| 82 | CB | LYS | A | 22 | −1.368 | 8.272 | 7.743 | 1.00 | 18.70 |
| 83 | CG | LYS | A | 22 | −0.747 | 7.544 | 8.920 | 1.00 | 19.20 |
| 84 | CD | LYS | A | 22 | −1.561 | 6.302 | 9.257 | 1.00 | 24.02 |
| 85 | CE | LYS | A | 22 | −0.937 | 5.501 | 10.385 | 1.00 | 26.29 |
| 86 | NZ | LYS | A | 22 | −1.695 | 4.243 | 10.642 | 1.00 | 31.12 |
| 87 | N | THR | A | 23 | 0.129 | 11.392 | 8.805 | 1.00 | 22.66 |
| 88 | CA | THR | A | 23 | 0.055 | 12.368 | 9.888 | 1.00 | 24.08 |
| 89 | C | THR | A | 23 | −1.202 | 13.214 | 9.711 | 1.00 | 21.06 |
| 90 | O | THR | A | 23 | −1.405 | 13.830 | 8.663 | 1.00 | 23.95 |
| 91 | CB | THR | A | 23 | 1.282 | 13.300 | 9.886 | 1.00 | 26.11 |
| 92 | OG1 | THR | A | 23 | 2.455 | 12.537 | 10.183 | 1.00 | 27.18 |
| 93 | CG2 | THR | A | 23 | 1.124 | 14.403 | 10.928 | 1.00 | 28.32 |
| 94 | N | GLY | A | 24 | −2.051 | 13.223 | 10.733 | 1.00 | 21.90 |
| 95 | CA | GLY | A | 24 | −3.274 | 14.005 | 10.679 | 1.00 | 22.03 |
| 96 | C | GLY | A | 24 | −4.435 | 13.317 | 9.990 | 1.00 | 23.84 |
| 97 | O | GLY | A | 24 | −5.507 | 13.909 | 98.26 | 1.00 | 23.60 |
| 98 | N | LYS | A | 25 | −4.229 | 12.064 | 9.592 | 1.00 | 22.63 |
| 99 | CA | LYS | A | 25 | −5.262 | 11.284 | 8.911 | 1.00 | 23.25 |
| 100 | C | LYS | A | 25 | −5.462 | 9.944 | 9.618 | 1.00 | 20.42 |
| 101 | O | LYS | A | 25 | −4.543 | 9.423 | 10.237 | 1.00 | 21.13 |
| 102 | CB | LYS | A | 25 | −4.862 | 11.045 | 7.451 | 1.00 | 24.79 |
| 103 | CG | LYS | A | 25 | −4.753 | 12.304 | 6.610 | 1.00 | 25.50 |
| 104 | CD | LYS | A | 25 | −6.116 | 12.920 | 6.345 | 1.00 | 26.69 |
| 105 | CE | LYS | A | 25 | −6.005 | 14.099 | 5.392 | 1.00 | 27.58 |
| 106 | NZ | LYS | A | 25 | −7.340 | 14.617 | 5.002 | 1.00 | 29.67 |
| 107 | N | LYS | A | 26 | −6.667 | 9.392 | 9.511 | 1.00 | 23.31 |
| 108 | CA | LYS | A | 26 | −7.015 | 8.126 | 10.151 | 1.00 | 25.30 |
| 109 | C | LYS | A | 26 | −6.273 | 6.899 | 9.630 | 1.00 | 24.83 |
| 110 | O | LYS | A | 26 | −6.049 | 5.933 | 10.364 | 1.00 | 25.48 |
| 111 | CB | LYS | A | 26 | −8.522 | 7.889 | 10.025 | 1.00 | 30.21 |
| 112 | CG | LYS | A | 26 | −9.365 | 8.792 | 10.908 | 1.00 | 37.09 |
| 113 | CD | LYS | A | 26 | −9.289 | 8.362 | 12.366 | 1.00 | 41.71 |
| 114 | CE | LYS | A | 26 | −9.908 | 6.986 | 12.566 | 1.00 | 43.59 |
| 115 | NZ | LYS | A | 26 | −9.866 | 6.557 | 13.990 | 1.00 | 47.44 |
| 116 | N | SER | A | 27 | −5.903 | 6.925 | 8.360 | 1.00 | 22.70 |
| 117 | CA | SER | A | 27 | −5.202 | 5.792 | 7.774 | 1.00 | 20.05 |
| 118 | C | SER | A | 27 | −4.535 | 6.246 | 6.495 | 1.00 | 17.55 |
| 119 | O | SER | A | 27 | −4.688 | 7.395 | 6.088 | 1.00 | 17.86 |
| 120 | CB | SER | A | 27 | −6.187 | 4.665 | 7.467 | 1.00 | 21.47 |
| 121 | OG | SER | A | 27 | −7.050 | 5.036 | 6.408 | 1.00 | 23.98 |
| 122 | N | PHE | A | 28 | −3.802 | 5.345 | 5.851 | 1.00 | 17.01 |
| 123 | CA | PHE | A | 28 | −3.127 | 5.709 | 4.619 | 1.00 | 15.33 |
| 124 | C | PHE | A | 28 | −4.120 | 5.823 | 3.467 | 1.00 | 17.01 |
| 125 | O | PHE | A | 28 | −3.894 | 6.578 | 2.521 | 1.00 | 16.01 |
| 126 | CB | PHE | A | 28 | −2.023 | 4.701 | 4.306 | 1.00 | 14.78 |
| 127 | CG | PHE | A | 28 | −0.889 | 4.731 | 5.296 | 1.00 | 14.62 |
| 128 | CD1 | PHE | A | 28 | −0.822 | 3.801 | 6.324 | 1.00 | 15.85 |
| 129 | CD2 | PHE | A | 28 | 0.094 | 5.717 | 5.215 | 1.00 | 15.29 |
| 130 | CE1 | PHE | A | 28 | 0.213 | 3.851 | 7.264 | 1.00 | 18.16 |
| 131 | CE2 | PHE | A | 28 | 1.132 | 5.777 | 6.150 | 1.00 | 18.50 |
| 132 | CZ | PHE | A | 28 | 1.190 | 4.843 | 7.173 | 1.00 | 17.62 |
| 133 | N | GLY | A | 29 | −5.216 | 5.074 | 3.560 | 1.00 | 17.92 |
| 134 | CA | GLY | A | 29 | −6.256 | 5.150 | 2.546 | 1.00 | 16.58 |
| 135 | C | GLY | A | 29 | −6.185 | 4.173 | 1.389 | 1.00 | 17.49 |
| 136 | O | GLY | A | 29 | −6.695 | 4.461 | 0.304 | 1.00 | 14.74 |
| 137 | N | ILE | A | 30 | −5.549 | 3.027 | 1.594 | 1.00 | 15.26 |
| 138 | CA | ILE | A | 30 | −5.476 | 2.052 | 0.520 | 1.00 | 16.94 |
| 139 | C | ILE | A | 30 | −6.135 | 0.744 | 0.907 | 1.00 | 18.42 |
| 140 | O | ILE | A | 30 | −6.018 | 0.285 | 2.044 | 1.00 | 20.16 |
| 141 | CB | ILE | A | 30 | −4.018 | 1.750 | 0.096 | 1.00 | 20.93 |
| 142 | CG1 | ILE | A | 30 | −3.235 | 1.158 | 1.269 | 1.00 | 19.75 |
| 143 | CG2 | ILE | A | 30 | −3.346 | 3.028 | −0.416 | 1.00 | 19.16 |
| 144 | CD1 | ILE | A | 30 | −1.871 | 0.644 | 0.879 | 1.00 | 26.53 |
| 145 | N | CYS | A | 31 | −6.858 | 0.162 | −0.043 | 1.00 | 17.47 |
| 146 | CA | CYS | A | 31 | −7.493 | −1.126 | 0.172 | 1.00 | 15.96 |
| 147 | C | CYS | A | 31 | −6.826 | −2.013 | −0.865 | 1.00 | 16.11 |
| 148 | O | CYS | A | 31 | −6.674 | −1.621 | −2.026 | 1.00 | 16.88 |
| 149 | CB | CYS | A | 31 | −8.998 | −1.046 | −0.053 | 1.00 | 21.03 |
| 150 | SG | CYS | A | 31 | −9.908 | −0.012 | 1.148 | 1.00 | 26.36 |
| 151 | N | ILE | A | 32 | −6.416 | −3.200 | −0.445 | 1.00 | 15.28 |
| 152 | CA | ILE | A | 32 | −5.692 | −4.091 | −1.335 | 1.00 | 16.47 |

TABLE 2-continued

| ATOM | ATOM TYPE | RESIDUE | PROTEIN # | # | X | Y | Z | OCC | B |
|---|---|---|---|---|---|---|---|---|---|
| 153 | C | ILE | A | 32 | −6.316 | −5.459 | −1.521 | 1.00 | 18.60 |
| 154 | O | ILE | A | 32 | −7.170 | −5.885 | −0.744 | 1.00 | 16.70 |
| 155 | CB | ILE | A | 32 | −4.252 | −4.298 | −0.820 | 1.00 | 15.06 |
| 156 | CG1 | ILE | A | 32 | −4.281 | −5.029 | 0.528 | 1.00 | 18.62 |
| 157 | CG2 | ILE | A | 32 | −3.561 | −2.951 | −0.644 | 1.00 | 17.61 |
| 158 | CD1 | ILE | A | 32 | −2.896 | −5.326 | 1.110 | 1.00 | 19.04 |
| 159 | N | VAL | A | 33 | −5.872 | −6.146 | −2.566 | 1.00 | 18.98 |
| 160 | CA | VAL | A | 33 | −6.354 | −7.490 | −2.855 | 1.00 | 20.33 |
| 161 | C | VAL | A | 33 | −5.270 | −8.281 | −3.563 | 1.00 | 19.38 |
| 162 | O | VAL | A | 33 | −4.383 | −7.712 | −4.198 | 1.00 | 19.61 |
| 163 | CB | VAL | A | 33 | −7.604 | −7.487 | −3.779 | 1.00 | 20.85 |
| 164 | CG1 | VAL | A | 33 | −8.732 | −6.711 | −3.134 | 1.00 | 23.75 |
| 165 | CG2 | VAL | A | 33 | −7.247 | −6.908 | −5.145 | 1.00 | 20.92 |
| 166 | N | ARG | A | 34 | −5.336 | −9.599 | −3.427 | 1.00 | 20.73 |
| 167 | CA | ARG | A | 34 | −4.401 | −10.474 | −4.112 | 1.00 | 23.91 |
| 168 | C | ARG | A | 34 | −4.973 | −10.522 | −5.517 | 1.00 | 26.01 |
| 169 | O | ARG | A | 34 | −6.189 | −10.624 | −5.684 | 1.00 | 26.84 |
| 170 | CB | ARG | A | 34 | −4.444 | −11.883 | −3.525 | 1.00 | 28.65 |
| 171 | CG | ARG | A | 34 | −3.653 | −12.090 | −2.262 | 1.00 | 34.27 |
| 172 | CD | ARG | A | 34 | −2.432 | −12.937 | −2.551 | 1.00 | 37.46 |
| 173 | NE | ARG | A | 34 | −1.255 | −12.113 | −2.785 | 1.00 | 42.86 |
| 174 | CZ | ARG | A | 34 | −0.107 | −12.570 | −3.270 | 1.00 | 41.70 |
| 175 | NH1 | ARG | A | 34 | 0.019 | −13.853 | −3.587 | 1.00 | 40.37 |
| 176 | NH2 | ARG | A | 34 | 0.921 | −11.746 | −3.416 | 1.00 | 39.64 |
| 177 | N | GLY | A | 35 | −4.114 | −10.446 | −6.522 | 1.00 | 25.55 |
| 178 | CA | GLY | A | 35 | −4.610 | −10.486 | −7.883 | 1.00 | 30.58 |
| 179 | C | GLY | A | 35 | −3.605 | −11.083 | −8.837 | 1.00 | 29.87 |
| 180 | O | GLY | A | 35 | −2.536 | −11.526 | −8.426 | 1.00 | 29.61 |
| 181 | N | GLU | A | 36 | −3.954 | −11.104 | −10.118 | 1.00 | 32.38 |
| 182 | CA | GLU | A | 36 | −3.062 | −11.643 | −11.132 | 1.00 | 34.53 |
| 183 | C | GLU | A | 36 | −3.269 | −10.942 | −12.462 | 1.00 | 32.84 |
| 184 | O | GLU | A | 36 | −4.377 | −10.523 | −12.794 | 1.00 | 32.47 |
| 185 | CB | GLU | A | 36 | −3.285 | −13.147 | −11.310 | 1.00 | 37.20 |
| 186 | CG | GLU | A | 36 | −4.704 | −13.528 | −11.687 | 1.00 | 43.25 |
| 187 | CD | GLU | A | 36 | −4.800 | −14.941 | −12.228 | 1.00 | 46.38 |
| 188 | OE1 | GLU | A | 36 | −4.189 | −15.852 | −11.631 | 1.00 | 49.84 |
| 189 | OE2 | GLU | A | 36 | −5.492 | −15.142 | −13.248 | 1.00 | 49.44 |
| 190 | N | VAL | A | 37 | −2.183 | −10.811 | −13.210 | 1.00 | 32.45 |
| 191 | CA | VAL | A | 37 | −2.217 | −10.175 | −14.517 | 1.00 | 33.12 |
| 192 | C | VAL | A | 37 | −1.389 | −11.046 | −15.442 | 1.00 | 35.13 |
| 193 | O | VAL | A | 37 | −0.413 | −11.662 | −15.012 | 1.00 | 33.62 |
| 194 | CB | VAL | A | 37 | −1.615 | −8.758 | −14.466 | 1.00 | 34.24 |
| 195 | CG1 | VAL | A | 37 | −2.525 | −7.842 | −13.672 | 1.00 | 35.68 |
| 196 | CG2 | VAL | A | 37 | −0.236 | −8.799 | −13.825 | 1.00 | 35.86 |
| 197 | N | LYS | A | 38 | −1.774 | −11.122 | −16.709 | 1.00 | 38.82 |
| 198 | CA | LYS | A | 38 | −1.011 | −11.952 | −17.620 | 1.00 | 43.96 |
| 199 | C | LYS | A | 38 | 0.152 | −11.193 | −18.231 | 1.00 | 46.68 |
| 200 | O | LYS | A | 38 | −0.026 | −10.271 | −19.029 | 1.00 | 49.76 |
| 201 | CB | LYS | A | 38 | −1.914 | −12.552 | −18.706 | 1.00 | 45.07 |
| 202 | CG | LYS | A | 38 | −2.599 | −11.565 | −19.628 | 1.00 | 48.70 |
| 203 | CD | LYS | A | 38 | −3.624 | −12.277 | −20.515 | 1.00 | 50.65 |
| 204 | CE | LYS | A | 38 | −3.013 | −13.465 | −21.260 | 1.00 | 51.68 |
| 205 | NZ | LYS | A | 38 | −4.018 | −14.196 | −22.092 | 1.00 | 51.21 |
| 206 | N | ASP | A | 39 | 1.339 | −11.552 | −17.780 | 1.00 | 47.72 |
| 207 | CA | ASP | A | 39 | 2.562 | −11.037 | −18.307 | 1.00 | 49.70 |
| 208 | C | ASP | A | 39 | 3.136 | −11.945 | −19.375 | 1.00 | 49.87 |
| 209 | O | ASP | A | 39 | 3.659 | −13.005 | −19.042 | 1.00 | 53.20 |
| 210 | CB | ASP | A | 39 | 3.507 | −10.853 | −17.129 | 1.00 | 51.18 |
| 211 | CG | ASP | A | 39 | 2.923 | −9.869 | −16.126 | 1.00 | 53.09 |
| 212 | OD1 | ASP | A | 39 | 2.037 | −9.078 | −16.524 | 1.00 | 52.91 |
| 213 | OD2 | ASP | A | 39 | 3.334 | −9.890 | −14.949 | 1.00 | 54.93 |
| 214 | N | SER | A | 40 | 2.917 | −11.577 | −20.614 | 1.00 | 49.44 |
| 215 | CA | SER | A | 40 | 3.272 | −12.395 | −21.767 | 1.00 | 47.54 |
| 216 | C | SER | A | 40 | 3.081 | −11.625 | −23.069 | 1.00 | 46.03 |
| 217 | O | SER | A | 40 | 2.091 | −10.881 | −23.182 | 1.00 | 44.12 |
| 218 | CB | SER | A | 40 | 2.448 | −13.684 | −21.783 | 1.00 | 48.56 |
| 219 | OG | SER | A | 40 | 1.200 | −13.485 | −22.424 | 1.00 | 49.91 |
| 220 | N | PRO | A | 41 | 2.971 | −13.323 | −24.083 | 1.00 | 43.78 |
| 221 | CA | PRO | A | 41 | 1.614 | −13.864 | −24.169 | 1.00 | 42.31 |
| 222 | C | PRO | A | 41 | 1.406 | −15.084 | −23.260 | 1.00 | 40.07 |
| 223 | O | PRO | A | 41 | −0.527 | −16.225 | −22.977 | 1.00 | 38.90 |
| 224 | CB | PRO | A | 41 | 1.518 | −14.371 | −25.612 | 1.00 | 41.94 |
| 225 | CG | PRO | A | 41 | 2.901 | −14.759 | −25.961 | 1.00 | 43.41 |
| 226 | CD | PRO | A | 41 | 3.797 | −13.862 | −25.155 | 1.00 | 44.30 |
| 227 | N | ASN | A | 42 | 1.682 | −16.520 | −22.512 | 1.00 | 38.23 |
| 228 | CA | ASN | A | 42 | 1.423 | −17.803 | −21.897 | 1.00 | 35.25 |

TABLE 2-continued

| ATOM | ATOM TYPE | RESIDUE | PROTEIN # | # | X | Y | Z | OCC | B |
|---|---|---|---|---|---|---|---|---|---|
| 229 | C | ASN | A | 42 | 1.815 | −17.784 | −20.434 | 1.00 | 31.91 |
| 230 | O | ASN | A | 42 | 1.998 | −18.941 | −19.860 | 1.00 | 27.12 |
| 231 | CB | ASN | A | 42 | 2.102 | −18.912 | −22.693 | 1.00 | 39.94 |
| 232 | CG | ASN | A | 42 | 1.574 | −18.972 | −24.114 | 1.00 | 44.65 |
| 233 | OD1 | ASN | A | 42 | 0.371 | −18.829 | −24.346 | 1.00 | 48.19 |
| 234 | ND2 | ASN | A | 42 | 2.468 | −19.179 | −25.072 | 1.00 | 47.86 |
| 235 | N | THR | A | 43 | 1.912 | −16.712 | −19.702 | 1.00 | 30.37 |
| 236 | CA | THR | A | 43 | 2.216 | −16.760 | −18.275 | 1.00 | 30.81 |
| 237 | C | THR | A | 43 | 1.458 | −15.684 | −17.517 | 1.00 | 28.36 |
| 238 | O | THR | A | 43 | 0.950 | −14.733 | −18.107 | 1.00 | 28.22 |
| 239 | CB | THR | A | 43 | 3.731 | −16.599 | −17.987 | 1.00 | 32.76 |
| 240 | OG1 | THR | A | 43 | 4.160 | −15.281 | −18.347 | 1.00 | 34.72 |
| 241 | CG2 | THR | A | 43 | 4.531 | −17.624 | −18.767 | 1.00 | 34.24 |
| 242 | N | LYS | A | 44 | 1.366 | −15.856 | −16.205 | 1.00 | 29.06 |
| 243 | CA | LYS | A | 44 | 0.679 | −14.897 | −15.356 | 1.00 | 30.26 |
| 244 | C | LYS | A | 44 | 1.527 | −14.602 | −14.134 | 1.00 | 32.10 |
| 245 | O | LYS | A | 44 | 2.353 | −15.420 | −13.722 | 1.00 | 30.01 |
| 246 | CB | LYS | A | 44 | −0.680 | −15.438 | −14.904 | 1.00 | 30.68 |
| 247 | CG | LYS | A | 44 | −1.739 | −15.492 | −15.995 | 1.00 | 32.42 |
| 248 | CD | LYS | A | 44 | −3.091 | −15.875 | −15.421 | 1.00 | 31.05 |
| 249 | CE | LYS | A | 44 | −4.174 | −15.828 | −16.481 | 1.00 | 37.43 |
| 250 | NZ | LYS | A | 44 | −5.494 | −16.232 | −15.926 | 1.00 | 38.00 |
| 251 | N | THR | A | 45 | 1.322 | −13.420 | −13.565 | 1.00 | 32.39 |
| 252 | CA | THR | A | 45 | 2.043 | −13.008 | −12.374 | 1.00 | 34.86 |
| 253 | C | THR | A | 45 | 1.005 | −12.675 | −11.314 | 1.00 | 34.46 |
| 254 | O | THR | A | 45 | −0.032 | −12.080 | −11.613 | 1.00 | 32.73 |
| 255 | CB | THR | A | 45 | 2.909 | −11.764 | −12.638 | 1.00 | 38.51 |
| 256 | OG1 | THR | A | 45 | 3.821 | −12.036 | −13.709 | 1.00 | 43.77 |
| 257 | CG2 | THR | A | 45 | 3.702 | −11.399 | −11.391 | 1.00 | 39.28 |
| 258 | N | THR | A | 46 | 1.277 | −13.080 | −10.081 | 1.00 | 34.07 |
| 259 | CA | THR | A | 46 | 0.367 | −12.821 | −8.977 | 1.00 | 33.79 |
| 260 | C | THR | A | 46 | 0.974 | −11.747 | −8.090 | 1.00 | 33.22 |
| 261 | O | THR | A | 46 | 2.185 | −11.520 | −8.115 | 1.00 | 33.17 |
| 262 | CB | THR | A | 46 | 0.145 | −14.083 | −8.133 | 1.00 | 38.52 |
| 263 | OG1 | THR | A | 46 | 1.418 | −14.628 | −7.761 | 1.00 | 41.84 |
| 264 | CG2 | THR | A | 46 | −0.648 | −15.123 | −8.918 | 1.00 | 37.93 |
| 265 | N | GLY | A | 47 | 0.136 | −11.075. | −7.313 | 1.00 | 27.90 |
| 266 | CA | GLY | A | 47 | 0.660 | −10.046 | −6.442 | 1.00 | 25.10 |
| 267 | C | GLY | A | 47 | −0.401 | −9.284 | −5.687 | 1.00 | 23.71 |
| 268 | O | GLY | A | 47 | −1.587 | −9.610 | −5.739 | 1.00 | 20.30 |
| 269 | N | ILE | A | 48 | 0.049 | −8.254 | −4.978 | 1.00 | 20.49 |
| 270 | CA | ILE | A | 48 | −0.818 | −7.399 | −4.187 | 1.00 | 18.04 |
| 271 | C | ILE | A | 48 | −1.154 | −6.169 | −5.018 | 1.00 | 18.19 |
| 272 | O | ILE | A | 48 | −0.261 | −5.463 | −5.471 | 1.00 | 19.44 |
| 273 | CB | ILE | A | 48 | −0.098 | −6.957 | −2.895 | 1.00 | 16.38 |
| 274 | CG1 | ILE | A | 48 | 0.204 | −8.183 | −2.033 | 1.00 | 16.06 |
| 275 | CG2 | ILE | A | 48 | −0.945 | −5.947 | −2.135 | 1.00 | 17.61 |
| 276 | CD1 | ILE | A | 48 | −1.016 | −8.863 | −1.480 | 1.00 | 19.99 |
| 277 | N | PHE | A | 49 | −2.442 | −5.915 | −5.217 | 1.00 | 15.69 |
| 278 | CA | PHE | A | 49 | −2.862 | −4.770 | −6.005 | 1.00 | 15.71 |
| 279 | C | PHE | A | 49 | −3.713 | −3.797 | −5.210 | 1.00 | 14.70 |
| 280 | O | PHE | A | 49 | −4.412 | −4.185 | −4.281 | 1.00 | 14.98 |
| 281 | CB | PHE | A | 49 | −3.664 | −5.231 | −7.222 | 1.00 | 17.87 |
| 282 | CG | PHE | A | 49 | −2.864 | −6.022 | −8.211 | 1.00 | 17.36 |
| 283 | CD1 | PHE | A | 49 | −2.562 | −7.356 | −7.974 | 1.00 | 20.93 |
| 284 | CD2 | PHE | A | 49 | −2.410 | −5.428 | −9.384 | 1.00 | 20.80 |
| 285 | CE1 | PHE | A | 49 | −1.815 | −8.094 | −8.893 | 1.00 | 20.69 |
| 286 | CE2 | PHE | A | 49 | −1.663 | −6.154 | −10.313 | 1.00 | 23.70 |
| 287 | CZ | PHE | A | 49 | −1.365 | −7.491 | −10.065 | 1.00 | 22.35 |
| 288 | N | ILE | A | 50 | −3.643 | −2.524 | −5.585 | 1.00 | 15.13 |
| 289 | CA | ILE | A | 50 | −4.460 | −1.510 | −4.937 | 1.00 | 13.79 |
| 290 | C | ILE | A | 50 | −5.839 | −1.677 | −5.571 | 1.00 | 16.79 |
| 291 | O | ILE | A | 50 | −5.985 | −1.559 | −6.790 | 1.00 | 16.76 |
| 292 | CB | ILE | A | 50 | −3.924 | −0.092 | −5.224 | 1.00 | 13.28 |
| 293 | CG1 | ILE | A | 50 | −2.565 | 0.090 | −4.534 | 1.00 | 16.33 |
| 294 | CG2 | ILE | A | 50 | −4.938 | 0.946 | −4.769 | 1.00 | 12.35 |
| 295 | CD1 | ILE | A | 50 | −1.925 | 1.453 | −4.771 | 1.00 | 18.26 |
| 296 | N | LYS | A | 51 | −6.841 | −1.974 | −4.752 | 1.00 | 14.91 |
| 297 | CA | LYS | A | 51 | −8.198 | −2.176 | −5.258 | 1.00 | 16.74 |
| 298 | C | LYS | A | 51 | −9.073 | −0.956 | −5.032 | 1.00 | 16.72 |
| 299 | O | LYS | A | 51 | −10.072 | −0.761 | −5.721 | 1.00 | 15.78 |
| 300 | CB | LYS | A | 51 | −8.849 | −3.373 | −4.569 | 1.00 | 22.48 |
| 301 | CG | LYS | A | 51 | −10.144 | −3.819 | −5.230 | 1.00 | 28.63 |
| 302 | CD | LYS | A | 51 | −11.190 | −4.225 | −4.206 | 1.00 | 35.73 |
| 303 | CE | LYS | A | 51 | −11.825 | −3.005 | −3.548 | 1.00 | 38.73 |
| 304 | NZ | LYS | A | 51 | −13.080 | −3.360 | −2.817 | 1.00 | 41.58 |

TABLE 2-continued

| ATOM | ATOM TYPE | RESIDUE | PROTEIN # | # | X | Y | Z | OCC | B |
|---|---|---|---|---|---|---|---|---|---|
| 305 | N | GLY | A | 52 | −8.703 | −0.139 | −4.052 | 1.00 | 18.59 |
| 306 | CA | GLY | A | 52 | −9.483 | 1.046 | −3.761 | 1.00 | 16.37 |
| 307 | C | GLY | A | 52 | −8.659 | 2.092 | −3.045 | 1.00 | 17.57 |
| 308 | O | GLY | A | 52 | −7.664 | 1.763 | −2.404 | 1.00 | 14.71 |
| 309 | N | ILE | A | 53 | −9.068 | 3.349 | −3.176 | 1.00 | 17.60 |
| 310 | CA | ILE | A | 53 | −8.389 | 4.464 | −2.521 | 1.00 | 17.11 |
| 311 | C | ILE | A | 53 | −9.436 | 5.321 | −1.814 | 1.00 | 17.44 |
| 312 | O | ILE | A | 53 | −10.435 | 5.709 | −2.410 | 1.00 | 17.74 |
| 313 | CB | ILE | A | 53 | −7.616 | 5.321 | −3.546 | 1.00 | 16.47 |
| 314 | CG1 | ILE | A | 53 | −6.378 | 4.549 | −4.016 | 1.00 | 15.92 |
| 315 | CG2 | ILE | A | 53 | −7.222 | 6.670 | −2.938 | 1.00 | 17.75 |
| 316 | CD1 | ILE | A | 53 | −5.534 | 5.288 | −5.025 | 1.00 | 23.81 |
| 317 | N | VAL | A | 54 | −9.197 | 5.614 | −0.541 | 1.00 | 14.72 |
| 318 | CA | VAL | A | 54 | −10.128 | 6.417 | 0.246 | 1.00 | 15.94 |
| 319 | C | VAL | A | 54 | −10.035 | 7.902 | −0.096 | 1.00 | 17.32 |
| 320 | O | VAL | A | 54 | −8.960 | 8.491 | −0.044 | 1.00 | 19.30 |
| 321 | CB | VAL | A | 54 | −9.855 | 6.258 | 1.756 | 1.00 | 17.69 |
| 322 | CG1 | VAL | A | 54 | −10.833 | 7.120 | 2.553 | 1.00 | 18.84 |
| 323 | CG2 | VAL | A | 54 | −9.981 | 4.791 | 2.148 | 1.00 | 18.31 |
| 324 | N | PRO | A | 55 | −11.169 | 8.532 | −0.440 | 1.00 | 20.11 |
| 325 | CA | PRO | A | 55 | −11.129 | 9.957 | −0.777 | 1.00 | 21.19 |
| 326 | C | PRO | A | 55 | −10.572 | 10.838 | 0.344 | 1.00 | 23.23 |
| 327 | O | PRO | A | 55 | −10.897 | 10.659 | 1.520 | 1.00 | 22.23 |
| 328 | CB | PRO | A | 55 | −12.588 | 10.281 | −1.139 | 1.00 | 23.74 |
| 329 | CG | PRO | A | 55 | −13.384 | 9.180 | −0.510 | 1.00 | 28.26 |
| 330 | CD | PRO | A | 55 | −12.511 | 7.969 | −0.655 | 1.00 | 20.45 |
| 331 | N | ASP | A | 56 | −9.712 | 11.774 | −0.047 | 1.00 | 23.74 |
| 332 | CA | ASP | A | 56 | −9.065 | 12.718 | 0.863 | 1.00 | 26.03 |
| 333 | C | ASP | A | 56 | −8.059 | 12.086 | 1.821 | 1.00 | 26.34 |
| 334 | O | ASP | A | 56 | −7.652 | 12.707 | 2.805 | 1.00 | 24.78 |
| 335 | CB | ASP | A | 56 | −10.104 | 13.494 | 1.673 | 1.00 | 27.76 |
| 336 | CG | ASP | A | 56 | −9.528 | 14.754 | 2.277 | 1.00 | 33.69 |
| 337 | OD1 | ASP | A | 56 | −8.977 | 15.563 | 1.503 | 1.00 | 34.65 |
| 338 | OD2 | ASP | A | 56 | −9.619 | 14.935 | 3.510 | 1.00 | 36.11 |
| 339 | N | SER | A | 57 | −7.662 | 10.850 | 1.537 | 1.00 | 22.74 |
| 340 | CA | SER | A | 57 | −6.685 | 10.156 | 2.370 | 1.00 | 21.57 |
| 341 | C | SER | A | 57 | −5.304 | 10.478 | 1.803 | 1.00 | 18.70 |
| 342 | O | SER | A | 57 | −5.194 | 11.069 | 0.734 | 1.00 | 19.88 |
| 343 | CB | SER | A | 57 | −6.911 | 8.645 | 2.293 | 1.00 | 19.93 |
| 344 | OG | SER | A | 57 | −6.603 | 8.173 | 0.987 | 1.00 | 17.04 |
| 345 | N | PRO | A | 58 | −4.229 | 10.106 | 2.521 | 1.00 | 17.52 |
| 346 | CA | PRO | A | 58 | −2.879 | 10.377 | 2.017 | 1.00 | 19.16 |
| 347 | C | PRO | A | 58 | −2.667 | 9.761 | 0.623 | 1.00 | 20.05 |
| 348 | O | PRO | A | 58 | −2.080 | 10.387 | −0.261 | 1.00 | 17.91 |
| 349 | CB | PRO | A | 58 | −1.983 | 9.731 | 3.074 | 1.00 | 20.94 |
| 350 | CG | PRO | A | 58 | −2.773 | 9.930 | 4.335 | 1.00 | 19.44 |
| 351 | CD | PRO | A | 58 | −4.184 | 9.585 | 3.899 | 1.00 | 21.52 |
| 352 | N | ALA | A | 59 | −3.147 | 8.533 | 0.437 | 1.00 | 18.47 |
| 353 | CA | ALA | A | 59 | −3.007 | 7.837 | −0.845 | 1.00 | 16.42 |
| 354 | C | ALA | A | 59 | −3.692 | 8.620 | −1.966 | 1.00 | 17.77 |
| 355 | O | ALA | A | 59 | −3.180 | 8.702 | −3.083 | 1.00 | 19.10 |
| 356 | CB | ALA | A | 59 | −3.613 | 6.431 | −0.750 | 1.00 | 16.33 |
| 357 | N | HIS | A | 60 | −4.854 | 9.182 | −1.661 | 1.00 | 17.53 |
| 358 | CA | HIS | A | 60 | −5.614 | 9.961 | −2.632 | 1.00 | 19.51 |
| 359 | C | HIS | A | 60 | −4.936 | 11.303 | −2.920 | 1.00 | 20.57 |
| 360 | O | HIS | A | 60 | −4.723 | 11.662 | −4.081 | 1.00 | 21.25 |
| 361 | CB | HIS | A | 60 | −7.035 | 10.188 | −2.102 | 1.00 | 19.50 |
| 362 | CG | HIS | A | 60 | −7.943 | 10.897 | −3.061 | 1.00 | 21.28 |
| 363 | ND1 | HIS | A | 60 | −7.920 | 10.668 | −4.420 | 1.00 | 25.98 |
| 364 | CD2 | HIS | A | 60 | −8.926 | 11.804 | −2.850 | 1.00 | 22.86 |
| 365 | CE1 | HIS | A | 60 | −8.850 | 11.404 | −5.005 | 1.00 | 25.00 |
| 366 | NE2 | HIS | A | 60 | −9.475 | 12.102 | −4.074 | 1.00 | 26.15 |
| 367 | N | LEU | A | 61 | −4.587 | 12.032 | −1.863 | 1.00 | 21.85 |
| 368 | CA | LEU | A | 61 | −3.947 | 13.337 | −2.016 | 1.00 | 23.92 |
| 369 | C | LEU | A | 61 | −2.585 | 13.235 | −2.686 | 1.00 | 26.27 |
| 370 | O | LEU | A | 61 | −2.150 | 14.161 | −3.374 | 1.00 | 26.99 |
| 371 | CB | LEU | A | 61 | −3.827 | 14.029 | −0.653 | 1.00 | 24.55 |
| 372 | CG | LEU | A | 61 | −5.169 | 14.329 | 0.022 | 1.00 | 27.93 |
| 373 | CD1 | LEU | A | 61 | −4.939 | 15.074 | 1.326 | 1.00 | 30.19 |
| 374 | CD2 | LEU | A | 61 | −6.043 | 15.151 | −0.913 | 1.00 | 31.00 |
| 375 | N | CYS | A | 62 | −1.918 | 12.101 | −2.490 | 1.00 | 26.18 |
| 376 | CA | CYS | A | 62 | −0.613 | 11.850 | −3.093 | 1.00 | 29.08 |
| 377 | C | CYS | A | 62 | −0.690 | 12.053 | −4.606 | 1.00 | 29.59 |
| 378 | O | CYS | A | 62 | 0.158 | 12.718 | −5.203 | 1.00 | 29.23 |
| 379 | CB | CYS | A | 62 | −0.176 | 10.418 | −2.777 | 1.00 | 29.35 |
| 380 | SG | CYS | A | 62 | 1.052 | 9.728 | −3.885 | 1.00 | 31.14 |

TABLE 2-continued

| ATOM | ATOM TYPE | RESIDUE | PROTEIN # | # | X | Y | Z | OCC | B |
|---|---|---|---|---|---|---|---|---|---|
| 381 | N | GLY | A | 63 | −1.717 | 11.472 | −5.220 | 1.00 | 28.43 |
| 382 | CA | GLY | A | 63 | −1.901 | 11.606 | −6.653 | 1.00 | 29.84 |
| 383 | C | GLY | A | 63 | −0.992 | 10.740 | −7.505 | 1.00 | 31.08 |
| 384 | O | GLY | A | 63 | −1.134 | 10.712 | −8.727 | 1.00 | 33.68 |
| 385 | N | ARG | A | 64 | −0.058 | 10.031 | −6.879 | 1.00 | 28.38 |
| 386 | CA | ARG | A | 64 | 0.857 | 9.180 | −7.632 | 1.00 | 28.97 |
| 387 | C | ARG | A | 64 | 0.586 | 7.691 | −7.445 | 1.00 | 23.41 |
| 388 | O | ARG | A | 64 | 1.405 | 6.848 | −7.815 | 1.00 | 24.05 |
| 389 | CB | ARG | A | 64 | 2.307 | 9.501 | −7.265 | 1.00 | 31.85 |
| 390 | CG | ARG | A | 64 | 2.744 | 10.894 | −7.706 | 1.00 | 39.01 |
| 391 | CD | ARG | A | 64 | 4.231 | 11.104 | −7.486 | 1.00 | 43.57 |
| 392 | NE | ARG | A | 64 | 4.694 | 12.381 | −8.022 | 1.00 | 48.91 |
| 393 | CZ | ARG | A | 64 | 4.658 | 12.713 | −9.309 | 1.00 | 51.14 |
| 394 | NH1 | ARG | A | 64 | 4.180 | 11.860 | −10.207 | 1.00 | 52.93 |
| 395 | NH2 | ARG | A | 64 | 5.098 | 13.901 | −9.701 | 1.00 | 52.56 |
| 396 | N | LEU | A | 65 | −0.562 | 7.379 | −6.858 | 1.00 | 20.20 |
| 397 | CA | LEU | A | 65 | −0.975 | 5.996 | −6.645 | 1.00 | 21.82 |
| 398 | C | LED | A | 65 | −2.284 | 5.802 | −7.395 | 1.00 | 22.82 |
| 399 | O | LEU | A | 65 | −3.195 | 6.623 | −7.287 | 1.00 | 24.07 |
| 400 | CB | LEU | A | 65 | −1.192 | 5.711 | −5.159 | 1.00 | 23.59 |
| 401 | CG | LEU | A | 65 | 0.057 | 5.560 | −4.288 | 1.00 | 22.65 |
| 402 | CD1 | LEU | A | 65 | −0.358 | 5.375 | −2.836 | 1.00 | 23.46 |
| 403 | CD2 | LEU | A | 65 | 0.873 | 4.362 | −4.756 | 1.00 | 24.37 |
| 404 | N | LYS | A | 66 | −2.376 | 4.717 | −8.153 | 1.00 | 20.11 |
| 405 | CA | LYS | A | 66 | −3.579 | 4.453 | −8.919 | 1.00 | 20.87 |
| 406 | C | LYS | A | 66 | −4.172 | 3.096 | −8.601 | 1.00 | 20.83 |
| 407 | O | LYS | A | 66 | −3.464 | 2.155 | −8.249 | 1.00 | 18.17 |
| 408 | CB | LYS | A | 66 | −3.271 | 4.513 | −10.421 | 1.00 | 23.02 |
| 409 | CG | LYS | A | 66 | −2.659 | 5.833 | −10.882 | 1.00 | 29.20 |
| 410 | CD | LYS | A | 66 | −3.581 | 7.005 | −10.580 | 1.00 | 35.15 |
| 411 | CE | LYS | A | 66 | −2.939 | 8.334 | −10.957 | 1.00 | 39.54 |
| 412 | NZ | LYS | A | 66 | −2.581 | 8.390 | −12.403 | 1.00 | 42.88 |
| 413 | N | VAL | A | 67 | −5.488 | 3.014 | −8.718 | 1.00 | 20.64 |
| 414 | CA | VAL | A | 67 | −6.181 | 1.762 | −8.509 | 1.00 | 17.49 |
| 415 | C | VAL | A | 67 | −5.637 | 0.868 | −9.611 | 1.00 | 17.56 |
| 416 | O | VAL | A | 67 | −5.550 | 1.292 | −10.767 | 1.00 | 18.49 |
| 417 | CB | VAL | A | 67 | −7.685 | 1.943 | −8.705 | 1.00 | 18.63 |
| 418 | CG1 | VAL | A | 67 | −8.385 | 0.589 | −8.657 | 1.00 | 21.47 |
| 419 | CG2 | VAL | A | 67 | −8.215 | 2.895 | −7.660 | 1.00 | 22.76 |
| 420 | N | GLY | A | 68 | −5.263 | −0.355 | −9.258 | 1.00 | 16.20 |
| 421 | CA | GLY | A | 68 | −4.710 | −1.269 | −10.242 | 1.00 | 17.41 |
| 422 | C | GLY | A | 68 | −3.198 | −1.397 | −10.128 | 1.00 | 16.65 |
| 423 | O | GLY | A | 68 | −2.601 | −2.311 | −10.697 | 1.00 | 17.02 |
| 424 | N | ASP | A | 69 | −2.566 | −0.475 | −9.404 | 1.00 | 17.37 |
| 425 | CA | ASP | A | 69 | −1.111 | −0.538 | −9.224 | 1.00 | 19.72 |
| 426 | C | ASP | A | 69 | −0.769 | −1.744 | −8.363 | 1.00 | 19.02 |
| 427 | O | ASP | A | 69 | −1.561 | −2.137 | −7.514 | 1.00 | 20.00 |
| 428 | CB | ASP | A | 69 | −0.580 | 0.699 | −8.491 | 1.00 | 18.60 |
| 429 | CG | ASP | A | 69 | −0.547 | 1.940 | −9.352 | 1.00 | 21.93 |
| 430 | OD1 | ASP | A | 69 | −0.636 | 1.826 | −10.589 | 1.00 | 20.56 |
| 431 | OD2 | ASP | A | 69 | −0.404 | 3.041 | −8.775 | 1.00 | 20.35 |
| 432 | N | ARG | A | 70 | 0.403 | −2.336 | −8.566 | 1.00 | 17.48 |
| 433 | CA | ARG | A | 70 | 0.791 | −3.450 | −7.715 | 1.00 | 19.10 |
| 434 | C | ARG | A | 70 | 1.854 | −2.971 | −6.723 | 1.00 | 20.57 |
| 435 | O | ARG | A | 70 | 2.681 | −2.116 | −7.043 | 1.00 | 21.01 |
| 436 | CB | ARG | A | 70 | 1.319 | −4.630 | −8.540 | 1.00 | 26.28 |
| 437 | CG | ARG | A | 70 | 2.501 | −4.330 | −9.420 | 1.00 | 37.99 |
| 438 | CD | ARG | A | 70 | 2.187 | −4.643 | −10.876 | 1.00 | 44.05 |
| 439 | NE | ARG | A | 70 | 1.152 | −3.760 | −11.410 | 1.00 | 47.64 |
| 440 | CZ | ARG | A | 70 | 0.740 | −3.770 | −12.674 | 1.00 | 46.17 |
| 441 | NH1 | ARG | A | 70 | 1.271 | −4.621 | −13.540 | 1.00 | 47.41 |
| 442 | NH2 | ARG | A | 70 | −0.192 | −2.915 | −13.075 | 1.00 | 45.27 |
| 443 | N | ILE | A | 71 | 1.802 | −3.500 | −5.509 | 1.00 | 17.74 |
| 444 | CA | ILE | A | 71 | 2.776 | −3.142 | −4.493 | 1.00 | 16.43 |
| 445 | C | ILE | A | 71 | 3.848 | −4.231 | −4.478 | 1.00 | 16.14 |
| 446 | O | ILE | A | 71 | 3.556 | −5.399 | −4.212 | 1.00 | 18.19 |
| 447 | CB | ILE | A | 71 | 2.109 | −3.032 | −3.108 | 1.00 | 17.38 |
| 448 | CG1 | ILE | A | 71 | 0.985 | −1.991 | −3.168 | 1.00 | 16.41 |
| 449 | CG2 | ILE | A | 71 | 3.146 | −2.631 | −2.062 | 1.00 | 17.81 |
| 450 | CD1 | ILE | A | 71 | 0.127 | −1.923 | −1.920 | 1.00 | 20.02 |
| 451 | N | LEU | A | 72 | 5.084 | −3.852 | −4.796 | 1.00 | 15.85 |
| 452 | CA | LEU | A | 72 | 6.182 | −4.811 | −4.826 | 1.00 | 17.95 |
| 453 | C | LEU | A | 72 | 6.829 | −4.970 | −3.457 | 1.00 | 19.40 |
| 454 | O | LEU | A | 72 | 7.159 | −6.082 | −3.045 | 1.00 | 19.33 |
| 455 | CB | LEU | A | 72 | 7.234 | −4.386 | −5.852 | 1.00 | 19.32 |
| 456 | CG | LEU | A | 72 | 6.747 | −4.305 | −7.303 | 1.00 | 21.53 |

TABLE 2-continued

| ATOM | ATOM TYPE | RESIDUE | PROTEIN # | # | X | Y | Z | OCC | B |
|---|---|---|---|---|---|---|---|---|---|
| 457 | CD1 | LEU | A | 72 | 7.920 | −3.970 | −8.222 | 1.00 | 22.31 |
| 458 | CD2 | LEU | A | 72 | 6.114 | −5.632 | −7.715 | 1.00 | 23.37 |
| 459 | N | SER | A | 73 | 7.017 | −3.860 | −2.754 | 1.00 | 18.28 |
| 460 | CA | SER | A | 73 | 7.619 | −3.924 | −1.429 | 1.00 | 20.21 |
| 461 | C | SER | A | 73 | 7.068 | −2.807 | −0.564 | 1.00 | 21.56 |
| 462 | O | SER | A | 73 | 6.516 | −1.829 | −1.072 | 1.00 | 17.93 |
| 463 | CB | SER | A | 73 | 9.146 | −3.823 | −1.513 | 1.00 | 19.58 |
| 464 | OG | SER | A | 73 | 9.572 | −2.553 | −1.966 | 1.00 | 22.61 |
| 465 | N | LEU | A | 74 | 7.212 | −2.974 | 0.745 | 1.00 | 20.67 |
| 466 | CA | LEU | A | 74 | 6.728 | −2.001 | 1.718 | 1.00 | 23.52 |
| 467 | C | LEU | A | 74 | 7.814 | −1.788 | 2.764 | 1.00 | 25.85 |
| 468 | O | LEU | A | 74 | 8.176 | −2.713 | 3.484 | 1.00 | 27.30 |
| 469 | CB | LEU | A | 74 | 5.453 | −2.531 | 2.376 | 1.00 | 27.14 |
| 470 | CG | LEU | A | 74 | 4.838 | −1.723 | 3.521 | 1.00 | 32.72 |
| 471 | CD1 | LEU | A | 74 | 4.536 | −0.312 | 3.063 | 1.00 | 37.70 |
| 472 | CD2 | LEU | A | 74 | 3.572 | −2.419 | 3.992 | 1.00 | 37.58 |
| 473 | N | ASN | A | 75 | 8.334 | −0.567 | 2.841 | 1.00 | 26.43 |
| 474 | CA | ASN | A | 75 | 9.402 | −0.256 | 3.784 | 1.00 | 28.43 |
| 475 | C | ASN | A | 75 | 10.550 | −1.253 | 3.649 | 1.00 | 31.10 |
| 476 | O | ASN | A | 75 | 11.100 | −1.729 | 4.643 | 1.00 | 31.61 |
| 477 | CB | ASN | A | 75 | 8.880 | −0.249 | 5.227 | 1.00 | 27.29 |
| 478 | CG | ASN | A | 75 | 8.030 | 0.971 | 5.530 | 1.00 | 29.35 |
| 479 | OD1 | ASN | A | 75 | 8.155 | 2.003 | 4.871 | 1.00 | 27.27 |
| 480 | ND2 | ASN | A | 75 | 7.172 | 0.865 | 6.540 | 1.00 | 31.00 |
| 481 | N | GLY | A | 76 | 10.897 | −1.570 | 2.405 | 1.00 | 32.52 |
| 482 | CA | GLY | A | 76 | 11.993 | −2.485 | 2.142 | 1.00 | 33.20 |
| 483 | C | GLY | A | 76 | 11.681 | −3.963 | 2.245 | 1.00 | 32.51 |
| 484 | O | GLY | A | 76 | 12.567 | −4.795 | 2.057 | 1.00 | 36.02 |
| 485 | N | LYS | A | 77 | 10.433 | −4.302 | 2.542 | 1.00 | 29.93 |
| 486 | CA | LYS | A | 77 | 10.049 | −5.701 | 2.659 | 1.00 | 29.79 |
| 487 | C | LYS | A | 77 | 9.285 | −6.179 | 1.430 | 1.00 | 29.00 |
| 488 | O | LYS | A | 77 | 8.268 | −5.597 | 1.059 | 1.00 | 24.92 |
| 489 | CB | LYS | A | 77 | 9.198 | −5.911 | 3.909 | 1.00 | 31.26 |
| 490 | CG | LYS | A | 77 | 8.847 | −7.365 | 4.175 | 1.00 | 37.46 |
| 491 | CD | LYS | A | 77 | 8.278 | −7.543 | 5.570 | 1.00 | 40.35 |
| 492 | CE | LYS | A | 77 | 8.085 | −9.013 | 5.905 | 1.00 | 44.10 |
| 493 | NZ | LYS | A | 77 | 7.616 | −9.195 | 7.308 | 1.00 | 47.09 |
| 494 | N | ASP | A | 78 | 9.794 | −7.241 | 0.807 | 1.00 | 27.51 |
| 495 | CA | ASP | A | 78 | 9.189 | −7.838 | −0.383 | 1.00 | 27.74 |
| 496 | C | ASP | A | 78 | 7.798 | −8.392 | −0.057 | 1.00 | 27.73 |
| 497 | O | ASP | A | 78 | 7.658 | −9.242 | 0.822 | 1.00 | 28.45 |
| 498 | CB | ASP | A | 78 | 10.098 | −8.969 | −0.885 | 1.00 | 32.43 |
| 499 | CG | ASP | A | 78 | 9.569 | −9.655 | −2.132 | 1.00 | 34.41 |
| 500 | OD1 | ASP | A | 78 | 10.165 | −10.683 | −2.525 | 1.00 | 37.38 |
| 501 | OD2 | ASP | A | 78 | 8.576 | −9.178 | −2.722 | 1.00 | 31.25 |
| 502 | N | VAL | A | 79 | 6.769 | −7.919 | −0.757 | 1.00 | 23.67 |
| 503 | CA | VAL | A | 79 | 5.413 | −8.402 | −0.502 | 1.00 | 22.06 |
| 504 | C | VAL | A | 79 | 4.767 | −9.017 | −1.742 | 1.00 | 21.42 |
| 505 | O | VAL | A | 79 | 3.547 | −9.215 | −1.789 | 1.00 | 21.14 |
| 506 | CB | VAL | A | 79 | 4.496 | −7.267 | 0.032 | 1.00 | 22.73 |
| 507 | CG1 | VAL | A | 79 | 5.036 | −6.743 | 1.356 | 1.00 | 23.63 |
| 508 | CG2 | VAL | A | 79 | 4.401 | −6.136 | −0.993 | 1.00 | 20.81 |
| 509 | N | ARG | A | 80 | 5.590 | −9.338 | −2.735 | 1.00 | 23.71 |
| 510 | CA | ARG | A | 80 | 5.090 | −9.921 | −3.977 | 1.00 | 26.41 |
| 511 | C | ARG | A | 80 | 4.225 | −11.158 | −3.762 | 1.00 | 26.30 |
| 512 | O | ARG | A | 80 | 3.229 | −11.348 | −4.456 | 1.00 | 27.24 |
| 513 | CB | ARG | A | 80 | 6.253 | −10.275 | −4.907 | 1.00 | 26.31 |
| 514 | CG | ARG | A | 80 | 7.031 | −9.073 | −5.438 | 1.00 | 33.01 |
| 515 | CD | ARG | A | 80 | 8.247 | −9.530 | −6.238 | 1.00 | 35.12 |
| 516 | NE | ARG | A | 80 | 9.016 | −8.421 | −6.800 | 1.00 | 39.41 |
| 517 | CZ | ARG | A | 80 | 9.607 | −7.472 | −6.080 | 1.00 | 40.04 |
| 518 | NH1 | ARG | A | 80 | 9.520 | −7.484 | −4.755 | 1.00 | 39.55 |
| 519 | NH2 | ARG | A | 80 | 10.300 | −6.516 | −6.685 | 1.00 | 40.92 |
| 520 | N | ASN | A | 81 | 4.596 | −11.995 | −2.799 | 1.00 | 24.93 |
| 521 | CA | ASN | A | 81 | 3.837 | −13.217 | −2.539 | 1.00 | 26.05 |
| 522 | C | ASN | A | 81 | 3.133 | −13.224 | −1.189 | 1.00 | 24.34 |
| 523 | O | ASN | A | 81 | 2.702 | −14.273 | −0.709 | 1.00 | 23.99 |
| 524 | CB | ASN | A | 81 | 4.761 | −14.436 | −2.636 | 1.00 | 29.81 |
| 525 | CG | ASN | A | 81 | 5.421 | −14.558 | −3.996 | 1.00 | 32.85 |
| 526 | OD1 | ASN | A | 81 | 4.757 | −14.463 | −5.026 | 1.00 | 36.03 |
| 527 | ND2 | ASN | A | 81 | 6.733 | −14.775 | −4.006 | 1.00 | 37.46 |
| 528 | N | SER | A | 82 | 3.001 | −12.050 | −0.582 | 1.00 | 22.65 |
| 529 | CA | SER | A | 82 | 2.354 | −11.949 | 0.717 | 1.00 | 22.25 |
| 530 | C | SER | A | 82 | 0.838 | −12.067 | 0.636 | 1.00 | 22.81 |
| 531 | O | SER | A | 82 | 0.227 | −11.835 | −0.413 | 1.00 | 20.59 |
| 532 | CB | SER | A | 82 | 2.717 | −10.614 | 1.385 | 1.00 | 23.81 |

TABLE 2-continued

| ATOM | ATOM TYPE | RESIDUE | PROTEIN # | # | X | Y | Z | OCC | B |
|---|---|---|---|---|---|---|---|---|---|
| 533 | OG | SER | A | 82 | 4.109 | −10.520 | 1.633 | 1.00 | 26.13 |
| 534 | N | THR | A | 83 | 0.239 | −12.455 | 1.755 | 1.00 | 19.03 |
| 535 | CA | THR | A | 83 | −1.206 | −12.550 | 1.860 | 1.00 | 20.57 |
| 536 | C | THR | A | 83 | −1.645 | −11.107 | 2.098 | 1.00 | 20.84 |
| 537 | O | THR | A | 83 | −0.819 | −10.268 | 2.466 | 1.00 | 18.95 |
| 538 | CB | THR | A | 83 | −1.620 | −13.385 | 3.080 | 1.00 | 26.24 |
| 539 | OG1 | THR | A | 83 | −1.035 | −12.820 | 4.263 | 1.00 | 23.12 |
| 540 | CG2 | THR | A | 83 | −1.150 | −14.825 | 2.925 | 1.00 | 27.52 |
| 541 | N | GLU | A | 84 | −2.922 | −10.807 | 1.892 | 1.00 | 20.34 |
| 542 | CA | GLU | A | 84 | −3.399 | −9.446 | 2.117 | 1.00 | 22.94 |
| 543 | C | GLU | A | 84 | −3.214 | −9.058 | 3.581 | 1.00 | 23.18 |
| 544 | O | GLU | A | 84 | −2.734 | −7.969 | 3.888 | 1.00 | 18.58 |
| 545 | CB | GLU | A | 84 | −4.876 | −9.306 | 1.745 | 1.00 | 26.18 |
| 546 | CG | GLU | A | 84 | −5.177 | −9.540 | 0.273 | 1.00 | 26.90 |
| 547 | CD | GLU | A | 84 | −5.658 | −10.949 | −0.009 | 1.00 | 30.67 |
| 548 | OE1 | GLU | A | 84 | −5.072 | −11.900 | 0.542 | 1.00 | 33.28 |
| 549 | OE2 | GLU | A | 84 | −6.619 | −11.103 | −0.792 | 1.00 | 35.22 |
| 550 | N | GLN | A | 85 | −3.584 | −9.958 | 4.486 | 1.00 | 20.72 |
| 551 | CA | GLN | A | 85 | −3.458 | −9.671 | 5.910 | 1.00 | 23.19 |
| 552 | C | GLN | A | 85 | −2.026 | −9.364 | 6.325 | 1.00 | 21.88 |
| 553 | O | GLN | A | 85 | −1.793 | −8.494 | 7.167 | 1.00 | 23.84 |
| 554 | CB | GLN | A | 85 | −3.983 | −10.842 | 6.741 | 1.00 | 25.39 |
| 555 | CG | GLN | A | 85 | −4.108 | −10.506 | 8.212 | 1.00 | 28.77 |
| 556 | CD | GLN | A | 85 | −5.008 | −9.309 | 8.446 | 1.00 | 30.50 |
| 557 | OE1 | GLN | A | 85 | −6.171 | −9.305 | 8.039 | 1.00 | 35.51 |
| 558 | NE2 | GLN | A | 85 | −4.476 | −8.287 | 9.103 | 1.00 | 31.04 |
| 559 | N | ALA | A | 86 | −1.067 | −10.079 | 5.743 | 1.00 | 20.85 |
| 560 | CA | ALA | A | 86 | 0.339 | −9.865 | 6.064 | 1.00 | 21.36 |
| 561 | C | ALA | A | 86 | 0.775 | −8.448 | 5.700 | 1.00 | 21.55 |
| 562 | O | ALA | A | 86 | 1.555 | −7.824 | 6.420 | 1.00 | 19.33 |
| 563 | CB | ALA | A | 86 | 1.211 | −10.881 | 5.332 | 1.00 | 21.91 |
| 564 | N | VAL | A | 87 | 0.280 | −7.941 | 4.575 | 1.00 | 21.49 |
| 565 | CA | VAL | A | 87 | 0.639 | −6.591 | 4.157 | 1.00 | 19.35 |
| 566 | C | VAL | A | 87 | −0.024 | −5.586 | 5.092 | 1.00 | 19.72 |
| 567 | O | VAL | A | 87 | 0.593 | −4.591 | 5.482 | 1.00 | 21.98 |
| 568 | CB | VAL | A | 87 | 0.195 | −6.309 | 2.707 | 1.00 | 19.29 |
| 569 | CG1 | VAL | A | 87 | 0.512 | −4.861 | 2.342 | 1.00 | 17.51 |
| 570 | CG2 | VAL | A | 87 | 0.908 | −7.264 | 1.752 | 1.00 | 19.33 |
| 571 | N | ILE | A | 88 | −1.278 | −5.846 | 5.451 | 1.00 | 18.68 |
| 572 | CA | ILE | A | 88 | −1.994 | −4.950 | 6.358 | 1.00 | 21.86 |
| 573 | C | ILE | A | 88 | −1.275 | −4.894 | 7.706 | 1.00 | 22.34 |
| 574 | O | ILE | A | 88 | −1.112 | −3.816 | 8.281 | 1.00 | 22.49 |
| 575 | CB | ILE | A | 88 | −3.455 | −5.404 | 6.583 | 1.00 | 21.24 |
| 576 | CG1 | ILE | A | 88 | −4.252 | −5.262 | 5.282 | 1.00 | 23.03 |
| 577 | CG2 | ILE | A | 88 | −4.101 | −4.571 | 7.683 | 1.00 | 23.99 |
| 578 | CD1 | ILE | A | 88 | −4.248 | −3.851 | 4.694 | 1.00 | 20.37 |
| 579 | N | ASP | A | 89 | −0.841 | −6.047 | 8.209 | 1.00 | 22.02 |
| 580 | CA | ASP | A | 89 | −0.130 | −6.070 | 9.486 | 1.00 | 25.89 |
| 581 | C | ASP | A | 89 | 1.145 | −5.237 | 9.387 | 1.00 | 25.29 |
| 582 | O | ASP | A | 89 | 1.468 | −4.474 | 10.298 | 1.00 | 23.98 |
| 583 | CB | ASP | A | 89 | 0.229 | −7.502 | 9.901 | 1.00 | 27.00 |
| 584 | CG | ASP | A | 89 | −0.994 | −8.360 | 10.166 | 1.00 | 33.00 |
| 585 | OD1 | ASP | A | 89 | −1.997 | −7.838 | 10.697 | 1.00 | 34.72 |
| 586 | OD2 | ASP | A | 89 | −0.950 | −9.567 | 9.852 | 1.00 | 38.32 |
| 587 | N | LEU | A | 90 | 1.866 | −5.384 | 8.279 | 1.00 | 23.99 |
| 588 | CA | LEU | A | 90 | 3.098 | −4.630 | 8.063 | 1.00 | 22.88 |
| 589 | C | LEU | A | 90 | 2.829 | −3.129 | 8.101 | 1.00 | 23.76 |
| 590 | O | LEU | A | 90 | 3.585 | −2.365 | 8.704 | 1.00 | 23.53 |
| 591 | CB | LEU | A | 90 | 3.721 | −4.994 | 6.712 | 1.00 | 23.69 |
| 592 | CG | LEU | A | 90 | 4.447 | −6.335 | 6.608 | 1.00 | 27.52 |
| 593 | CD1 | LEU | A | 90 | 4.850 | −6.598 | 5.155 | 1.00 | 27.76 |
| 594 | CD2 | LEU | A | 90 | 5.672 | −6.308 | 7.513 | 1.00 | 30.93 |
| 595 | N | ILE | A | 91 | 1.754 | −2.707 | 7.446 | 1.00 | 21.18 |
| 596 | CA | ILE | A | 91 | 1.400 | −1.296 | 7.421 | 1.00 | 23.16 |
| 597 | C | ILE | A | 91 | 1.054 | −0.781 | 8.816 | 1.00 | 24.58 |
| 598 | O | ILE | A | 91 | 1.479 | 0.307 | 9.202 | 1.00 | 23.67 |
| 599 | CB | ILE | A | 91 | 0.196 | −1.034 | 6.495 | 1.00 | 24.32 |
| 600 | CG1 | ILE | A | 91 | 0.560 | −1.391 | 5.054 | 1.00 | 24.43 |
| 601 | CG2 | ILE | A | 91 | −0.214 | 0.441 | 6.573 | 1.00 | 22.39 |
| 602 | CD1 | ILE | A | 91 | −0.610 | −1.276 | 4.087 | 1.00 | 20.94 |
| 603 | N | LYS | A | 92 | 0.287 | −1.563 | 9.571 | 1.00 | 24.10 |
| 604 | CA | LYS | A | 92 | −0.112 | −1.153 | 10.915 | 1.00 | 27.33 |
| 605 | C | LYS | A | 92 | 1.063 | −1.105 | 11.881 | 1.00 | 30.69 |
| 606 | O | LYS | A | 92 | 1.020 | −0.405 | 12.894 | 1.00 | 30.02 |
| 607 | CB | LYS | A | 92 | −1.205 | −2.082 | 11.450 | 1.00 | 32.57 |
| 608 | CG | LYS | A | 92 | −2.525 | −1.939 | 10.707 | 1.00 | 37.58 |

TABLE 2-continued

| ATOM | ATOM TYPE | RESIDUE | PROTEIN # | # | X | Y | Z | OCC | B |
|---|---|---|---|---|---|---|---|---|---|
| 609 | CD | LYS | A | 92 | −3.625 | −2.805 | 11.305 | 1.00 | 41.03 |
| 610 | CE | LYS | A | 92 | −4.952 | −2.545 | 10.598 | 1.00 | 44.34 |
| 611 | NZ | LYS | A | 92 | −6.075 | −3.346 | 11.161 | 1.00 | 47.53 |
| 612 | N | GLU | A | 93 | 2.120 | −1.839 | 11.558 | 1.00 | 28.47 |
| 613 | CA | GLU | A | 93 | 3.310 | −1.869 | 12.394 | 1.00 | 29.74 |
| 614 | C | GLU | A | 93 | 4.194 | −0.659 | 12.134 | 1.00 | 32.59 |
| 615 | O | GLU | A | 93 | 5.107 | −0.371 | 12.908 | 1.00 | 32.24 |
| 616 | CB | GLU | A | 93 | 4.095 | −3.148 | 12.133 | 1.00 | 29.79 |
| 617 | CG | GLU | A | 93 | 3.481 | −4.371 | 12.779 | 1.00 | 33.41 |
| 618 | CD | GLU | A | 93 | 4.078 | −5.654 | 12.257 | 1.00 | 34.91 |
| 619 | OE1 | GLU | A | 93 | 5.215 | −5.609 | 11.746 | 1.00 | 35.85 |
| 620 | OE2 | GLU | A | 93 | 3.416 | −6.707 | 12.366 | 1.00 | 39.39 |
| 621 | N | ALA | A | 94 | 3.920 | 0.050 | 11.044 | 1.00 | 31.48 |
| 622 | CA | ALA | A | 94 | 4.695 | 1.230 | 10.698 | 1.00 | 32.82 |
| 623 | C | ALA | A | 94 | 4.233 | 2.416 | 11.542 | 1.00 | 34.20 |
| 624 | O | ALA | A | 94 | 3.144 | 2.400 | 12.112 | 1.00 | 34.37 |
| 625 | CB | ALA | A | 94 | 4.538 | 1.543 | 9.213 | 1.00 | 32.91 |
| 626 | N | ASP | A | 95 | 5.068 | 3.443 | 11.630 | 1.00 | 36.18 |
| 627 | CA | ASP | A | 95 | 4.711 | 4.622 | 12.405 | 1.00 | 37.81 |
| 628 | C | ASP | A | 95 | 3.684 | 5.432 | 11.619 | 1.00 | 37.60 |
| 629 | O | ASP | A | 95 | 2.532 | 5.021 | 11.477 | 1.00 | 42.33 |
| 630 | CB | ASP | A | 95 | 5.951 | 5.463 | 12.684 | 1.00 | 41.16 |
| 631 | N | PHE | A | 96 | 4.111 | 6.575 | 11.097 | 1.00 | 32.84 |
| 632 | CA | PHE | A | 96 | 3.229 | 7.436 | 10.326 | 1.00 | 29.81 |
| 633 | C | PHE | A | 96 | 3.550 | 7.382 | 8.838 | 1.00 | 26.72 |
| 634 | O | PHE | A | 96 | 2.819 | 7.942 | 8.027 | 1.00 | 24.12 |
| 635 | CB | PHE | A | 96 | 3.339 | 8.885 | 10.812 | 1.00 | 34.43 |
| 636 | CG | PHE | A | 96 | 4.740 | 9.434 | 10.787 | 1.00 | 40.06 |
| 637 | CD1 | PHE | A | 96 | 5.724 | 8.913 | 11.627 | 1.00 | 43.72 |
| 638 | CD2 | PHE | A | 96 | 5.079 | 10.471 | 9.924 | 1.00 | 42.75 |
| 639 | CE1 | PHE | A | 96 | 7.026 | 9.418 | 11.606 | 1.00 | 45.22 |
| 640 | CE2 | PHE | A | 96 | 6.377 | 10.984 | 9.894 | 1.00 | 45.27 |
| 641 | CZ | PHE | A | 96 | 7.352 | 10.455 | 10.737 | 1.00 | 45.98 |
| 642 | N | LYS | A | 97 | 4.639 | 6.709 | 8.479 | 1.00 | 27.21 |
| 643 | CA | LYS | A | 97 | 5.020 | 6.629 | 7.074 | 1.00 | 26.82 |
| 644 | C | LYS | A | 97 | 5.318 | 5.237 | 6.542 | 1.00 | 25.63 |
| 645 | O | LYS | A | 97 | 5.792 | 4.350 | 7.256 | 1.00 | 24.11 |
| 646 | CB | LYS | A | 97 | 6.238 | 7.519 | 6.799 | 1.00 | 29.78 |
| 647 | CG | LYS | A | 97 | 6.044 | 8.977 | 7.165 | 1.00 | 34.08 |
| 648 | CD | LYS | A | 97 | 7.049 | 9.899 | 6.472 | 1.00 | 40.23 |
| 649 | CE | LYS | A | 97 | 8.496 | 9.449 | 6.654 | 1.00 | 42.13 |
| 650 | NZ | LYS | A | 97 | 8.857 | 8.324 | 5.742 | 1.00 | 45.59 |
| 651 | N | ILE | A | 98 | 5.029 | 5.059 | 5.261 | 1.00 | 24.38 |
| 652 | CA | ILE | A | 98 | 5.300 | 3.803 | 4.584 | 1.00 | 21.39 |
| 653 | C | ILE | A | 98 | 5.845 | 4.165 | 3.210 | 1.00 | 22.28 |
| 654 | O | ILE | A | 98 | 5.335 | 5.079 | 2.555 | 1.00 | 21.76 |
| 655 | CB | ILE | A | 98 | 4.024 | 2.935 | 4.418 | 1.00 | 23.12 |
| 656 | CG1 | ILE | A | 98 | 2.956 | 3.698 | 3.629 | 1.00 | 22.59 |
| 657 | CG2 | ILE | A | 98 | 3.500 | 2.514 | 5.784 | 1.00 | 21.44 |
| 658 | CD1 | ILE | A | 98 | 1.738 | 2.849 | 3.247 | 1.00 | 24.31 |
| 659 | N | GLU | A | 99 | 6.907 | 3.480 | 2.795 | 1.00 | 19.89 |
| 660 | CA | GLU | A | 99 | 7.483 | 3.726 | 1.486 | 1.00 | 20.67 |
| 661 | C | GLU | A | 99 | 7.080 | 2.533 | 0.644 | 1.00 | 19.97 |
| 662 | O | GLU | A | 99 | 7.369 | 1.391 | 0.995 | 1.00 | 18.78 |
| 663 | CB | GLU | A | 99 | 9.007 | 3.828 | 1.546 | 1.00 | 23.03 |
| 664 | CG | GLU | A | 99 | 9.592 | 4.333 | 0.238 | 1.00 | 31.84 |
| 665 | CD | GLU | A | 99 | 11.093 | 4.527 | 0.279 | 1.00 | 36.88 |
| 666 | OE1 | GLU | A | 99 | 11.627 | 5.151 | −0.665 | 1.00 | 40.16 |
| 667 | OE2 | GLU | A | 99 | 11.736 | 4.058 | 1.242 | 1.00 | 38.91 |
| 668 | N | LEU | A | 100 | 6.409 | 2.808 | −0.465 | 1.00 | 18.51 |
| 669 | CA | LEU | A | 100 | 5.923 | 1.755 | −1.340 | 1.00 | 19.87 |
| 670 | C | LEU | A | 100 | 6.646 | 1.702 | −2.673 | 1.00 | 17.15 |
| 671 | O | LEU | A | 100 | 6.836 | 2.731 | −3.315 | 1.00 | 17.50 |
| 672 | CB | LEU | A | 100 | 4.431 | 1.966 | −1.609 | 1.00 | 19.54 |
| 673 | CG | LEU | A | 100 | 3.499 | 2.052 | −0.398 | 1.00 | 22.21 |
| 674 | CD1 | LEU | A | 100 | 2.158 | 2.651 | −0.807 | 1.00 | 25.72 |
| 675 | CD2 | LEU | A | 100 | 3.313 | 0.670 | 0.188 | 1.00 | 28.05 |
| 676 | N | GLU | A | 101 | 7.057 | 0.499 | −3.069 | 1.00 | 17.59 |
| 677 | CA | GLU | A | 101 | 7.696 | 0.284 | −4.365 | 1.00 | 17.08 |
| 678 | C | GLU | A | 101 | 6.460 | −0.115 | −5.160 | 1.00 | 15.68 |
| 679 | O | GLU | A | 101 | 5.846 | −1.147 | −4.876 | 1.00 | 15.57 |
| 680 | CB | GLU | A | 101 | 8.688 | −0.880 | −4.307 | 1.00 | 19.35 |
| 681 | CG | GLU | A | 101 | 9.436 | −1.123 | −5.617 | 1.00 | 19.73 |
| 682 | CD | GLU | A | 101 | 10.372 | −2.320 | −5.546 | 1.00 | 22.41 |
| 683 | OE1 | GLU | A | 101 | 11.025 | −2.631 | −6.561 | 1.00 | 25.00 |
| 684 | OE2 | GLU | A | 101 | 10.449 | −2.957 | −4.478 | 1.00 | 26.40 |

TABLE 2-continued

| ATOM | ATOM TYPE | RESIDUE | PROTEIN # | # | X | Y | Z | OCC | B |
|---|---|---|---|---|---|---|---|---|---|
| 685 | N | ILE | A | 102 | 6.106 | 0.709 | −6.137 | 1.00 | 14.89 |
| 686 | CA | ILE | A | 102 | 4.898 | 0.519 | −6.936 | 1.00 | 18.89 |
| 687 | C | ILE | A | 102 | 5.186 | 0.224 | −8.404 | 1.00 | 20.07 |
| 688 | O | ILE | A | 102 | 6.075 | 0.824 | −8.997 | 1.00 | 17.87 |
| 689 | CB | ILE | A | 102 | 4.025 | 1.813 | −6.883 | 1.00 | 17.08 |
| 690 | CG1 | ILE | A | 102 | 3.560 | 2.089 | −5.450 | 1.00 | 17.90 |
| 691 | CG2 | ILE | A | 102 | 2.853 | 1.716 | −7.852 | 1.00 | 19.47 |
| 692 | CD1 | ILE | A | 102 | 2.642 | 1.042 | −4.881 | 1.00 | 14.90 |
| 693 | N | GLN | A | 103 | 4.439 | −0.715 | −8.981 | 1.00 | 21.80 |
| 694 | CA | GLN | A | 103 | 4.576 | −1.015 | −10.404 | 1.00 | 20.15 |
| 695 | C | GLN | A | 103 | 3.254 | −0.534 | −10.986 | 1.00 | 22.70 |
| 696 | O | GLN | A | 103 | 2.188 | −1.013 | −10.592 | 1.00 | 21.47 |
| 697 | CB | GLN | A | 103 | 4.763 | −2.508 | −10.654 | 1.00 | 20.57 |
| 698 | CG | GLN | A | 103 | 5.103 | −2.818 | −12.109 | 1.00 | 25.32 |
| 699 | CD | GLN | A | 103 | 5.329 | −4.287 | −12.350 | 1.00 | 28.71 |
| 700 | OE1 | GLN | A | 103 | 5.827 | −4.996 | −11.478 | 1.00 | 32.58 |
| 701 | NE2 | GLN | A | 103 | 4.977 | −4.757 | −13.542 | 1.00 | 27.66 |
| 702 | N | THR | A | 104 | 3.325 | 0.419 | −11.911 | 1.00 | 24.92 |
| 703 | CA | THR | A | 104 | 2.126 | 1.016 | −12.489 | 1.00 | 26.59 |
| 704 | C | THR | A | 104 | 2.057 | 1.060 | −14.012 | 1.00 | 33.14 |
| 705 | O | THR | A | 104 | 3.030 | 0.759 | −14.704 | 1.00 | 30.91 |
| 706 | CB | THR | A | 104 | 1.972 | 2.461 | −11.985 | 1.00 | 26.40 |
| 707 | OG1 | THR | A | 104 | 0.729 | 3.005 | −12.440 | 1.00 | 26.52 |
| 708 | CG2 | THR | A | 104 | 3.120 | 3.327 | −12.511 | 1.00 | 27.84 |
| 709 | N | PHE | A | 105 | 0.886 | 1.467 | −14.503 | 1.00 | 37.06 |
| 710 | CA | PHE | A | 105 | 0.595 | 1.602 | −15.927 | 1.00 | 41.44 |
| 711 | C | PHE | A | 105 | 0.428 | 0.253 | −16.610 | 1.00 | 44.41 |
| 712 | O | PHE | A | 105 | −0.598 | 0.078 | −17.297 | 1.00 | 45.58 |
| 713 | CB | PHE | A | 105 | 1.685 | 2.414 | −16.612 | 1.00 | 42.58 |
| 714 |  | PHE | A | 105 |  |  |  |  |  |
| 715 | N | GLY | B | 12 | −2.824 | 24.380 | 44.686 | 1.00 | 41.18 |
| 716 | CA | GLY | B | 12 | −3.795 | 25.328 | 44.075 | 1.00 | 38.01 |
| 717 | C | GLY | B | 12 | −3.833 | 25.218 | 42.563 | 1.00 | 35.77 |
| 718 | O | GLY | B | 12 | −4.400 | 24.276 | 42.011 | 1.00 | 37.68 |
| 719 | N | GLU | B | 13 | −3.221 | 26.183 | 41.890 | 1.00 | 33.16 |
| 720 | CA | GLU | B | 13 | −3.193 | 26.191 | 40.436 | 1.00 | 29.03 |
| 721 | C | GLU | B | 13 | −1.955 | 25.512 | 39.871 | 1.00 | 25.26 |
| 722 | O | GLU | B | 13 | −0.972 | 25.276 | 40.578 | 1.00 | 21.19 |
| 723 | CB | GLU | B | 13 | −3.252 | 27.624 | 39.914 | 1.00 | 31.29 |
| 724 | CG | GLU | B | 13 | −4.539 | 28.349 | 40.225 | 1.00 | 41.35 |
| 725 | CD | GLU | B | 13 | −4.590 | 29.711 | 39.572 | 1.00 | 45.87 |
| 726 | OE1 | GLU | B | 13 | −3.741 | 30.564 | 39.912 | 1.00 | 48.62 |
| 727 | OE2 | GLU | B | 13 | −5.474 | 29.926 | 38.714 | 1.00 | 49.26 |
| 728 | N | LEU | B | 14 | −2.012 | 25.213 | 38.580 | 1.00 | 21.48 |
| 729 | CA | LEU | B | 14 | −0.900 | 24.568 | 37.907 | 1.00 | 19.08 |
| 730 | C | LEU | B | 14 | −0.922 | 24.888 | 36.420 | 1.00 | 18.50 |
| 731 | O | LEU | B | 14 | −1.989 | 24.951 | 35.810 | 1.00 | 17.43 |
| 732 | CB | LEU | B | 14 | −0.982 | 23.055 | 38.084 | 1.00 | 21.39 |
| 733 | CG | LEU | B | 14 | 0.235 | 22.288 | 37.567 | 1.00 | 23.76 |
| 734 | CD1 | LEU | B | 14 | 1.406 | 22.532 | 38.509 | 1.00 | 27.00 |
| 735 | CD2 | LEU | B | 14 | −0.079 | 20.804 | 37.480 | 1.00 | 27.03 |
| 736 | N | ILE | B | 15 | 0.255 | 25.110 | 35.848 | 1.00 | 16.49 |
| 737 | CA | ILE | B | 15 | 0.358 | 25.367 | 34.416 | 1.00 | 14.99 |
| 738 | C | ILE | B | 15 | 0.886 | 24.062 | 33.842 | 1.00 | 17.09 |
| 739 | O | ILE | B | 15 | 1.896 | 23.541 | 34.311 | 1.00 | 16.73 |
| 740 | CB | ILE | B | 15 | 1.362 | 26.504 | 34.092 | 1.00 | 16.30 |
| 741 | CG1 | ILE | B | 15 | 0.860 | 27.823 | 34.681 | 1.00 | 20.80 |
| 742 | CG2 | ILE | B | 15 | 1.539 | 26.644 | 32.570 | 1.00 | 19.63 |
| 743 | CD1 | ILE | B | 15 | 1.853 | 28.977 | 34.542 | 1.00 | 20.78 |
| 744 | N | HIS | B | 16 | 0.177 | 23.515 | 32.860 | 1.00 | 15.23 |
| 745 | CA | HIS | B | 16 | 0.596 | 22.279 | 32.231 | 1.00 | 14.89 |
| 746 | C | HIS | B | 16 | 0.318 | 22.345 | 30.742 | 1.00 | 16.56 |
| 747 | O | HIS | B | 16 | −0.322 | 23.284 | 30.276 | 1.00 | 15.60 |
| 748 | CB | HIS | B | 16 | −0.101 | 21.074 | 32.876 | 1.00 | 15.29 |
| 749 | CG | HIS | B | 16 | −1.590 | 21.080 | 32.737 | 1.00 | 18.06 |
| 750 | ND1 | HIS | B | 16 | −2.272 | 20.095 | 32.059 | 1.00 | 22.45 |
| 751 | CD2 | HIS | B | 16 | −2.530 | 21.937 | 33.204 | 1.00 | 20.71 |
| 752 | CE1 | HIS | B | 16 | −3.569 | 20.343 | 32.113 | 1.00 | 22.22 |
| 753 | NE2 | HIS | B | 16 | −3.752 | 21.455 | 32.801 | 1.00 | 22.31 |
| 754 | N | MET | B | 17 | 0.818 | 21.362 | 29.998 | 1.00 | 14.87 |
| 755 | CA | MET | B | 17 | 0.639 | 21.344 | 28.550 | 1.00 | 16.62 |
| 756 | C | MET | B | 17 | −0.350 | 20.279 | 28.113 | 1.00 | 18.65 |
| 757 | O | MET | B | 17 | −0.330 | 19.150 | 28.609 | 1.00 | 18.22 |
| 758 | CB | MET | B | 17 | 1.979 | 21.092 | 27.844 | 1.00 | 17.48 |
| 759 | CG | MET | B | 17 | 3.027 | 22.165 | 28.050 | 1.00 | 21.72 |
| 760 | SD | MET | B | 17 | 2.511 | 23.775 | 27.445 | 1.00 | 24.06 |

TABLE 2-continued

| ATOM | ATOM TYPE | RESIDUE | PROTEIN # | # | X | Y | Z | OCC | B |
|---|---|---|---|---|---|---|---|---|---|
| 761 | CE | MET | B | 17 | 2.446 | 23.478 | 25.683 | 1.00 | 27.91 |
| 762 | N | VAL | B | 18 | −1.226 | 20.655 | 27.189 | 1.00 | 18.33 |
| 763 | CA | VAL | B | 18 | −2.211 | 19.729 | 26.660 | 1.00 | 20.10 |
| 764 | C | VAL | B | 18 | −2.203 | 19.820 | 25.145 | 1.00 | 19.21 |
| 765 | O | VAL | B | 18 | −2.361 | 20.897 | 24.580 | 1.00 | 17.81 |
| 766 | CB | VAL | B | 18 | −3.639 | 20.052 | 27.153 | 1.00 | 20.22 |
| 767 | CG1 | VAL | B | 18 | −4.645 | 19.169 | 26.425 | 1.00 | 23.94 |
| 768 | CG2 | VAL | B | 18 | −3.743 | 19.816 | 28.658 | 1.00 | 20.20 |
| 769 | N | THR | B | 19 | −2.003 | 18.686 | 24.490 | 1.00 | 21.46 |
| 770 | CA | THR | B | 19 | −2.014 | 18.662 | 23.038 | 1.00 | 22.86 |
| 771 | C | THR | B | 19 | −3.314 | 18.012 | 22.596 | 1.00 | 21.71 |
| 772 | O | THR | B | 19 | −3.657 | 16.923 | 23.055 | 1.00 | 22.92 |
| 773 | CB | THR | B | 19 | −0.834 | 17.847 | 22.474 | 1.00 | 25.52 |
| 774 | OG1 | THR | B | 19 | 0.394 | 18.536 | 22.741 | 1.00 | 29.18 |
| 775 | CG2 | THR | B | 19 | −0.991 | 17.653 | 20.968 | 1.00 | 24.32 |
| 776 | N | LEU | B | 20 | −4.049 | 18.700 | 21.732 | 1.00 | 21.87 |
| 777 | CA | LEU | B | 20 | −5.295 | 18.167 | 21.206 | 1.00 | 20.98 |
| 778 | C | LEU | B | 20 | −5.052 | 17.823 | 19.743 | 1.00 | 22.11 |
| 779 | O | LEU | B | 20 | −4.489 | 18.618 | 18.990 | 1.00 | 20.92 |
| 780 | CB | LEU | B | 20 | −6.431 | 19.187 | 21.327 | 1.00 | 19.25 |
| 781 | CG | LEU | B | 20 | −6.914 | 19.510 | 22.746 | 1.00 | 21.16 |
| 782 | CD1 | LEU | B | 20 | −8.098 | 20.451 | 22.676 | 1.00 | 19.80 |
| 783 | CD2 | LEU | B | 20 | −7.305 | 18.220 | 23.466 | 1.00 | 20.88 |
| 784 | N | ASP | B | 21 | −5.478 | 16.627 | 19.365 | 1.00 | 20.47 |
| 785 | CA | ASP | B | 21 | −5.315 | 16.108 | 18.014 | 1.00 | 20.88 |
| 786 | C | ASP | B | 21 | −6.719 | 15.819 | 17.485 | 1.00 | 21.16 |
| 787 | O | ASP | B | 21 | −7.432 | 14.989 | 18.047 | 1.00 | 20.06 |
| 788 | CB | ASP | B | 21 | −4.494 | 14.819 | 18.087 | 1.00 | 23.74 |
| 789 | CG | ASP | B | 21 | −4.125 | 14.283 | 16.728 | 1.00 | 28.18 |
| 790 | OD1 | ASP | B | 21 | −4.994 | 14.283 | 15.837 | 1.00 | 21.93 |
| 791 | OD2 | ASP | B | 21 | −2.964 | 13.853 | 16.562 | 1.00 | 35.94 |
| 792 | N | LYS | B | 22 | −7.130 | 16.499 | 16.417 | 1.00 | 17.29 |
| 793 | CA | LYS | B | 22 | −8.472 | 16.268 | 15.899 | 1.00 | 18.02 |
| 794 | C | LYS | B | 22 | −8.502 | 15.328 | 14.703 | 1.00 | 21.13 |
| 795 | O | LYS | B | 22 | −9.383 | 15.427 | 13.852 | 1.00 | 19.47 |
| 796 | CB | LYS | B | 22 | −9.158 | 17.592 | 15.546 | 1.00 | 22.05 |
| 797 | CG | LYS | B | 22 | −8.537 | 18.352 | 14.387 | 1.00 | 24.03 |
| 798 | CD | LYS | B | 22 | −9.347 | 19.595 | 14.074 | 1.00 | 26.87 |
| 799 | CE | LYS | B | 22 | −8.776 | 20.351 | 12.887 | 1.00 | 28.24 |
| 800 | NZ | LYS | B | 22 | −9.514 | 21.628 | 12.657 | 1.00 | 33.85 |
| 801 | N | THR | B | 23 | −7.540 | 14.414 | 14.647 | 1.00 | 22.56 |
| 802 | CA | THR | B | 23 | −7.496 | 13.445 | 13.556 | 1.00 | 25.34 |
| 803 | C | THR | B | 23 | −8.835 | 12.709 | 13.553 | 1.00 | 26.07 |
| 804 | O | THR | B | 23 | −9.259 | 12.182 | 14.580 | 1.00 | 28.00 |
| 805 | CB | THR | B | 23 | −6.351 | 12.419 | 13.755 | 1.00 | 27.31 |
| 806 | OG1 | THR | B | 23 | −5.085 | 13.084 | 13.652 | 1.00 | 24.33 |
| 807 | CG2 | THR | B | 23 | −6.424 | 11.314 | 12.694 | 1.00 | 25.40 |
| 808 | N | GLY | B | 24 | −9.508 | 12.698 | 12.407 | 1.00 | 29.73 |
| 809 | CA | GLY | B | 24 | −10.786 | 12.014 | 12.307 | 1.00 | 30.82 |
| 810 | C | GLY | B | 24 | −11.937 | 12.719 | 13.002 | 1.00 | 33.78 |
| 811 | O | GLY | B | 24 | −12.992 | 12.124 | 13.218 | 1.00 | 34.98 |
| 812 | N | LYS | B | 25 | −11.738 | 13.984 | 13.358 | 1.00 | 33.59 |
| 813 | CA | LYS | B | 25 | −12.771 | 14.774 | 14.025 | 1.00 | 32.68 |
| 814 | C | LYS | B | 25 | −13.026 | 16.065 | 13.253 | 1.00 | 31.82 |
| 815 | O | LYS | B | 25 | −12.178 | 16.507 | 12.479 | 1.00 | 31.80 |
| 816 | CB | LYS | B | 25 | −12.346 | 15.101 | 15.457 | 1.00 | 32.07 |
| 817 | CG | LYS | B | 25 | −12.367 | 13.909 | 16.404 | 1.00 | 33.59 |
| 818 | CD | LYS | B | 25 | −13.792 | 13.475 | 16.708 | 1.00 | 36.55 |
| 819 | CE | LYS | B | 25 | −13.828 | 12.403 | 17.778 | 1.00 | 36.99 |
| 820 | NZ | LYS | B | 25 | −15.228 | 12.040 | 18.129 | 1.00 | 39.61 |
| 821 | N | LYS | B | 26 | −14.190 | 16.671 | 13.476 | 1.00 | 31.80 |
| 822 | CA | LYS | B | 26 | −14.567 | 17.903 | 12.784 | 1.00 | 33.54 |
| 823 | C | LYS | B | 26 | −13.988 | 19.169 | 13.415 | 1.00 | 32.10 |
| 824 | O | LYS | B | 26 | −13.865 | 20.203 | 12.754 | 1.00 | 32.50 |
| 825 | CB | LYS | B | 26 | −16.096 | 18.014 | 12.714 | 1.00 | 36.86 |
| 826 | CG | LYS | B | 26 | −16.777 | 18.209 | 14.061 | 1.00 | 42.90 |
| 827 | CD | LYS | B | 26 | −18.285 | 17.967 | 13.977 | 1.00 | 47.87 |
| 828 | CE | LYS | B | 26 | −18.964 | 18.886 | 12.965 | 1.00 | 50.01 |
| 829 | NZ | LYS | B | 26 | −18.845 | 20.323 | 13.336 | 1.00 | 53.27 |
| 830 | N | SER | B | 27 | −13.632 | 19.091 | 14.692 | 1.00 | 28.48 |
| 831 | CA | SER | B | 27 | −13.068 | 20.244 | 15.387 | 1.00 | 26.93 |
| 832 | C | SER | B | 27 | −12.415 | 19.792 | 16.683 | 1.00 | 23.49 |
| 833 | O | SER | B | 27 | −12.504 | 18.622 | 17.055 | 1.00 | 21.51 |
| 834 | CB | SER | B | 27 | −14.162 | 21.259 | 15.705 | 1.00 | 28.61 |
| 835 | OG | SER | B | 27 | −15.034 | 20.750 | 16.697 | 1.00 | 34.48 |
| 836 | N | PHE | B | 28 | −11.761 | 20.718 | 17.376 | 1.00 | 20.81 |

TABLE 2-continued

| ATOM | ATOM TYPE | RESIDUE | PROTEIN # | # | X | Y | Z | OCC | B |
|---|---|---|---|---|---|---|---|---|---|
| 837 | CA | PHE | B | 28 | −11.111 | 20.365 | 18.627 | 1.00 | 18.61 |
| 838 | C | PHE | B | 28 | −12.132 | 20.231 | 19.753 | 1.00 | 18.00 |
| 839 | O | PHE | B | 28 | −11.955 | 19.421 | 20.663 | 1.00 | 20.46 |
| 840 | CB | PHE | B | 28 | −10.032 | 21.393 | 18.971 | 1.00 | 18.32 |
| 841 | CG | PHE | B | 28 | −8.872 | 21.376 | 18.019 | 1.00 | 16.19 |
| 842 | CD1 | PHE | B | 28 | −8.766 | 22.332 | 17.015 | 1.00 | 17.25 |
| 843 | CD2 | PHE | B | 28 | −7.914 | 20.366 | 18.091 | 1.00 | 16.35 |
| 844 | CE1 | PHE | B | 28 | −7.722 | 22.284 | 16.091 | 1.00 | 19.01 |
| 845 | CE2 | PHE | B | 28 | −6.861 | 20.311 | 17.166 | 1.00 | 18.64 |
| 846 | CZ | PHE | B | 28 | −6.769 | 21.269 | 16.170 | 1.00 | 18.42 |
| 847 | N | GLY | B | 29 | −13.198 | 21.021 | 19.686 | 1.00 | 18.85 |
| 848 | CA | GLY | B | 29 | −14.243 | 20.929 | 20.691 | 1.00 | 20.66 |
| 849 | C | GLY | B | 29 | −14.196 | 21.895 | 21.861 | 1.00 | 19.42 |
| 850 | O | GLY | B | 29 | −14.688 | 21.579 | 22.944 | 1.00 | 17.12 |
| 851 | N | ILE | B | 30 | −13.605 | 23.067 | 21.672 | 1.00 | 18.58 |
| 852 | CA | ILE | B | 30 | −13.572 | 24.027 | 22.765 | 1.00 | 19.17 |
| 853 | C | ILE | B | 30 | −14.226 | 25.343 | 22.388 | 1.00 | 19.80 |
| 854 | O | ILE | B | 30 | −14.124 | 25.803 | 21.250 | 1.00 | 21.00 |
| 855 | CB | ILE | B | 30 | −12.125 | 24.329 | 23.251 | 1.00 | 22.16 |
| 856 | CG1 | ILE | B | 30 | −11.290 | 24.926 | 22.120 | 1.00 | 21.20 |
| 857 | CG2 | ILE | B | 30 | −11.484 | 23.060 | 23.787 | 1.00 | 21.97 |
| 858 | CD1 | ILE | B | 30 | −9.964 | 25.509 | 22.591 | 1.00 | 25.90 |
| 859 | N | CYS | B | 31 | −14.923 | 25.935 | 23.346 | 1.00 | 18.30 |
| 860 | CA | CYS | B | 31 | −15.544 | 27.230 | 23.134 | 1.00 | 18.24 |
| 861 | C | CYS | B | 31 | −14.875 | 28.113 | 24.177 | 1.00 | 18.48 |
| 862 | O | CYS | B | 31 | −14.741 | 27.723 | 25.340 | 1.00 | 18.78 |
| 863 | CB | CYS | B | 31 | −17.047 | 27.166 | 23.356 | 1.00 | 23.28 |
| 864 | SG | CYS | B | 31 | −17.945 | 26.095 | 22.182 | 1.00 | 28.08 |
| 865 | N | ILE | B | 32 | −14.451 | 29.295 | 23.757 | 1.00 | 16.58 |
| 866 | CA | ILE | B | 32 | −13.731 | 30.188 | 24.652 | 1.00 | 18.37 |
| 867 | C | ILE | B | 32 | −14.374 | 31.548 | 24.854 | 1.00 | 19.18 |
| 868 | O | ILE | B | 32 | −15.242 | 31.967 | 24.090 | 1.00 | 19.56 |
| 869 | CB | ILE | B | 32 | −12.304 | 30.411 | 24.131 | 1.00 | 15.35 |
| 870 | CG1 | ILE | B | 32 | −12.360 | 31.105 | 22.759 | 1.00 | 18.59 |
| 871 | CG2 | ILE | B | 32 | −11.580 | 29.077 | 24.004 | 1.00 | 17.99 |
| 872 | CD1 | ILE | B | 32 | −11.005 | 31.427 | 22.177 | 1.00 | 16.93 |
| 873 | N | VAL | B | 33 | −13.941 | 32.230 | 25.908 | 1.00 | 18.93 |
| 874 | CA | VAL | B | 33 | −14.435 | 33.564 | 26.218 | 1.00 | 19.22 |
| 875 | C | VAL | B | 33 | −13.315 | 34.331 | 26.889 | 1.00 | 20.35 |
| 876 | O | VAL | B | 33 | −12.408 | 33.739 | 27.469 | 1.00 | 15.75 |
| 877 | CB | VAL | B | 33 | −15.635 | 33.548 | 27.200 | 1.00 | 21.37 |
| 878 | CG1 | VAL | B | 33 | −16.806 | 32.798 | 26.591 | 1.00 | 26.48 |
| 879 | CG2 | VAL | B | 33 | −15.212 | 32.932 | 28.533 | 1.00 | 21.37 |
| 880 | N | ARG | B | 34 | −13.376 | 35.651 | 26.796 | 1.00 | 21.18 |
| 881 | CA | ARG | B | 34 | −12.381 | 36.487 | 27.445 | 1.00 | 24.58 |
| 882 | C | ARG | B | 34 | −12.975 | 36.730 | 28.828 | 1.00 | 24.64 |
| 883 | O | ARG | B | 34 | −14.169 | 37.000 | 28.957 | 1.00 | 21.51 |
| 884 | CB | ARG | B | 34 | −12.213 | 37.806 | 26.684 | 1.00 | 29.78 |
| 885 | CG | ARG | B | 34 | −10.976 | 38.594 | 27.077 | 1.00 | 39.78 |
| 886 | CD | ARG | B | 34 | −10.573 | 39.573 | 25.980 | 1.00 | 41.05 |
| 887 | NE | ARG | B | 34 | −9.261 | 40.163 | 26.236 | 1.00 | 48.23 |
| 888 | CZ | ARG | B | 34 | −9.021 | 41.088 | 27.159 | 1.00 | 51.91 |
| 889 | NH1 | ARG | B | 34 | −10.007 | 41.541 | 27.921 | 1.00 | 53.71 |
| 890 | NH2 | ARG | B | 34 | −7.791 | 41.556 | 27.327 | 1.00 | 55.04 |
| 891 | N | GLY | B | 35 | −12.154 | 36.599 | 29.864 | 1.00 | 25.59 |
| 892 | CA | GLY | B | 35 | −12.659 | 36.804 | 31.206 | 1.00 | 29.33 |
| 893 | C | GLY | B | 35 | −11.586 | 37.322 | 32.132 | 1.00 | 30.77 |
| 894 | O | GLY | B | 35 | −10.472 | 37.610 | 31.706 | 1.00 | 30.07 |
| 895 | N | GLU | B | 36 | −11.924 | 37.448 | 33.409 | 1.00 | 36.31 |
| 896 | CA | GLU | B | 36 | −10.964 | 37.932 | 34.384 | 1.00 | 37.34 |
| 897 | C | GLU | B | 36 | −11.117 | 37.209 | 35.707 | 1.00 | 36.60 |
| 898 | O | GLU | B | 36 | −12.132 | 36.562 | 35.971 | 1.00 | 35.32 |
| 899 | CB | GLU | B | 36 | −11.129 | 39.437 | 34.600 | 1.00 | 40.28 |
| 900 | CG | GLU | B | 36 | −12.540 | 39.869 | 34.956 | 1.00 | 44.80 |
| 901 | CD | GLU | B | 36 | −12.597 | 41.290 | 35.485 | 1.00 | 47.87 |
| 902 | OE1 | GLU | B | 36 | −11.984 | 42.186 | 34.866 | 1.00 | 50.53 |
| 903 | OE2 | GLU | B | 36 | −13.262 | 41.511 | 36.519 | 1.00 | 49.08 |
| 904 | N | VAL | B | 37 | −10.090 | 37.323 | 36.534 | 1.00 | 35.84 |
| 905 | CA | VAL | B | 37 | −10.087 | 36.697 | 37.842 | 1.00 | 35.44 |
| 906 | C | VAL | B | 37 | −9.054 | 37.418 | 38.687 | 1.00 | 36.12 |
| 907 | O | VAL | B | 37 | −8.061 | 37.925 | 38.164 | 1.00 | 33.45 |
| 908 | CB | VAL | B | 37 | −9.730 | 35.222 | 37.716 | 1.00 | 35.17 |
| 909 | N | LYS | B | 38 | −9.295 | 37.485 | 39.989 | 1.00 | 37.72 |
| 910 | CA | LYS | B | 38 | −8.347 | 38.137 | 40.874 | 1.00 | 39.96 |
| 911 | C | LYS | B | 38 | −7.164 | 37.205 | 41.079 | 1.00 | 40.44 |
| 912 | O | LYS | B | 38 | −7.315 | 36.100 | 41.598 | 1.00 | 42.04 |

TABLE 2-continued

| ATOM | ATOM TYPE | RESIDUE | PROTEIN # | # | X | Y | Z | OCC | B |
|---|---|---|---|---|---|---|---|---|---|
| 913 | CB | LYS | B | 38 | −8.997 | 38.466 | 42.219 | 1.00 | 41.55 |
| 914 | CG | LYS | B | 38 | −10.044 | 39.563 | 42.146 | 1.00 | 45.36 |
| 915 | CD | LYS | B | 38 | −10.377 | 40.088 | 43.535 | 1.00 | 49.10 |
| 916 | CE | LYS | B | 38 | −11.299 | 41.295 | 43.464 | 1.00 | 51.56 |
| 917 | NZ | LYS | B | 38 | −11.509 | 41.913 | 44.804 | 1.00 | 53.04 |
| 918 | N | ASP | B | 39 | −5.992 | 37.648 | 40.645 | 1.00 | 41.57 |
| 919 | CA | ASP | B | 39 | −4.774 | 36.865 | 40.786 | 1.00 | 43.82 |
| 920 | C | ASP | B | 39 | −4.065 | 37.287 | 42.068 | 1.00 | 43.65 |
| 921 | O | ASP | B | 39 | −2.959 | 36.833 | 42.365 | 1.00 | 45.19 |
| 922 | CB | ASP | B | 39 | −3.870 | 37.083 | 39.571 | 1.00 | 45.70 |
| 923 | CG | ASP | B | 39 | −3.588 | 38.547 | 39.311 | 1.00 | 48.78 |
| 924 | OD1 | ASP | B | 39 | −4.542 | 39.354 | 39.351 | 1.00 | 48.52 |
| 925 | OD2 | ASP | B | 39 | −2.415 | 38.890 | 39.056 | 1.00 | 50.44 |
| 926 | N | SER | B | 40 | −4.722 | 38.166 | 42.818 | 1.00 | 41.43 |
| 927 | CA | SER | B | 40 | −4.204 | 38.662 | 44.086 | 1.00 | 40.54 |
| 928 | C | SER | B | 40 | −5.316 | 39.466 | 44.756 | 1.00 | 39.41 |
| 929 | O | SER | B | 40 | −6.332 | 39.780 | 44.132 | 1.00 | 36.82 |
| 930 | CB | SER | B | 40 | −2.970 | 39.543 | 43.864 | 1.00 | 41.76 |
| 931 | OG | SER | B | 40 | −3.331 | 40.883 | 43.595 | 1.00 | 46.56 |
| 932 | N | PRO | B | 41 | −5.140 | 39.818 | 46.037 | 1.00 | 38.70 |
| 933 | CA | PRO | B | 41 | −6.183 | 40.584 | 46.722 | 1.00 | 35.80 |
| 934 | C | PRO | B | 41 | −6.522 | 41.942 | 46.109 | 1.00 | 33.69 |
| 935 | O | PRO | B | 41 | −7.674 | 42.374 | 46.159 | 1.00 | 33.18 |
| 936 | CB | PRO | B | 41 | −5.636 | 40.707 | 48.142 | 1.00 | 39.49 |
| 937 | CG | PRO | B | 41 | −4.149 | 40.731 | 47.924 | 1.00 | 40.69 |
| 938 | CD | PRO | B | 41 | −3.969 | 39.627 | 46.910 | 1.00 | 40.09 |
| 939 | N | ASN | B | 42 | −5.534 | 42.604 | 45.517 | 1.00 | 30.71 |
| 940 | CA | ASN | B | 42 | −5.766 | 43.924 | 44.944 | 1.00 | 30.12 |
| 941 | C | ASN | B | 42 | −5.534 | 44.043 | 43.446 | 1.00 | 27.53 |
| 942 | O | ASN | B | 42 | −5.343 | 45.143 | 42.934 | 1.00 | 23.27 |
| 943 | CB | ASN | B | 42 | −4.900 | 44.956 | 45.666 | 1.00 | 33.80 |
| 944 | CG | ASN | B | 42 | −5.143 | 44.970 | 47.157 | 1.00 | 36.93 |
| 945 | OD1 | ASN | B | 42 | −6.273 | 45.155 | 47.610 | 1.00 | 38.54 |
| 946 | ND2 | ASN | B | 42 | −4.079 | 44.773 | 47.932 | 1.00 | 42.44 |
| 947 | N | THR | B | 43 | −5.539 | 42.923 | 42.736 | 1.00 | 27.36 |
| 948 | CA | THR | B | 43 | −5.335 | 42.979 | 41.295 | 1.00 | 28.86 |
| 949 | C | THR | B | 43 | −6.167 | 41.932 | 40.576 | 1.00 | 28.42 |
| 950 | O | THR | B | 43 | −6.634 | 40.966 | 41.178 | 1.00 | 28.03 |
| 951 | CB | THR | B | 43 | −3.860 | 42.749 | 40.904 | 1.00 | 30.55 |
| 952 | OG1 | THR | B | 43 | −3.486 | 41.403 | 41.222 | 1.00 | 35.90 |
| 953 | CG2 | THR | B | 43 | −2.949 | 43.719 | 41.640 | 1.00 | 32.50 |
| 954 | N | LYS | B | 44 | −6.354 | 42.144 | 39.280 | 1.00 | 29.22 |
| 955 | CA | LYS | B | 44 | −7.104 | 41.215 | 38.451 | 1.00 | 31.74 |
| 956 | C | LYS | B | 44 | −6.326 | 40.976 | 37.172 | 1.00 | 33.64 |
| 957 | O | LYS | B | 44 | −5.469 | 41.773 | 36.796 | 1.00 | 31.42 |
| 958 | CB | LYS | B | 44 | −8.481 | 41.780 | 38.099 | 1.00 | 33.26 |
| 959 | CG | LYS | B | 44 | −9.505 | 41.694 | 39.211 | 1.00 | 37.59 |
| 960 | CD | LYS | B | 44 | −10.887 | 42.047 | 38.689 | 1.00 | 38.04 |
| 961 | CE | LYS | B | 44 | −11.959 | 41.759 | 39.722 | 1.00 | 41.94 |
| 962 | NZ | LYS | B | 44 | −13.318 | 42.100 | 39.209 | 1.00 | 45.75 |
| 963 | N | THR | B | 45 | −6.620 | 39.864 | 36.513 | 1.00 | 33.14 |
| 964 | CA | THR | B | 45 | −5.968 | 39.529 | 35.259 | 1.00 | 36.03 |
| 965 | C | THR | B | 45 | −7.069 | 39.063 | 34.315 | 1.00 | 35.75 |
| 966 | O | THR | B | 45 | −7.937 | 38.282 | 34.705 | 1.00 | 34.33 |
| 967 | CB | THR | B | 45 | −4.917 | 38.410 | 35.446 | 1.00 | 38.11 |
| 968 | OG1 | THR | B | 45 | −4.216 | 38.208 | 34.214 | 1.00 | 41.48 |
| 969 | CG2 | THR | B | 45 | −5.581 | 37.104 | 35.872 | 1.00 | 38.31 |
| 970 | N | THR | B | 46 | −7.051 | 39.573 | 33.088 | 1.00 | 35.53 |
| 971 | CA | THR | B | 46 | −8.053 | 39.209 | 32.094 | 1.00 | 34.31 |
| 972 | C | THR | B | 46 | −7.408 | 38.328 | 31.030 | 1.00 | 33.33 |
| 973 | O | THR | B | 46 | −6.422 | 38.720 | 30.415 | 1.00 | 36.24 |
| 974 | CB | THR | B | 46 | −8.645 | 40.468 | 31.418 | 1.00 | 37.28 |
| 975 | OG1 | THR | B | 46 | −9.184 | 41.341 | 32.418 | 1.00 | 40.63 |
| 976 | CG2 | THR | B | 46 | −9.753 | 40.087 | 30.449 | 1.00 | 36.65 |
| 977 | N | GLY | B | 47 | −7.965 | 37.139 | 30.816 | 1.00 | 28.76 |
| 978 | CA | GLY | B | 47 | −7.404 | 36.237 | 29.828 | 1.00 | 21.69 |
| 979 | C | GLY | B | 47 | −8.446 | 35.428 | 29.075 | 1.00 | 18.25 |
| 980 | O | GLY | B | 47 | −9.636 | 35.718 | 29.141 | 1.00 | 19.67 |
| 981 | N | ILE | B | 48 | −7.977 | 34.412 | 28.354 | 1.00 | 18.27 |
| 982 | CA | ILE | B | 48 | −8.835 | 33.528 | 27.567 | 1.00 | 17.81 |
| 983 | C | ILE | B | 48 | −9.165 | 32.281 | 28.383 | 1.00 | 16.83 |
| 984 | O | ILE | B | 48 | −8.268 | 31.574 | 28.836 | 1.00 | 19.68 |
| 985 | CB | ILE | B | 48 | −8.123 | 33.098 | 26.267 | 1.00 | 18.21 |
| 986 | CG1 | ILE | B | 48 | −7.826 | 34.331 | 25.406 | 1.00 | 16.82 |
| 987 | CG2 | ILE | B | 48 | −8.992 | 32.107 | 25.488 | 1.00 | 18.65 |
| 988 | CD1 | ILE | B | 48 | −9.057 | 35.035 | 24.896 | 1.00 | 21.03 |

TABLE 2-continued

| ATOM | ATOM TYPE | RESIDUE | PROTEIN # | # | X | Y | Z | OCC | B |
|---|---|---|---|---|---|---|---|---|---|
| 989 | N | PHE | B | 49 | −10.451 | 32.006 | 28.558 | 1.00 | 16.18 |
| 990 | CA | PHE | B | 49 | −10.863 | 30.853 | 29.339 | 1.00 | 15.10 |
| 991 | C | PHE | B | 49 | −11.708 | 29.890 | 28.536 | 1.00 | 16.71 |
| 992 | O | PHE | B | 49 | −12.385 | 30.284 | 27.591 | 1.00 | 17.17 |
| 993 | CB | PHE | B | 49 | −11.670 | 31.298 | 30.555 | 1.00 | 17.54 |
| 994 | CG | PHE | B | 49 | −10.888 | 32.116 | 31.540 | 1.00 | 18.64 |
| 995 | CD1 | PHE | B | 49 | −10.605 | 33.454 | 31.286 | 1.00 | 20.81 |
| 996 | CD2 | PHE | B | 49 | −10.436 | 31.545 | 32.726 | 1.00 | 20.58 |
| 997 | CE1 | PHE | B | 49 | −9.883 | 34.214 | 32.199 | 1.00 | 23.63 |
| 998 | CE2 | PHE | B | 49 | −9.711 | 32.299 | 33.650 | 1.00 | 25.37 |
| 999 | CZ | PHE | B | 49 | −9.435 | 33.636 | 33.383 | 1.00 | 21.55 |
| 1000 | N | ILE | B | 50 | −11.666 | 28.622 | 28.923 | 1.00 | 15.50 |
| 1001 | CA | ILE | B | 50 | −12.488 | 27.627 | 28.260 | 1.00 | 16.84 |
| 1002 | C | ILE | B | 50 | −13.875 | 27.765 | 28.890 | 1.00 | 18.22 |
| 1003 | O | ILE | B | 50 | −14.034 | 27.592 | 30.100 | 1.00 | 20.21 |
| 1004 | CB | ILE | B | 50 | −11.942 | 26.206 | 28.492 | 1.00 | 16.56 |
| 1005 | CG1 | ILE | B | 50 | −10.582 | 26.062 | 27.802 | 1.00 | 19.70 |
| 1006 | CG2 | ILE | B | 50 | −12.944 | 25.169 | 27.973 | 1.00 | 17.94 |
| 1007 | CD1 | ILE | B | 50 | −9.943 | 24.687 | 27.959 | 1.00 | 21.65 |
| 1008 | N | LYS | B | 51 | −14.871 | 28.095 | 28.074 | 1.00 | 16.57 |
| 1009 | CA | LYS | B | 51 | −16.236 | 28.273 | 28.568 | 1.00 | 18.28 |
| 1010 | C | LYS | B | 51 | −17.084 | 27.023 | 28.373 | 1.00 | 20.49 |
| 1011 | O | LYS | B | 51 | −18.094 | 26.825 | 29.053 | 1.00 | 18.75 |
| 1012 | CB | LYS | B | 51 | −16.906 | 29.451 | 27.855 | 1.00 | 22.98 |
| 1013 | CG | LYS | B | 51 | −18.158 | 29.963 | 28.555 | 1.00 | 27.57 |
| 1014 | CD | LYS | B | 51 | −17.828 | 30.461 | 29.958 | 1.00 | 34.68 |
| 1015 | CE | LYS | B | 51 | −19.071 | 30.960 | 30.689 | 1.00 | 38.53 |
| 1016 | NZ | LYS | B | 51 | −18.740 | 31.458 | 32.059 | 1.00 | 39.98 |
| 1017 | N | GLY | B | 52 | −16.681 | 26.179 | 27.433 | 1.00 | 20.02 |
| 1018 | CA | GLY | B | 52 | −17.440 | 24.969 | 27.194 | 1.00 | 19.97 |
| 1019 | C | GLY | B | 52 | −16.638 | 23.970 | 26.398 | 1.00 | 20.13 |
| 1020 | O | GLY | B | 52 | −15.716 | 24.345 | 25.672 | 1.00 | 18.09 |
| 1021 | N | ILE | B | 53 | −16.990 | 22.698 | 26.545 | 1.00 | 19.27 |
| 1022 | CA | ILE | B | 53 | −16.327 | 21.613 | 25.834 | 1.00 | 18.30 |
| 1023 | C | ILE | B | 53 | −17.401 | 20.800 | 25.109 | 1.00 | 20.38 |
| 1024 | O | ILE | B | 53 | −18.428 | 20.467 | 25.692 | 1.00 | 21.35 |
| 1025 | CB | ILE | B | 53 | −15.562 | 20.707 | 26.821 | 1.00 | 20.43 |
| 1026 | CG1 | ILE | B | 53 | −14.352 | 21.470 | 27.375 | 1.00 | 20.36 |
| 1027 | CG2 | ILE | B | 53 | −15.127 | 19.414 | 26.138 | 1.00 | 21.65 |
| 1028 | CD1 | ILE | B | 53 | −13.585 | 20.720 | 28.439 | 1.00 | 27.59 |
| 1029 | N | VAL | B | 54 | −17.165 | 20.492 | 23.837 | 1.00 | 18.61 |
| 1030 | CA | VAL | B | 54 | −18.134 | 19.724 | 23.053 | 1.00 | 18.93 |
| 1031 | C | VAL | B | 54 | −18.052 | 18.235 | 23.386 | 1.00 | 18.08 |
| 1032 | O | VAL | B | 54 | −16.986 | 17.630 | 23.313 | 1.00 | 18.41 |
| 1033 | CB | VAL | B | 54 | −17.886 | 19.897 | 21.536 | 1.00 | 21.36 |
| 1034 | CG1 | VAL | B | 54 | −18.914 | 19.091 | 20.742 | 1.00 | 22.71 |
| 1035 | CG2 | VAL | B | 54 | −17.949 | 21.372 | 21.165 | 1.00 | 18.66 |
| 1036 | N | PRO | B | 55 | −19.186 | 17.620 | 23.750 | 1.00 | 21.89 |
| 1037 | CA | PRO | B | 55 | −19.134 | 16.193 | 24.073 | 1.00 | 21.85 |
| 1038 | C | PRO | B | 55 | −18.618 | 15.332 | 22.919 | 1.00 | 23.12 |
| 1039 | O | PRO | B | 55 | −18.953 | 15.563 | 21.753 | 1.00 | 22.89 |
| 1040 | CB | PRO | B | 55 | −20.581 | 15.871 | 24.473 | 1.00 | 25.61 |
| 1041 | CG | PRO | B | 55 | −21.391 | 16.923 | 23.770 | 1.00 | 29.51 |
| 1042 | CD | PRO | B | 55 | −20.543 | 18.159 | 23.927 | 1.00 | 21.25 |
| 1043 | N | ASP | B | 56 | −17.785 | 14.359 | 23.268 | 1.00 | 23.93 |
| 1044 | CA | ASP | B | 56 | −17.188 | 13.417 | 22.321 | 1.00 | 27.16 |
| 1045 | C | ASP | B | 56 | −16.130 | 14.030 | 21.405 | 1.00 | 26.33 |
| 1046 | O | ASP | B | 56 | −15.704 | 13.401 | 20.438 | 1.00 | 24.15 |
| 1047 | CB | ASP | B | 56 | −18.269 | 12.754 | 21.460 | 1.00 | 32.02 |
| 1048 | CG | ASP | B | 56 | −17.758 | 11.518 | 20.745 | 1.00 | 36.24 |
| 1049 | OD1 | ASP | B | 56 | −18.223 | 11.235 | 19.621 | 1.00 | 43.25 |
| 1050 | OD2 | ASP | B | 56 | −16.891 | 10.822 | 21.315 | 1.00 | 38.06 |
| 1051 | N | SER | B | 57 | −15.702 | 15.250 | 21.711 | 1.00 | 23.57 |
| 1052 | CA | SER | B | 57 | −14.686 | 15.924 | 20.907 | 1.00 | 22.19 |
| 1053 | C | SER | B | 57 | −13.306 | 15.617 | 21.477 | 1.00 | 21.26 |
| 1054 | O | SER | B | 57 | −13.186 | 15.040 | 22.555 | 1.00 | 20.83 |
| 1055 | CB | SER | B | 57 | −14.902 | 17.436 | 20.945 | 1.00 | 23.47 |
| 1056 | OG | SER | B | 57 | −14.629 | 17.931 | 22.249 | 1.00 | 19.36 |
| 1057 | N | PRO | B | 58 | −12.240 | 15.986 | 20.748 | 1.00 | 20.43 |
| 1058 | CA | PRO | B | 58 | −10.888 | 15.733 | 21.244 | 1.00 | 21.11 |
| 1059 | C | PRO | B | 58 | −10.692 | 16.364 | 22.629 | 1.00 | 19.81 |
| 1060 | O | PRO | B | 58 | −10.087 | 15.765 | 23.516 | 1.00 | 20.58 |
| 1061 | CB | PRO | B | 58 | −10.008 | 16.392 | 20.185 | 1.00 | 22.60 |
| 1062 | CG | PRO | B | 58 | −10.790 | 16.150 | 18.920 | 1.00 | 20.70 |
| 1063 | CD | PRO | B | 58 | −12.211 | 16.467 | 19.353 | 1.00 | 21.41 |
| 1064 | N | ALA | B | 59 | −11.212 | 17.576 | 22.809 | 1.00 | 18.66 |

TABLE 2-continued

| ATOM | ATOM TYPE | RESIDUE | PROTEIN # | # | X | Y | Z | OCC | B |
|---|---|---|---|---|---|---|---|---|---|
| 1065 | CA | ALA | B | 59 | −11.073 | 18.275 | 24.088 | 1.00 | 18.36 |
| 1066 | C | ALA | B | 59 | −11.731 | 17.491 | 25.214 | 1.00 | 19.71 |
| 1067 | O | ALA | B | 59 | −11.197 | 17.402 | 26.321 | 1.00 | 20.25 |
| 1068 | CB | ALA | B | 59 | −11.689 | 19.667 | 23.999 | 1.00 | 18.61 |
| 1069 | N | HIS | B | 60 | −12.896 | 16.925 | 24.923 | 1.00 | 19.26 |
| 1070 | CA | HIS | B | 60 | −13.633 | 16.156 | 25.917 | 1.00 | 21.47 |
| 1071 | C | HIS | B | 60 | −12.964 | 14.808 | 26.183 | 1.00 | 23.57 |
| 1072 | O | HIS | B | 60 | −12.751 | 14.429 | 27.336 | 1.00 | 25.22 |
| 1073 | CB | HIS | B | 60 | −15.075 | 15.953 | 25.434 | 1.00 | 22.14 |
| 1074 | CG | HIS | B | 60 | −15.948 | 15.231 | 26.411 | 1.00 | 26.58 |
| 1075 | ND1 | HIS | B | 60 | −15.946 | 15.512 | 27.761 | 1.00 | 30.15 |
| 1076 | CD2 | HIS | B | 60 | −16.881 | 14.266 | 26.229 | 1.00 | 26.02 |
| 1077 | CE1 | HIS | B | 60 | −16.839 | 14.752 | 28.368 | 1.00 | 27.82 |
| 1078 | NE2 | HIS | B | 60 | −17.421 | 13.987 | 27.462 | 1.00 | 29.87 |
| 1079 | N | LEU | B | 61 | −12.624 | 14.094 | 25.116 | 1.00 | 23.66 |
| 1080 | CA | LEU | B | 61 | −11.991 | 12.785 | 25.244 | 1.00 | 25.54 |
| 1081 | C | LEU | B | 61 | −10.624 | 12.881 | 25.917 | 1.00 | 26.58 |
| 1082 | O | LEU | B | 61 | −10.205 | 11.964 | 26.629 | 1.00 | 22.89 |
| 1083 | CB | LEU | B | 61 | −11.861 | 12.128 | 23.864 | 1.00 | 26.67 |
| 1084 | CG | LEU | B | 61 | −13.187 | 11.862 | 23.144 | 1.00 | 29.82 |
| 1085 | CD1 | LEU | B | 61 | −12.917 | 11.300 | 21.761 | 1.00 | 31.31 |
| 1086 | CD2 | LEU | B | 61 | −14.038 | 10.895 | 23.962 | 1.00 | 33.02 |
| 1087 | N | CYS | B | 62 | −9.936 | 13.995 | 25.686 | 1.00 | 25.40 |
| 1088 | CA | CYS | B | 62 | −8.625 | 14.235 | 26.280 | 1.00 | 29.56 |
| 1089 | C | CYS | B | 62 | −8.679 | 14.057 | 27.796 | 1.00 | 28.96 |
| 1090 | O | CYS | B | 62 | −7.819 | 13.400 | 28.384 | 1.00 | 30.95 |
| 1091 | CB | CYS | B | 62 | −8.156 | 15.652 | 25.932 | 1.00 | 28.61 |
| 1092 | SG | CYS | B | 62 | −7.016 | 16.386 | 27.109 | 1.00 | 33.39 |
| 1093 | N | GLY | B | 63 | −9.691 | 14.652 | 28.422 | 1.00 | 27.61 |
| 1094 | CA | GLY | B | 63 | −9.851 | 14.540 | 29.862 | 1.00 | 29.92 |
| 1095 | C | GLY | B | 63 | −8.927 | 15.411 | 30.696 | 1.00 | 30.81 |
| 1096 | O | GLY | B | 63 | −9.049 | 15.453 | 31.921 | 1.00 | 34.63 |
| 1097 | N | ARG | B | 64 | −8.009 | 16.116 | 30.048 | 1.00 | 29.20 |
| 1098 | CA | ARG | B | 64 | −7.078 | 16.965 | 30.779 | 1.00 | 29.14 |
| 1099 | C | ARG | B | 64 | −7.418 | 18.447 | 30.687 | 1.00 | 25.81 |
| 1100 | O | ARG | B | 64 | −6.640 | 19.297 | 31.125 | 1.00 | 24.65 |
| 1101 | CB | ARG | B | 64 | −5.649 | 16.732 | 30.282 | 1.00 | 31.02 |
| 1102 | CG | ARG | B | 64 | −5.172 | 15.288 | 30.413 | 1.00 | 38.59 |
| 1103 | CD | ARG | B | 64 | −5.634 | 14.666 | 31.727 | 1.00 | 41.71 |
| 1104 | NE | ARG | B | 64 | −5.439 | 15.566 | 32.860 | 1.00 | 48.58 |
| 1105 | CZ | ARG | B | 64 | −5.844 | 15.306 | 34.099 | 1.00 | 51.15 |
| 1106 | NH1 | ARG | B | 64 | −6.468 | 14.166 | 34.369 | 1.00 | 53.36 |
| 1107 | NH2 | ARG | B | 64 | −5.631 | 16.187 | 35.068 | 1.00 | 51.92 |
| 1108 | N | LEU | B | 65 | −8.575 | 18.748 | 30.107 | 1.00 | 23.15 |
| 1109 | CA | LEU | B | 65 | −9.027 | 20.123 | 29.960 | 1.00 | 22.91 |
| 1110 | C | LEU | B | 65 | −10.330 | 20.291 | 30.722 | 1.00 | 25.57 |
| 1111 | O | LEU | B | 65 | −11.240 | 19.471 | 30.606 | 1.00 | 26.12 |
| 1112 | CB | LEU | B | 65 | −9.250 | 20.466 | 28.486 | 1.00 | 24.95 |
| 1113 | CG | LEU | B | 65 | −8.013 | 20.532 | 27.591 | 1.00 | 26.47 |
| 1114 | CD1 | LEU | B | 65 | −8.439 | 20.780 | 26.151 | 1.00 | 27.28 |
| 1115 | CD2 | LEU | B | 65 | −7.087 | 21.647 | 28.078 | 1.00 | 25.96 |
| 1116 | N | LYS | B | 66 | −10.412 | 21.356 | 31.508 | 1.00 | 21.71 |
| 1117 | CA | LYS | B | 66 | −11.605 | 21.615 | 32.292 | 1.00 | 21.66 |
| 1118 | C | LYS | B | 66 | −12.213 | 22.958 | 31.950 | 1.00 | 21.49 |
| 1119 | O | LYS | B | 66 | −11.500 | 23.910 | 31.624 | 1.00 | 19.66 |
| 1120 | CB | LYS | B | 66 | −11.276 | 21.590 | 33.790 | 1.00 | 25.77 |
| 1121 | CG | LYS | B | 66 | −11.123 | 20.196 | 34.389 | 1.00 | 34.04 |
| 1122 | CD | LYS | B | 66 | −9.955 | 19.433 | 33.791 | 1.00 | 40.20 |
| 1123 | CE | LYS | B | 66 | −9.835 | 18.041 | 34.407 | 1.00 | 43.80 |
| 1124 | NZ | LYS | B | 66 | −8.638 | 17.302 | 33.908 | 1.00 | 45.22 |
| 1125 | N | VAL | B | 67 | −13.538 | 23.029 | 32.005 | 1.00 | 20.98 |
| 1126 | CA | VAL | B | 67 | −14.211 | 24.290 | 31.763 | 1.00 | 19.38 |
| 1127 | C | VAL | B | 67 | −13.665 | 25.162 | 32.883 | 1.00 | 20.90 |
| 1128 | O | VAL | B | 67 | −13.542 | 24.701 | 34.021 | 1.00 | 20.35 |
| 1129 | CB | VAL | B | 67 | −15.739 | 24.158 | 31.923 | 1.00 | 22.63 |
| 1130 | CG1 | VAL | B | 67 | −16.394 | 25.523 | 31.812 | 1.00 | 24.38 |
| 1131 | CG2 | VAL | B | 67 | −16.287 | 23.217 | 30.872 | 1.00 | 20.33 |
| 1132 | N | GLY | B | 68 | −13.315 | 26.403 | 32.563 | 1.00 | 18.63 |
| 1133 | CA | GLY | B | 68 | −12.767 | 27.294 | 33.572 | 1.00 | 20.83 |
| 1134 | C | GLY | B | 68 | −11.259 | 27.465 | 33.469 | 1.00 | 18.18 |
| 1135 | O | GLY | B | 68 | −10.698 | 28.399 | 34.049 | 1.00 | 20.13 |
| 1136 | N | ASP | B | 69 | −10.599 | 26.563 | 32.743 | 1.00 | 17.28 |
| 1137 | CA | ASP | B | 69 | −9.150 | 26.633 | 32.552 | 1.00 | 17.52 |
| 1138 | C | ASP | B | 69 | −8.796 | 27.842 | 31.703 | 1.00 | 17.47 |
| 1139 | O | ASP | B | 69 | −9.576 | 28.247 | 30.845 | 1.00 | 17.96 |
| 1140 | CB | ASP | B | 69 | −8.621 | 25.396 | 31.817 | 1.00 | 17.68 |

TABLE 2-continued

| ATOM | ATOM TYPE | RESIDUE | PROTEIN | # | X | Y | Z | OCC | B |
|---|---|---|---|---|---|---|---|---|---|
| 1141 | CG | ASP | B | 69 | −8.537 | 24.172 | 32.695 | 1.00 | 19.27 |
| 1142 | OD1 | ASP | B | 69 | −8.648 | 24.306 | 33.929 | 1.00 | 19.80 |
| 1143 | OD2 | ASP | B | 69 | −8.335 | 23.070 | 32.139 | 1.00 | 20.19 |
| 1144 | N | ARG | B | 70 | −7.619 | 28.413 | 31.934 | 1.00 | 15.13 |
| 1145 | CA | ARG | B | 70 | −7.170 | 29.548 | 31.142 | 1.00 | 16.62 |
| 1146 | C | ARG | B | 70 | −6.159 | 29.067 | 30.103 | 1:00 | 18.06 |
| 1147 | O | ARG | B | 70 | −5.355 | 28.179 | 30.376 | 1:00 | 19.92 |
| 1148 | CB | ARG | B | 70 | −6.506 | 30.613 | 32.025 | 1.00 | 18.90 |
| 1149 | CG | ARG | B | 70 | −5.978 | 31.784 | 31.211 | 1.00 | 26.36 |
| 1150 | CD | ARG | B | 70 | −5.344 | 32.889 | 32.059 | 1.00 | 33.45 |
| 1151 | NE | ARG | B | 70 | −4.820 | 33.941 | 31.189 | 1.00 | 36.92 |
| 1152 | CZ | ARG | B | 70 | −4.241 | 35.061 | 31.604 | 1.00 | 35.90 |
| 1153 | NH1 | ARG | B | 70 | −4.097 | 35.305 | 32.898 | 1.00 | 42.41 |
| 1154 | NH2 | ARG | B | 70 | −3.812 | 35.947 | 30.715 | 1.00 | 41.50 |
| 1155 | N | ILE | B | 71 | −6.210 | 29.639 | 28.905 | 1.00 | 15.56 |
| 1156 | CA | ILE | B | 71 | −5.257 | 29.274 | 27.865 | 1.00 | 14.32 |
| 1157 | C | ILE | B | 71 | −4.212 | 30.392 | 27.863 | 1.00 | 16.65 |
| 1158 | O | ILE | B | 71 | −4.543 | 31.555 | 27.610 | 1.00 | 16.91 |
| 1159 | CB | ILE | B | 71 | −5.946 | 29.185 | 26.476 | 1.00 | 17.28 |
| 1160 | CG1 | ILE | B | 71 | −7.042 | 28.114 | 26.509 | 1.00 | 18.00 |
| 1161 | CG2 | ILE | B | 71 | −4.922 | 28.840 | 25.404 | 1.00 | 16.14 |
| 1162 | CD1 | ILE | B | 71 | −7.851 | 28.000 | 25.224 | 1.00 | 19.89 |
| 1163 | N | LEU | B | 72 | −2.964 | 30.048 | 28.178 | 1.00 | 14.97 |
| 1164 | CA | LEU | B | 72 | −1.893 | 31.046 | 28.218 | 1.00 | 18.76 |
| 1165 | C | LEU | B | 72 | −1.234 | 31.216 | 26.856 | 1.00 | 19.13 |
| 1166 | O | LEU | B | 72 | −0.857 | 32.325 | 26.473 | 1.00 | 21.43 |
| 1167 | CB | LEU | B | 72 | −0.838 | 30.663 | 29.266 | 1.00 | 19.34 |
| 1168 | CG | LEU | B | 72 | −1.324 | 30.554 | 30.720 | 1.00 | 21.53 |
| 1169 | CD1 | LEU | B | 72 | −0.152 | 30.196 | 31.632 | 1.00 | 22.97 |
| 1170 | CD2 | LEU | B | 72 | −1.953 | 31.863 | 31.170 | 1.00 | 22.47 |
| 1171 | N | SER | B | 73 | −1.085 | 30.116 | 26.131 | 1.00 | 17.13 |
| 1172 | CA | SER | B | 73 | −0.492 | 30.173 | 24.801 | 1.00 | 20.23 |
| 1173 | C | SER | B | 73 | −1.006 | 29.025 | 23.945 | 1.00 | 20.07 |
| 1174 | O | SER | B | 73 | −1.480 | 28.005 | 24.462 | 1.00 | 15.74 |
| 1175 | CB | SER | B | 73 | 1.040 | 30.130 | 24.873 | 1.00 | 20.86 |
| 1176 | OG | SER | B | 73 | 1.524 | 28.860 | 25.262 | 1.00 | 21.43 |
| 1177 | N | LEU | B | 74 | −0.919 | 29.215 | 22.634 | 1.00 | 19.20 |
| 1178 | CA | LEU | B | 74 | −1.365 | 28.229 | 21.658 | 1.00 | 22.45 |
| 1179 | C | LEU | B | 74 | −0.231 | 28.043 | 20.663 | 1.00 | 24.68 |
| 1180 | O | LEU | B | 74 | 0.161 | 28.988 | 19.976 | 1.00 | 27.80 |
| 1181 | CB | LEU | B | 74 | −2.626 | 28.735 | 20.944 | 1.00 | 25.18 |
| 1182 | CG | LEU | B | 74 | −3.280 | 27.895 | 19.837 | 1.00 | 28.01 |
| 1183 | CD1 | LEU | B | 74 | −2.442 | 27.916 | 18.572 | 1.00 | 34.13 |
| 1184 | CD2 | LEU | B | 74 | −3.472 | 26.485 | 20.330 | 1.00 | 32.72 |
| 1185 | N | ASN | B | 75 | 0.298 | 26.827 | 20.597 | 1.00 | 24.79 |
| 1186 | CA | ASN | B | 75 | 1.406 | 26.522 | 19.705 | 1.00 | 30.33 |
| 1187 | C | ASN | B | 75 | 2.549 | 27.508 | 19.895 | 1.00 | 32.19 |
| 1188 | O | ASN | B | 75 | 3.171 | 27.955 | 18.930 | 1.00 | 34.42 |
| 1189 | CB | ASN | B | 75 | 0.944 | 26.526 | 18.246 | 1.00 | 32.11 |
| 1190 | CG | ASN | B | 75 | 0.024 | 25.371 | 17.932 | 1.00 | 33.87 |
| 1191 | OD1 | ASN | B | 75 | 0.168 | 24.284 | 18.490 | 1.00 | 29.58 |
| 1192 | ND2 | ASN | B | 75 | −0.921 | 25.591 | 17.025 | 1.00 | 36.42 |
| 1193 | N | GLY | B | 76 | 2.807 | 27.854 | 21.151 | 1.00 | 32.23 |
| 1194 | CA | GLY | B | 76 | 3.891 | 28.764 | 21.461 | 1.00 | 34.09 |
| 1195 | C | GLY | B | 76 | 3.549 | 30.237 | 21.413 | 1.00 | 33.15 |
| 1196 | O | GLY | B | 76 | 4.326 | 31.061 | 21.890 | 1.00 | 36.47 |
| 1197 | N | LYS | B | 77 | 2.401 | 30.581 | 20.838 | 1.00 | 31.85 |
| 1198 | CA | LYS | B | 77 | 2.007 | 31.981 | 20.761 | 1.00 | 29.73 |
| 1199 | C | LYS | B | 77 | 1.224 | 32.415 | 21.987 | 1.00 | 28.44 |
| 1200 | O | LYS | B | 77 | 0.218 | 31.804 | 22.346 | 1.00 | 23.91 |
| 1201 | CB | LYS | B | 77 | 1.168 | 32.249 | 19.512 | 1.00 | 33.24 |
| 1202 | CG | LYS | B | 77 | 0.770 | 33.713 | 19.368 | 1.00 | 39.06 |
| 1203 | CD | LYS | B | 77 | 0.124 | 33.988 | 18.024 | 1.00 | 42.55 |
| 1204 | CE | LYS | B | 77 | −0.105 | 35.478 | 17.818 | 1.00 | 44.99 |
| 1205 | NZ | LYS | B | 77 | −0.456 | 35.773 | 16.400 | 1.00 | 47.67 |
| 1206 | N | ASP | B | 78 | 1.698 | 33.479 | 22.624 | 1.00 | 25.87 |
| 1207 | CA | ASP | B | 78 | 1.051 | 34.022 | 23.806 | 1.00 | 28.01 |
| 1208 | C | ASP | B | 78 | −0.309 | 34.613 | 23.432 | 1.00 | 27.74 |
| 1209 | O | ASP | B | 78 | −0.402 | 35.465 | 22.549 | 1.00 | 26.76 |
| 1210 | CB | ASP | B | 78 | 1.962 | 35.088 | 24.430 | 1.00 | 30.69 |
| 1211 | CG | ASP | B | 78 | 1.257 | 35.931 | 25.464 | 1.00 | 32.77 |
| 1212 | OD1 | ASP | B | 78 | 0.468 | 35.376 | 26.249 | 1.00 | 30.82 |
| 1213 | OD2 | ASP | B | 78 | 1.503 | 37.158 | 25.497 | 1.00 | 37.89 |
| 1214 | N | VAL | B | 79 | −1.367 | 34.144 | 24.090 | 1.00 | 24.51 |
| 1215 | CA | VAL | B | 79 | −2.712 | 34.642 | 23.809 | 1.00 | 21.36 |
| 1216 | C | VAL | B | 79 | −3.354 | 35.282 | 25.035 | 1.00 | 23.50 |

TABLE 2-continued

| ATOM | ATOM TYPE | RESIDUE | PROTEIN # | # | X | Y | Z | OCC | B |
|---|---|---|---|---|---|---|---|---|---|
| 1217 | O | VAL | B | 79 | −4.557 | 35.537 | 25.055 | 1.00 | 22.14 |
| 1218 | CB | VAL | B | 79 | −3.639 | 33.510 | 23.297 | 1.00 | 24.07 |
| 1219 | CG1 | VAL | B | 79 | −3.176 | 33.046 | 21.927 | 1.00 | 22.30 |
| 1220 | CG2 | VAL | B | 79 | −3.639 | 32.336 | 24.290 | 1.00 | 22.12 |
| 1221 | N | ARG | B | 80 | −2.543 | 35.557 | 26.050 | 1.00 | 23.55 |
| 1222 | CA | ARG | B | 80 | −3.046 | 36.160 | 27.276 | 1.00 | 26.70 |
| 1223 | C | ARG | B | 80 | −3.896 | 37.403 | 27.024 | 1.00 | 25.83 |
| 1224 | O | ARG | B | 80 | −4.897 | 37.617 | 27.702 | 1.00 | 28.77 |
| 1225 | CB | ARG | B | 80 | −1.882 | 36.502 | 28.211 | 1.00 | 28.52 |
| 1226 | CG | ARG | B | 80 | −1.123 | 35.283 | 28.739 | 1.00 | 33.22 |
| 1227 | CD | ARG | B | 80 | 0.051 | 35.716 | 29.603 | 1.00 | 36.26 |
| 1228 | NE | ARG | B | 80 | 0.794 | 34.592 | 30.168 | 1.00 | 39.03 |
| 1229 | CZ | ARG | B | 80 | 1.483 | 33.703 | 29.457 | 1.00 | 39.63 |
| 1230 | NH1 | ARG | B | 80 | 1.532 | 33.793 | 28.133 | 1.00 | 39.40 |
| 1231 | NH2 | ARG | B | 80 | 2.136 | 32.725 | 30.072 | 1.00 | 40.94 |
| 1232 | N | ASN | B | 81 | −3.508 | 38.222 | 26.050 | 1.00 | 25.88 |
| 1233 | CA | ASN | B | 81 | −4.269 | 39.430 | 25.749 | 1.00 | 26.84 |
| 1234 | C | ASN | B | 81 | −4.958 | 39.440 | 24.388 | 1.00 | 26.30 |
| 1235 | O | ASN | B | 81 | −5.301 | 40.502 | 23.871 | 1.00 | 24.53 |
| 1236 | CB | ASN | B | 81 | −3.375 | 40.665 | 25.875 | 1.00 | 32.54 |
| 1237 | CG | ASN | B | 81 | −3.249 | 41.140 | 27.307 | 1.00 | 37.02 |
| 1238 | OD1 | ASN | B | 81 | −2.639 | 40.476 | 28.141 | 1.00 | 37.65 |
| 1239 | ND2 | ASN | B | 81 | −3.844 | 42.290 | 27.603 | 1.00 | 41.90 |
| 1240 | N | SER | B | 82 | −5.185 | 38.259 | 23.822 | 1.00 | 23.95 |
| 1241 | CA | SER | B | 82 | −5.828 | 38.160 | 22.517 | 1.00 | 21.52 |
| 1242 | C | SER | B | 82 | −7.347 | 38.256 | 22.576 | 1.00 | 20.97 |
| 1243 | O | SER | B | 82 | −7.970 | 37.972 | 23.600 | 1.00 | 18.51 |
| 1244 | CB | SER | B | 82 | −5.450 | 36.837 | 21.837 | 1.00 | 24.21 |
| 1245 | OG | SER | B | 82 | −4.055 | 36.751 | 21.602 | 1.00 | 26.69 |
| 1246 | N | THR | B | 83 | −7.941 | 38.675 | 21.466 | 1.00 | 19.25 |
| 1247 | CA | THR | B | 83 | −9.388 | 38.745 | 21.380 | 1.00 | 19.88 |
| 1248 | C | THR | B | 83 | −9.792 | 37.285 | 21.170 | 1.00 | 18.77 |
| 1249 | O | THR | B | 83 | −8.952 | 36.457 | 20.811 | 1.00 | 19.91 |
| 1250 | CB | THR | B | 83 | −9.846 | 39.573 | 20.161 | 1.00 | 22.91 |
| 1251 | OG1 | THR | B | 83 | −9.322 | 38.981 | 18.964 | 1.00 | 23.18 |
| 1252 | CG2 | THR | B | 83 | −9.342 | 41.009 | 20.269 | 1.00 | 23.89 |
| 1253 | N | GLU | B | 84 | −11.058 | 36.963 | 21.397 | 1.00 | 18.96 |
| 1254 | CA | GLU | B | 84 | −11.508 | 35.593 | 21.210 | 1.00 | 20.79 |
| 1255 | C | GLU | B | 84 | −11.350 | 35.177 | 19.757 | 1.00 | 20.89 |
| 1256 | O | GLU | B | 84 | −10.814 | 34.109 | 19.462 | 1.00 | 18.19 |
| 1257 | CB | GLU | B | 84 | −12.970 | 35.436 | 21.627 | 1.00 | 23.07 |
| 1258 | CG | GLU | B | 84 | −13.222 | 35.709 | 23.096 | 1.00 | 27.14 |
| 1259 | CD | GLU | B | 84 | −13.747 | 37.105 | 23.347 | 1.00 | 28.72 |
| 1260 | OE1 | GLU | B | 84 | −13.283 | 38.048 | 22.673 | 1.00 | 30.70 |
| 1261 | OE2 | GLU | B | 84 | −14.619 | 37.257 | 24.227 | 1.00 | 34.13 |
| 1262 | N | GLN | B | 85 | −11.804 | 36.032 | 18.848 | 1.00 | 20.20 |
| 1263 | CA | GLN | B | 85 | −11.715 | 35.718 | 17.426 | 1.00 | 20.93 |
| 1264 | C | GLN | B | 85 | −10.285 | 35.455 | 16.982 | 1.00 | 20.21 |
| 1265 | O | GLN | B | 85 | −10.043 | 34.580 | 16.151 | 1.00 | 23.17 |
| 1266 | CB | GLN | B | 85 | −12.306 | 36.846 | 16.582 | 1.00 | 22.70 |
| 1267 | CG | GLN | B | 85 | −12.443 | 36.463 | 15.112 | 1.00 | 25.03 |
| 1268 | CD | GLN | B | 85 | −13.324 | 35.247 | 14.926 | 1.00 | 20.74 |
| 1269 | OE1 | GLN | B | 85 | −14.478 | 35.236 | 15.349 | 1.00 | 24.85 |
| 1270 | NE2 | GLN | B | 85 | −12.785 | 34.213 | 14.295 | 1.00 | 23.78 |
| 1271 | N | ALA | B | 86 | −9.337 | 36.214 | 17.524 | 1.00 | 21.23 |
| 1272 | CA | ALA | B | 86 | −7.935 | 36.033 | 17.169 | 1.00 | 22.12 |
| 1273 | C | ALA | B | 86 | −7.470 | 34.623 | 17.517 | 1.00 | 23.39 |
| 1274 | O | ALA | B | 86 | −6.728 | 33.993 | 16.757 | 1.00 | 24.35 |
| 1275 | CB | ALA | B | 86 | −7.068 | 37.061 | 17.894 | 1.00 | 23.94 |
| 1276 | N | VAL | B | 87 | −7.899 | 34.130 | 18.674 | 1.00 | 20.62 |
| 1277 | CA | VAL | B | 87 | −7.517 | 32.792 | 19.103 | 1.00 | 20.36 |
| 1278 | C | VAL | B | 87 | −8.165 | 31.737 | 18.211 | 1.00 | 20.06 |
| 1279 | O | VAL | B | 87 | −7.522 | 30.751 | 17.829 | 1.00 | 22.42 |
| 1280 | CB | VAL | B | 87 | −7.925 | 32.536 | 20.564 | 1.00 | 17.94 |
| 1281 | CG1 | VAL | B | 87 | −7.495 | 31.131 | 20.979 | 1.00 | 20.37 |
| 1282 | CG2 | VAL | B | 87 | −7.279 | 33.588 | 21.477 | 1.00 | 18.89 |
| 1283 | N | ILE | B | 88 | −9.436 | 31.945 | 17.883 | 1.00 | 19.18 |
| 1284 | CA | ILE | B | 88 | −10.157 | 31.013 | 17.019 | 1.00 | 20.79 |
| 1285 | C | ILE | B | 88 | −9.455 | 30.940 | 15.667 | 1.00 | 22.10 |
| 1286 | O | ILE | B | 88 | −9.254 | 29.851 | 15.122 | 1.00 | 21.93 |
| 1287 | CB | ILE | B | 88 | −11.619 | 31.455 | 16.811 | 1.00 | 20.67 |
| 1288 | CG1 | ILE | B | 88 | −12.373 | 31.417 | 18.146 | 1.00 | 20.72 |
| 1289 | CG2 | ILE | B | 88 | −12.309 | 30.543 | 15.795 | 1.00 | 20.45 |
| 1290 | CD1 | ILE | B | 88 | −12.427 | 30.039 | 18.801 | 1.00 | 21.00 |
| 1291 | N | ASP | B | 89 | −9.074 | 32.096 | 15.127 | 1.00 | 23.00 |
| 1292 | CA | ASP | B | 89 | −8.380 | 32.124 | 13.843 | 1.00 | 27.10 |

TABLE 2-continued

| ATOM | ATOM TYPE | RESIDUE | PROTEIN # | # | X | Y | Z | OCC | B |
|---|---|---|---|---|---|---|---|---|---|
| 1293 | C | ASP | B | 89 | −7.106 | 31.288 | 13.926 | 1.00 | 27.08 |
| 1294 | O | ASP | B | 89 | −6.826 | 30.487 | 13.040 | 1.00 | 24.72 |
| 1295 | CB | ASP | B | 89 | −8.022 | 33.560 | 13.428 | 1.00 | 28.04 |
| 1296 | CG | ASP | B | 89 | −9.241 | 34.398 | 13.087 | 1.00 | 30.60 |
| 1297 | OD1 | ASP | B | 89 | −10.292 | 33.823 | 12.733 | 1.00 | 34.68 |
| 1298 | OD2 | ASP | B | 89 | −9.143 | 35.642 | 13.155 | 1.00 | 32.69 |
| 1299 | N | LEU | B | 90 | −6.332 | 31.477 | 14.991 | 1.00 | 27.55 |
| 1300 | CA | LEU | B | 90 | −5.101 | 30.718 | 15.171 | 1.00 | 28.67 |
| 1301 | C | LEU | B | 90 | −5.390 | 29.220 | 15.199 | 1.00 | 27.78 |
| 1302 | O | LEU | B | 90 | −4.692 | 28.431 | 14.565 | 1.00 | 29.40 |
| 1303 | CB | LEU | B | 90 | −4.401 | 31.125 | 16.471 | 1.00 | 31.51 |
| 1304 | CG | LEU | B | 90 | −3.695 | 32.483 | 16.480 | 1.00 | 35.55 |
| 1305 | CD1 | LEU | B | 90 | −3.152 | 32.773 | 17.873 | 1.00 | 39.29 |
| 1306 | CD2 | LEU | B | 90 | −2.567 | 32.475 | 15.461 | 1.00 | 37.91 |
| 1307 | N | ILE | B | 91 | −6.422 | 28.831 | 15.937 | 1.00 | 26.23 |
| 1308 | CA | ILE | B | 91 | −6.783 | 27.424 | 16.034 | 1.00 | 25.84 |
| 1309 | C | ILE | B | 91 | −7.197 | 26.843 | 14.680 | 1.00 | 27.61 |
| 1310 | O | ILE | B | 91 | −6.801 | 25.733 | 14.332 | 1.00 | 26.07 |
| 1311 | CB | ILE | B | 91 | −7.930 | 27.213 | 17.037 | 1.00 | 26.78 |
| 1312 | CG1 | ILE | B | 91 | −7.463 | 27.592 | 18.446 | 1.00 | 23.79 |
| 1313 | CG2 | ILE | B | 91 | −8.383 | 25.754 | 17.007 | 1.00 | 23.99 |
| 1314 | CD1 | ILE | B | 91 | −8.570 | 27.592 | 19.483 | 1.00 | 24.05 |
| 1315 | N | LYS | B | 92 | −7.984 | 27.592 | 13.916 | 1.00 | 28.06 |
| 1316 | CA | LYS | B | 92 | −8.423 | 27.109 | 12.612 | 1.00 | 33.30 |
| 1317 | C | LYS | B | 92 | −7.273 | 27.051 | 11.607 | 1.00 | 35.42 |
| 1318 | O | LYS | B | 92 | −7.351 | 26.339 | 10.605 | 1.00 | 37.61 |
| 1319 | CB | LYS | B | 92 | −9.568 | 27.978 | 12.085 | 1.00 | 32.99 |
| 1320 | CG | LYS | B | 92 | −10.840 | 27.859 | 12.924 | 1.00 | 32.83 |
| 1321 | CD | LYS | B | 92 | −12.008 | 28.629 | 12.322 | 1.00 | 31.89 |
| 1322 | CE | LYS | B | 92 | −13.297 | 28.346 | 13.090 | 1.00 | 35.18 |
| 1323 | NZ | LYS | B | 92 | −14.486 | 29.050 | 12.522 | 1.00 | 31.54 |
| 1324 | N | GLU | B | 93 | −6.201 | 27.787 | 11.881 | 1.00 | 35.90 |
| 1325 | CA | GLU | B | 93 | −5.038 | 27.783 | 10.997 | 1.00 | 39.09 |
| 1326 | C | GLU | B | 93 | −4.228 | 26.509 | 11.218 | 1.00 | 39.35 |
| 1327 | O | GLU | B | 93 | −3.378 | 26.151 | 10.401 | 1.00 | 37.43 |
| 1328 | CB | GLU | B | 93 | −4.152 | 29.003 | 11.264 | 1.00 | 40.87 |
| 1329 | CG | GLU | B | 93 | −4.711 | 30.311 | 10.731 | 1.00 | 46.43 |
| 1330 | CD | GLU | B | 93 | −3.895 | 31.512 | 11.171 | 1.00 | 49.56 |
| 1331 | OE1 | GLU | B | 93 | −2.656 | 31.483 | 11.011 | 1.00 | 51.45 |
| 1332 | OE2 | GLU | B | 93 | −4.493 | 32.488 | 11.673 | 1.00 | 53.68 |
| 1333 | N | ALA | B | 94 | −4.499 | 25.831 | 12.330 | 1.00 | 37.39 |
| 1334 | CA | ALA | B | 94 | −3.801 | 24.597 | 12.665 | 1.00 | 37.90 |
| 1335 | C | ALA | B | 94 | −4.236 | 23.474 | 11.730 | 1.00 | 37.01 |
| 1336 | O | ALA | B | 94 | −5.389 | 23.414 | 11.307 | 1.00 | 38.58 |
| 1337 | CB | ALA | B | 94 | −4.082 | 24.217 | 14.115 | 1.00 | 37.44 |
| 1338 | N | ASP | B | 95 | −3.308 | 22.579 | 11.417 | 1.00 | 37.34 |
| 1339 | CA | ASP | B | 95 | −3.596 | 21.470 | 10.522 | 1.00 | 36.65 |
| 1340 | C | ASP | B | 95 | −4.456 | 20.397 | 11.187 | 1.00 | 34.17 |
| 1341 | O | ASP | B | 95 | −5.567 | 20.114 | 10.736 | 1.00 | 36.10 |
| 1342 | CB | ASP | B | 95 | −2.289 | 20.848 | 10.032 | 1.00 | 41.06 |
| 1343 | CG | ASP | B | 95 | −2.483 | 19.982 | 8.810 | 1.00 | 46.21 |
| 1344 | OD1 | ASP | B | 95 | −3.342 | 19.073 | 8.854 | 1.00 | 47.72 |
| 1345 | OD2 | ASP | B | 95 | −1.775 | 20.213 | 7.805 | 1.00 | 47.55 |
| 1346 | N | PHE | B | 96 | −3.947 | 19.802 | 12.260 | 1.00 | 27.73 |
| 1347 | CA | PHE | B | 96 | −4.688 | 18.756 | 12.948 | 1.00 | 25.35 |
| 1348 | C | PHE | B | 96 | −4.447 | 18.728 | 14.452 | 1.00 | 22.98 |
| 1349 | O | PHE | B | 96 | −5.128 | 18.004 | 15.171 | 1.00 | 21.18 |
| 1350 | CB | PHE | B | 96 | −4.330 | 17.391 | 12.354 | 1.00 | 25.87 |
| 1351 | CG | PHE | B | 96 | −2.952 | 16.921 | 12.713 | 1.00 | 23.56 |
| 1352 | CD1 | PHE | B | 96 | −2.754 | 16.071 | 13.796 | 1.00 | 23.18 |
| 1353 | CD2 | PHE | B | 96 | −1.846 | 17.360 | 11.996 | 1.00 | 27.58 |
| 1354 | CE1 | PHE | B | 96 | −1.476 | 15.669 | 14.161 | 1.00 | 25.27 |
| 1355 | CE2 | PHE | B | 96 | −0.562 | 16.963 | 12.354 | 1.00 | 26.13 |
| 1356 | CZ | PHE | B | 96 | −0.377 | 16.117 | 13.439 | 1.00 | 26.87 |
| 1357 | N | LYS | B | 97 | −3.479 | 19.501 | 14.935 | 1.00 | 22.11 |
| 1358 | CA | LYS | B | 97 | −3.215 | 19.509 | 16.370 | 1.00 | 20.93 |
| 1359 | C | LYS | B | 97 | −2.839 | 20.884 | 16.902 | 1.00 | 20.31 |
| 1360 | O | LYS | B | 97 | −2.303 | 21.722 | 16.182 | 1.00 | 19.54 |
| 1361 | CB | LYS | B | 97 | −2.103 | 18.512 | 16.719 | 1.00 | 25.46 |
| 1362 | CG | LYS | B | 97 | −0.714 | 18.915 | 16.256 | 1.00 | 30.07 |
| 1363 | CD | LYS | B | 97 | 0.310 | 17.847 | 16.613 | 1.00 | 36.74 |
| 1364 | CE | LYS | B | 97 | 1.709 | 18.230 | 16.156 | 1.00 | 39.98 |
| 1365 | NZ | LYS | B | 97 | 2.227 | 19.429 | 16.875 | 1.00 | 45.01 |
| 1366 | N | ILE | B | 98 | −3.140 | 21.112 | 18.174 | 1.00 | 19.87 |
| 1367 | CA | ILE | B | 98 | −2.799 | 22.374 | 18.811 | 1.00 | 18.95 |
| 1368 | C | ILE | B | 98 | −2.223 | 22.047 | 20.180 | 1.00 | 22.13 |

TABLE 2-continued

| ATOM | ATOM TYPE | RESIDUE | PROTEIN # | # | X | Y | Z | OCC | B |
|---|---|---|---|---|---|---|---|---|---|
| 1369 | O | ILE | B | 98 | −2.712 | 21.149 | 20.872 | 1.00 | 19.55 |
| 1370 | CB | ILE | B | 98 | −4.031 | 23.301 | 18.975 | 1.00 | 20.34 |
| 1371 | CG1 | ILE | B | 98 | −5.158 | 22.565 | 19.703 | 1.00 | 19.19 |
| 1372 | CG2 | ILE | B | 98 | −4.487 | 23.802 | 17.608 | 1.00 | 19.27 |
| 1373 | CD1 | ILE | B | 98 | −6.386 | 23.433 | 20.000 | 1.00 | 19.42 |
| 1374 | N | GLU | B | 99 | −1.160 | 22.755 | 20.539 | 1.00 | 18.79 |
| 1375 | CA | GLU | B | 99 | −0.497 | 22.567 | 21.822 | 1.00 | 23.65 |
| 1376 | C | GLU | B | 99 | −0.956 | 23.722 | 22.694 | 1.00 | 20.46 |
| 1377 | O | GLU | B | 99 | −0.712 | 24.884 | 22.374 | 1.00 | 21.74 |
| 1378 | CB | GLU | B | 99 | 1.024 | 22.617 | 21.647 | 1.00 | 28.81 |
| 1379 | CG | GLU | B | 99 | 1.591 | 21.527 | 20.750 | 1.00 | 39.76 |
| 1380 | CD | GLU | B | 99 | 3.074 | 21.720 | 20.464 | 1.00 | 46.75 |
| 1381 | OE1 | GLU | B | 99 | 3.857 | 21.871 | 21.428 | 1.00 | 49.07 |
| 1382 | OE2 | GLU | B | 99 | 3.456 | 21.719 | 19.273 | 1.00 | 51.53 |
| 1383 | N | LEU | B | 100 | −1.626 | 23.404 | 23.793 | 1.00 | 17.62 |
| 1384 | CA | LEU | B | 100 | −2.134 | 24.434 | 24.682 | 1.00 | 17.01 |
| 1385 | C | LEU | B | 100 | −1.386 | 24.499 | 26.002 | 1.00 | 15.82 |
| 1386 | O | LEU | B | 100 | −1.156 | 23.473 | 26.635 | 1.00 | 18.54 |
| 1387 | CB | LEU | B | 100 | −3.613 | 24.177 | 24.984 | 1.00 | 16.35 |
| 1388 | CG | LEU | B | 100 | −4.573 | 24.094 | 23.796 | 1.00 | 19.30 |
| 1389 | CD1 | LEU | B | 100 | −5.936 | 23.577 | 24.252 | 1.00 | 24.09 |
| 1390 | CD2 | LEU | B | 100 | −4.703 | 25.462 | 23.164 | 1.00 | 23.00 |
| 1391 | N | GLU | B | 101 | −0.995 | 25.706 | 26.402 | 1.00 | 14.90 |
| 1392 | CA | GLU | B | 101 | −0.353 | 25.900 | 27.702 | 1.00 | 13.89 |
| 1393 | C | GLU | B | 101 | −1.568 | 26.300 | 28.532 | 1.00 | 13.00 |
| 1394 | O | GLU | B | 101 | −2.164 | 27.355 | 28.307 | 1.00 | 15.93 |
| 1395 | CB | GLU | B | 101 | 0.662 | 27.045 | 27.668 | 1.00 | 15.98 |
| 1396 | CG | GLU | B | 101 | 1.360 | 27.259 | 29.011 | 1.00 | 16.10 |
| 1397 | CD | GLU | B | 101 | 2.319 | 28.433 | 28.991 | 1.00 | 21.06 |
| 1398 | OE1 | GLU | B | 101 | 2.533 | 29.000 | 27.901 | 1.00 | 22.79 |
| 1399 | OE2 | GLU | B | 101 | 2.854 | 28.787 | 30.064 | 1.00 | 22.08 |
| 1400 | N | ILE | B | 102 | −1.929 | 25.440 | 29.476 | 1.00 | 13.47 |
| 1401 | CA | ILE | B | 102 | −3.110 | 25.617 | 30.308 | 1.00 | 16.45 |
| 1402 | C | ILE | B | 102 | −2.811 | 25.902 | 31.775 | 1.00 | 16.00 |
| 1403 | O | ILE | B | 102 | −1.911 | 25.303 | 32.352 | 1.00 | 15.39 |
| 1404 | CB | ILE | B | 102 | −3.967 | 24.323 | 30.268 | 1.00 | 15.64 |
| 1405 | CG1 | ILE | B | 102 | −4.370 | 24.004 | 28.826 | 1.00 | 18.75 |
| 1406 | CG2 | ILE | B | 102 | −5.184 | 24.458 | 31.183 | 1.00 | 17.18 |
| 1407 | CD1 | ILE | B | 102 | −5.325 | 24.999 | 28.228 | 1.00 | 16.74 |
| 1408 | N | GLN | B | 103 | −3.570 | 26.822 | 32.367 | 1.00 | 18.33 |
| 1409 | CA | GLN | B | 103 | −3.432 | 27.104 | 33.793 | 1.00 | 19.08 |
| 1410 | C | GLN | B | 103 | −4.758 | 26.637 | 34.387 | 1.00 | 19.66 |
| 1411 | O | GLN | B | 103 | −5.817 | 27.172 | 34.051 | 1.00 | 20.06 |
| 1412 | CB | GLN | B | 103 | −3.232 | 28.590 | 34.070 | 1.00 | 19.81 |
| 1413 | CG | GLN | B | 103 | −2.986 | 28.863 | 35.550 | 1.00 | 23.12 |
| 1414 | CD | GLN | B | 103 | −2.513 | 30.272 | 35.803 | 1.00 | 26.34 |
| 1415 | OE1 | GLN | B | 103 | −1.770 | 30.835 | 35.000 | 1.00 | 29.24 |
| 1416 | NE2 | GLN | B | 103 | −2.930 | 30.850 | 36.927 | 1.00 | 24.88 |
| 1417 | N | THR | B | 104 | −4.690 | 25.630 | 35.252 | 1.00 | 22.23 |
| 1418 | CA | THR | B | 104 | −5.882 | 25.040 | 35.859 | 1.00 | 25.78 |
| 1419 | C | THR | B | 104 | −5.815 | 24.977 | 37.380 | 1.00 | 30.40 |
| 1420 | O | THR | B | 104 | −4.784 | 25.273 | 37.983 | 1.00 | 28.96 |
| 1421 | CB | THR | B | 104 | −6.079 | 23.595 | 35.351 | 1.00 | 25.32 |
| 1422 | OG1 | THR | B | 104 | −7.294 | 23.049 | 35.882 | 1.00 | 26.46 |
| 1423 | CG2 | THR | B | 104 | −4.915 | 22.718 | 35.802 | 1.00 | 25.32 |
| 1424 | N | PHE | B | 105 | −6.931 | 24.582 | 37.986 | 1.00 | 34.95 |
| 1425 | CA | PHE | B | 105 | −7.015 | 24.430 | 39.433 | 1.00 | 39.35 |
| 1426 | C | PHE | B | 105 | −6.960 | 22.933 | 39.727 | 1.00 | 43.72 |
| 1427 | O | PHE | B | 105 | −7.561 | 22.133 | 39.008 | 1.00 | 44.71 |
| 1428 | CB | PHE | B | 105 | −8.320 | 25.021 | 39.951 | 1.00 | 38.87 |
| 1429 | N | ASP | B | 106 | −6.232 | 22.549 | 40.770 | 1.00 | 47.66 |
| 1430 | CA | ASP | B | 106 | −6.121 | 21.139 | 41.129 | 1.00 | 51.57 |
| 1431 | C | ASP | B | 106 | −5.948 | 20.958 | 42.632 | 1.00 | 52.47 |
| 1432 | O | ASP | B | 106 | −5.903 | 21.980 | 43.349 | 1.00 | 55.25 |
| 1433 | CB | ASP | B | 106 | −4.938 | 20.500 | 40.399 | 1.00 | 52.59 |
| 1434 | CG | ASP | B | 106 | −3.601 | 21.027 | 40.883 | 1.00 | 52.79 |
| 1435 | OD1 | ASP | B | 106 | −3.385 | 22.255 | 40.815 | 1.00 | 53.14 |
| 1436 | OD2 | ASP | B | 106 | −2.766 | 20.211 | 41.330 | 1.00 | 52.51 |
| 1437 | | ASP | B | 106 | | | | | |
| 1438 | N | THR | C | 3 | −23.318 | 29.266 | 21.119 | 1.00 | 44.20 |
| 1439 | CA | THR | C | 3 | −21.935 | 29.543 | 21.608 | 1.00 | 44.09 |
| 1440 | C | THR | C | 3 | −21.140 | 30.285 | 20.534 | 1.00 | 40.71 |
| 1441 | O | THR | C | 3 | −20.878 | 29.758 | 19.450 | 1.00 | 38.11 |
| 1442 | CB | THR | C | 3 | −21.230 | 28.237 | 21.982 | 1.00 | 45.21 |
| 1443 | OG1 | THR | C | 3 | −19.858 | 28.508 | 22.285 | 1.00 | 51.49 |
| 1444 | CG2 | THR | C | 3 | −21.342 | 27.229 | 20.849 | 1.00 | 47.02 |

TABLE 2-continued

| ATOM | ATOM TYPE | RESIDUE | PROTEIN # | # | X | Y | Z | OCC | B |
|---|---|---|---|---|---|---|---|---|---|
| 1445 | N | GLU | C | 4 | −20.743 | 31.509 | 20.859 | 1.00 | 37.61 |
| 1446 | CA | GLU | C | 4 | −20.040 | 32.373 | 19.921 | 1.00 | 36.50 |
| 1447 | C | GLU | C | 4 | −18.643 | 32.008 | 19.421 | 1.00 | 34.44 |
| 1448 | O | GLU | C | 4 | −18.406 | 32.044 | 18.215 | 1.00 | 37.34 |
| 1449 | CB | GLU | C | 4 | −20.023 | 33.801 | 20.473 | 1.00 | 40.01 |
| 1450 | CG | GLU | C | 4 | −19.620 | 34.851 | 19.453 | 1.00 | 44.22 |
| 1451 | CD | GLU | C | 4 | −20.122 | 36.234 | 19.818 | 1.00 | 46.71 |
| 1452 | OE1 | GLU | C | 4 | −21.353 | 36.398 | 19.957 | 1.00 | 49.32 |
| 1453 | OE2 | GLU | C | 4 | −19.293 | 37.156 | 19.965 | 1.00 | 50.57 |
| 1454 | N | PHE | C | 5 | −17.714 | 31.663 | 20.308 | 1.00 | 27.88 |
| 1455 | CA | PHE | C | 5 | −16.357 | 31.351 | 19.841 | 1.00 | 24.24 |
| 1456 | C | PHE | C | 5 | −15.911 | 29.914 | 20.076 | 1.00 | 2391 |
| 1457 | O | PHE | C | 5 | −15.359 | 29.595 | 21.130 | 1.00 | 23.28 |
| 1458 | CB | PHE | C | 5 | −15.345 | 32.294 | 20.494 | 1.00 | 22.91 |
| 1459 | CG | PHE | C | 5 | −15.676 | 33.746 | 20.318 | 1.00 | 24.05 |
| 1460 | CD1 | PHE | C | 5 | −16.341 | 34.448 | 21.321 | 1.00 | 23.19 |
| 1461 | CD2 | PHE | C | 5 | −15.336 | 34.409 | 19.145 | 1.00 | 24.94 |
| 1462 | CE1 | PHE | C | 5 | −16.661 | 35.791 | 21.158 | 1.00 | 24.05 |
| 1463 | CE2 | PHE | C | 5 | −15.654 | 35.757 | 18.971 | 1.00 | 26.21 |
| 1464 | CZ | PHE | C | 5 | −16.316 | 36.447 | 19.979 | 1.00 | 24.09 |
| 1465 | N | CYS | C | 6 | −16.128 | 29.050 | 19.090 | 1.00 | 20.17 |
| 1466 | CA | CYS | C | 6 | −15.741 | 27.650 | 19.240 | 1.00 | 20.71 |
| 1467 | C | CYS | C | 6 | −14.899 | 27.155 | 18.071 | 1.00 | 22.38 |
| 1468 | O | CYS | C | 6 | −15.030 | 27.642 | 16.950 | 1.00 | 21.10 |
| 1469 | CB | CYS | C | 6 | −16.977 | 26.759 | 19.347 | 1.00 | 25.55 |
| 1470 | SG | CYS | C | 6 | −18.275 | 27.242 | 20.531 | 1.00 | 29.99 |
| 1471 | N | ALA | C | 7 | −14.048 | 26.171 | 18.338 | 1.00 | 20.87 |
| 1472 | CA | ALA | C | 7 | −13.191 | 25.602 | 17.304 | 1.00 | 22.32 |
| 1473 | C | ALA | C | 7 | −12.827 | 24.164 | 17.645 | 1.00 | 23.15 |
| 1474 | O | ALA | C | 7 | −12.048 | 23.561 | 16.874 | 1.00 | 20.38 |
| 1475 | CB | ALA | C | 7 | −11.920 | 26.445 | 17.150 | 1.00 | 19.92 |
| 1476 | OXT | ALA | C | 7 | −13.328 | 23.660 | 18.677 | 1.00 | 21.77 |
| 1477 | | ALA | C | 7 | | | | | |
| 1478 | N | THR | D | 3 | −15.296 | −3.229 | 2.536 | 1.00 | 40.96 |
| 1479 | CA | THR | D | 3 | −14.133 | −3.861 | 1.846 | 1.00 | 43.40 |
| 1480 | C | THR | D | 3 | −13.016 | −4.171 | 2.845 | 1.00 | 42.71 |
| 1481 | O | THR | D | 3 | −12.502 | −3.280 | 3.524 | 1.00 | 42.89 |
| 1482 | CB | THR | D | 3 | −13.601 | −2.936 | 0.730 | 1.00 | 43.84 |
| 1483 | OG1 | THR | D | 3 | −12.478 | −3.545 | 0.081 | 1.00 | 47.34 |
| 1484 | CG2 | THR | D | 3 | −13.197 | −1.592 | 1.307 | 1.00 | 45.56 |
| 1485 | N | GLU | D | 4 | −12.653 | −5.445 | 2.940 | 1.00 | 42.32 |
| 1486 | CA | GLU | D | 4 | −11.613 | −5.864 | 3.870 | 1.00 | 41.03 |
| 1487 | C | GLU | D | 4 | −10.221 | −5.532 | 3.349 | 1.00 | 38.23 |
| 1488 | O | GLU | D | 4 | −10.050 | −5.191 | 2.187 | 1.00 | 38.91 |
| 1489 | CB | GLU | D | 4 | −11.741 | −7.366 | 4.154 | 1.00 | 45.60 |
| 1490 | CG | GLU | D | 4 | −11.787 | −8.254 | 2.919 | 1.00 | 48.48 |
| 1491 | CD | GLU | D | 4 | −12.313 | −9.651 | 3.221 | 1.00 | 50.69 |
| 1492 | OE1 | GLU | D | 4 | −13.497 | −9.771 | 3.602 | 1.00 | 53.00 |
| 1493 | OE2 | GLU | D | 4 | −11.549 | −10.630 | 3.078 | 1.00 | 50.91 |
| 1494 | N | PHE | D | 5 | −9.231 | −5.602 | 4.227 | 1.00 | 35.71 |
| 1495 | CA | PHE | D | 5 | −7.854 | −5.312 | 3.850 | 1.00 | 26.58 |
| 1496 | C | PHE | D | 5 | −7.620 | −3.866 | 3.423 | 1.00 | 23.70 |
| 1497 | O | PHE | D | 5 | −7.214 | −3.594 | 2.293 | 1.00 | 21.21 |
| 1498 | CB | PHE | D | 5 | −7.413 | −6.256 | 2.733 | 1.00 | 27.60 |
| 1499 | CG | PHE | D | 5 | −7.673 | −7.702 | 3.037 | 1.00 | 27.05 |
| 1500 | CD1 | PHE | D | 5 | −8.165 | −8.555 | 2.054 | 1.00 | 25.07 |
| 1501 | CD2 | PHE | D | 5 | −7.442 | −8.207 | 4.311 | 1.00 | 26.26 |
| 1502 | CE1 | PHE | D | 5 | −8.425 | −9.892 | 2.337 | 1.00 | 26.61 |
| 1503 | CE2 | PHE | D | 5 | −7.698 | −9.546 | 4.605 | 1.00 | 29.34 |
| 1504 | CZ | PHE | D | 5 | −8.191 | −10.388 | 3.613 | 1.00 | 27.22 |
| 1505 | N | CYS | D | 6 | −7.886 | −2.938 | 4.333 | 1.00 | 21.13 |
| 1506 | CA | CYS | D | 6 | −7.654 | −1.526 | 4.059 | 1.00 | 20.21 |
| 1507 | C | CYS | D | 6 | −6.824 | −1.006 | 5.225 | 1.00 | 23.47 |
| 1508 | O | CYS | D | 6 | −6.951 | −1.496 | 6.349 | 1.00 | 21.16 |
| 1509 | CB | CYS | D | 6 | −8.961 | −0.735 | 3.999 | 1.00 | 23.91 |
| 1510 | SG | CYS | D | 6 | −10.232 | −1.203 | 2.773 | 1.00 | 28.50 |
| 1511 | N | ALA | D | 7 | −5.980 | −0.017 | 4.959 | 1.00 | 20.97 |
| 1512 | CA | ALA | D | 7 | −5.137 | 0.566 | 5.999 | 1.00 | 22.00 |
| 1513 | C | ALA | D | 7 | −4.744 | 1.989 | 5.622 | 1.00 | 23.22 |
| 1514 | O | ALA | D | 7 | −5.284 | 2.501 | 4.618 | 1.00 | 20.96 |
| 1515 | CB | ALA | D | 7 | −3.894 | −0.282 | 6.201 | 1.00 | 24.79 |
| 1516 | OXT | ALA | D | 7 | −3.905 | 2.572 | 6.340 | 1.00 | 20.40 |
| 1518 | O | HOH | | 1001 | −6.648 | 21.260 | 32.953 | 1.00 | 19.49 |
| 1519 | O | HOH | | 1002 | 1.870 | 18.994 | 31.260 | 1.00 | 19.39 |
| 1520 | O | HOH | | 1003 | −3.156 | 8.943 | −5.664 | 1.00 | 23.24 |
| 1521 | O | HOH | | 1004 | −11.145 | 17.253 | 29.023 | 1.00 | 24.18 |

TABLE 2-continued

| ATOM | ATOM TYPE | RESIDUE | PROTEIN # | # | X | Y | Z | OCC | B |
|---|---|---|---|---|---|---|---|---|---|
| 1522 | O | HOH | | 1005 | 9.924 | 7.134 | -7.909 | 1.00 | 20.21 |
| 1523 | O | HOH | | 1006 | -13.198 | 38.564 | 19.429 | 1.00 | 24.10 |
| 1524 | O | HOH | | 1007 | -6.216 | 14.863 | 21.320 | 1.00 | 30.11 |
| 1525 | O | HOH | | 1008 | 1.633 | 26.579 | 23.658 | 1.00 | 23.84 |
| 1526 | O | HOH | | 1009 | 1.749 | 11.472 | 2.127 | 1.00 | 27.61 |
| 1527 | O | HOH | | 1010 | -6.645 | 5.483 | -9.459 | 1.00 | 34.93 |
| 1528 | O | HOH | | 1011 | 9.718 | -0.472 | -0.159 | 1.00 | 24.34 |
| 1529 | O | HOH | | 1012 | -16.047 | 37.424 | 15.531 | 1.00 | 25.19 |
| 1530 | O | HOH | | 1013 | 1.363 | 4.799 | -9.672 | 1.00 | 21.76 |
| 1531 | O | HOH | | 1014 | -2.242 | 11.871 | 13.188 | 1.00 | 28.77 |
| 1532 | O | HOH | | 1015 | -14.646 | 20.598 | 32.888 | 1.00 | 37.62 |
| 1533 | O | HOH | | 1016 | -4.884 | -12.498 | 3.796 | 1.00 | 29.31 |
| 1534 | O | HOH | | 1017 | -7.932 | 20.086 | 36.757 | 1.00 | 43.40 |
| 1535 | O | HOH | | 1018 | -8.756 | 10.806 | 8.051 | 1.00 | 32.08 |
| 1536 | O | HOH | | 1019 | -0.245 | 32.921 | 35.012 | 1.00 | 31.75 |
| 1537 | O | HOH | | 1020 | -9.660 | 25.404 | 36.204 | 1.00 | 29.99 |
| 1538 | O | HOH | | 1021 | -9.786 | -5.289 | -0.220 | 1.00 | 29.19 |
| 1539 | O | HOH | | 1022 | -7.662 | 23.676 | 12.690 | 1.00 | 32.19 |
| 1540 | O | HOH | | 1023 | 0.794 | 2.461 | 10.659 | 1.00 | 30.11 |
| 1541 | O | HOH | | 1024 | 3.476 | -7.680 | -11.566 | 1.00 | 33.34 |
| 1542 | O | HOH | | 1025 | 6.560 | 9.963 | -2.504 | 1.00 | 37.18 |
| 1543 | O | HOH | | 1026 | -1.322 | 20.491 | 13.052 | 1.00 | 29.09 |
| 1544 | O | HOH | | 1027 | -1.434 | 0.623 | -12.859 | 1.00 | 31.22 |
| 1545 | O | HOH | | 1028 | -7.924 | 29.123 | 36.542 | 1.00 | 47.17 |
| 1546 | O | HOH | | 1029 | -11.179 | 23.707 | 14.359 | 1.00 | 36.41 |
| 1547 | O | HOH | | 1030 | -15.525 | 32.889 | 15.892 | 1.00 | 37.64 |
| 1548 | O | HOH | | 1031 | -6.908 | -3.544 | -8.512 | 1.00 | 26.90 |
| 1549 | O | HOH | | 1032 | -5.197 | 33.987 | 28.584 | 1.00 | 33.38 |
| 1550 | O | HOH | | 1033 | -5.065 | 35.449 | 15.210 | 1.00 | 28.55 |
| 1551 | O | HOH | | 1034 | 3.162 | -9.168 | 8.118 | 1.00 | 38.48 |
| 1552 | O | HOH | | 1035 | -10.163 | 10.712 | 4.139 | 1.00 | 32.94 |
| 1553 | O | HOH | | 1036 | -6.578 | 31.739 | 35.152 | 1.00 | 68.12 |
| 1554 | O | HOH | | 1037 | -3.256 | 2.532 | 8.888 | 1.00 | 27.77 |
| 1555 | O | HOH | | 1038 | -18.706 | 35.864 | 16.663 | 1.00 | 36.66 |
| 1556 | O | HOH | | 1039 | -7.354 | 37.792 | 26.293 | 1.00 | 32.16 |
| 1557 | O | HOH | | 1040 | -3.846 | -3.833 | -12.578 | 1.00 | 34.83 |
| 1558 | O | HOH | | 1041 | 2.724 | -7.990 | -4.675 | 1.00 | 36.47 |
| 1559 | O | HOH | | 1042 | -8.569 | 12.780 | 17.246 | 1.00 | 32.11 |
| 1560 | O | HOH | | 1043 | 9.555 | 7.630 | -1.931 | 1.00 | 35.76 |
| 1561 | O | HOH | | 1044 | -12.186 | 29.911 | 35.761 | 1.00 | 34.35 |
| 1562 | O | HOH | | 1045 | -0.917 | 13.130 | 6.088 | 1.00 | 29.01 |
| 1563 | O | HOH | | 1046 | -2.410 | 9.144 | 11.777 | 1.00 | 38.90 |
| 1564 | O | HOH | | 1047 | -0.516 | 24.228 | 43.048 | 1.00 | 32.93 |
| 1565 | O | HOH | | 1048 | 7.328 | 2.281 | -19.522 | 1.00 | 42.42 |
| 1566 | O | HOH | | 1049 | -12.071 | 42.614 | 31.433 | 1.00 | 50.01 |
| 1567 | O | HOH | | 1050 | 7.762 | -6.699 | -11.493 | 1.00 | 32.72 |
| 1568 | O | HOH | | 1051 | -10.687 | 14.805 | -1.131 | 1.00 | 54.85 |
| 1569 | O | HOH | | 1052 | -7.050 | 37.428 | 13.621 | 1.00 | 42.96 |
| 1570 | O | HOH | | 1053 | -2.061 | 16.025 | 26.160 | 1.00 | 37.55 |
| 1571 | O | HOH | | 1054 | 4.229 | -20.729 | -19.937 | 1.00 | 35.46 |
| 1572 | O | HOH | | 1055 | -18.239 | 29.528 | 17.147 | 1.00 | 43.10 |
| 1573 | O | HOH | | 1056 | 6.345 | -2.095 | 8.515 | 1.00 | 41.75 |
| 1574 | O | HOH | | 1057 | -9.023 | 44.941 | 46.222 | 1.00 | 35.93 |
| 1575 | O | HOH | | 1058 | -16.192 | 23.431 | 18.379 | 1.00 | 37.92 |
| 1576 | O | HOH | | 1059 | 3.344 | 31.621 | 27.507 | 1.00 | 38.83 |
| 1577 | O | | HOH | 1060 | 5.088 | -14.887 | -14.175 | 1.00 | 46.82 |
| 1578 | O | | HOH | 1061 | -5.344 | 12.427 | -6.742 | 1.00 | 40.53 |
| 1579 | O | | HOH | 1062 | -18.179 | 15.613 | 18.975 | 1.00 | 40.58 |
| 1580 | O | | HOH | 1063 | -12.230 | 31.939 | 9.216 | 1.00 | 53.98 |
| 1581 | O | | HOH | 1064 | -7.971 | -3.637 | 7.742 | 1.00 | 61.28 |
| 1582 | O | | HOH | 1065 | 11.963 | -8.472 | 2.096 | 1.00 | 42.64 |
| 1583 | O | | HOH | 1066 | 7.599 | -12.274 | -1.758 | 1.00 | 44.02 |
| 1584 | O | | HOH | 1067 | -0.567 | 12.758 | 0.489 | 1.00 | 60.92 |
| 1585 | O | | HOH | 1068 | -1.987 | 38.141 | 23.537 | 1.00 | 42.92 |
| 1586 | O | | HOH | 1069 | 1.224 | -11.295 | 9.371 | 1.00 | 42.23 |
| 1587 | O | | HOH | 1070 | -13.315 | 9.865 | 2.738 | 1.00 | 40.65 |
| 1588 | O | | HOH | 1071 | 4.437 | 4.899 | -18.136 | 1.00 | 61.64 |
| 1589 | O | | HOH | 1072 | -9.997 | 40.236 | 16.626 | 1.00 | 39.79 |
| 1590 | O | | HOH | 1073 | -2.755 | 41.209 | 37.339 | 1.00 | 44.78 |
| 1591 | O | | HOH | 1074 | -5.453 | 16.739 | 8.755 | 1.00 | 52.83 |
| 1592 | O | | HOH | 1075 | -15.067 | 29.611 | 31.870 | 1.00 | 27.68 |
| 1593 | O | | HOH | 1076 | 1.164 | 21.550 | 43.361 | 1.00 | 61.33 |
| 1594 | O | | HOH | 1077 | -1.189 | 17.795 | 31.214 | 1.00 | 30.52 |
| 1595 | O | | HOH | 1078 | 3.448 | 17.404 | 29.320 | 1.00 | 32.94 |
| 1596 | O | | HOH | 1079 | -0.463 | 14.731 | 17.908 | 1.00 | 67.21 |
| 1597 | O | | HOH | 1080 | -2.784 | 11.582 | 18.036 | 1.00 | 81.78 |

TABLE 2-continued

| ATOM | ATOM TYPE | RESIDUE | PROTEIN # | # | X | Y | Z | OCC | B |
|---|---|---|---|---|---|---|---|---|---|
| 1598 | O | | HOH | 1081 | −8.939 | 11.256 | 21.552 | 1.00 | 44.36 |
| 1599 | O | | HOH | 1082 | −10.876 | 12.216 | 19.288 | 1.00 | 31.71 |
| 1600 | O | | HOH | 1083 | −4.131 | 12.556 | 20.856 | 1.00 | 56.78 |
| 1601 | O | | HOH | 1084 | −16.330 | 15.274 | 15.029 | 1.00 | 36.81 |
| 1602 | O | | HOH | 1085 | −17.763 | 31.318 | 23.499 | 1.00 | 25.50 |
| 1603 | O | | HOH | 1086 | −14.941 | 36.649 | 33.874 | 1.00 | 47.47 |
| 1604 | O | | HOH | 1087 | −17.601 | 28.829 | 33.543 | 1.00 | 36.73 |
| 1605 | O | | HOH | 1088 | −19.455 | 34.130 | 29.721 | 1.00 | 58.84 |
| 1606 | O | | HOH | 1089 | −19.358 | 33.783 | 24.471 | 1.00 | 44.72 |
| 1607 | O | | HOH | 1090 | 3.558 | −8.574 | −8.256 | 1.00 | 36.65 |
| 1608 | O | | HOH | 1091 | −7.426 | 9.606 | 5.483 | 1.00 | 40.97 |
| 1609 | O | | HOH | 1092 | −8.347 | 7.280 | −7.803 | 1.00 | 42.79 |
| 1610 | O | | HOH | 1093 | −7.123 | −13.084 | 5.877 | 1.00 | 38.01 |
| 1611 | O | | HOH | 1094 | −2.809 | 13.897 | 3.832 | 1.00 | 30.64 |
| 1612 | O | | HOH | 1095 | −3.327 | 46.840 | 43.164 | 1.00 | 35.45 |
| 1613 | O | | HOH | 1096 | −15.711 | 39.463 | 17.828 | 1.00 | 45.38 |
| 1614 | O | | HOH | 1097 | 2.034 | 12.943 | −1.497 | 1.00 | 41.49 |
| 1615 | O | | HOH | 1098 | 1.789 | 33.283 | 32.748 | 1.00 | 43.58 |
| 1616 | O | | HOH | 1099 | −13.871 | 44.168 | 36.925 | 1.00 | 51.49 |
| 1617 | O | | HOH | 1100 | −5.143 | −7.904 | −11.011 | 1.00 | 46.78 |
| 1618 | O | | HOH | 1101 | 2.905 | 36.911 | 29.322 | 1.00 | 52.90 |
| 1619 | O | | HOH | 1102 | 9.603 | 4.287 | −20.394 | 1.00 | 48.45 |
| 1620 | O | | HOH | 1103 | −8.017 | 2.828 | 4.797 | 1.00 | 34.64 |
| 1621 | O | | HOH | 1104 | 10.572 | 7.302 | 2.494 | 1.00 | 39.10 |
| 1622 | O | | HOH | 1105 | 0.248 | 4.601 | 13.840 | 1.00 | 48.79 |
| 1623 | O | | HOH | 1106 | −0.395 | 23.215 | 14.483 | 1.00 | 54.44 |
| 1624 | O | | HOH | 1107 | 11.823 | −5.324 | −4.054 | 1.00 | 36.83 |
| 1625 | O | | HOH | 1108 | −13.835 | 31.734 | 12.981 | 1.00 | 45.64 |
| 1626 | O | | HOH | 1109 | −8.371 | 13.663 | 9.683 | 1.00 | 34.64 |
| 1627 | O | | HOH | 1110 | −13.628 | 13.419 | 29.932 | 1.00 | 39.21 |
| 1628 | O | | HOH | 1111 | −1.903 | 36.556 | 36.793 | 1.00 | 45.05 |
| 1629 | O | | HOH | 1112 | −14.518 | 9.223 | 19.276 | 1.00 | 57.27 |
| 1630 | O | | HOH | 1113 | 4.138 | 34.827 | 21.612 | 1.00 | 42.94 |
| 1631 | O | | HOH | 1114 | −10.866 | −8.254 | −0.615 | 1.00 | 43.48 |
| 1632 | O | | HOH | 1115 | 4.698 | −12.941 | −7.343 | 1.00 | 60.47 |
| 1633 | O | | HOH | 1116 | −2.932 | 16.510 | 6.667 | 1.00 | 79.26 |
| 1634 | O | | HOH | 1117 | −0.031 | 16.739 | 8.174 | 1.00 | 71.38 |
| 1635 | O | | HOH | 1118 | −8.612 | 6.701 | 5.028 | 1.00 | 62.42 |
| 1636 | O | | HOH | 1119 | −5.875 | −17.912 | −13.208 | 1.00 | 48.98 |
| 1637 | O | | HOH | 1120 | −1.554 | −15.923 | −4.768 | 1.00 | 53.88 |
| 1638 | O | | HOH | 1121 | 2.304 | −15.607 | −4.954 | 1.00 | 51.06 |
| 1639 | O | | HOH | 1122 | −6.437 | 17.203 | 3.597 | 1.00 | 41.16 |
| 1640 | O | | HOH | 1123 | −6.094 | 9.041 | −6.831 | 1.00 | 36.98 |
| 1641 | O | | HOH | 1124 | −3.521 | 12.123 | −9.771 | 1.00 | 57.07 |
| 1642 | O | | HOH | 1125 | −1.496 | 11.323 | −13.482 | 1.00 | 52.46 |
| 1643 | O | | HOH | 1126 | 1.581 | 1.938 | 16.978 | 1.00 | 62.28 |
| 1644 | O | | HOH | 1127 | 12.057 | 1.396 | 0.833 | 1.00 | 60.20 |
| 1645 | O | | HOH | 1128 | 12.815 | −1.539 | −8.304 | 1.00 | 50.94 |
| 1646 | O | | HOH | 1129 | 15.039 | −3.251 | −9.664 | 1.00 | 46.12 |
| 1647 | O | | HOH | 1130 | −1.717 | 32.912 | 41.182 | 1.00 | 52.68 |
| 1648 | O | | HOH | 1131 | −4.625 | 33.996 | 39.007 | 1.00 | 50.37 |
| 1649 | O | | HOH | 1132 | −17.900 | 12.797 | 17.409 | 1.00 | 64.63 |
| 1650 | O | | HOH | 1133 | −16.755 | 12.026 | 14.455 | 1.00 | 77.44 |
| 1651 | O | | HOH | 1134 | −16.415 | 39.649 | 21.797 | 1.00 | 40.49 |
| 1652 | O | | HOH | 1135 | −2.905 | 36.921 | 16.824 | 1.00 | 41.22 |
| 1653 | O | | HOH | 1136 | −16.085 | 30.016 | 14.670 | 1.00 | 69.03 |
| 1654 | O | | HOH | 1137 | 3.816 | 15.385 | 8.414 | 1.00 | 50.37 |
| 1655 | O | | HOH | 1138 | 0.109 | −10.190 | −22.019 | 1.00 | 63.01 |
| 1656 | O | | HOH | 1139 | 4.301 | −14.459 | −10.124 | 1.00 | 56.73 |
| 1657 | O | | HOH | 1140 | −7.274 | −6.583 | −8.742 | 1.00 | 39.87 |
| 1658 | O | | HOH | 1141 | 5.165 | −10.242 | 6.021 | 1.00 | 49.99 |
| 1659 | O | | HOH | 1142 | 11.080 | −10.915 | −5.579 | 1.00 | 51.07 |
| 1660 | O | | HOH | 1143 | 10.047 | −6.771 | −9.373 | 1.00 | 56.45 |
| 1661 | O | | HOH | 1144 | −8.718 | −6.685 | 6.994 | 1.00 | 55.03 |
| 1662 | O | | HOH | 1145 | −10.703 | −2.849 | 6.332 | 1.00 | 46.14 |
| 1663 | O | | HOH | 1146 | 9.326 | −0.521 | 9.559 | 1.00 | 69.26 |
| 1664 | O | | HOH | 1147 | 7.301 | −4.411 | 10.646 | 1.00 | 47.66 |
| 1665 | O | | HOH | 1148 | 10.068 | 5.756 | 5.280 | 1.00 | 53.49 |
| 1666 | O | | HOH | 1149 | 3.03 | 21.594 | 33.057 | 1.00 | 101.30 |
| 1667 | O | | HOH | 1150 | 3.131 | 20.433 | 23.935 | 1.00 | 50.77 |
| 1668 | O | | HOH | 1151 | −14.389 | 32.669 | 32.745 | 1.00 | 50.00 |
| 1669 | O | | HOH | 1152 | −15.767 | 27.767 | 35.884 | 1.00 | 52.03 |
| 1670 | O | | HOH | 1153 | −17.147 | 30.782 | 37.687 | 1.00 | 47.87 |
| 1671 | O | | HOH | 1154 | −21.990 | 28.556 | 31.375 | 1.00 | 36.17 |
| 1672 | O | | HOH | 1155 | −23.114 | 29.749 | 33.891 | 1.00 | 42.15 |
| 1673 | O | | HOH | 1156 | −4.307 | 18.756 | 35.827 | 1.00 | 49.49 |

TABLE 2-continued

| ATOM | ATOM TYPE | RESIDUE | PROTEIN # | # | X | Y | Z | OCC | B |
|---|---|---|---|---|---|---|---|---|---|
| 1674 | O | | HOH | 1157 | −4.355 | 33.867 | 35.136 | 1.00 | 39.12 |
| 1675 | O | | HOH | 1158 | −0.232 | 12.344 | 15.591 | 1.00 | 59.12 |
| 1676 | O | | HOH | 1159 | −4.563 | 9.516 | 15.817 | 1.00 | 62.92 |
| 1677 | O | | HOH | 1160 | −15.293 | 13.117 | 11.731 | 1.00 | 56.39 |
| 1678 | O | | HOH | 1161 | −18.374 | 11.150 | 24.452 | 1.00 | 49.62 |
| 1679 | O | | HOH | 1162 | −8.305 | 13.725 | 23.235 | 1.00 | 58.60 |
| 1680 | O | | HOH | 1163 | 3.954 | 24.408 | 18.919 | 1.00 | 47.73 |
| 1681 | O | | HOH | 1164 | 1.194 | 21.898 | 17.497 | 1.00 | 47.83 |
| 1682 | O | | HOH | 1165 | −11.180 | −5.255 | −8.381 | 1.00 | 50.36 |
| 1683 | O | | HOH | 1166 | −12.227 | −3.531 | −11.978 | 1.00 | 60.60 |
| 1684 | O | | HOH | 1167 | −6.569 | −4.957 | −11.425 | 1.00 | 73.07 |
| 1685 | O | | HOH | 1168 | −4.454 | 0.407 | −13.393 | 1.00 | 57.20 |
| 1686 | O | | HOH | 1169 | −10.140 | −2.532 | −14.075 | 1.00 | 68.05 |
| 1687 | O | | HOH | 1170 | −7.694 | −0.711 | −12.721 | 1.00 | 51.03 |
| 1688 | O | | HOH | 1171 | 7.732 | −12.271 | −8.162 | 1.00 | 53.12 |
| 1689 | O | | HOH | 1172 | −5.537 | −14.500 | 1.044 | 1.00 | 52.35 |

References

The references listed below as well as all references cited in the specification are incorporated herein by reference to the extent that they supplement, explain, provide a background for or teach methodology, techniques and/or compositions employed herein.

Adelman et al. (1983) *DNA* 2:183
Altschul et al., (1990) *J. Mol. Biol.* 215: 403-10
*Animal Cell Culture* (1986) (Freshney, ed.)
Ausubel et al., (1989) *Current Protocols in Molecular Biology*, Greene Publishing Associates and Wiley Interscience, New York
Bahner et al., (2000) *J. Biol. Chem.* 275: 2901-2904
Bodanszky et al. (1976) *Peptide Synthesis*, John Wiley & Sons, Second Edition
Brenman et al., 1996
Buffers. *A Guide for the Preparation and Use of Buffers in Biological Systems*, (Gueffroy, ed.) Calbiochem Corporation (1975)
Cho et al., (1992) *Neuron* 9:929-942
Crea et al., (1978) *Proc. Nat. Acad. Sci. U.S.A.* 75: 5765
Creighton, (1983) *Proteins: Structures and Molecular Principles*, W. H. Freeman & Co., New York
Daniels et al., (1998) *Nat. Struct. Biol.* 5: 317-325
Doyle et al., (1996) *Cell* 85: 1067-1076
Fanning & Anderson, (1999) *Curr. Opin. Cell Biol.* 11: 432-439
Fields et al. (1990) *Int. J. Peptide Protein Res.*, 35:161-214
Fitch et al., *Proc. Natl. Acad. Sci. U.S.A.* 80: 1382-1386 (1983)
Gomperts, (1996) *Cell* 84: 659-662
Gribskov et al., (1986) *Nucl. Acids. Res.* 14: 6745
Henikoff & Henikoff, (1989) *Proc Natl Acad Sci U.S.A.* 89: 10915
Hillier et al., (1999) *Science* 284: 812-815
Hoskins et al., (1996) *Development* 122: 97-111
*Immobilized Cells and Enzymes* (1986) (IRL Press)
Itoh et al., (1993) *J. Cell Biol.* 121: 491-502
Janson & Rydén (eds), (1998) *Protein Purification: Principles, High Resolution Methods, and Applications* (2$^{nd}$ ed.), Wiley-Liss, New York
Johnstone & Thorpe, (1987) *Immunochemistry in Practice*, (2$^{nd}$ ed.)
Karlin & Altschul, (1993) *Proc Natl Acad Sci U.S.A.* 90: 5873-5887
Kennedy, (1995) *Trends Biochem Sci* 20: 350
Kimple et al., (2001) *EMBO J.* 20: 4414-4422
Kornau et al., (1995) *Science* 269: 1737-1740
Kyte & Doolittle, (1982), *J. Mol. Biol.* 157: 105-132
Maniatis et al., (1982) *Molecular Cloning: A Laboratory Manual; DNA Cloning: A Practical Approach*, Volumes I and II (1985) (Glover, ed.)
McOmie, (1973) *Protective Groups in Organic Chemistry*, Plenum Press, New York, N.Y.
Meienhofer, (1983) *Hormonal Proteins and Peptides*, Vol. 2, p. 46
Merrifield, (1969) *Adv. Enzymol.* 32:221-96
Messing et al., (1981) *Third Cleveland Symposium on Macromolecules and Recombinant DNA*, (Walton, ed.) Elsevier, Amsterdam
Montell, (1999) *Annu Rev Cell Dev Biol* 15: 231-268
Morais Cabral et al., (1996) *Nature* 382: 649-652
Needleman et al., (1970) *J. Mol. Biol.* 48: 443-453
Nicholls et al., (1991) *Proteins* 11: 282
*Nucleic Acid Hybridization* (1985) (Hames & Higgins, eds.)
Ogez et al., (1989) *Biotech. Adv.* 7: 467-488
*Oligonucleotide Synthesis* (1984) (Gait, ed.)
Perbal, (1984) *A Practical Guide to Molecular Cloning*
Ponting et al., (1995) *Trend. Biol. Sci.* 20: 102-103
Sambrook et al., (1989) *Molecular Cloning: A Laboratory Manual*, Cold Spring Harbor Press
Schroder et al. (1965) *The Peptides*, Vol. 1, Academic Press, New York, N.Y.
Schwartz et al., eds., (1979), *Atlas of Protein Sequence and Structure*, National Biomedical Research Foundation, pp. 357-358
Scott & Zuker, (1998) *Nature* 395: 805-808
Scott et al., (1995) *Neuron* 15: 919-927
Shieh et al., (1997) *Proc. Natl. Acad. Sci. U.S.A.* 94: 12682-12687
Simske et al., (1996) *Cell* 85: 195-204
Smith et al., (1981) *Adv. Appl. Math.* 2:482
Sofer, (1986) Bio/Technology 4: 712-715
Songyang et al., (1997) *Science* 275: 73-77
Steward et al. (1969) *Solid Phase Peptide Synthesis*, W. H. Freeman Co., San Francisco, Calif.
*Transcription and Translation* (1984) (Hames & Higgins, eds)
Tsunoda et al., (1997) *Nature* 388: 243-249
U.S. Pat. No. 4,244,946
U.S. Pat. No. 4,554,101
van Huizen et al., (1998) *EMBO J.* 17: 2285-2297

Wallen et al. (1983) *Eur. J. Biochem.* 133: 681-686
Wells et al., (1985) *Gene* 34: 315
Wes et al., (1999) *Nat Neurosci* 2: 447-453
Wetmur & Davidson, (1968) *J. Mol. Biol.* 31: 349-70
Woods et al., (1991) *Cell* 66: 451-464
Xu et al., (1998) *J. Cell Biol.* 142: 545-555

It will be understood that various details of the invention can be changed without departing from the scope of the invention. Furthermore, the foregoing description is for the purpose of illustration only, and not for the purpose of limitation—the invention being defined by the claims appended hereto.

---

What is claimed is:

1. A method for purifying a target protein, said method comprising:
   a) providing a fusion protein comprising the target protein and the PDZ1 domain of InaD in a host cell;
   b) contacting a composition comprising said fusion protein with NorpA or a fragment of NorpA that binds to the PDZ1 domain of the fusion protein,
   c) removing uncomplexed components from the composition, and
   d) recovering the fusion protein comprising the target protein from NorpA or a fragment of NorpA that binds to the PDZ1 domain.

2. The method of claim 1, wherein the PDZ1 domain comprises SEQ ID NO: 8.

3. The method of claim 1, wherein the NorpA sequence comprises a functional enzyme.

4. The method of claim 3, wherein the enzyme is selected from the group consisting of alkaline phosphatase, horseradish peroxidase, an enzyme that yields a colored product, an enzyme that yields a fluorescent product, an enzyme that degrades a colored substrate, an enzyme that degrades a fluorescent substrate, an enzyme that yields a product that yields a colored product when assayed with a second reagent, and an enzyme that yields a product that yields a fluorescent product when assayed with a second reagent.

5. The method of claim 1, wherein the NorpA or a fragment of NorpA that binds to the PDZ1 domain is immobilized on a support.

6. The method of claim 5, wherein the support comprises a matrix.

7. The method of claim 6, wherein the matrix is selected from the group consisting of a polysaccharide-based gel, glass beads, nitrocellulose, a membrane, a plastic plate, and a carboxymethylated dextran.

8. The method of claim 1, wherein the removal of uncomplexed components comprising washing buffer over the NorpA or fragment of NorpA that binds to the PDZ1 domain.

9. The method of claim 1, wherein the recovery of the fusion protein comprising the target protein comprises eluting the target protein away from NorpA or a fragment of NorpA that binds to the PDZ1 domain with a compound selected from te group consisiting of DTT, BME, DTE, and GSH.

10. A method for purifying a target protein, said method comprising:
    a) providing a fusion protein comprising the target protein and NorpA or a fragment of NorpA that binds to the PDZ1 domain of InaD in a host cell;
    b) contacting a composition comprising said fusion protein with the PDZ1 domain of InaD,
    c) removing uncomplexed components from the composition, and
    d) recovering the fusion protein comprising the target protein from the PDZ1 domain of InaD.

11. The method of claim 10, wherein the NorpA sequence comprises a sequence selected from the group consisting of SEQ ID NO: 1, 2, and 9.

12. The method of claim 10, wherein the PDZ1 domain comprises a functional enzyme.

13. The method of claim 12, wherein the enzyme is selected from the group consisting of alkaline phosphatase, horseradish peroxidase, an enzyme that yields a colored product, an enzyme that yields a fluorescent product, an enzyme that degrades a colored substrate, an enzyme that degrades a fluorescent substrate, an enzyme that yields a product that yields a colored product when assayed with a second reagent, and an enzyme that yields a product that yields a fluorescent product when assayed with a second reagent.

14. The method of claim 10, wherein the PDZ1 domain is immobilized on a support.

15. The method of claim 14, wherein the support comprises a matrix.

16. The method of claim 15, wherein the matrix is selected from the group consisting of a polysaccharide-based gel, glass beads, nitrocellulose, a membrane, a plastic plate, and a carboxymethylated dextran.

17. The method of claim 10, wherein the removal of uncomplexed components comprising washing buffer over the PDZ1 domain.

18. The method of claim 10, wherein the recovery of the fusion protein comprising the target protein comprises eluting the target protein away from the PDZ1 domain with a compound selected from te group consisting of DTT, BME, DTE, and GSH.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Drosophila melanogaster

<400> SEQUENCE: 1

Thr Glu Phe Cys Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Artificial NorpA tag
<220> FEATURE:
<221> NAME/KEY: PEPTIDE
<222> LOCATION: (1)..(5)
<223> OTHER INFORMATION: X is any amino acid
<220> FEATURE:
<221> NAME/KEY: PEPTIDE
<222> LOCATION: (1)..(5)
<223> OTHER INFORMATION: Synthesized peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

Xaa Xaa Xaa Cys Xaa
1               5

<210> SEQ ID NO 3
<211> LENGTH: 2025
<212> TYPE: DNA
<213> ORGANISM: Drosophila melanogaster
<220> FEATURE:
<221> NAME/KEY: CDS
<222> LOCATION: (1)..(2025)

<400> SEQUENCE: 3 atg gtt cag ttc ctg ggc aaa cag ggc acc gcg ggt gag ctc att cac      48
Met Val Gln Phe Leu Gly Lys Gln Gly Thr Ala Gly Glu Leu Ile His
1               5                   10                  15 atg gtg acc ctg gac aag acg ggc aag aag tcc ttc ggc atc tgc ata      96
Met Val Thr Leu Asp Lys Thr Gly Lys Lys Ser Phe Gly Ile Cys Ile
                20                  25                  30 gtg cgc ggc gag gtg aag gat tcg ccc aac acc aag aca acc ggc atc     144
Val Arg Gly Glu Val Lys Asp Ser Pro Asn Thr Lys Thr Thr Gly Ile
            35                  40                  45 ttc atc aag ggc att gtg ccc gac agt ccc gcg cat ctg tgt ggt cgc     192
Phe Ile Lys Gly Ile Val Pro Asp Ser Pro Ala His Leu Cys Gly Arg
        50                  55                  60
```

```
cta aag gtt ggc gat cgg atc ctc tcg ctc aac gga aag gat gtg cgc        240
Leu Lys Val Gly Asp Arg Ile Leu Ser Leu Asn Gly Lys Asp Val Arg
 65              70                  75                  80 aac tcc acc gaa cag gcg gtc atc gat ctc atc aag gag gcg gac ttc        288
Asn Ser Thr Glu Gln Ala Val Ile Asp Leu Ile Lys Glu Ala Asp Phe
                 85                  90                  95 aag atc gag ctg gag att cag acc ttc gac aag agc gat gag cag cag        336
Lys Ile Glu Leu Glu Ile Gln Thr Phe Asp Lys Ser Asp Glu Gln Gln
            100                 105                 110 gcc aag tca gat ccg cgg agc aat ggc tac atg cag gcc aag aac aag        384
Ala Lys Ser Asp Pro Arg Ser Asn Gly Tyr Met Gln Ala Lys Asn Lys
        115                 120                 125 ttc aat cag gag cag acc acc aac aac aat gcg tcc gga ggt cag gga        432
Phe Asn Gln Glu Gln Thr Thr Asn Asn Asn Ala Ser Gly Gly Gln Gly
    130                 135                 140 atg ggg caa ggt cag ggt cag ggt cag gga atg gct ggc atg aac cgg        480
Met Gly Gln Gly Gln Gly Gln Gly Gln Gly Met Ala Gly Met Asn Arg
145                 150                 155                 160 cag caa tcg atg cag aag cgg aat acc aca ttc acg gcc tcg atg cgt        528
Gln Gln Ser Met Gln Lys Arg Asn Thr Thr Phe Thr Ala Ser Met Arg
                165                 170                 175 cag aag cat agt aac tac gcc gac gag gat gac gag gac acc cgg gac        576
Gln Lys His Ser Asn Tyr Ala Asp Glu Asp Asp Glu Asp Thr Arg Asp
            180                 185                 190 atg acc ggt cgc att cgc acg gag gcg ggt tat gag atc gat cga gcc        624
Met Thr Gly Arg Ile Arg Thr Glu Ala Gly Tyr Glu Ile Asp Arg Ala
        195                 200                 205 tcc gcc ggt aat tgc aaa ctt aat aag cag gaa aag gat cgc gac aag        672
Ser Ala Gly Asn Cys Lys Leu Asn Lys Gln Glu Lys Asp Arg Asp Lys
    210                 215                 220 gag cag gaa gat gaa ttt ggc tac acg atg gct aag atc aac aag cgg        720
Glu Gln Glu Asp Glu Phe Gly Tyr Thr Met Ala Lys Ile Asn Lys Arg
225                 230                 235                 240 tac aac atg atg aag gat ctg cgc agg atc gag gtc cag agg gac gcc        768
Tyr Asn Met Met Lys Asp Leu Arg Arg Ile Glu Val Gln Arg Asp Ala
                245                 250                 255 agc aag cca ctg gga ctc gca ctc gct ggc cac aag gac cgc cag aag        816
Ser Lys Pro Leu Gly Leu Ala Leu Ala Gly His Lys Asp Arg Gln Lys
            260                 265                 270 atg gcc tgc ttt gtt gcc ggt gtg gat ccc aac gga gca ttg ggc agc        864
Met Ala Cys Phe Val Ala Gly Val Asp Pro Asn Gly Ala Leu Gly Ser
        275                 280                 285 gtg gac att aag ccg ggc gac gag atc gtc gag gtc aac ggc aat gtg        912
Val Asp Ile Lys Pro Gly Asp Glu Ile Val Glu Val Asn Gly Asn Val
    290                 295                 300 ctt aag aat cgc tgc cac ttg aac gcc tcc gcc gtg ttc aag aac gtg        960
Leu Lys Asn Arg Cys His Leu Asn Ala Ser Ala Val Phe Lys Asn Val
305                 310                 315                 320 gat ggg gat aag ctc gtg atg atc acc tcg cga cgc aag ccc aac gat       1008
Asp Gly Asp Lys Leu Val Met Ile Thr Ser Arg Arg Lys Pro Asn Asp
                325                 330                 335 gag ggc atg tgc gtc aag ccc atc aaa aag ttc ccc acc gcg tct gat       1056
Glu Gly Met Cys Val Lys Pro Ile Lys Lys Phe Pro Thr Ala Ser Asp
            340                 345                 350 gag act aag ttt atc ttc gac cag ttt ccc aag gcg cgc acg gtg cag       1104
Glu Thr Lys Phe Ile Phe Asp Gln Phe Pro Lys Ala Arg Thr Val Gln
        355                 360                 365 gtg cgc aag gag ggt ttc ctg ggc atc atg gtc atc tat ggc aag cac       1152
Val Arg Lys Glu Gly Phe Leu Gly Ile Met Val Ile Tyr Gly Lys His
    370                 375                 380
```

```
gct gag gtg ggc agt ggc att ttc atc tcg gat ctg aga gag gga tcg    1200
Ala Glu Val Gly Ser Gly Ile Phe Ile Ser Asp Leu Arg Glu Gly Ser
385             390                 395                 400 aat gcc gag ttg gcg ggc gtg aaa gtg ggc gac atg ctg ctg gcc gtt    1248
Asn Ala Glu Leu Ala Gly Val Lys Val Gly Asp Met Leu Leu Ala Val
            405                 410                 415 aat cag gat gta aca ctg gaa tcc aac tac gat gat gct act gga ctg    1296
Asn Gln Asp Val Thr Leu Glu Ser Asn Tyr Asp Asp Ala Thr Gly Leu
        420                 425                 430 ctt aaa cgt gcc gag ggc gta gtg acc atg att cta ttg act ctc aag    1344
Leu Lys Arg Ala Glu Gly Val Val Thr Met Ile Leu Leu Thr Leu Lys
    435                 440                 445 agc gag gag gcg ata aag gct gag aag gca gcg gaa gag aaa aag aag    1392
Ser Glu Glu Ala Ile Lys Ala Glu Lys Ala Ala Glu Glu Lys Lys Lys
450                 455                 460 gag gag gcc aag aaa gag gag gaa aag cca cag gaa ccc gcc aca gcc    1440
Glu Glu Ala Lys Lys Glu Glu Glu Lys Pro Gln Glu Pro Ala Thr Ala
465             470                 475                 480 gag atc aag ccg aac aaa aag ata ctc att gag ttg aag gtg gaa aag    1488
Glu Ile Lys Pro Asn Lys Lys Ile Leu Ile Glu Leu Lys Val Glu Lys
            485                 490                 495 aag cca atg ggc gtc atc gtc tgc ggc ggc aag aac aac cat gtc acg    1536
Lys Pro Met Gly Val Ile Val Cys Gly Gly Lys Asn Asn His Val Thr
        500                 505                 510 act ggc tgt gta atc acc cac gtt tat ccg gag gga caa gtg gca gcc    1584
Thr Gly Cys Val Ile Thr His Val Tyr Pro Glu Gly Gln Val Ala Ala
    515                 520                 525 gac aag cgc ctc aag atc ttt gac cac att tgc gat ata aat ggt acg    1632
Asp Lys Arg Leu Lys Ile Phe Asp His Ile Cys Asp Ile Asn Gly Thr
530                 535                 540 cca atc cac gtg gga tcc atg acg aca ctg aag gtc cat cag tta ttc    1680
Pro Ile His Val Gly Ser Met Thr Thr Leu Lys Val His Gln Leu Phe
545             550                 555                 560 cac acc aca tac gag aag gcg gtc acc cta acg gtc ttc cgc gct gat    1728
His Thr Thr Tyr Glu Lys Ala Val Thr Leu Thr Val Phe Arg Ala Asp
            565                 570                 575 cct ccg gaa ctg gaa aag ttt aac gtt gac ctt atg aaa aaa gca ggc    1776
Pro Pro Glu Leu Glu Lys Phe Asn Val Asp Leu Met Lys Lys Ala Gly
        580                 585                 590 aag gag ctg ggc ctg tcg ctg tct ccc aac gaa att gga tgc acc atc    1824
Lys Glu Leu Gly Leu Ser Leu Ser Pro Asn Glu Ile Gly Cys Thr Ile
    595                 600                 605 gcg gac ttg att caa gga caa tac ccg gag att gac agc aaa ctg cag    1872
Ala Asp Leu Ile Gln Gly Gln Tyr Pro Glu Ile Asp Ser Lys Leu Gln
610                 615                 620 cgc ggc gat att atc acc aaa ttc aat ggc gat gcc ttg gag ggt ctt    1920
Arg Gly Asp Ile Ile Thr Lys Phe Asn Gly Asp Ala Leu Glu Gly Leu
625                 630                 635                 640 ccg ttc cag gtg tgc tac gcc ttg ttc aag gga gcc aac ggc aag gta    1968
Pro Phe Gln Val Cys Tyr Ala Leu Phe Lys Gly Ala Asn Gly Lys Val
            645                 650                 655 tcg atg gaa gtg aca cga ccc aag ccc act cta cgt acg gag gca ccc    2016
Ser Met Glu Val Thr Arg Pro Lys Pro Thr Leu Arg Thr Glu Ala Pro
        660                 665                 670 aag gcc tag                                                        2025
Lys Ala
```

<210> SEQ ID NO 4
<211> LENGTH: 674
<212> TYPE: PRT
<213> ORGANISM: Drosophila melanogaster

<400> SEQUENCE: 4

```
Met Val Gln Phe Leu Gly Lys Gln Gly Thr Ala Gly Glu Leu Ile His
1               5                   10                  15
Met Val Thr Leu Asp Lys Thr Gly Lys Ser Phe Gly Ile Cys Ile
            20                  25                  30
Val Arg Gly Glu Val Lys Asp Ser Pro Asn Thr Lys Thr Thr Gly Ile
            35                  40                  45
Phe Ile Lys Gly Ile Val Pro Asp Ser Pro Ala His Leu Cys Gly Arg
        50                  55                  60
Leu Lys Val Gly Asp Arg Ile Leu Ser Leu Asn Gly Lys Asp Val Arg
65                  70                  75                  80
Asn Ser Thr Glu Gln Ala Val Ile Asp Leu Ile Lys Glu Ala Asp Phe
                85                  90                  95
Lys Ile Glu Leu Glu Ile Gln Thr Phe Asp Lys Ser Asp Glu Gln Gln
            100                 105                 110
Ala Lys Ser Asp Pro Arg Ser Asn Gly Tyr Met Gln Ala Lys Asn Lys
        115                 120                 125
Phe Asn Gln Glu Gln Thr Thr Asn Asn Ala Ser Gly Gly Gln Gly
    130                 135                 140
Met Gly Gln Gly Gln Gly Gln Gly Gln Gly Met Ala Gly Met Asn Arg
145                 150                 155                 160
Gln Gln Ser Met Gln Lys Arg Asn Thr Thr Phe Thr Ala Ser Met Arg
                165                 170                 175
Gln Lys His Ser Asn Tyr Ala Asp Glu Asp Asp Glu Asp Thr Arg Asp
            180                 185                 190
Met Thr Gly Arg Ile Arg Thr Glu Ala Gly Tyr Glu Ile Asp Arg Ala
        195                 200                 205
Ser Ala Gly Asn Cys Lys Leu Asn Lys Gln Glu Lys Asp Arg Asp Lys
    210                 215                 220
Glu Gln Glu Asp Glu Phe Gly Tyr Thr Met Ala Lys Ile Asn Lys Arg
225                 230                 235                 240
Tyr Asn Met Met Lys Asp Leu Arg Arg Ile Glu Val Gln Arg Asp Ala
                245                 250                 255
Ser Lys Pro Leu Gly Leu Ala Leu Ala Gly His Lys Asp Arg Gln Lys
            260                 265                 270
Met Ala Cys Phe Val Ala Gly Val Asp Pro Asn Gly Ala Leu Gly Ser
        275                 280                 285
Val Asp Ile Lys Pro Gly Asp Glu Ile Val Glu Val Asn Gly Asn Val
    290                 295                 300
Leu Lys Asn Arg Cys His Leu Asn Ala Ser Ala Val Phe Lys Asn Val
305                 310                 315                 320
Asp Gly Asp Lys Leu Val Met Ile Thr Ser Arg Arg Lys Pro Asn Asp
                325                 330                 335
Glu Gly Met Cys Val Lys Pro Ile Lys Lys Phe Pro Thr Ala Ser Asp
            340                 345                 350
Glu Thr Lys Phe Ile Phe Asp Gln Phe Pro Lys Ala Arg Thr Val Gln
        355                 360                 365
Val Arg Lys Glu Gly Phe Leu Gly Ile Met Val Ile Tyr Gly Lys His
    370                 375                 380
```

```
Ala Glu Val Gly Ser Gly Ile Phe Ile Ser Asp Leu Arg Glu Gly Ser
385                 390                 395                 400

Asn Ala Glu Leu Ala Gly Val Lys Val Gly Asp Met Leu Leu Ala Val
            405                 410                 415

Asn Gln Asp Val Thr Leu Glu Ser Asn Tyr Asp Asp Ala Thr Gly Leu
        420                 425                 430

Leu Lys Arg Ala Glu Gly Val Val Thr Met Ile Leu Leu Thr Leu Lys
    435                 440                 445

Ser Glu Glu Ala Ile Lys Ala Glu Lys Ala Ala Glu Glu Lys Lys Lys
450                 455                 460

Glu Glu Ala Lys Lys Glu Glu Lys Pro Gln Glu Pro Ala Thr Ala
465                 470                 475                 480

Glu Ile Lys Pro Asn Lys Lys Ile Leu Ile Glu Leu Lys Val Glu Lys
                485                 490                 495

Lys Pro Met Gly Val Ile Val Cys Gly Gly Lys Asn Asn His Val Thr
                500                 505                 510

Thr Gly Cys Val Ile Thr His Val Tyr Pro Glu Gly Gln Val Ala Ala
            515                 520                 525

Asp Lys Arg Leu Lys Ile Phe Asp His Ile Cys Asp Ile Asn Gly Thr
530                 535                 540

Pro Ile His Val Gly Ser Met Thr Thr Leu Lys Val His Gln Leu Phe
545                 550                 555                 560

His Thr Thr Tyr Glu Lys Ala Val Thr Leu Thr Val Phe Arg Ala Asp
                565                 570                 575

Pro Pro Glu Leu Glu Lys Phe Asn Val Asp Leu Met Lys Lys Ala Gly
            580                 585                 590

Lys Glu Leu Gly Leu Ser Leu Ser Pro Asn Glu Ile Gly Cys Thr Ile
        595                 600                 605

Ala Asp Leu Ile Gln Gly Gln Tyr Pro Glu Ile Asp Ser Lys Leu Gln
    610                 615                 620

Arg Gly Asp Ile Ile Thr Lys Phe Asn Gly Asp Ala Leu Glu Gly Leu
625                 630                 635                 640

Pro Phe Gln Val Cys Tyr Ala Leu Phe Lys Gly Ala Asn Gly Lys Val
                645                 650                 655

Ser Met Glu Val Thr Arg Pro Lys Pro Thr Leu Arg Thr Glu Ala Pro
            660                 665                 670

Lys Ala

<210> SEQ ID NO 5
<211> LENGTH: 3288
<212> TYPE: DNA
<213> ORGANISM: Drosophila melanogaster
<220> FEATURE:
<221> NAME/KEY: CDS
<222> LOCATION: (1)..(3288)

<400> SEQUENCE: 5 atg acc aag aag tac gag ttc gat tgg atc att ccg gtt ccg ccg gaa     48
Met Thr Lys Lys Tyr Glu Phe Asp Trp Ile Ile Pro Val Pro Pro Glu
1               5                   10                  15 ttg acc acg ggc tgc gtt ttc gat cgc tgg ttc gaa aac gaa aag gag     96
Leu Thr Thr Gly Cys Val Phe Asp Arg Trp Phe Glu Asn Glu Lys Glu
            20                  25                  30 aca aag gag aat gac ttt gag cgt gat gcc ctc ttc aag gtc gat gaa    144
Thr Lys Glu Asn Asp Phe Glu Arg Asp Ala Leu Phe Lys Val Asp Glu
        35                  40                  45
```

-continued

| | | |
|---|---|---|
| tac gga ttt ttc ctg tac tgg aaa agt gag ggc agg gat ggc gat gtc<br>Tyr Gly Phe Phe Leu Tyr Trp Lys Ser Glu Gly Arg Asp Gly Asp Val<br>50 55 60 | 192 | |
| ata gag ctc tgc caa gtg agc gac att cgt gcg ggc gga aca cca aag<br>Ile Glu Leu Cys Gln Val Ser Asp Ile Arg Ala Gly Gly Thr Pro Lys<br>65 70 75 80 | 240 | |
| gat ccg aag ata ctt gat aag gtg acg aag aag aac ggc acc aat ata<br>Asp Pro Lys Ile Leu Asp Lys Val Thr Lys Lys Asn Gly Thr Asn Ile<br>85 90 95 | 288 | |
| ccg gaa ctg gat aag cga tcc ctg acg atc tgt tcg aac acg gac tat<br>Pro Glu Leu Asp Lys Arg Ser Leu Thr Ile Cys Ser Asn Thr Asp Tyr<br>100 105 110 | 336 | |
| atc aat ata aca tat cac cat gtt att tgt cca gat gcg gca aca gcc<br>Ile Asn Ile Thr Tyr His His Val Ile Cys Pro Asp Ala Ala Thr Ala<br>115 120 125 | 384 | |
| aag agc tgg caa aag aac ttg cgt ctc atc acg cat aat aac cgc gcc<br>Lys Ser Trp Gln Lys Asn Leu Arg Leu Ile Thr His Asn Asn Arg Ala<br>130 135 140 | 432 | |
| acg aat gtg tgc ccg cgc gtc aac ctg atg aag cat tgg atg cga ttg<br>Thr Asn Val Cys Pro Arg Val Asn Leu Met Lys His Trp Met Arg Leu<br>145 150 155 160 | 480 | |
| agt tac tgc gta gag aag agt gga aaa att ccg gtt aaa acg ctg gcc<br>Ser Tyr Cys Val Glu Lys Ser Gly Lys Ile Pro Val Lys Thr Leu Ala<br>165 170 175 | 528 | |
| aaa acc ttt gca tcc ggc aaa acg gag aaa ttg gtg tac acg tgc ata<br>Lys Thr Phe Ala Ser Gly Lys Thr Glu Lys Leu Val Tyr Thr Cys Ile<br>180 185 190 | 576 | |
| aag gat gcc ggt ctg ccc gat gat aaa aac gca acg atg acc aag gag<br>Lys Asp Ala Gly Leu Pro Asp Asp Lys Asn Ala Thr Met Thr Lys Glu<br>195 200 205 | 624 | |
| cag ttc acc ttc gac aag ttc tac gcc ttg tac cac aag gtg tgt ccc<br>Gln Phe Thr Phe Asp Lys Phe Tyr Ala Leu Tyr His Lys Val Cys Pro<br>210 215 220 | 672 | |
| cga aac gac att gag gag ctc ttc acc tcc atc acc aag ggc aag cag<br>Arg Asn Asp Ile Glu Glu Leu Phe Thr Ser Ile Thr Lys Gly Lys Gln<br>225 230 235 240 | 720 | |
| gac ttt atc agt ttg gag caa ttt att cag ttt atg aac gac aaa cag<br>Asp Phe Ile Ser Leu Glu Gln Phe Ile Gln Phe Met Asn Asp Lys Gln<br>245 250 255 | 768 | |
| cgc gat ccg cgg atg aac gaa att ctg tac cct ctc tac gag gag aaa<br>Arg Asp Pro Arg Met Asn Glu Ile Leu Tyr Pro Leu Tyr Glu Glu Lys<br>260 265 270 | 816 | |
| cgt tgc acg gag atc atc aac gat tac gag cta gat gag gag aaa aag<br>Arg Cys Thr Glu Ile Ile Asn Asp Tyr Glu Leu Asp Glu Glu Lys Lys<br>275 280 285 | 864 | |
| aag aac gtt caa atg tcg ttg gac gga ttt aag cgc tat cta atg tcc<br>Lys Asn Val Gln Met Ser Leu Asp Gly Phe Lys Arg Tyr Leu Met Ser<br>290 295 300 | 912 | |
| gac gaa aac gca ccc gta ttc ctg gac cgg ctg gat ttc tac atg gaa<br>Asp Glu Asn Ala Pro Val Phe Leu Asp Arg Leu Asp Phe Tyr Met Glu<br>305 310 315 320 | 960 | |
| atg gat cag cca ctg gcc cat tac tat atc aac agc tcg cat aat acc<br>Met Asp Gln Pro Leu Ala His Tyr Tyr Ile Asn Ser Ser His Asn Thr<br>325 330 335 | 1008 | |
| tac cta tcc ggt cgt cag atc ggc ggc aaa agt tcc gtg gaa atg tac<br>Tyr Leu Ser Gly Arg Gln Ile Gly Gly Lys Ser Ser Val Glu Met Tyr<br>340 345 350 | 1056 | |
| cga cag aca ctc ttg gca ggt tgt cgc tgt gtg gag ctg gat tgc tgg<br>Arg Gln Thr Leu Leu Ala Gly Cys Arg Cys Val Glu Leu Asp Cys Trp<br>355 360 365 | 1104 | |

```
aac gga aag ggt gag gac gag gag cca att gtc acc cac ggt cac gcc    1152
Asn Gly Lys Gly Glu Asp Glu Glu Pro Ile Val Thr His Gly His Ala
    370             375                 380 tac tgc act gaa atc ctc ttt aag gac tgc atc cag gcg att gcg gat    1200
Tyr Cys Thr Glu Ile Leu Phe Lys Asp Cys Ile Gln Ala Ile Ala Asp
385             390                 395                     400 tgc gcc ttc gtg tcc tcc gag tat ccg gta atc ctg tcc ttc gaa aac    1248
Cys Ala Phe Val Ser Ser Glu Tyr Pro Val Ile Leu Ser Phe Glu Asn
                405                 410                 415 cac tgc aac cgc gcc cag caa tac aag ttg gcc aaa tac tgt gat gac    1296
His Cys Asn Arg Ala Gln Gln Tyr Lys Leu Ala Lys Tyr Cys Asp Asp
            420                 425                 430 ttc ttc ggc gat ctg ctg cta aag gag ccg cta cca gat cga ccg ctg    1344
Phe Phe Gly Asp Leu Leu Leu Lys Glu Pro Leu Pro Asp Arg Pro Leu
        435                 440                 445 gat ccg ggc ctt ccg ttg ccg cca ccc tgc aaa ctg aag cgt aag atc    1392
Asp Pro Gly Leu Pro Leu Pro Pro Pro Cys Lys Leu Lys Arg Lys Ile
450                 455                 460 ctc atc aag aac aag cga atg aag cca gaa gtg gaa aag gtc gag ctg    1440
Leu Ile Lys Asn Lys Arg Met Lys Pro Glu Val Glu Lys Val Glu Leu
465                 470                 475                 480 gag ctc tgg ctg aag ggc gaa ctc aaa acg gat gac gat ccg gaa gag    1488
Glu Leu Trp Leu Lys Gly Glu Leu Lys Thr Asp Asp Asp Pro Glu Glu
            485                 490                 495 gac gcc agt gcg ggc aag ccg cca gag gca gcc gcc gca ccc gca ccc    1536
Asp Ala Ser Ala Gly Lys Pro Pro Glu Ala Ala Ala Ala Pro Ala Pro
                500                 505                 510 gcc ccg gaa gca gcc gcc gcc gcc gaa gga gcg gcc gag ggg ggc ggt    1584
Ala Pro Glu Ala Ala Ala Ala Ala Glu Gly Ala Ala Glu Gly Gly Gly
        515                 520                 525 gga gcg gag gcc gaa gcc gcc gct gcc aac tac agc ggc tcc acc acc    1632
Gly Ala Glu Ala Glu Ala Ala Ala Asn Tyr Ser Gly Ser Thr Thr
    530                 535                 540 aac gtg cat ccg tgg ctc tcc tcc atg gtc aat tac gcg cag ccc atc    1680
Asn Val His Pro Trp Leu Ser Ser Met Val Asn Tyr Ala Gln Pro Ile
545             550                 555                 560 aag ttc cag ggc ttc gac aag gca atc gaa aag aat att gcc cac aac    1728
Lys Phe Gln Gly Phe Asp Lys Ala Ile Glu Lys Asn Ile Ala His Asn
                565                 570                 575 atg tcc tcg ttt gcg gaa tcg gcg ggc atg aac tac ttg aag cag agc    1776
Met Ser Ser Phe Ala Glu Ser Ala Gly Met Asn Tyr Leu Lys Gln Ser
            580                 585                 590 tcc atc gac ttt gtc aat tac aac aag cgt cag atg tcg cga att tat    1824
Ser Ile Asp Phe Val Asn Tyr Asn Lys Arg Gln Met Ser Arg Ile Tyr
        595                 600                 605 ccg aag ggc aca cga gcg gac tcc tca aac tat atg ccg cag gtg ttc    1872
Pro Lys Gly Thr Arg Ala Asp Ser Ser Asn Tyr Met Pro Gln Val Phe
610                 615                 620 tgg aac gcc ggc tgc cag atg gtc tca ctc aat ttc cag agc tcc gat    1920
Trp Asn Ala Gly Cys Gln Met Val Ser Leu Asn Phe Gln Ser Ser Asp
625                 630                 635                 640 tta ccc atg caa ctc aac cag ggc aag ttc gag tat aat ggc ggc tgt    1968
Leu Pro Met Gln Leu Asn Gln Gly Lys Phe Glu Tyr Asn Gly Gly Cys
            645                 650                 655 ggc tat cta cta aaa ccg gat ttc atg cgt cga gcc gac aag gat ttt    2016
Gly Tyr Leu Leu Lys Pro Asp Phe Met Arg Arg Ala Asp Lys Asp Phe
        660                 665                 670 gat ccg ttt gcc gat gcg ccg gtg gac ggt gtg att gcg gcc cag tgt    2064
Asp Pro Phe Ala Asp Ala Pro Val Asp Gly Val Ile Ala Ala Gln Cys
    675                 680                 685
```

| | |
|---|---|
| tcc gtt aaa gtg att gcc ggc caa ttc ttg tcc gac aag aaa gtg ggc<br>Ser Val Lys Val Ile Ala Gly Gln Phe Leu Ser Asp Lys Lys Val Gly<br>690                      695                      700 | 2112 |
| acc tat gtg gag gtg gac atg ttt gga ttg ccc tcg gac acg gtg aaa<br>Thr Tyr Val Glu Val Asp Met Phe Gly Leu Pro Ser Asp Thr Val Lys<br>705                    710                      715                    720 | 2160 |
| aaa gag ttt cga acg cgt ttg gtc gcc aat aat ggc ctg aat cca gtt<br>Lys Glu Phe Arg Thr Arg Leu Val Ala Asn Asn Gly Leu Asn Pro Val<br>                    725                      730                    735 | 2208 |
| tac aat gag gat ccc ttt gtg ttc cgc aaa gtg gtc ctt ccg gac ttg<br>Tyr Asn Glu Asp Pro Phe Val Phe Arg Lys Val Val Leu Pro Asp Leu<br>              740                      745                    750 | 2256 |
| gct gtg cta aga ttt ggc gtt tat gaa gaa agc gga aag att ctg ggt<br>Ala Val Leu Arg Phe Gly Val Tyr Glu Glu Ser Gly Lys Ile Leu Gly<br>755                    760                      765 | 2304 |
| caa cgt att ctg ccg ctg gac ggt ttg cag gct ggc tat cgg cat gtt<br>Gln Arg Ile Leu Pro Leu Asp Gly Leu Gln Ala Gly Tyr Arg His Val<br>770                    775                      780 | 2352 |
| tcc ctg cgc acg gag gct aac ttc ccc atg tcg ttg ccc atg ttg ttc<br>Ser Leu Arg Thr Glu Ala Asn Phe Pro Met Ser Leu Pro Met Leu Phe<br>785                    790                      795                    800 | 2400 |
| gtg aat atc gag cta aag atc tac gta cct gac ggc ttt gag gac ttc<br>Val Asn Ile Glu Leu Lys Ile Tyr Val Pro Asp Gly Phe Glu Asp Phe<br>                    805                      810                    815 | 2448 |
| atg gcc atg ttg tcg gat ccg cga ggt ttc gcc ggt gcc gct aag cag<br>Met Ala Met Leu Ser Asp Pro Arg Gly Phe Ala Gly Ala Ala Lys Gln<br>              820                      825                    830 | 2496 |
| caa aac gaa cag atg aag gca ctt ggc att gag gag cag agc ggc ggt<br>Gln Asn Glu Gln Met Lys Ala Leu Gly Ile Glu Glu Gln Ser Gly Gly<br>835                    840                      845 | 2544 |
| gcc gcc cga gat gct ggc aag gcc aaa gag gag gaa aag aag gag cca<br>Ala Ala Arg Asp Ala Gly Lys Ala Lys Glu Glu Glu Lys Lys Glu Pro<br>850                    855                      860 | 2592 |
| cca cta gtc ttt gag cct gtc acg ttg gaa tct ctg cgc cag gag aaa<br>Pro Leu Val Phe Glu Pro Val Thr Leu Glu Ser Leu Arg Gln Glu Lys<br>865                    870                      875                    880 | 2640 |
| ggc ttc caa aag gtg ggc aaa aag caa atc aag gag ctc gac acc ctg<br>Gly Phe Gln Lys Val Gly Lys Lys Gln Ile Lys Glu Leu Asp Thr Leu<br>                    885                      890                    895 | 2688 |
| cgc aag aag cat gcc aag gag cgc acc tcg gtg caa aag acc cag aat<br>Arg Lys Lys His Ala Lys Glu Arg Thr Ser Val Gln Lys Thr Gln Asn<br>              900                      905                    910 | 2736 |
| gcg gcc atc gac aag ttg atc aag ggc aag agc aaa gac gac att cgt<br>Ala Ala Ile Asp Lys Leu Ile Lys Gly Lys Ser Lys Asp Asp Ile Arg<br>915                    920                      925 | 2784 |
| aac gat gcc aac atc aag aat tcg atc aat gac cag acc aag cag tgg<br>Asn Asp Ala Asn Ile Lys Asn Ser Ile Asn Asp Gln Thr Lys Gln Trp<br>930                    935                      940 | 2832 |
| acc gac atg atc gcc agg cac cgc aag gag gaa tgg gac atg ctg cgc<br>Thr Asp Met Ile Ala Arg His Arg Lys Glu Glu Trp Asp Met Leu Arg<br>945                    950                      955                    960 | 2880 |
| caa cat gtc cag gac tcg cag gac gcc atg aag gca ctg atg ctc acc<br>Gln His Val Gln Asp Ser Gln Asp Ala Met Lys Ala Leu Met Leu Thr<br>                    965                      970                    975 | 2928 |
| gtt cag gcg gcg cag atc aag cag ctg gag gat cgt cat gcc agg gac<br>Val Gln Ala Ala Gln Ile Lys Gln Leu Glu Asp Arg His Ala Arg Asp<br>              980                      985                    990 | 2976 |
| atc aag gat ctg aat gcc aag caa gca aag atg tcg gcg gat acc gcc<br>Ile Lys Asp Leu Asn Ala Lys Gln Ala Lys Met Ser Ala Asp Thr Ala<br>995                    1000                     1005 | 3024 |

-continued

| | | |
|---|---|---|
| aag gag gta caa aac gac aag acc ttg aag act aag aac gaa aag<br>Lys Glu Val Gln Asn Asp Lys Thr Leu Lys Thr Lys Asn Glu Lys<br>    1010                      1015                    1020 | | 3069 |
| gat cgt cgg ctg cgt gag aag cgc cag aac aat gtg aag cgc ttc<br>Asp Arg Arg Leu Arg Glu Lys Arg Gln Asn Asn Val Lys Arg Phe<br>    1025                      1030                    1035 | | 3114 |
| atg gag gaa aag aag caa atc gga gtt aag cag ggt cgt gcg atg<br>Met Glu Glu Lys Lys Gln Ile Gly Val Lys Gln Gly Arg Ala Met<br>1040                      1045                    1050 | | 3159 |
| gag aaa cta aag ttg gcg cat tcg aag cag atc gag gaa ttc agt<br>Glu Lys Leu Lys Leu Ala His Ser Lys Gln Ile Glu Glu Phe Ser<br>    1055                      1060                    1065 | | 3204 |
| acc gac gtg caa aag ctt atg gac atg tac aaa atc gag gag gag<br>Thr Asp Val Gln Lys Leu Met Asp Met Tyr Lys Ile Glu Glu Glu<br>1070                      1075                    1080 | | 3249 |
| gcg tat aag acg caa gga aaa acg gaa ttt tgt gcc taa<br>Ala Tyr Lys Thr Gln Gly Lys Thr Glu Phe Cys Ala<br>    1085                      1090                    1095 | | 3288 |

<210> SEQ ID NO 6
<211> LENGTH: 1095
<212> TYPE: PRT
<213> ORGANISM: Drosophila melanogaster

<400> SEQUENCE: 6

Met Thr Lys Lys Tyr Glu Phe Asp Trp Ile Ile Pro Val Pro Pro Glu
1               5                   10                  15

Leu Thr Thr Gly Cys Val Phe Asp Arg Trp Phe Glu Asn Glu Lys Glu
            20                  25                  30

Thr Lys Glu Asn Asp Phe Glu Arg Asp Ala Leu Phe Lys Val Asp Glu
        35                  40                  45

Tyr Gly Phe Phe Leu Tyr Trp Lys Ser Glu Gly Arg Asp Gly Asp Val
    50                  55                  60

Ile Glu Leu Cys Gln Val Ser Asp Ile Arg Ala Gly Gly Thr Pro Lys
65                  70                  75                  80

Asp Pro Lys Ile Leu Asp Lys Val Thr Lys Lys Asn Gly Thr Asn Ile
                85                  90                  95

Pro Glu Leu Asp Lys Arg Ser Leu Thr Ile Cys Ser Asn Thr Asp Tyr
            100                 105                 110

Ile Asn Ile Thr Tyr His His Val Ile Cys Pro Asp Ala Ala Thr Ala
        115                 120                 125

Lys Ser Trp Gln Lys Asn Leu Arg Leu Ile Thr His Asn Asn Arg Ala
    130                 135                 140

Thr Asn Val Cys Pro Arg Val Asn Leu Met Lys His Trp Met Arg Leu
145                 150                 155                 160

Ser Tyr Cys Val Glu Lys Ser Gly Lys Ile Pro Val Lys Thr Leu Ala
                165                 170                 175

Lys Thr Phe Ala Ser Gly Lys Thr Glu Lys Leu Val Tyr Thr Cys Ile
            180                 185                 190

Lys Asp Ala Gly Leu Pro Asp Asp Lys Asn Ala Thr Met Thr Lys Glu
        195                 200                 205

Gln Phe Thr Phe Asp Lys Phe Tyr Ala Leu Tyr His Lys Val Cys Pro
    210                 215                 220

Arg Asn Asp Ile Glu Glu Leu Phe Thr Ser Ile Thr Lys Gly Lys Gln
225                 230                 235                 240

Asp Phe Ile Ser Leu Glu Gln Phe Ile Gln Phe Met Asn Asp Lys Gln
                245                 250                 255

-continued

```
Arg Asp Pro Arg Met Asn Glu Ile Leu Tyr Pro Leu Tyr Glu Glu Lys
            260                 265                 270

Arg Cys Thr Glu Ile Ile Asn Asp Tyr Glu Leu Asp Glu Glu Lys Lys
            275                 280                 285

Lys Asn Val Gln Met Ser Leu Asp Gly Phe Lys Arg Tyr Leu Met Ser
            290                 295                 300

Asp Glu Asn Ala Pro Val Phe Leu Asp Arg Leu Asp Phe Tyr Met Glu
305                 310                 315                 320

Met Asp Gln Pro Leu Ala His Tyr Tyr Ile Asn Ser Ser His Asn Thr
            325                 330                 335

Tyr Leu Ser Gly Arg Gln Ile Gly Gly Lys Ser Ser Val Glu Met Tyr
            340                 345                 350

Arg Gln Thr Leu Leu Ala Gly Cys Arg Cys Val Glu Leu Asp Cys Trp
            355                 360                 365

Asn Gly Lys Gly Glu Asp Glu Glu Pro Ile Val Thr His Gly His Ala
            370                 375                 380

Tyr Cys Thr Glu Ile Leu Phe Lys Asp Cys Ile Gln Ala Ile Ala Asp
385                 390                 395                 400

Cys Ala Phe Val Ser Ser Glu Tyr Pro Val Ile Leu Ser Phe Glu Asn
            405                 410                 415

His Cys Asn Arg Ala Gln Gln Tyr Lys Leu Ala Lys Tyr Cys Asp Asp
            420                 425                 430

Phe Phe Gly Asp Leu Leu Leu Lys Glu Pro Leu Pro Asp Arg Pro Leu
            435                 440                 445

Asp Pro Gly Leu Pro Leu Pro Pro Cys Lys Leu Lys Arg Lys Ile
450                 455                 460

Leu Ile Lys Asn Lys Arg Met Lys Pro Glu Val Glu Lys Val Glu Leu
465                 470                 475                 480

Glu Leu Trp Leu Lys Gly Glu Leu Lys Thr Asp Asp Pro Glu Glu
            485                 490                 495

Asp Ala Ser Ala Gly Lys Pro Pro Glu Ala Ala Ala Pro Ala Pro
            500                 505                 510

Ala Pro Glu Ala Ala Ala Ala Glu Gly Ala Ala Glu Gly Gly Gly
            515                 520                 525

Gly Ala Glu Ala Glu Ala Ala Ala Asn Tyr Ser Gly Ser Thr Thr
            530                 535                 540

Asn Val His Pro Trp Leu Ser Ser Met Val Asn Tyr Ala Gln Pro Ile
545                 550                 555                 560

Lys Phe Gln Gly Phe Asp Lys Ala Ile Glu Lys Asn Ile Ala His Asn
            565                 570                 575

Met Ser Ser Phe Ala Glu Ser Ala Gly Met Asn Tyr Leu Lys Gln Ser
            580                 585                 590

Ser Ile Asp Phe Val Asn Tyr Asn Lys Arg Gln Met Ser Arg Ile Tyr
            595                 600                 605

Pro Lys Gly Thr Arg Ala Asp Ser Ser Asn Tyr Met Pro Gln Val Phe
            610                 615                 620

Trp Asn Ala Gly Cys Gln Met Val Ser Leu Asn Phe Gln Ser Ser Asp
625                 630                 635                 640

Leu Pro Met Gln Leu Asn Gln Gly Lys Phe Glu Tyr Asn Gly Gly Cys
            645                 650                 655

Gly Tyr Leu Leu Lys Pro Asp Phe Met Arg Arg Ala Asp Lys Asp Phe
            660                 665                 670
```

-continued

```
Asp Pro Phe Ala Asp Ala Pro Val Asp Gly Val Ile Ala Ala Gln Cys
            675                 680                 685

Ser Val Lys Val Ile Ala Gly Gln Phe Leu Ser Asp Lys Lys Val Gly
690                 695                 700

Thr Tyr Val Glu Val Asp Met Phe Gly Leu Pro Ser Asp Thr Val Lys
705                 710                 715                 720

Lys Glu Phe Arg Thr Arg Leu Val Ala Asn Asn Gly Leu Asn Pro Val
                725                 730                 735

Tyr Asn Glu Asp Pro Phe Val Phe Arg Lys Val Val Leu Pro Asp Leu
            740                 745                 750

Ala Val Leu Arg Phe Gly Val Tyr Glu Glu Ser Gly Lys Ile Leu Gly
        755                 760                 765

Gln Arg Ile Leu Pro Leu Asp Gly Leu Gln Ala Gly Tyr Arg His Val
    770                 775                 780

Ser Leu Arg Thr Glu Ala Asn Phe Pro Met Ser Leu Pro Met Leu Phe
785                 790                 795                 800

Val Asn Ile Glu Leu Lys Ile Tyr Val Pro Asp Gly Phe Glu Asp Phe
                805                 810                 815

Met Ala Met Leu Ser Asp Pro Arg Gly Phe Ala Gly Ala Ala Lys Gln
            820                 825                 830

Gln Asn Glu Gln Met Lys Ala Leu Gly Ile Glu Glu Gln Ser Gly Gly
        835                 840                 845

Ala Ala Arg Asp Ala Gly Lys Ala Lys Glu Glu Lys Lys Glu Pro
    850                 855                 860

Pro Leu Val Phe Glu Pro Val Thr Leu Glu Ser Leu Arg Gln Glu Lys
865                 870                 875                 880

Gly Phe Gln Lys Val Gly Lys Lys Gln Ile Lys Glu Leu Asp Thr Leu
                885                 890                 895

Arg Lys Lys His Ala Lys Glu Arg Thr Ser Val Gln Lys Thr Gln Asn
            900                 905                 910

Ala Ala Ile Asp Lys Leu Ile Lys Gly Lys Ser Lys Asp Asp Ile Arg
        915                 920                 925

Asn Asp Ala Asn Ile Lys Asn Ser Ile Asn Asp Gln Thr Lys Gln Trp
    930                 935                 940

Thr Asp Met Ile Ala Arg His Arg Lys Glu Glu Trp Asp Met Leu Arg
945                 950                 955                 960

Gln His Val Gln Asp Ser Gln Asp Ala Met Lys Ala Leu Met Leu Thr
                965                 970                 975

Val Gln Ala Ala Gln Ile Lys Gln Leu Glu Asp Arg His Ala Arg Asp
            980                 985                 990

Ile Lys Asp Leu Asn Ala Lys  Ala Lys Met Ser Ala  Asp Thr Ala
        995                 1000                1005

Lys Glu  Val Gln Asn Asp Lys  Thr Leu Lys Thr Lys  Asn Glu Lys
        1010                1015                1020

Asp Arg  Arg Leu Arg Glu Lys  Arg Gln Asn Asn Val  Lys Arg Phe
        1025                1030                1035

Met Glu  Glu Lys Lys Gln Ile  Gly Val Lys Gln Gly  Arg Ala Met
        1040                1045                1050

Glu Lys  Leu Lys Leu Ala His  Ser Lys Gln Ile Glu  Glu Phe Ser
        1055                1060                1065
```

```
            Thr Asp Val Gln Lys Leu Met Asp Met Tyr Lys Ile Glu Glu Glu
                1070                1075                1080

Ala Tyr Lys Thr Gln Gly Lys Thr Glu Phe Cys Ala
                1085                1090            1095

<210> SEQ ID NO 7
<211> LENGTH: 303
<212> TYPE: DNA
<213> ORGANISM: Drosophila melanogaster
<220> FEATURE:
<221> NAME/KEY: CDS
<222> LOCATION: (1)..(303)

<400> SEQUENCE: 7 ggc gcc atg gcg ggt gag ctc att cac atg gtg acc ctg gac aag acg      48
Gly Ala Met Ala Gly Glu Leu Ile His Met Val Thr Leu Asp Lys Thr
1               5                   10                  15 ggc aag aag tcc ttc ggc atc tgc ata gtg cgc ggc gag gtg aag gat      96
Gly Lys Lys Ser Phe Gly Ile Cys Ile Val Arg Gly Glu Val Lys Asp
            20                  25                  30 tcg ccc aac acc aag aca acc ggc atc ttc atc aag ggc att gtg ccc     144
Ser Pro Asn Thr Lys Thr Thr Gly Ile Phe Ile Lys Gly Ile Val Pro
        35                  40                  45 gac agt ccc gcg cat ctg tgt ggt cgc cta aag gtt ggc gat cgg atc     192
Asp Ser Pro Ala His Leu Cys Gly Arg Leu Lys Val Gly Asp Arg Ile
    50                  55                  60 ctc tcg ctc aac gga aag gat gtg cgc aac tcc acc gaa cag gcg gtc     240
Leu Ser Leu Asn Gly Lys Asp Val Arg Asn Ser Thr Glu Gln Ala Val
65                  70                  75                  80 atc gat ctc atc aag gag gcg gac ttc aag atc gag ctg gag att cag     288
Ile Asp Leu Ile Lys Glu Ala Asp Phe Lys Ile Glu Leu Glu Ile Gln
                85                  90                  95 acc ttc gac aag tga                                                  303
Thr Phe Asp Lys
            100

<210> SEQ ID NO 8
<211> LENGTH: 100
<212> TYPE: PRT
<213> ORGANISM: Drosophila melanogaster

<400> SEQUENCE: 8

Gly Ala Met Ala Gly Glu Leu Ile His Met Val Thr Leu Asp Lys Thr
1               5                   10                  15

Gly Lys Lys Ser Phe Gly Ile Cys Ile Val Arg Gly Glu Val Lys Asp
            20                  25                  30

Ser Pro Asn Thr Lys Thr Thr Gly Ile Phe Ile Lys Gly Ile Val Pro
        35                  40                  45

Asp Ser Pro Ala His Leu Cys Gly Arg Leu Lys Val Gly Asp Arg Ile
    50                  55                  60

Leu Ser Leu Asn Gly Lys Asp Val Arg Asn Ser Thr Glu Gln Ala Val
65                  70                  75                  80

Ile Asp Leu Ile Lys Glu Ala Asp Phe Lys Ile Glu Leu Glu Ile Gln
                85                  90                  95

Thr Phe Asp Lys
            100

<210> SEQ ID NO 9
<211> LENGTH: 7
<212> TYPE: PRT
<213> ORGANISM: Drosophila melanogaster
```

```
<400> SEQUENCE: 9

Gly Leu Thr Glu Phe Cys Ala
1               5

<210> SEQ ID NO 10
<211> LENGTH: 25
<212> TYPE: DNA
<213> ORGANISM: Artificial Sequence
<220> FEATURE:
<223> OTHER INFORMATION: Sense oligonucleotide that encodes the
      C-terminal five amino acids of NorpA (Thr-Glu-Phe-Cys-Ala) flanked
      by NotI half-site, partially complementary to SEQ ID NO: 11
<220> FEATURE:
<221> NAME/KEY: misc_structure
<222> LOCATION: (1)..(25)

<400> SEQUENCE: 10
ggccgcacgg aattttgtgc ctaat                                          25

<210> SEQ ID NO 11
<211> LENGTH: 25
<212> TYPE: DNA
<213> ORGANISM: Artificial Sequence
<220> FEATURE:
<223> OTHER INFORMATION: Antisense oligonucleotide that encodes the
      C-terminal five amino acids of NorpA (Thr-Glu-Phe-Cys-Ala) flanked
      by XbaI half-sites, partially complementary to SEQ ID NO: 10
<220> FEATURE:
<221> NAME/KEY: misc_feature
<222> LOCATION: (1)..(25)

<400> SEQUENCE: 11
ctagattagg cacaaaattc cgtgc                                          25

<210> SEQ ID NO 12
<211> LENGTH: 30
<212> TYPE: DNA
<213> ORGANISM: Artificial Sequence
<220> FEATURE:
<223> OTHER INFORMATION: Sense primer used to amplify nucleotides
      encoding residues 13-10 of InaD, with flanking Kpn I site
<220> FEATURE:
<221> NAME/KEY: misc_feature
<222> LOCATION: (1)..(30)

<400> SEQUENCE: 12
tggtaccgag ctcattcaca tggtgaccct                                     30

<210> SEQ ID NO 13
<211> LENGTH: 29
<212> TYPE: DNA
<213> ORGANISM: Artificial Sequence
<220> FEATURE:
<223> OTHER INFORMATION: Anti-sense primer used to amplify nucleotides
      encoding residues 13-107 of InaD, with flanking Bgl II site
<220> FEATURE:
<221> NAME/KEY: misc_feature
<222> LOCATION: (1)..(29)

<400> SEQUENCE: 13
cagatcttct tgtcgaaggt ctgaatctc                                      29
```